(12) United States Patent
Choi

(10) Patent No.: US 9,504,668 B2
(45) Date of Patent: Nov. 29, 2016

(54) PHENYL ALKYL CARBAMATE COMPOUNDS FOR USE IN PREVENTING OR TREATING EPILEPSY OR EPILEPSY-RELATED SYNDROME

(71) Applicant: BIO-PHARM SOLUTIONS CO., LTD., Gyeonggi-do (KR)

(72) Inventor: Yong Moon Choi, Pine Brook, NJ (US)

(73) Assignee: BIO-PHARM SOLUTIONS CO., LTD. (KR)

( * ) Notice: Subject to any disclaimer, the term of this patent is extended or adjusted under 35 U.S.C. 154(b) by 0 days.

(21) Appl. No.: 14/774,287

(22) PCT Filed: Mar. 11, 2014

(86) PCT No.: PCT/KR2014/002006
§ 371 (c)(1),
(2) Date: Sep. 10, 2015

(87) PCT Pub. No.: WO2014/142519
PCT Pub. Date: Sep. 18, 2014

(65) Prior Publication Data
US 2016/0023999 A1  Jan. 28, 2016

Related U.S. Application Data

(60) Provisional application No. 61/776,926, filed on Mar. 12, 2013.

(51) Int. Cl.
*A61K 31/045* (2006.01)
*A61K 31/325* (2006.01)
*C07C 271/12* (2006.01)
*C07C 271/24* (2006.01)
*A61K 31/03* (2006.01)
*A61K 31/27* (2006.01)

(52) U.S. Cl.
CPC ............. *A61K 31/325* (2013.01); *A61K 31/03* (2013.01); *A61K 31/27* (2013.01); *C07C 271/12* (2013.01); *C07C 271/24* (2013.01); *C07C 2101/02* (2013.01); *C07C 2101/14* (2013.01); *C07C 2102/42* (2013.01)

(58) Field of Classification Search
CPC .. C07C 271/24; C07C 271/12; A61K 31/045
USPC .................... 514/730; 560/32, 115, 163, 164
See application file for complete search history.

(56) References Cited

U.S. PATENT DOCUMENTS

| | | |
|---|---|---|
| 3,265,728 A | 8/1966 | Bossinger et al. |
| 5,258,397 A | 11/1993 | Lepage et al. |
| 2001/0034365 A1 | 10/2001 | Choi et al. |
| 2004/0171679 A1* | 9/2004 | Plata-Salaman ....... A61K 31/27 514/483 |
| 2012/0184762 A1 | 7/2012 | Choi |

FOREIGN PATENT DOCUMENTS

| | | |
|---|---|---|
| KR | 10-0467760 | 1/2005 |
| WO | WO 2012-002773 A2 | 1/2012 |

OTHER PUBLICATIONS

International Search Report prepared by the Korean Intellectual Property Office on Jun. 26, 2014, for International Application No. PCT/KR2014/002006.
Kung, et al. "Carbamate derivatives of felbamate as potential anticonvulsant agents", Medicinal Chemistry Research, 2010, vol. 19, No. 5, pp. 498-513.
Official Action for Korea Patent Application No. Oct. 2015-7026369, dated Sep. 07, 2016, 5 pages.
Official Action for Japan Patent Application No. 2015/562914, dated Sep. 08, 2016, 4 pages.

* cited by examiner

*Primary Examiner* — T. Victor Oh
(74) *Attorney, Agent, or Firm* — Sheridan Ross P.C.

(57) ABSTRACT

The present invention provides a pharmaceutical composition for preventing and/or treating a epilepsy or epilepsy-related syndrome, for example an intractable epilepsy or its related syndrome such as drug-resistant epilepsy, comprising the phenyl alkyl carbamate compound as an active ingredient, and a use of the phenyl alkyl carbamate compound for preventing and/or treating epilepsy or epilepsy-related syndrome.

16 Claims, No Drawings

PHENYL ALKYL CARBAMATE COMPOUNDS FOR USE IN PREVENTING OR TREATING EPILEPSY OR EPILEPSY-RELATED SYNDROME

CROSS REFERENCE TO RELATED APPLICATIONS

This application is a national stage application under 35 U.S.C. 371 and claims the benefit of PCT Application No. PCT/KR2014/002006 having an international filing date of Mar. 11, 2014, which designated the United States, which PCT application claimed the benefit of U.S. Provisional Application No. 61/776,926 filed Mar. 12, 2013, the disclosures of each of which are incorporated herein by reference.

TECHNICAL FIELD

The present invention provides a pharmaceutical composition for preventing and/or treating a epilepsy or epilepsy-related syndrome, for example an intractable epilepsy or its related syndrome such as drug-resistant epilepsy, comprising the phenyl alkyl carbamate compound as an active ingredient, and a use of the phenyl alkyl carbamate compound for preventing and/or treating epilepsy or epilepsy-related syndrome.

BACKGROUND OF THE INVENTION

Epilepsy and its related syndromes may be classified according to whether the associated seizures are partial or generalized, and whether the etiology is idiopathic or symptomatic/cryptogenic. Several important syndromes can be further grouped according to age of onset and prognosis.

Epilepsy is a chronic brain disease in which epileptic seizures are the predominant feature. Generally, most epilepsies and diseases associated therewith are difficult to treat, since epilepsies are not etiologically elucidated. Thus, administration of an antiepileptic agent is a common approach toward suppressing epileptic seizures or inhibiting propagation of focal seizures to other portions.

The older established antiepileptic drugs (AEDs) such as phenyloin, carbamazepine, clonazepam, ethosuximide, valproic acid and barbiturates are widely prescribed but suffer from a range of side effect. Furthermore, there is a significant group of patients (20-30%) that are resistant to the currently available therapeutic agents. Fifty million people in the world have epilepsy, and there are between 16 and 51 cases of new-onset epilepsy per 100,000 people every year. A community-based study in southern France estimated that up to 22.5% of patients with epilepsy have drug-resistant epilepsy. Patients with drug-resistant epilepsy have increased risks of premature death, injuries, psychosocial dysfunction, and a reduced quality of life.

One study showed that the use-dependent blockade of the fast sodium current in dentate granule cells by carbamazepine was lost in hippocampi resected from patients with carbamazepine-resistant temporal-lobe epilepsy, although this finding did not extend to lamotrigine, which has a pharmacologic action similar to that of carbamazepine. Altered expression of subtypes of the γ-aminobutyric acid type A ($GABA_A$) receptor has also been observed in patients with drug-resistant temporal-lobe epilepsy. Whether these changes result in reduced sensitivity to antiepileptic drugs that act on the receptor is unknown.

Since 1989 several new drugs have been launched, including felbamate, gabapentin, lamotrigine, oxcarbazepine, tiagabine, topimarate, vigabartrin, zonisamide and levetiracetam. While many of new drugs AEDs show improved efficacies and side-effect profiles, patients with intractable epilepsy remain untreated. Because of the need to individualize therapy, no rigid set of guidelines can be applied to determine medical intractability. There is still a need for improved medication.

SUMMARY OF THE INVENTION

An embodiment provides a pharmaceutical composition for the prevention and the treatment of an epilepsy or a epilepsy-related syndrome, comprising a phenyl alkyl carbamate compound of the following Chemical Formula 1, an enantiomer or a diastereomer thereof, or a mixture of enantiomers or diastereomers; or a pharmaceutically acceptable salt thereof.

Another embodiment is to provide a method of preventing and/or treating an epilepsy or a epilepsy-related syndrome in a subject comprising administering a pharmaceutically effective amount of a phenyl alkyl carbamate compound represented by Chemical Formula 1; a racemate, an enantiomer, a diastereomer, a mixture of enantiomers, or a mixture of diastereomers thereof; or a pharmaceutically acceptable salt thereof, to the subject in need.

Still other embodiment is to provide a phenyl alkyl carbamate compound represented by Chemical Formula 1; a racemate, an enantiomer, a diastereomer, a mixture of enantiomers, or a mixture of diastereomers thereof; or a pharmaceutically acceptable salt thereof, for use in the prevention and/or treatment of epilepsy or the manufacture of a pharmaceutical composition for preventing and/or treating an epilepsy or a epilepsy-related syndrome.

DETAILED DESCRIPTION OF THE EMBODIMENTS

Continuing its research work in the field of epilepsy, the present inventors, as results of studies on the development of the drugs useful for prevention and/or treatment of an epilepsy or a epilepsy-related syndrome, found that a substituted phenyl alkyl carbamate compounds of the following Chemical Formula 1 exhibits remarkably excellent anti-epilepsy activity in various emulation models and simultaneously has very low toxicity, and completed the invention.

An embodiment of the present invention provides a pharmaceutical composition for prevention and/or treatment of an epilepsy or a epilepsy-related syndrome, comprising an organic compound, i.e., phenyl carbamate derivatives, more particularly, a phenyl alkyl carbamate compound represented by following Chemical Formula I; a racemate, an enantiomer, a diastereomer, a mixture of enantiomers, or a mixture of diastereomers thereof; or a pharmaceutically acceptable salt thereof:

[Chemical Formula I]

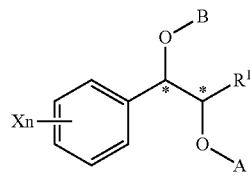

wherein,

X is a halogen, for example, chlorine, fluorine, iodine, or bromine, n, that means the number of substituent X, is an integer from 1 to 5, for example, 1 or 2, wherein X is the same or different each other, when n is 2 or larger, R¹ is a hydrogen or linear or branched $C_1$-$C_4$ alkyl group, for example, methyl group, ethyl group, isopropyl group, or butyl group, A is selected from the group consisting of an allyl, a $C_1$-$C_{19}$ linear or branched alkyl group (such as a methyl, t-butyl, benzyl, p-methoxybezyl, 2-napthylmethyl, trityl group etc.), a $C_2$-$C_8$ alkoxy alky ether group (such as a methoxy methy (MOM), methoxyethoxymethyl (MEM), thertahydropyranyl (THP), benzyloxymethyl (BOM), methylthiomethyl (MTM), trimethylsilylethoxymethyl (SEM), ethoxyethyl (EE) group etc.), and a carbamoyl derivative represented by

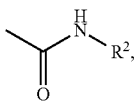

B is selected from the group consisting of an allyl, a $C_1$-$C_{19}$ linear or branched alkyl group (such as a methyl, t-butyl, benzyl, p-methoxybenzyl, 2-napthylmethyl, trityl group etc.), a $C_2$-$C_8$ alkoxy alky ether group (such as a methoxy methy (MOM), methoxyethoxymethyl (MEM), thertahydropyranyl (THP), benzyloxymethyl (BOM), methylthiomethyl (MTM), trimethylsilylethoxymethyl (SEM), ethoxyethyl (EE) group etc.), and a carbamoyl derivative represented by

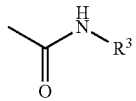

and

R² and R³ may be the same as or different from each other, and independently selected from the group consisting of hydrogen, a linear or branched lower alkyl group of $C_1$-$C_4$, for example $C_1$-$C_3$, a cycloalkyl group of $C_3$-$C_8$, for example $C_3$-$C_7$, and benzyl group, and more specifically, R² and R³ may be the same as or different from each other, and independently selected from the group consisting of hydrogen, methyl group, propyl group, isopropyl group, cyclopropyl group, cyclohexyl group, bicycloheptane group, and benzyl group.

In an embodiment, when A is a carbamoyl group, B is an allyl, a linear or branched $C_1$-$C_{19}$ alkyl group or a $C_2$-$C_8$ alkoxy alky ether group; when B is a carbamoyl group, A is an allyl, a linear or branched $C_1$-$C_{19}$ alkyl group or a $C_2$-$C_8$ alkoxy alky ether group; or A and B are carbamoyl derivative at the same time.

In an embodiment of Chemical Formula 1, the $C_1$-$C_{19}$ linear or branched alkyl group is independently linear or branched $C_1$-$C_6$ lower aliphatic alkyl such as methyl, ethyl, t-butyl and the like; a substituted or unsubstituted $C_3$-$C_{19}$ cycloaliphatic and substituted or unsubstituted $C_6$-$C_{18}$ aromatic group such as benzyl, naphtyl, trityl and the like. The cycloaliphatic group and the aromatic group may be substituted with at least one selected from the group consisting of hydrogen, $C_1$-$C_6$ lower alkyl and $C_1$-$C_6$ alkoxy group.

The examples of $C_1$-$C_6$ lower aliphatic alkyl include methyl, ethyl, propyl, t-butyl, pantyl, hexyl and the like. The examples of $C_6$-$C_{18}$ aromatic group is benzyl such as benzyl, methylbenzyl, methoxybenzyl and the like, naphtyl such as 2-naphtylmethyl, trityl group and the like.

Another embodiment provides a pharmaceutical composition containing a phenyl alkyl carbamate derivertive compound represented by Chemical Formula I; a racemate, an enantiomer, a diastereomer, a mixture of enantiomers, or a mixture of diastereomers thereof; or a pharmaceutically acceptable salt thereof, as an active ingredient.

Since the compound has two chiral carbons at the 1$^{st}$ and 2$^{nd}$ positions from the X substituted phenyl alkyl carbamate derivative group, they may be in the form of a racemate, an enantiomer, a diastereomer, a mixture of enantiomers, or a mixture of diastereomers.

In a concrete embodiment, the compound may be selected from the group consisting of:
1-(2-chlorophenyl)-1-carbamoyloxypropyl-2-carbamate,
1-(2-chlorophenyl)-1-carbamoyloxypropyl-2-N-methylcarbamate,
1-(2-chlorophenyl)-1-carbamoyloxypropyl-2-N-propylcarbamate
1-(2-chlorophenyl)-1-carbamoyloxybutyl-2-carbamate,
1-(2-chlorophenyl)-1-carbamoyloxy-3-methyl-butyl-2-carbamate,
1-(2-chlorophenyl)-1-carbamoyloxyhexyl-2-carbamate,
1-(2-iodophenyl)-1-carbamoyloxypropyl-2-carbamate,
1-(2-iodophenyl)-1-carbamoyloxybutyl-2-carbamate,
1-(2-iodophenyl)-1-carbamoyloxy-3-methyl-butyl-2-carbamate,
1-(2-iodophenyl)-1-carbamoyloxyhexyl-2-carbamate,
1-(2-fluorophenyl)-1-carbamoyloxypropyl-2-carbamate,
1-(2-fluorophenyl)-1-carbamoyloxybutyl-2-carbamate,
1-(2-fluorophenyl)-1-carbamoyloxy-3-methyl-butyl-2-carbamate,
1-(2-fluorophenyl)-1-carbamoyloxyhexyl-2-carbamate,
1-(2,4-dichlorophenyl)-1-carbamoyloxypropyl-2-carbamate,
1-(2,4-dichlorophenyl)-1-carbamoyloxybutyl-2-carbamate,
1-(2,4-dichlorophenyl)-1-carbamoyloxy-3-methyl-butyl-2-carbamate,
1-(2,4-dichlorophenyl)-1-carbamoyloxyhexyl-2-carbamate,
1-(2,6-dichlorophenyl)-1-carbamoyloxypropyl-2-carbamate,
1-(2,6-dichlorophenyl)-1-carbamoyloxybutyl-2-carbamate,
1-(2,6-dichlorophenyl)-1-carbamoyloxy-3-methyl-butyl-2-carbamate,
1-(2,6-dichlorophenyl)-1-carbamoyloxyhexyl-2-carbamate,
1-(2,4-difluorophenyl)-1-carbamoyloxypropyl-2-carbamate
1-(2,5-difluorophenyl)-1-carbamoyloxypropyl-2-carbamate
1-(2,6-difluorophenyl)-1-carbamoyloxypropyl-2-carbamate
1-(2-chloro-6-fluorophenyl)-1-carbamoyloxypropyl-2-carbamate
1-(2-chlorophenyl)-1-(methoxy)-ethyl-2-carbamate,
1-(2-fluorophenyl)-1-(methoxy)-ethyl-2-carbamate,
1-(2-iodophenyl)-1-(methoxy)-ethyl-2-carbamate,
1-(2-iodophenyl)-1-(methoxy)-propyl-2-carbamate,
1-(2-iodophenyl)-1-(methoxy)-propyl-2-N-methylcarbamate,
1-(2-iodophenyl)-1-(methoxy)-propyl-2-N-propylcarbamate,
1-(2-iodophenyl)-1-(methoxy)-propyl-2-N-isopropylcarbamate,
1-(2-iodophenyl)-1-(methoxy)-propyl-2-N-cyclopropylcarbamate,
1-(2-iodophenyl)-1-(methoxy)-propyl-2-N-cyclohexylcarbamate,
1-(2-iodophenyl)-1-(methoxy)-propyl-2-N-benzylcarbamate,
1-(2-iodophenyl)-1-(methoxy)-propyl-2-N-bicyclo[2,2,1]heptanecarbamate 1-(2-iodophenyl)-1-(methoxy)-butyl-2-carbamate,
1-(2-iodophenyl)-1-(methoxy)-butyl-2-N-m ethylcarbamate,
1-(2-iodophenyl)-1-(methoxy)-butyl-2-N-propylcarbamate,
1-(2-iodophenyl)-1-(methoxy)-butyl-2-N-isopropylcarbamate,
1-(2-iodophenyl)-1-(methoxy)-butyl-2-N-cyclopropylcarbamate,
1-(2-iodophenyl)-1-(methoxy)-butyl-2-N-cyclohexylcarbamate,
1-(2-iodophenyl)-1-(methoxy)-butyl-2-N-benzylcarbamate,
1-(2-iodophenyl)-1-(methoxy)-butyl-2-N-bicyclo[2,2,1]heptanecarbamate,
1-(2-iodophenyl)-1-(methoxy)3-methyl-butyl-2-carbamate,
1-(2-iodophenyl)-1-(methoxy)-3-methyl-butyl-2-N-methylcarbamate,
1-(2-iodophenyl)-1-(methoxy)-3-methyl-butyl-2-N-propylcarbamate,
1-(2-iodophenyl)-1-(methoxy)-3-methyl-butyl-2-N-isopropylcarbamate,
1-(2-iodophenyl)-1-(methoxy)-3-methyl-butyl-2-N-cyclopropylcarbamate,
1-(2-iodophenyl)-1-(methoxy)-3-methyl-butyl-2-N-cyclohexylcarbamate,
1-(2-iodophenyl)-1-(methoxy)-3-methyl-butyl-2-N-benzylcarbamate,
1-(2-iodophenyl)-1-(methoxy)-3-methyl-butyl-2-N-bicyclo[2,2,1]heptanecarbamate,
1-(2-iodophenyl)-1-(methoxy)-hexyl-2-carbamate,
1-(2-iodophenyl)-1-(methoxy)-hexyl-2-N-methylcarbamate,
1-(2-iodophenyl)-1-(methoxy)-hexyl-2-N-propylcarbamate,
1-(2-iodophenyl)-1-(methoxy)-hexyl-2-N-isopropylcarbamate,
1-(2-iodophenyl)-1-(methoxy)-hexyl-2-N-cyclopropylcarbamate,
1-(2-iodophenyl)-1-(methoxy)-hexyl-2-N-cyclohexylcarbamate,
1-(2-iodophenyl)-1-(methoxy)-hexyl-2-N-benzylcarbamate,
1-(2-iodophenyl)-1-(methoxy)-hexyl-2-N-bicyclo[2,2,1]heptanecarbamate,
1-(3-iodophenyl)-1-(methoxy)-propyl-2-carbamate,
1-(3-iodophenyl)-1-(methoxy)-butyl-2-carbamate,
1-(3-iodophenyl)-1-(methoxy)3-methyl-butyl-2-carbamate,
1-(3-iodophenyl)-1-(methoxy)-hexyl-2-carbamate,
1-(2-fluorophenyl)-1-(methoxy)-propyl-2-carbamate,
1-(2-fluorophenyl)-1-(methoxy)-propyl-2-N-methylcarbamate,
1-(2-fluorophenyl)-1-(methoxy)-propyl-2-N-propylcarbamate,
1-(2-fluorophenyl)-1-(methoxy)-propyl-2-N-isopropylcarbamate,
1-(2-fluorophenyl)-1-(methoxy)-propyl-2-N-cyclopropylcarbamate,
1-(2-fluorophenyl)-1-(methoxy)-propyl-2-N-cyclohexylcarbamate,
1-(2-fluorophenyl)-1-(methoxy)-propyl-2-N-benzylcarbamate,
1-(2-fluorophenyl)-1-(methoxy)-propyl-2-N-bicyclo[2,2,1]heptanecarbamate
1-(2-fluorophenyl)-1-(methoxy)-butyl-2-carbamate,
1-(2-fluorophenyl)-1-(methoxy)-3-methyl-butyl-2-carbamate,
1-(2-fluorophenyl)-1-(methoxy)-hexyl-2-carbamate,
1-(4-fluorophenyl)-1-(methoxy)-proyl-2-carbamate,
1-(4-fluorophenyl)-1-(methoxy)-butyl-2-carbamate,
1-(4-fluorophenyl)-1-(methoxy)-3-methyl-butyl-2-carbamate,
1-(4-fluorophenyl)-1-(methoxy)-hexyl-2-carbamate,
1-(2-chlorophenyl)-1-(methoxy)-propyl-2-carbamate,
1-(2-chlorophenyl)-1-(methoxy)-propyl-2-N-methylcarbamate,
1-(2-chlorophenyl)-1-(methoxy)-propyl-2-N-propylcarbamate,
1-(2-chlorophenyl)-1-(methoxy)-propyl-2-N-isopropylcarbamate,
1-(2-chlorophenyl)-1-(methoxy)-propyl-2-N-cyclopropylcarbamate,
1-(2-chlorophenyl)-1-(methoxy)-propyl-2-N-cyclohexylcarbamate,
1-(2-chlorophenyl)-1-(methoxy)-propyl-2-N-benzylcarbamate,
1-(2-chlorophenyl)-1-(methoxy)-propyl-2-N-bicyclo[2,2,1]heptanecarbamate
1-(2-chlorophenyl)-1-(methoxy)-butyl-2-carbamate,
1-(2-chlorophenyl)-1-(methoxy)-3-methyl-butyl-2-carbamate,
1-(2-chlorophenyl)-1-(methoxy)-hexyl-2-carbamate,
1-(2,3-dichlorophenyl)-1-(methoxy)-propyl-2-carbamate,
1-(2,4-dichlorophenyl)-1-(methoxy)-propyl-2-carbamate,
1-(2,4-dichlorophenyl)-1-(methoxy)-butyl-2-carbamate,
1-(2,4-dichlorophenyl)-1-(methoxy)-3-methyl-butyl-2-carbamate,
1-(2,4-dichlorophenyl)-1-(methoxy)-hexyl-2-carbamate,
1-(2,6-dichlorophenyl)-1-(methoxy)-propyl-2-carbamate,
1-(2,6-dichlorophenyl)-1-(methoxy)-butyl-2-carbamate,
1-(2,6-dichlorophenyl)-1-(methoxy)-3-methyl-butyl-2-carbamate,
1-(2,6-dichlorophenyl)-1-(methoxy)-hexyl-2-carbamate,
1-(2-chlorophenyl)-1-(methoxymethoxy)-ethyl-2-carbamate,
1-(2-fluorophenyl)-1-(methoxymethoxy)-ethyl-2-carbamate,
1-(2-iodophenyl)-1-(methoxymethoxy)-ethyl-2-carbamate,
1-(2-chlorophenyl)-1-(methoxymethoxy)-propyl-2-carbamate,
1-(2-chlorophenyl)-1-(methoxymethoxy)-propyl-2-N-methylcarbamate,
1-(2-chlorophenyl)-1-(methoxymethoxy)-propyl-2-N-propylcarbamate,
1-(2-chlorophenyl)-1-(methoxymethoxy)-propyl-2-N-isopropylcarbamate,
1-(2-chlorophenyl)-1-(methoxymethoxy)-propyl-2-N-cyclopropylcarbamate,
1-(2-chlorophenyl)-1-(methoxymethoxy)-propyl-2-N-cyclohexylcarbamate,
1-(2-chlorophenyl)-1-(methoxymethoxy)-propyl-2-N-benzylcarbamate,
1-(2-chlorophenyl)-1-(methoxymethoxy)-propyl-2-N-bicyclo[2,2,1]heptanecarbamate
1-(2-chlorophenyl)-1-(methoxymethoxy)-butyl-2-carbamate,
1-(2-chlorophenyl)-1-(methoxymethoxy)-3-methyl-butyl-2-carbamate,
1-(2-chlorophenyl)-1-(methoxymethoxy)-hexyl-2-carbamate,
1-(2,3-dichlorophenyl)-1-(methoxymethoxy)-propyl-2-carbamate,
1-(2,4-dichlorophenyl)-1-(methoxymethoxy)-propyl-2-carbamate,
1-(2,4-dichlorophenyl)-1-(methoxymethoxy)-butyl-2-carbamate, 1-(2,4-dichlorophenyl)-1-(methoxymethoxy)-3-methyl-butyl-2-carbamate,
1-(2,4-dichlorophenyl)-1-(methoxymethoxy)-hexyl-2-carbamate,
1-(2,5-dichlorophenyl)-1-(methoxymethoxy)-propyl-2-carbamate,
1-(2,6-dichlorophenyl)-1-(methoxymethoxy)-propyl-2-carbamate,
1-(2,6-dichlorophenyl)-1-(methoxymethoxy)-butyl-2-carbamate,
1-(2,6-dichlorophenyl)-1-(methoxymethoxy)-3-methyl-butyl-2-carbamate,
1-(2,6-dichlorophenyl)-1-(methoxymethoxy)-hexyl-2-carbamate,
1-(2-fluorophenyl)-1-(methoxymethoxy)-propyl-2-carbamate,
1-(2-fluorophenyl)-1-(methoxymethoxy)-propyl-2-N-methylcarbamate,
1-(2-fluorophenyl)-1-(methoxymethoxy)-propyl-2-N-propylcarbamate,
1-(2-fluorophenyl)-1-(methoxymethoxy)-propyl-2-N-isopropylcarbamate,
1-(2-fluorophenyl)-1-(methoxymethoxy)-propyl-2-N-cyclopropylcarbamate,
1-(2-fluorophenyl)-1-(methoxymethoxy)-propyl-2-N-cyclohexylcarbamate,
1-(2-fluorophenyl)-1-(methoxymethoxy)-propyl-2-N-benzylcarbamate,
1-(2-fluorophenyl)-1-(methoxymethoxy)-propyl-2-N-bicyclo[2,2,1]heptanecarbamate
1-(2-fluorophenyl)-1-(methoxymethoxy)-butyl-2-carbamate,
1-(2-fluorophenyl)-1-(methoxymethoxy)-3-methyl-butyl-2-carbamate,
1-(2-fluorophenyl)-1-(methoxymethoxy)-hexyl-2-carbamate,
1-(4-fluorophenyl)-1-(methoxymethoxy)-propyl-2-carbamate,
1-(4-fluorophenyl)-1-(methoxymethoxy)-butyl-2-carbamate,
1-(4-fluorophenyl)-1-(methoxymethoxy)-3-methyl-butyl-2-carbamate,
1-(4-fluorophenyl)-1-(methoxymethoxy)-hexyl-2-carbamate,
1-(2,6-difluorophenyl)-1-(methoxymethoxy)-propyl-2-carbamate,
1-(2-iodophenyl)-1-(methoxymethoxy)-propyl-2-carbamate,
1-(2-iodophenyl)-1-(methoxymethoxy)-propyl-2-N-methylcarbamate,
1-(2-iodophenyl)-1-(methoxymethoxy)-propyl-2-N-propylcarbamate,
1-(2-iodophenyl)-1-(methoxymethoxy)-propyl-2-N-isopropylcarbamate,
1-(2-iodophenyl)-1-(methoxymethoxy)-propyl-2-N-cyclopropylcarbamate,
1-(2-iodophenyl)-1-(methoxymethoxy)-propyl-2-N-cyclohexylcarbamate,
1-(2-iodophenyl)-1-(methoxymethoxy)-propyl-2-N-benzylcarbamate,
1-(2-iodophenyl)-1-(methoxymethoxy)-propyl-2-N-bicyclo[2,2,1]heptanecarbamate
1-(2-iodophenyl)-1-(methoxymethoxy)-butyl-2-carbamate,
1-(2-iodophenyl)-1-(methoxymethoxy)-butyl-2-N-methylcarbamate,
1-(2-iodophenyl)-1-(methoxymethoxy)-butyl-2-N-propylcarbamate,
1-(2-iodophenyl)-1-(methoxymethoxy)-butyl-2-N-isopropylcarbamate,
1-(2-iodophenyl)-1-(methoxymethoxy)-butyl-2-N-cyclopropylcarbamate,
1-(2-iodophenyl)-1-(methoxymethoxy)-butyl-2-N-cyclohexylcarbamate,
1-(2-iodophenyl)-1-(methoxymethoxy)-butyl-2-N-benzylcarbamate,
1-(2-iodophenyl)-1-(methoxymethoxy)-butyl-2-N-bicyclo[2,2,1]heptanecarbamate
1-(2-iodophenyl)-1-(methoxymethoxy)-3-methyl-butyl-2-carbamate,
1-(2-iodophenyl)-1-(methoxymethoxy)-3-methyl-butyl-2-N-methylcarbamate,
1-(2-iodophenyl)-1-(methoxymethoxy)-3-methyl-butyl-2-N-propylcarbamate,
1-(2-iodophenyl)-1-(methoxymethoxy)-3-methyl-butyl-2-N-isopropylcarbamate,
1-(2-iodophenyl)-1-(methoxymethoxy)-3-methyl-butyl-2-N-cyclopropylcarbamate,
1-(2-iodophenyl)-1-(methoxymethoxy)-3-methyl-butyl-2-N-cyclohexylcarbamate,
1-(2-iodophenyl)-1-(methoxymethoxy)-3-methyl-butyl-2-N-benzylcarbamate,
1-(2-iodophenyl)-1-(methoxymethoxy)-3-methyl-butyl-2-N-bicyclo[2,2,1]heptanecarbamate,
1-(2-iodophenyl)-1-(methoxymethoxy)-hexyl-2-carbamate,
1-(2-iodophenyl)-1-(methoxymethoxy)-hexyl-2-N-methylcarbamate,
1-(2-iodophenyl)-1-(methoxymethoxy)-hexyl-2-N-propylcarbamate,
1-(2-iodophenyl)-1-(methoxymethoxy)-hexyl-2-N-isopropylcarbamate,
1-(2-iodophenyl)-1-(methoxymethoxy)-hexyl-2-N-cyclopropylcarbamate,
1-(2-iodophenyl)-1-(methoxymethoxy)-hexyl-2-N-cyclohexylcarbamate,
1-(2-iodophenyl)-1-(methoxymethoxy)-hexyl-2-N-benzylcarbamate,
1-(2-iodophenyl)-1-(methoxymethoxy)-hexyl-2-N-bicyclo[2,2,1]heptanecarbamate
1-(3-iodophenyl)-1-(methoxymethoxy)-propyl-2-carbamate,
1-(3-iodophenyl)-1-(methoxymethoxy)-butyl-2-carbamate,
1-(3-iodophenyl)-1-(methoxymethoxy)-3-methyl-butyl-2-carbamate,
1-(3-iodophenyl)-1-(methoxymethoxy)-hexyl-2-carbamate,
1-(2-chlorophenyl)-2-(methoxymethoxy)-propyl-1-carbamate,
1-(2-chlorophenyl)-2-(methoxy)-propyl-1-carbamate,
1-(2-fluorophenyl)-2-(methoxymethoxy)-propyl-1-carbamate,
1-(2-fluorophenyl)-2-(methoxy)-propyl-1-carbamate
1-(2-iodophenyl)-2-(methoxymethoxy)-propyl-1-carbamate,
1-(2-iodophenyl)-2-(methoxy)-propyl-1-carbamate and,
a racemate of the compound, an enantiomer of the compound, a diastereomer of the compound, a mixture of enantiomers of the compound, or a mixture of diastereomers of the compound.

In an embodiment, the phenyl alkyl carbamate compound is selected from the group consisting of:
1-(2-chlorophenyl)-(S)-1-carbamoyloxypropyl-(S)-2-carbamate,
1-(2-chlorophenyl)-(S)-1-carbamoyloxypropyl-(S)-2-N-methylcarbamate, 1-(2-chlorophenyl)-(S)-1-carbamoyloxypropyl-(S)-2-N-propylcarbamate
1-(2-chlorophenyl)-(S)-1-carbamoyloxybutyl-(S)-2-carbamate,
1-(2-chlorophenyl)-(S)-1-carbamoyloxy-3-methyl-butyl-(S)-2-carbamate,
1-(2-chlorophenyl)-(S)-1-carbamoyloxyhexyl-(S)-2-carbamate,
1-(2-iodophenyl)-(S)-1-carbamoyloxypropyl-(S)-2-carbamate,
1-(2-iodophenyl)-(S)-1-carbamoyloxybutyl-(S)-2-carbamate,
1-(2-iodophenyl)-(S)-1-carbamoyloxy-3-methyl-butyl-(S)-2-carbamate,
1-(2-iodophenyl)-(S)-1-carbamoyloxyhexyl-(S)-2-carbamate,
1-(2-fluorophenyl)-(S)-1-carbamoyloxypropyl-(S)-2-carbamate,
1-(2-fluorophenyl)-(S)-1-carbamoyloxybutyl-(S)-2-carbamate,
1-(2-fluorophenyl)-(S)-1-carbamoyloxy-3-methyl-butyl-(S)-2-carbamate,
1-(2-fluorophenyl)-(S)-1-carbamoyloxyhexyl-(S)-2-carbamate,
1-(2,4-dichlorophenyl)-(S)-1-carbamoyloxypropyl-(S)-2-carbamate,
1-(2,4-dichlorophenyl)-(S)-1-carbamoyloxybutyl-(S)-2-carbamate,
1-(2,4-dichlorophenyl)-(S)-1-carbamoyloxy-3-methyl-butyl-2-carbamate,
1-(2,4-dichlorophenyl)-(S)-1-carbamoyloxyhexyl-(S)-2-carbamate,
1-(2,6-dichlorophenyl)-(S)-1-carbamoyloxypropyl-(S)-2-carbamate,
1-(2,6-dichlorophenyl)-(S)-1-carbamoyloxybutyl-(S)-2-carbamate,
1-(2,6-dichlorophenyl)-(S)-1-carbamoyloxy-3-methyl-butyl-(S)-2-carbamate,
1-(2,6-dichlorophenyl)-(S)-1-carbamoyloxyhexyl-(S)-2-carbamate,
1-(2-chloro-6-fluorophenyl)-(S)-1-carbamoyloxypropyl-(S)-2-carbamate
1-(2-chlorophenyl)-(S)-1-(methoxy)-ethyl-2-carbamate,
1-(2-fluorophenyl)-(S)-1-(methoxy)-ethyl-2-carbamate,
1-(2-iodophenyl)-(S)-1-(methoxy)-ethyl-2-carbamate,
1-(2-iodophenyl)-(S)-1-(methoxy)-propyl-(S)-2-carbamate,
1-(2-iodophenyl)-(S)-1-(methoxy)-propyl-(S)-2-N-methylcarbamate,
1-(2-iodophenyl)-(S)-1-(methoxy)-propyl-(S)-2-N-propylcarbamate,
1-(2-iodophenyl)-(S)-1-(methoxy)-propyl-(S)-2-N-isopropylcarbamate,
1-(2-iodophenyl)-(S)-1-(methoxy)-propyl-(S)-2-N-cyclopropylcarbamate,
1-(2-iodophenyl)-(S)-1-(methoxy)-propyl-(S)-2-N-cyclohexylcarbamate,
1-(2-iodophenyl)-(S)-1-(methoxy)-propyl-(S)-2-N-benzylcarbamate,
1-(2-iodophenyl)-(S)-1-(methoxy)-propyl-(S)-2-N-bicyclo[2,2,1]heptanecarbamate
1-(2-iodophenyl)-(S)-1-(methoxy)-butyl(S)-2-carbamate,
1-(2-iodophenyl)-(S)-1-(methoxy)-butyl-(S)-2-N-methylcarbamate,
1-(2-iodophenyl)-(S)-1-(methoxy)-butyl-(S)-2-N-propylcarbamate,
1-(2-iodophenyl)-(S)-1-(methoxy)-butyl-(S)-2-N-isopropylcarbamate,
1-(2-iodophenyl)-(S)-1-(methoxy)-butyl-(S)-2-N-cyclopropylcarbamate,
1-(2-iodophenyl)-(S)-1-(methoxy)-butyl-(S)-2-N-cyclohexylcarbamate,
1-(2-iodophenyl)-(S)-1-(methoxy)-butyl-(S)-2-N-benzylcarbamate,
1-(2-iodophenyl)-(S)-1-(methoxy)-butyl-(S)-2-N-bicyclo[2,2,1]heptanecarbamate,
1-(2-iodophenyl)-(S)-1-(methoxy)3-methyl-butyl-(S)-2-carbamate,
1-(2-iodophenyl)-(S)-1-(methoxy)-3-methyl-butyl-(S)-2-N-methylcarbamate,
1-(2-iodophenyl)-(S)-1-(methoxy)-3-methyl-butyl-(S)-2-N-propylcarbamate,
1-(2-iodophenyl)-(S)-1-(methoxy)-3-methyl-butyl-(S)-2-N-isopropylcarbamate,
1-(2-iodophenyl)-(S)-1-(methoxy)-3-methyl-butyl-(S)-2-N-cyclopropylcarbamate,
1-(2-iodophenyl)-(S)-1-(methoxy)-3-methyl-butyl-(S)-2-N-cyclohexylcarbamate,
1-(2-iodophenyl)-(S)-1-(methoxy)-3-methyl-butyl-(S)-2-N-benzylcarbamate,
1-(2-iodophenyl)-(S)-1-(methoxy)-3-methyl-butyl-(S)-2-N-bicyclo[2,2,1]heptanecarbamate,
1-(2-iodophenyl)-(S)-1-(methoxy)-hexyl-(S)-2-carbamate,
1-(2-iodophenyl)-(S)-1-(methoxy)-hexyl-(S)-2-N-methylcarbamate,
1-(2-iodophenyl)-(S)-1-(methoxy)-hexyl-(S)-2-N-propylcarbamate,
1-(2-iodophenyl)-(S)-1-(methoxy)-hexyl-(S)-2-N-isopropylcarbamate,
1-(2-iodophenyl)-(S)-1-(methoxy)-hexyl-(S)-2-N-cyclopropylcarbamate,
1-(2-iodophenyl)-(S)-1-(methoxy)-hexyl-(S)-2-N-cyclohexylcarbamate,
1-(2-iodophenyl)-(S)-1-(methoxy)-hexyl-(S)-2-N-benzylcarbamate,
1-(2-iodophenyl)-(S)-1-(methoxy)-hexyl-(S)-2-N-bicyclo[2,2,1]heptanecarbamate,
1-(3-iodophenyl)-(S)-1-(methoxy)-propyl-(S)-2-carbamate,
1-(3-iodophenyl)-(S)-1-(methoxy)-butyl-(S)-2-carbamate,
1-(3-iodophenyl)-(S)-1-(methoxy)3-methyl-butyl-(S)-2-carbamate,
1-(3-iodophenyl)-(S)-1-(methoxy)-hexyl-(S)-2-carbamate,
1-(2-fluorophenyl)-(S)-1-(methoxy)-propyl-(S)-2-carbamate,
1-(2-fluorophenyl)-(S)-1-(methoxy)-propyl-(S)-2-N-methylcarbamate,
1-(2-fluorophenyl)-(S)-1-(methoxy)-propyl-(S)-2-N-propylcarbamate,
1-(2-fluorophenyl)-(S)-1-(methoxy)-propyl-(S)-2-N-isopropylcarbamate,
1-(2-fluorophenyl)-(S)-1-(methoxy)-propyl-(S)-2-N-cyclopropylcarbamate,
1-(2-fluorophenyl)-(S)-1-(methoxy)-propyl-(S)-2-N-cyclohexylcarbamate,
1-(2-fluorophenyl)-(S)-1-(methoxy)-propyl-(S)-2-N-benzylcarbamate,
1-(2-fluorophenyl)-(S)-1-(methoxy)-propyl-(S)-2-N-bicyclo[2,2,1]heptanecarbamate
1-(4-fluorophenyl)-(S)-1-(methoxy)-proyl-(S)-2-carbamate,
1-(4-fluorophenyl)-(S)-1-(methoxy)-butyl-(S)-2-carbamate,
1-(4-fluorophenyl)-(S)-1-(methoxy)-3-methyl-butyl-(S)-2-carbamate,
1-(4-fluorophenyl)-(S)-1-(methoxy)-hexyl-(S)-2-carbamate,
1-(2-chlorophenyl)-(S)-1-(methoxy)-propyl-(S)-2-carbamate, 1-(2-chlorophenyl)-(S)-1-(methoxy)-propyl-(S)-2-N-methylcarbamate,
1-(2-chlorophenyl)-(S)-1-(methoxy)-propyl-(S)-2-N-propylcarbamate,
1-(2-chlorophenyl)-(S)-1-(methoxy)-propyl-(S)-2-N-isopropylcarbamate,
1-(2-chlorophenyl)-(S)-1-(methoxy)-propyl-(S)-2-N-cyclopropylcarbamate,
1-(2-chlorophenyl)-(S)-1-(methoxy)-propyl-(S)-2-N-cyclohexylcarbamate,
1-(2-chlorophenyl)-(S)-1-(methoxy)-propyl-(S)-2-N-benzylcarbamate,
1-(2-chlorophenyl)-(S)-1-(methoxy)-propyl-(S)-2-N-bicyclo[2,2,1]heptanecarbamate
1-(2-chlorophenyl)-(S)-1-(methoxy)-butyl-(S)-2-carbamate,
1-(2-chlorophenyl)-(S)-1-(methoxy)-3-methyl-butyl-(S)-2-carbamate,
1-(2-chlorophenyl)-(S)-1-(methoxy)-hexyl-(S)-2-carbamate,
1-(2,3-dichlorophenyl)-(S)-1-(methoxy)-propyl-(S)-2-carbamate,
1-(2,4-dichlorophenyl)-(S)-1-(methoxy)-propyl-(S)-2-carbamate,
1-(2,4-dichlorophenyl)-(S)-1-(methoxy)-butyl-(S)-2-carbamate,
1-(2,4-dichlorophenyl)-(S)-1-(methoxy)-3-methyl-butyl-(S)-2-carbamate,
1-(2,4-dichlorophenyl)-(S)-1-(methoxy)-hexyl-(S)-2-carbamate,
1-(2,6-dichlorophenyl)-(S)-1-(methoxy)-propyl-(S)-2-carbamate,
1-(2,6-dichlorophenyl)-(S)-1-(methoxy)-butyl-(S)-2-carbamate,
1-(2,6-dichlorophenyl)-(S)-1-(methoxy)-3-methyl-butyl-(S)-2-carbamate,
1-(2,6-dichlorophenyl)-(S)-1-(methoxy)-hexyl-(S)-2-carbamate,
1-(2-chlorophenyl)-(S)-1-(methoxymethoxy)-ethyl-(S)-2-carbamate,
1-(2-fluorophenyl)-(S)-1-(methoxymethoxy)-ethyl-(S)-2-carbamate,
1-(2-iodophenyl)-(S)-1-(methoxymethoxy)-ethyl-(S)-2-carbamate,
1-(2-chlorophenyl)-(S)-1-(methoxymethoxy)-propyl-(S)-2-carbamate,
1-(2-chlorophenyl)-(S)-1-(methoxymethoxy)-propyl-(S)-2-N-methylcarbamate,
1-(2-chlorophenyl)-(S)-1-(methoxymethoxy)-propyl-(S)-2-N-propylcarbamate,
1-(2-chlorophenyl)-(S)-1-(methoxymethoxy)-propyl-(S)-2-N-isopropylcarbamate,
1-(2-chlorophenyl)-(S)-1-(methoxymethoxy)-propyl-(S)-2-N-cyclopropylcarbamate,
1-(2-chlorophenyl)-(S)-1-(methoxymethoxy)-propyl-(S)-2-N-cyclohexylcarbamate,
1-(2-chlorophenyl)-(S)-1-(methoxymethoxy)-propyl-2-N-benzylcarbamate,
1-(2-chlorophenyl)-(S)-1-(methoxymethoxy)-propyl-2-N-bicyclo[2,2,1]heptanecarbamate
1-(2-chlorophenyl)-(S)-1-(methoxymethoxy)-butyl-(S)-2-carbamate,
1-(2-chlorophenyl)-(S)-1-(methoxymethoxy)-3-methyl-butyl-(S)-2-carbamate,
1-(2-chlorophenyl)-(S)-1-(methoxymethoxy)-hexyl-(S)-2-carbamate,
1-(2,3-dichlorophenyl)-(S)-1-(methoxymethoxy)-propyl-(S)-2-carbamate,
1-(2,4-dichlorophenyl)-(S)-1-(methoxymethoxy)-propyl-(S)-2-carbamate,
1-(2,4-dichlorophenyl)-(S)-1-(methoxymethoxy)-butyl-(S)-2-carbamate,
1-(2,4-dichlorophenyl)-(S)-1-(methoxymethoxy)-3-methyl-butyl-(S)-2-carbamate,
1-(2,4-dichlorophenyl)-(S)-1-(methoxymethoxy)-hexyl-(S)-2-carbamate,
1-(2,5-dichlorophenyl)-(S)-1-(methoxymethoxy)-propyl-(S)-2-carbamate,
1-(2,6-dichlorophenyl)-(S)-1-(methoxymethoxy)-propyl-(S)-carbamate,
1-(2,6-dichlorophenyl)-(S)-1-(methoxymethoxy)-butyl-(S)-2-carbamate,
1-(2,6-dichlorophenyl)-(S)-1-(methoxymethoxy)-3-methyl-butyl-(S)-2-carbamate,
1-(2,6-dichlorophenyl)-(S)-1-(methoxymethoxy)-hexyl-(S)-2-carbamate,
1-(2-fluorophenyl)-(S)-1-(methoxymethoxy)-propyl-(S)-2-carbamate,
1-(2-fluorophenyl)-(S)-1-(methoxymethoxy)-propyl-(S)-2-N-methylcarbamate,
1-(2-fluorophenyl)-(S)-1-(methoxymethoxy)-propyl-(S)-2-N-propylcarbamate,
1-(2-fluorophenyl)-(S)-1-(methoxymethoxy)-propyl-(S)-2-N-isopropylcarbamate,
1-(2-fluorophenyl)-(S)-1-(methoxymethoxy)-propyl-(S)-2-N-cyclopropylcarbamate,
1-(2-fluorophenyl)-(S)-1-(methoxymethoxy)-propyl-(S)-2-N-cyclohexylcarbamate,
1-(2-fluorophenyl)-(S)-1-(methoxymethoxy)-propyl-(S)-2-N-benzylcarbamate,
1-(2-fluorophenyl)-(S)-1-(methoxymethoxy)-propyl-(S)-2-N-bicyclo[2,2,1]heptanecarbamate
1-(2-fluorophenyl)-(S)-1-(methoxymethoxy)-butyl-(S)-2-carbamate,
1-(2-fluorophenyl)-(S)-1-(methoxymethoxy)-3-methyl-butyl-(S)-2-carbamate,
1-(2-fluorophenyl)-(S)-1-(methoxymethoxy)-hexyl-(S)-2-carbamate,
1-(4-fluorophenyl)-(S)-1-(methoxymethoxy)-propyl-(S)-2-carbamate,
1-(4-fluorophenyl)-(S)-1-(methoxymethoxy)-butyl-(S)-2-carbamate,
1-(4-fluorophenyl)-(S)-1-(methoxymethoxy)-3-methyl-butyl-(S)-2-carbamate,
1-(4-fluorophenyl)-(S)-1-(methoxymethoxy)-hexyl-(S)-2-carbamate,
1-(2,6-difluorophenyl)-(S)-1-(methoxymethoxy)-propyl-(S)-2-carbamate,
1-(2-iodophenyl)-(S)-1-(methoxymethoxy)-propyl-(S)-2-carbamate,
1-(2-iodophenyl)-(S)-1-(methoxymethoxy)-propyl-(S)-2-N-methylcarbamate,
1-(2-iodophenyl)-(S)-1-(methoxymethoxy)-propyl-(S)-2-N-propylcarbamate,
1-(2-iodophenyl)-(S)-1-(methoxymethoxy)-propyl-(S)-2-N-isopropylcarbamate,
1-(2-iodophenyl)-(S)-1-(methoxymethoxy)-propyl-(S)-2-N-cyclopropylcarbamate,
1-(2-iodophenyl)-(S)-1-(methoxymethoxy)-propyl-(S)-2-N-cyclohexylcarbamate,
1-(2-iodophenyl)-(S)-1-(methoxymethoxy)-propyl-(S)-2-N-benzylcarbamate,
1-(2-iodophenyl)-(S)-1-(methoxymethoxy)-propyl-2-N-bicyclo[2,2,1]heptanecarbamate 1-(2-iodophenyl)-(S)-1-(methoxymethoxy)-butyl-(S)-2-carbamate,
1-(2-iodophenyl)-(S)-1-(methoxymethoxy)-butyl-(S)-2-N-methylcarbamate,
1-(2-iodophenyl)-(S)-1-(methoxymethoxy)-butyl-(S)-2-N-propylcarbamate,
1-(2-iodophenyl)-(S)-1-(methoxymethoxy)-butyl-(S)-2-N-isopropylcarbamate,
1-(2-iodophenyl)-(S)-1-(methoxymethoxy)-butyl-(S)-2-N-cyclopropylcarbamate,
1-(2-iodophenyl)-(S)-1-(methoxymethoxy)-butyl-(S)-2-N-cyclohexylcarbamate,
1-(2-iodophenyl)-(S)-1-(methoxymethoxy)-butyl-(S)-2-N-benzylcarbamate,
1-(2-iodophenyl)-(S)-1-(methoxymethoxy)-butyl-(S)-2-N-bicyclo[2,2,1]heptanecarbamate
1-(2-iodophenyl)-(S)-1-(methoxymethoxy)-3-methyl-butyl-(S)-2-carbamate,
1-(2-iodophenyl)-(S)-1-(methoxymethoxy)-3-methyl-butyl-(S)-2-N-methylcarbamate,
1-(2-iodophenyl)-(S)-1-(methoxymethoxy)-3-methyl-butyl-(S)-2-N-propylcarbamate,
1-(2-iodophenyl)-(S)-1-(methoxymethoxy)-3-methyl-butyl-(S)-2-N-isopropylcarbamate,
1-(2-iodophenyl)-(S)-1-(methoxymethoxy)-3-methyl-butyl-(S)-2-N-cyclopropylcarbamate,
1-(2-iodophenyl)-(S)-1-(methoxymethoxy)-3-methyl-butyl-(S)-2-N-cyclohexylcarbamate,
1-(2-iodophenyl)-(S)-1-(methoxymethoxy)-3-methyl-butyl-(S)-2-N-benzylcarbamate,
1-(2-iodophenyl)-(S)-1-(methoxymethoxy)-3-methyl-butyl-(S)-2-N-bicyclo[2,2,1]heptanecarbamate,
1-(2-iodophenyl)-(S)-1-(methoxymethoxy)-hexyl-2-carbamate,
1-(2-iodophenyl)-(S)-1-(methoxymethoxy)-hexyl-(S)-2-N-methylcarbamate,
1-(2-iodophenyl)-(S)-1-(methoxymethoxy)-hexyl-(S)-2-N-propylcarbamate,
1-(2-iodophenyl)-(S)-1-(methoxymethoxy)-hexyl-(S)-2-N-isopropylcarbamate,
1-(2-iodophenyl)-(S)-1-(methoxymethoxy)-hexyl-(S)-2-N-cyclopropylcarbamate,
1-(2-iodophenyl)-(S)-1-(methoxymethoxy)-hexyl-(S)-2-N-cyclohexylcarbamate,
1-(2-iodophenyl)-(S)-1-(methoxymethoxy)-hexyl-(S)-2-N-benzylcarbamate,
1-(2-iodophenyl)-(S)-1-(methoxymethoxy)-hexyl-(S)-2-N-bicyclo[2,2,1]heptanecarbamate
1-(3-iodophenyl)-(S)-1-(methoxymethoxy)-propyl-(S)-2-carbamate,
1-(3-iodophenyl)-(S)-1-(methoxymethoxy)-butyl-(S)-2-carbamate,
1-(3-iodophenyl)-(S)-1-(methoxymethoxy)-3-methyl-butyl-(S)-2-carbamate,
1-(3-iodophenyl)-(S)-1-(methoxymethoxy)-hexyl-(S)-2-carbamate,
1-(2-chlorophenyl)-(S)-2-(methoxymethoxy)-propyl-(S)-1-carbamate,
1-(2-chlorophenyl)-(S)-2-(methoxy)-propyl-(S)-1-carbamate,
1-(2-fluorophenyl)-(S)-2-(methoxymethoxy)-propyl-(S)-1-carbamate,
1-(2-fluorophenyl)-(S)-2-(methoxy)-propyl-(S)-1-carbamate
1-(2-iodophenyl)-(S)-2-(methoxymethoxy)-propyl-(S)-1-carbamate,
1-(2-iodophenyl)-(S)-2-(methoxy)-propyl-(S)-1-carbamate
1-(2-chlorophenyl)-(R)-1-carbamoyloxypropyl-(R)-2-carbamate,
1-(2-iodophenyl)-(R)-1-carbamoyloxypropyl-(R)-2-carbamate,
1-(2-fluorophenyl)-(R)-1-carbamoyloxypropyl-(R)-2-carbamate,
1-(2,4-dichlorophenyl)-(R)-1-carbamoyloxypropyl-(R)-2-carbamate,
1-(2,6-dichlorophenyl)-(R)-1-carbamoyloxypropyl-(R)-2-carbamate,
1-(2,4-difluorophenyl)-(R)-1-carbamoyloxypropyl(R)-2-carbamate
1-(2,5-difluorophenyl)-(R)-1-carbamoyloxypropyl-(R)-2-carbamate
1-(2,6-difluorophenyl)-(R)-1-carbamoyloxypropyl-(R)-2-carbamate
1-(2-chloro-6-fluorophenyl)-(R)-1-carbamoyloxypropyl-(R)-2-carbamate
1-(2-iodophenyl)-(R)-1-(methoxy)-propyl-(R)-2-carbamate,
1-(2-iodophenyl)-(R)-1-(methoxy)-butyl(R)-2-carbamate,
1-(2-iodophenyl)-(R)-1-(methoxy)3-methyl-butyl-(R)-2-carbamate,
1-(2-iodophenyl)-(R)-1-(methoxy)-hexyl-(R)-2-carbamate,
1-(3-iodophenyl)-(R)-1-(methoxy)-propyl-(R)-2-carbamate,
1-(3-iodophenyl)-(R)-1-(methoxy)-butyl-(R)-2-carbamate,
1-(3-iodophenyl)-(R)-1-(methoxy)3-methyl-butyl-(R)-2-carbamate,
1-(3-iodophenyl)-(R)-1-(methoxy)-hexyl-(R)-2-carbamate,
1-(2-fluorophenyl)-(R)-1-(methoxy)-propyl-(R)-2-carbamate,
1-(4-fluorophenyl)-(R)-1-(methoxy)-proyl-(R)-2-carbamate,
1-(4-fluorophenyl)-(R)-1-(methoxy)-butyl-(R)-2-carbamate,
1-(4-fluorophenyl)-(R)-1-(methoxy)-3-methyl-butyl-(R)-2-carbamate,
1-(4-fluorophenyl)-(R)-1-(methoxy)-hexyl-(R)-2-carbamate,
1-(2-chlorophenyl)-(R)-1-(methoxy)-propyl-(R)-2-carbamate,
1-(2-chlorophenyl)-(R)-1-(methoxy)-propyl-(R)-2-N-methylcarbamate,
1-(2-chlorophenyl)-(R)-1-(methoxy)-propyl-(R)-2-N-propylcarbamate,
1-(2-chlorophenyl)-(R)-1-(methoxy)-propyl-(R)-2-N-isopropylcarbamate,
1-(2-chlorophenyl)-(R)-1-(methoxy)-propyl-(R)-2-N-cyclopropylcarbamate,
1-(2-chlorophenyl)-(R)-1-(methoxy)-propyl-(R)-2-N-cyclohexylcarbamate,
1-(2-chlorophenyl)-(R)-1-(methoxy)-propyl-(R)-2-N-benzylcarbamate,
1-(2-chlorophenyl)-(R)-1-(methoxy)-propyl-(R)-2-N-bicyclo[2,2,1]heptanecarbamate
1-(2-chlorophenyl)-(R)-1-(methoxy)-butyl-(R)-2-carbamate,
1-(2-chlorophenyl)-(R)-1-(methoxy)-3-methyl-butyl-(R)-2-carbamate,
1-(2-chlorophenyl)-(R)-1-(methoxy)-hexyl-(R)-2-carbamate,
1-(2,3-dichlorophenyl)-(R)-1-(methoxy)-propyl-(R)-2-carbamate,
1-(2,4-dichlorophenyl)-(R)-1-(methoxy)-propyl-(R)-2-carbamate,
1-(2,4-dichlorophenyl)-(R)-1-(methoxy)-butyl(R)-2-carbamate, 1-(2,4-dichlorophenyl)-(R)-1-(methoxy)-3-methyl-butyl-(R)-2-carbamate,
1-(2,4-dichlorophenyl)-(R)-1-(methoxy)-hexyl-(R)-2-carbamate,
1-(2,6-dichlorophenyl)-(R)-1-(methoxy)-propyl-(R)-2-carbamate,
1-(2,6-dichlorophenyl)-(R)-1-(methoxy)-butyl-(R)-2-carbamate,
1-(2,6-dichlorophenyl)-(R)-1-(methoxy)-3-methyl-butyl-(R)-2-carbamate,
1-(2,6-dichlorophenyl)-(R)-1-(methoxy)-hexyl-(R)-2-carbamate,
1-(2-chlorophenyl)-(R)-1-(methoxymethoxy)-ethyl-(R)-2-carbamate,
1-(2-fluorophenyl)-(R)-1-(methoxymethoxy)-ethyl-(R)-2-carbamate,
1-(2-iodophenyl)-(R)-1-(methoxymethoxy)-ethyl-(R)-2-carbamate,
1-(2-chlorophenyl)-(R)-1-(methoxymethoxy)-propyl-(R)-2-carbamate,
1-(2-chlorophenyl)-(R)-1-(methoxymethoxy)-propyl-(R)-2-N-methylcarbamate,
1-(2-chlorophenyl)-(R)-1-(methoxymethoxy)-propyl-(R)-2-N-propyl carbamate,
1-(2-chlorophenyl)-(R)-1-(methoxymethoxy)-propyl-(R)-2-N-isopropylcarbamate,
1-(2-chlorophenyl)-(R)-1-(methoxymethoxy)-propyl-(R)-2-N-cyclopropylcarbamate,
1-(2-chlorophenyl)-(R)-1-(methoxymethoxy)-propyl-(R)-2-N-cyclohexylcarbamate,
1-(2-chlorophenyl)-(R)-1-(methoxymethoxy)-propyl-(R)-2-N-benzylcarbamate,
1-(2-chlorophenyl)-(R)-1-(methoxymethoxy)-propyl-(R)-2-N-bicyclo[2,2,1]heptanecarbamate
1-(2-chlorophenyl)-(R)-1-(methoxymethoxy)-butyl-(R)-2-carbamate,
1-(2-chlorophenyl)-(R)-1-(methoxymethoxy)-3-methyl-butyl-(R)-2-carbamate,
1-(2-chlorophenyl)-(R)-1-(methoxymethoxy)-hexyl-(R)-2-carbamate,
1-(2,3-dichlorophenyl)-(R)-1-(methoxymethoxy)-propyl-(R)-2-carbamate,
1-(2,4-dichlorophenyl)-(R)-1-(methoxymethoxy)-propyl-(R)-2-carbamate,
1-(2,4-dichlorophenyl)-(R)-1-(methoxymethoxy)-butyl-(R)-2-carbamate,
1-(2,4-dichlorophenyl)-(R)-1-(methoxymethoxy)-3-methyl-butyl-(R)-2-carbamate,
1-(2,4-dichlorophenyl)-(R)-1-(methoxymethoxy)-hexyl-(R)-2-carbamate,
1-(2,5-dichlorophenyl)-(R)-1-(methoxymethoxy)-propyl-(R)-2-carbamate,
1-(2,6-dichlorophenyl)-(R)-1-(methoxymethoxy)-propyl-(R)-carbamate,
1-(2,6-dichlorophenyl)-(R)-1-(methoxymethoxy)-butyl-(R)-2-carbamate,
1-(2,6-dichlorophenyl)-(R)-1-(methoxymethoxy)-3-methyl-butyl-(R)-2-carbamate,
1-(2,6-dichlorophenyl)-(R)-1-(methoxymethoxy)-hexyl-(R)-2-carbamate,
1-(2-fluorophenyl)-(R)-1-(methoxymethoxy)-propyl-(R)-2-carbamate,
1-(4-fluorophenyl)-(R)-1-(methoxymethoxy)-propyl-(R)-2-carbamate,
1-(4-fluorophenyl)-(R)-1-(methoxymethoxy)-butyl-(R)-2-carbamate,
1-(4-fluorophenyl)-(R)-1-(methoxymethoxy)-3-methyl-butyl-(R)-2-carbamate,
1-(4-fluorophenyl)-(R)-1-(methoxymethoxy)-hexyl-(R)-2-carbamate,
1-(2-iodophenyl)-(R)-1-(methoxymethoxy)-propyl-(R)-2-carbamate,
1-(2-iodophenyl)-(R)-1-(methoxymethoxy)-butyl-(R)-2-carbamate,
1-(2-iodophenyl)-(R)-1-(methoxymethoxy)-3-methyl-butyl-(R)-2-carbamate,
1-(2-iodophenyl)-(R)-1-(methoxymethoxy)-hexyl-(R)-2-carbamate,
1-(3-iodophenyl)-(R)-1-(methoxymethoxy)-propyl-(R)-2-carbamate,
1-(3-iodophenyl)-(R)-1-(methoxymethoxy)-butyl-(R)-2-carbamate,
1-(3-iodophenyl)-(R)-1-(methoxymethoxy)-3-methyl-butyl-(R)-2-carbamate,
1-(3-iodophenyl)-(R)-1-(methoxymethoxy)-hexyl-(R)-2-carbamate,
1-(2-chlorophenyl)-(S)-1-carbamoyloxypropyl-(R)-2-carbamate,
1-(2-chlorophenyl)-(R)-1-carbamoyloxypropyl-(S)-2-carbamate,
1-(2-chlorophenyl)-(S)-1-(methoxy)-propyl-(R)-2-carbamate,
1-(2-chlorophenyl)-(R)-1-(methoxy)-propyl-(S)-2-carbamate,
1-(2-chlorophenyl)-(S)-1-(methoxymethoxy)-propyl-(R)-2-carbamate, and
1-(2-chlorophenyl)-(R)-1-(methoxymethoxy)-propyl-(S)-2-carbamate.

Two substances in the form of regioisomers of a single carbamate of diol having halogen substituent at phenyl ring may be separated by flash column chromatography to obtain two kinds of single carbamate compounds.

Alternatively, the compound may be in the form of a pharmaceutically acceptable salt. The pharmaceutically acceptable salt may include an additional salt of acid or base, and its stereochemical isomer. For example, the compound may be in the form of an additional salt of an organic or inorganic acid. The salt may not be specially limited, and include any salts that maintain the activities of their parent compounds, with no undesirable effects, in the subject, when they are administered to the subject. Such salts may include inorganic and organic salts, such as salts of acetic acid, nitric acid, aspartic acid, sulfonic acid, sulfuric acid, maleic acid, glutamic acid, formic acid, succinic acid, phosphoric acid, phthalic acid, tannic acid, tartaric acid, hydrobromic acid, propionic acid, benzene sulfonic acid, benzoic acid, stearic acid, lactic acid, bicarbonic acid, bisulfuric acid, bitartaric acid, oxalic acid, butyric acid, calcium edetate, carbonic acid, chlorobezoic acid, citric acid, edetic acid, toluenesulfonic acid, fumaric acid, gluceptic acid, esilic acid, pamoic acid, gluconic acid, methyl nitric acid, malonic acid, hydrochloric acid, hydroiodic, hydroxynaphtholic acid, isethionic acid, lactobionic acid, mandelic acid, mucic acid, naphthylic acid, muconic acid, p-nitromethanesulfonic acid, hexamic acid, pantothenic acid, monohydrogen phosphoric acid, dihydrogen phosphoric acid, salicylic acid, sulfamic acid, sulfanilic acid, methane sulfonic acid, and the like. The additional salts of base may include salts of akali metal or alkaline earth metal, such as salts of ammonium, lithium, sodium, potassium, magnesium, calcium, and the like; salts having an organic base, such as benzathine, N-methyl-D-glucamine, hydrabamine, and the like; and salts having an amino acid such as arginine, lysine, and the like. In addition, these salts may be converted to a released form by treating with a proper base or acid.

The carbamate compound of the present invention may prepared by the following reaction formula.

Reaction Formula I

Synthesis of Diol-1

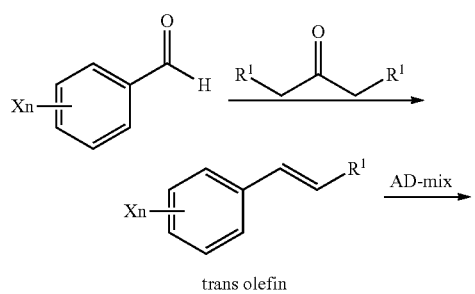

Diol

A diol compound used in the synthesis of the carbamate compound may be synthesized by dihydroxylation of a trans-olefin compound. A diol compound having optical activity may be synthesized using a sharpless asymmetric dihydroxylation catalyst.

Reaction Formula II

Synthesis of Diol-2

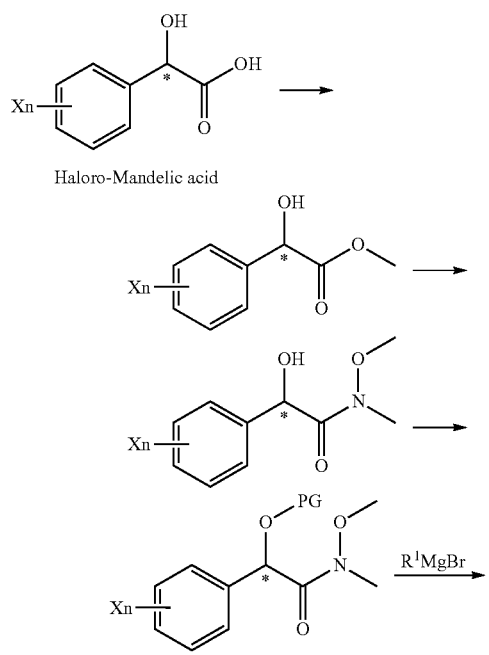

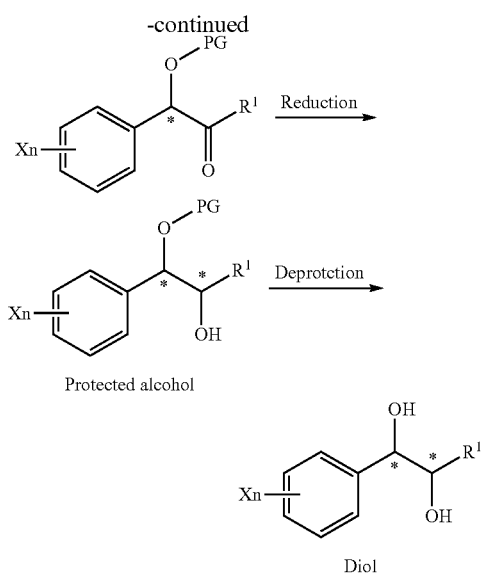

Protected alcohol

Diol

PG = Protecting Group

As indicated in the Reaction Formula II, the optically active substance of diol may also be synthesized using a reduction reagent after synthesizing a hydroxy-ketone compound using Haloro-Mandelic acid. In the Reaction Formula II, PG may be Trialkyl Silyl group (TMS, TES, TIPS, TBDMS, TBDPS), Ether group[MOM (Mothoxymethyl ether), MEM (2-Methoxyethoxymethyl ether), BOM (Benzyloxymethyl ether). MTM (Methylthiomethyl ether), SEM (2-(Trimethylsilyl)ethoxymethyl ether), PMBM (p-Methoxybenzyl ether), THP (Tetrahydropyranyl ether), Allyl ether, Trityl ether, Ester group[Ac (acetate), Bz (Benzoate), Pv (Pivaloate), Cbz (Benzyl carbonate), BOC (t-Butyl carbonate), Fmoc (9-Fulorenylmethyl)carbaonate, Alloc (Allyl Carbonate), Troc (Trichloroehtyl carbonate), or p-Methoxybenzoate, Methyl carbonate, and so on.

Reaction Formula III

Carbamation Reaction-1

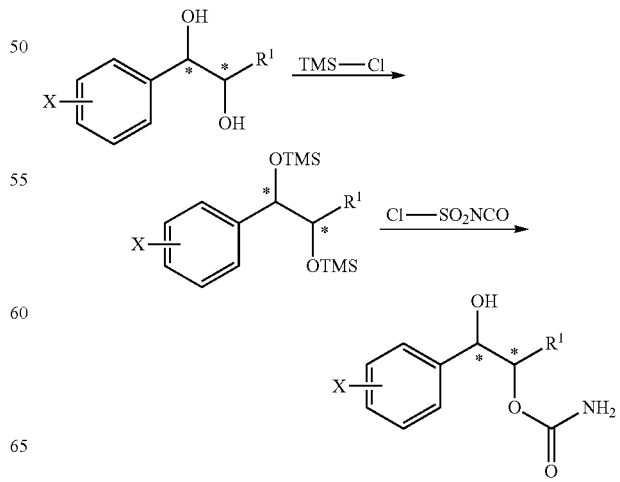

As a highly selectivity form of regioisomer of single carbamate of diol having halogen substituent at phenyl ring.

Reaction Formula IV

Carbamation Reaction-2

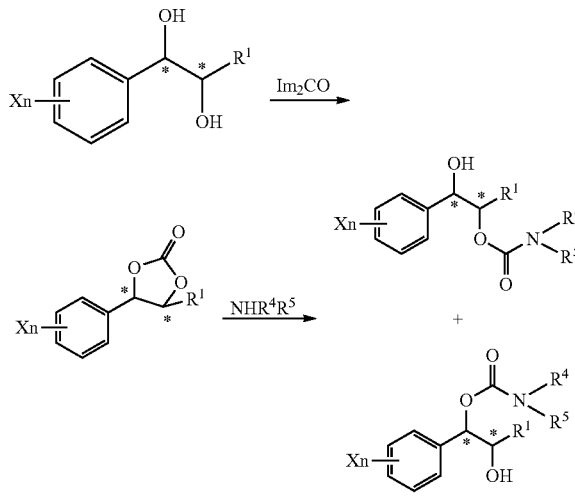

Two substances in the form of regioisomers of a single carbamate of diol having halogen substituent at phenyl ring may be separated by flash column chromatography to obtain two kinds of single carbamate compounds.

Reaction Formula V

Substitution Reaction

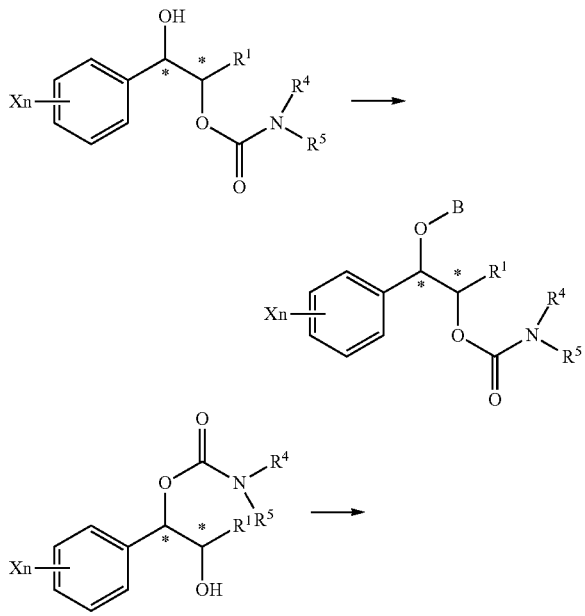

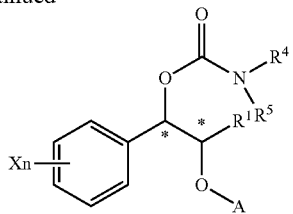

$R^1$ is a hydrogen or linear or branched $C_1$-$C_4$ alkyl group, for example, methyl group, ethyl group, isopropyl group, or butyl group, A is selected from the group consisting of an allyl, a $C_1$-$C_{19}$ linear or branched alkyl group (such as a methyl, t-butyl, benzyl, p-methoxybezyl, 2-napthylmethyl, trityl group etc.), a $C_2$-$C_8$ alkoxy alky ether group (such as a methoxy methy (MOM), methoxyethoxymethyl (MEM), thertahydropyranyl (THP), benzyloxymethyl (BOM), methylthiomethyl (MTM), trimethylsilylethoxymethyl (SEM), ethoxyethyl (EE) group etc.), and a carbamoyl derivative represented by

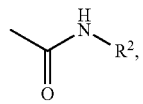

B is selected from the group consisting of an allyl, a $C_1$-$C_{19}$ linear or branched alkyl group (such as a methyl, t-butyl, benzyl, p-methoxybenzyl, 2-napthylmethyl, trityl group etc.), a $C_2$-$C_8$ alkoxy alky ether group (such as a methoxy methy (MOM), methoxyethoxymethyl (MEM), thertahydropyranyl (THP), benzyloxymethyl (BOM), methylthiomethyl (MTM), trimethylsilylethoxymethyl (SEM), ethoxyethyl (EE) group etc.), and a carbamoyl derivative represented by

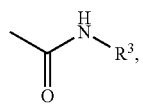

and $R^2$ and $R^3$ may be the same as or different from each other, and independently selected from the group consisting of hydrogen, a linear or branched lower alkyl group of $C_1$-$C_4$, for example $C_1$-$C_3$, a cycloalkyl group of $C_3$-$C_8$, for example $C_3$-$C_7$, and benzyl group, and more specifically, $R^2$ and $R^3$ may be the same as or different from each other, and independently selected from the group consisting of hydrogen, methyl group, propyl group, isopropyl group, cyclopropyl group, cyclohexyl group, bicycloheptane group, and benzyl group.

In an embodiment, when A is a carbamoyl group, B is an allyl, linear or branched $C_1$-$C_{19}$ alkyl group or a $C_2$-$C_8$ alkoxy alky ether group; when B is a carbamoyl group, A is an allyl, a linear or branched $C_1$-$C_{19}$ alkyl group or a $C_2$-$C_8$ alkoxy alky ether group; or A and B are carbamoyl derivative at the same time.

In an embodiment of Chemical Formula 1, the $C_1$-$C_{19}$ linear or branched alkyl group is independently linear or branched $C_1$-$C_6$ lower aliphatic alkyl such as methyl, ethyl, t-butyl and the like; a substituted or unsubstituted $C_3$-$C_{19}$ cycloaliphatic and substituted or unsubstituted $C_6$-$C_{18}$ aromatic group such as benzyl, naphtyl, trityl and the like. The cycloaliphatic group and the aromatic group may be substituted with at least one selected from the group consisting of hydrogen, $C_1$-$C_6$ lower alkyl and $C_1$-$C_6$ alkoxy group.

The examples of $C_1$-$C_6$ lower aliphatic alkyl include methyl, ethyl, propyl, t-butyl, pantyl, hexyl and the like. The examples of $C_6$-$C_{18}$ aromatic group is benzyl such as benzyl, methylbenzyl, methoxybenzyl and the like, naphtyl such as 2-naphtylmethyl, trityl group and the like.

A and B is independently $C_2$-$C_8$ alkoxy alky ether group such as such as a methoxy methy (MOM), methoxyethoxymethyl (MEM), thertahydropyranyl (THP), benzyl oxymethyl (BOM), methylthiomethyl (MTM), trimethylsilylethoxymethyl (SEM), ethoxyethyl (EE) group and the like.

$R^2$ and $R^3$ may be independently selected from the group consisting of hydrogen, a linear or branched alkyl group of $C_1$-$C_4$, for example $C_1$-$C_3$ alkyl, a cycloalkyl group of $C_3$-$C_8$, for example benzyl group, and more specifically, $R^2$ and $R^3$ may be selected from the group consisting of hydrogen, methyl group, propyl group, isopropyl group, cyclopropyl group, cyclohexyl group, bicycloheptane group, and benzyl group.

Another embodiment provides a method of prevention and/or treatment of a an epilepsy or a epilepsy-related syndrome, comprising administering a pharmaceutically effective amount of a phenyl carbamate compound represented by Chemical Formula 1; a racemate, an enantiomer, a diastereomer, a mixture of enantiomers, or a mixture of diastereomers thereof; or a pharmaceutically acceptable salt thereof, to a subject in need of preventing and/or treating drug-resistant epilepsy or drug-resistant epilepsy-related symptom. The method can be applied for preventing and/or treating drug-resistant epilepsy or drug-resistant epilepsy-related symptom.

The method may further comprise a step of identifying the subject in need of preventing and/or treating an epilepsy or a epilepsy-related syndrome, prior to the step of administering. Another embodiment provides a phenyl carbamate compound represented by Chemical Formula 1; a racemate, an enantiomer, a diastereomer, a mixture of enantiomers, or a mixture of diastereomers thereof; or a pharmaceutically acceptable salt thereof, for use in the prevention and/or treatment of an epilepsy or a epilepsy-related syndrome.

Another embodiment provides a use of a phenyl carbamate compound represented by Chemical Formula 1; a racemate, an enantiomer, a diastereomer, a mixture of enantiomers, or a mixture of diastereomers thereof; or a pharmaceutically acceptable salt thereof for the manufacture of a pharmaceutical composition for preventing and/or treating an epilepsy or a epilepsy-related syndrome.

In an embodiment, the present invention relates to a therapeutic or preventive agent for epilepsy and epilepsy-related syndrome, preferable an intractable epilepsy and its related syndrome.

The characteristics of intractable epilepsy include 1) high occurrence of partial seizure followed by a generalized seizure (particularly temporal lobe epilepsy); 2) high occurrence of symptomatic epilepsy caused by an organic lesion in the brain; 3) long-term absence of treatment from the onset to consultation of a specialist and high occurrence of seizures; and 4) high occurrence of status epilepticus in the anamnesis. In other words, the temporal lobe is likely to be a portion of the brain responsible for intractable epilepsy. It is indicated that epilepsy becomes more intractable by changing of the nature thereof and evolving as acquired seizures are repeated.

Intractable epilepsy is categorized into three clinical types, i.e., (a) localization-related epilepsies and syndromes, (b) generalized epilepsies and syndromes, and (c) epilepsies and syndromes undetermined, whether focal or generalized.

Examples of (a) localization-related epilepsies and syndromes include temporal lobe epilepsies, frontal lobe epilepsies, and multi-lobe epilepsies. Temporal lobe epilepsies and frontal lobe epilepsies are typical examples of intractable epilepsy. Multi-lobe epilepsies are considered to be caused by two or more lobes.

Examples of (b) generalized epilepsies and syndromes include myoclonic epilepsy.

Examples of (c) epilepsies and syndromes undetermined, whether focal or generalized, include severe myoclonic epilepsy, which exhibits a variety of seizure types. In particular, tonic-clonic seizures frequently occur, to thereby often lead to status epilepticus. Thus, special treatment conducted by a specialist for epilepsy is strongly required (Masako WATANABE, et al., Igakuno Ayumi, 183 (1):103-108, 1997).

Seizures associated with intractable epilepsy are categorized into a variety of types, e.g., tonic seizures, tonic-clonic seizures, atypical absence seizures, atonic seizures, myoclonic seizures, clonic seizures, simple partial seizures, complex partial seizures, and secondary generalized seizures. Of these, for tonic and atonic seizures, attention must be paid to injuries resulting from falls.

In addition, complex partial seizures may cause a behavior-caused accident during disturbance of consciousness. In intractable epilepsies, "complex partial seizures" associated with temporal lobe epilepsies and frontal lobe epilepsies occur at relatively high frequency in adults. Although said seizures occur at low frequency in children, the seizures are also intractable as in the case of adults (Progress of Epileptology, No. 2, Haruo AKIMOTO and Toshio YAMAUCHI, Iwanami Gakujutsu Shuppan, 1991, p 51-85).

In the present description, the term "intractable epilepsy" refers to epilepsies or seizures associated therewith corresponding to the following four epilepsies or seizures associated therewith:

(1) epilepsies difficult to treat in which suppression of seizures associated therewith cannot be controlled through a conventional pharmaceutical treatment (Masako WATANABE, et al., Igaku-no Ayumi, 183(1):103-108, 1997);

(2) epilepsies corresponding to the following (a) to (c): (a) localization-related epilepsies such as temporal lobe epilepsis and cortical epilepsis; (b) generalized epilepsies and myoclonic epilepsy; and (c) epilepsies and syndromes undetermined, whether focal or generalized, such as severe myoclonic epilepsy;

(3) seizures associated with the above-described intractable epilepsis including tonic seizures, tonic-clonic seizures, atypical absence seizures, atonic seizures, myoclonic seizures, clonic seizures, simple partial seizures, complex partial seizures, and secondary generalized seizures; and (4) epilepsies such as epilepsies following brain surgery, traumatic epilepsies, and relapsed epilepsies following surgery for epilepsy.

The antiepileptic agent of the present invention is effective for the above four types of intractable epilepsies. Of these, the antiepileptic agent of the present invention is particularly effective for localization-related epilepsies corresponding to (2) (a); seizures such as secondary generalized seizures, complex partial seizures and status epilepticus corresponding to (3) and status epilepticus; and epilepsies following brain surgery, traumatic epilepsies, and relapsed epilepsies following surgery for epilepsy corresponding to (4). The antiepileptic agent of the present invention has a possibly excellent effect to epilepsies such as localization-related epilepsies, temporal lobe epilepsies, and cortical epilepsies.

"Temporal lobe epilepsy," which is one type of intractable epilepsy, is an epilepsy having a seizure focus in the temporal lobe, and is categorized under symptomatic and localization-related epilepsies, which also include frontal lobe epilepsies, parietal lobe epilepsies, and occipital lobe epilepsies, based on the international classification of epilepsy.

The syndromes of temporal lobe epilepsy vary in accordance with a focus-localized site and type of seizure propagation, in that the temporal lobe has an anatomically complex structure including neocortex, allocortex, and paleocortex. Temporal lobe epilepsy, as previously defined as a psychomotor seizure, mostly causes complex partial seizures as clinically observed seizures, and also causes simple partial seizures, secondary generalized seizures, and combinations thereof.

Simple partial seizures include autonomic and mental symptoms and sensory symptoms such as olfaction, audition, or vision, sometimes concomitant with symptoms of experiences such as deja-vu and jamais-vu. Complex partial seizures often exhibit motion stopping followed by eating-function automatism, and are divided into amygdala-hippocampus seizures and lateral temporal lobe seizures according to localization. In the case of temporal lobe epilepsy, 70-80% of the seizures are hippocampus seizures, in which aura, motion stopping, lip automatism, and clouding of consciousness are successively developed to result in amnesia. When the focus is in the amygdala, there are caused autonomic symptoms such as dysphoria in the epigastrium; phobia; and olfactory hallucination. Lateral temporal lobe seizures include auditory illusion, hallucination, and a dreamy state, and disturbance of speech when the focus is in the dominant hemisphere. Temporal lobe epilepsy exhibits a long-term psychosis-like state in addition to other symptoms and recognition-and-memory disorder more frequently than do other epilepsies (Medical Dictionary, Nanzando). Treatment of temporal lobe epilepsy is carried out through pharmacotherapy employing a maximum dose of a combination of drugs, or through surgical treatment.

"Cortex epilepsy, which is one type of intractable epilepsy, is an epilepsy having a focus in the cerebral cortex, and is classified as symptomatic epilepsy belonging to localization-related (focal) epilepsies and syndromes in the international classification of epilepsy. In the international classification, seizures associated with cortex epilepsy are classified as simple partial seizures, which are partial seizures without reduction of consciousness. Accordingly, an electroencephalogram taken during a seizure associated with cortex epilepsy (not always recorded on the scalp) exhibits localized contralateral electric discharge from the corresponding cortical field. The cortex epilepsy is classified as temporal lobe epilepsy, parietal lobe epilepsy, or occipital lobe epilepsy.

"Traumatic epilepsy," which is one type of intractable epilepsy, in a broad sense, is divided into two epilepsies, i.e., "early epilepsy" and "late epilepsy." "Early epilepsy" is caused through stimulation of the brain induced by convulsion within a week after suffering a trauma, and is not a true epilepsy. In contrast, "late epilepsy" is a true epilepsy that is caused one or more weeks after suffering a trauma. Most of the traumatic epilepsies are caused by formation of a focus at a traumatically damaged portion of the cortex, and they are considered to be typical examples of partial epilepsies.

"A secondary generalized seizure," which is one of the symptoms associated with intractable epilepsy, is one type of partial seizure, which exhibit a clinical syndrome and an electrocephalogram feature observed as excitation of neurons that shows initiation of a seizure in a limited portion of one cerebral hemisphere. The secondary generalized seizure is initiated as a simple partial seizure (without impairment of consciousness) or a complex partial seizure (with impairment of consciousness), and develops to general convulsion induced through secondary generalization. The main symptom thereof is convulsion such as a tonic-clonic seizure, a tonic seizure, or a clonic seizure.

"A complex partial seizure," which is one of the symptoms associated with intractable epilepsy, refers to a partial seizure with impairment of consciousness, and is similar to a seizure that has conventionally been called a psycho-motor seizure or a seizure associated with temporal lobe epilepsy. In the international classification draft (1981), the complex partial seizure is defined as a seizure with impairment of consciousness exhibiting an electrocephalogram during a seizure in which unilateral or bilateral electric discharge attributed to a focus in a diffuse or a temporal or front-temporal portion.

Clinically, an epileptic seizure results from a sudden and abnormal electrical discharge originating from a collection of interconnected neurons in the brain or elsewhere in the nervous system. Depending on the type of epilepsy involved, the resulting nerve cell activity may be manifested by a wide variety of clinical symptoms such as uncontrollable motor movements, changes in the patient's level of consciousness and the like. Epilepsy and epileptic seizures and syndromes may be classified in a variety of ways (See, The Treatment of Epilepsy, Principles & Practice, Third Edition, Elaine Wyllie, M.D. Editor, Lippincott Williams & Wilkins, 2001). However, as used herein the terms; "epilepsy", "epileptic seizures" and "epileptic syndromes" are meant to include all known types of epileptic seizures and syndromes including; partial seizures, including simple, complex and partial seizures evolving to generalized tonic-clonic convulsions and generalized seizures, both convulsive and nonconvulsive and unclassified epileptic seizures.

Patients with epilepsy whose seizures do not successfully respond to antiepileptic drug (AED) therapy are considered to have drug-resistant epilepsy (DRE). This condition is also referred to as intractable, medically refractory, or pharmacoresistant epilepsy. The International League Against Epilepsy (ILAE) defines drug resistant epilepsy as a failure of adequate trials of two tolerated and appropriately chosen and used AED schedules (whether as monotherapies or in combination) to achieve sustained seizure freedom.

As used herein, the term "anti-epileptic drug(s)" or "AED(s)" generally encompasses pharmacological agents that reduce the frequency or likelihood of a seizure. There are many drug classes that comprise the set of antiepileptic drugs (AEDs), and many different mechanisms of action are represented. For example, some medications are believed to increase the seizure threshold, thereby making the brain less likely to initiate a seizure. Other medications retard the spread of neural bursting activity and tend to prevent the propagation or spread of seizure activity. Some. AEDs, such as the Benzodiazepines, act via the GABA receptor and globally suppress neural activity. However, other AEDs may act by modulating a neuronal calcium channel, a neuronal potassium channel, a neuronal NMDA channel, a neuronal AMPA channel, a neuronal metabotropic type channel, a neuronal sodium channel, and/or a neuronal kainite channel. The phrase "Anti-epileptic drugs that block sodium channels", "sodium-channel-blocking AEDs" used herein refers to anti-epileptic drugs that block sodium channels. The sodium-channel-blocking AEDs can be selected from the group consisting of topiramate, carbamazepine, oxcarbazepine, phenytoin, lamotrigine, zonisamide, felbamate, ethosuximide, and valproate (valproic acid), as well as other existing or new AEDs which may be identified to block sodium channels in the future.

As used herein, the terms "subject" or "patient" are used herein interchangeably and as used herein, refer to a human being, who has been the object of treatment, observation or experiment.

The pharmaceutical composition may be formulated in various forms for oral or parenteral administration. For example, the pharmaceutical composition may be formulated in the oral administration form, such as a tablet, pill, soft or hard capsule, liquid, suspension, emulsion, syrup, granules, elixirs, and the like. In addition to the active ingredient, the oral administration form may further include pharmaceutically acceptable and conventional components, for example, a diluent such as lactose, dextrose, sucrose, mannitol, sorbitol, cellulose, glycine, and the like; a lubricant such as silica, talc, stearic acid, magnesium or calcium salt thereof, polyethyleneglycol, and the like. In the case that the oral administration form is a tablet, it may further include a binder such as magnesium aluminium silicate, starch paste, gelatin, tragacanth, methylcellulose, sodium carboxymethylcellulose, polyvinylpirrolidine, and the like; and optionally include one or more additives selected from the group consisting of a disintegrant such as starch, agar, arginic acid or sodium salt thereof, an absorbent, a colorant, a flavoring, a sweetener, and the like. Alternatively, the pharmaceutical composition may also be formulated in a parenteral administration form, which can be administered by subcutaneous injection, intravenous injection, intramuscular injection, injection into thoracic cavity, and the like. In order to formulate the parenteral administration form, the pharmaceutical composition may be prepared as a solution or suspension wherein the active ingredient is dissolved in water together with a stabilizer and/or a buffering agent, and such solution or suspension formulation may be prepared as a dosage form in ample or vial.

The pharmaceutical composition may be sterilized, and/or include further additives such as a preservative, a stabilizer, a hydrating agent, an emulsification accelerator, a salt and/or buffering agent for osmoregulation, and the like, and/or further therapeutically effective ingredients. The pharmaceutical composition may be formulated by any conventional method for mixing, granulating, coating, and the like.

The pharmaceutical composition may be administered to a mammal including human, in the pharmaceutically effective amount of 0.01 to 750 mg/kg (body weight), preferably 0.1 to 500 mg/kg (body weight) per one day, based on the active ingredient. The pharmaceutically effective amount may refers to an amount capable of exhibiting a desired effect, i.e., an effect of treating and/or preventing epilepsy. The pharmaceutically effective amount may be administered through oral or parenteral pathway (e.g., an intravenous injection, an intramusclular injection, etc.), one or two or more times per one day.

The pharmaceutically effective amount and the administration pathway of the present pharmaceutical composition may be properly adjusted by a person skilled in the relevant field considering the conditions of the subject (patient), desired effects, and the like. The subject may be a mammal including human or cells and/or tissues obtained therefrom.

EXAMPLE

The present invention is further explained in more detail with reference to the following examples. These examples, however, should not be interpreted as limiting the scope of the present invention in any manner.

Preparation Example 1

Synthesis of 1-(2-chlorophenyl)-trans-1-propene

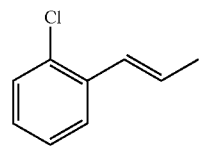

48 ml of 2-chlorobenzenaldehyde (0.42 mol) and 49.7 ml of 3-pentanone (0.47 mol) were dissolved in 600 mL of hexane in flask, and then stirred with raising the temperature. 53.6 ml of Boron trifluoride etherate ($BF_3OEt_2$, 0.42 mol) was added to the resultant under reflux conditions. When the reaction was completed, water was added thereto. After layer separation, the obtained organic layer was washed twice with 1M sodium hydroxide solution (1M NaOH), and then the separated organic layer was washed with water. The separated organic layer was dehydrated with anhydrous magnesium sulfate ($MgSO_4$) and concentrated. The concentrated residue was purified by a silica gel column chromatography to produce the title compound (38 g, yield 58%). $^1H$ NMR (400 MHz, $CDCl_3$) δ1.94 (d, J=4.8 Hz, 3H), 6.24 (m, 1H), 6.78 (d, J=14 Hz, 1H), 7.11~7.51 (m, 4H)

Preparation Example 2

Synthesis of 1-(2-chlorophenyl)-trans-1-butene

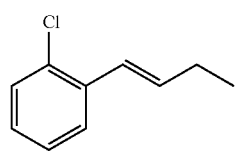

The substantially same method as described in Preparation Example 1 was conducted, except that 3-heptanone was used instead of 3-pentanone, to obtain the title compound (2.9 g, yield 83%).

$^1H$ NMR (400 MHz, $CDCl_3$) δ1.14 (d, J=7.6 Hz, 3H), 2.29~2.33 (m, 2H), 6.28 (dt, J=16 Hz, 6.4 Hz, 1H), 6.78 (d, J=15.6 Hz, 1H), 7.13~7.54 (m, 4H)

Preparation Example 3

Synthesis of 1-(2-chlorophenyl)-3-methyl-trans-1-butene

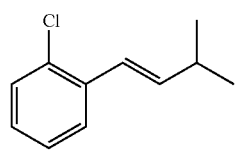

The substantially same method as described in Preparation Example 1 was conducted, except that 2,6-dimethylheptan-4-one was used instead of 3-pentanone, to obtain the title compound (8.0 g, yield 50~90%).

$^1$H NMR (400 MHz, CDCl$_3$) δ1.14 (d, J=6.8 Hz, 6H), 2.25~2.57 (m, 1H), 6.20 (dd, J=16 Hz, 7.2 Hz, 1H), 7.64 (d, J=16 Hz, 1H), 7.12~7.54 (m, 4H)

Preparation Example 4

Synthesis of 1-(2-chlorophenyl)-trans-1-hexene

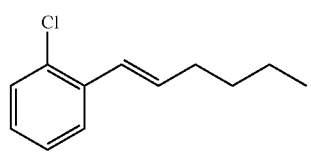

The substantially same method as described in Preparation Example 1 was conducted, except that 6-undecanone was used instead of 3-pentanone, to obtain the title compound (10 g, yield 85%).

$^1$H NMR (400 MHz, CDCl$_3$) δ0.96 (t, J=7.2 Hz, 3H), 1.33~1.56 (m, 4H), 2.26~2.32 (m, 4H), 6.24 (dt, J=15.6 Hz, 7 Hz, 1H), 6.78 (d, J=16 Hz, 1H), 7.13~7.54 (m, 4H)

Preparation Example 5

Synthesis of 1-(2,4-dichlorophenyl)-trans-1-propene

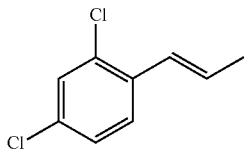

The substantially same method as described in Preparation Example 1 was conducted, except that 2,4-dichlorobenzenaldehyde was used instead of 2-chlorobenzenaldehyde, to obtain the title compound (2.4 g, yield 57%).

$^1$H NMR (400 MHz, CDCl$_3$) δ1.95 (dd, J=6.8 Hz, 1.6 Hz, 3H), 6.24 (m, 1H), 6.72 (d, J=15.6 Hz, 1H), 7.18~7.44 (m, 3H)

Preparation Example 6

Synthesis of 1-(2,4-dichlorophenyl)-trans-1-butene

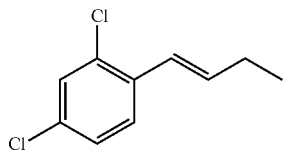

The substantially same method as described in Preparation Example 5 was conducted, except that 3-heptanone was used instead of 3-pentanone, to obtain the title compound (2.1 g, yield 90%).

$^1$H NMR (400 MHz, CDCl$_3$) δ1.14 (d, J=7.6 Hz, 3H), 2.20~2.33 (m, 2H), 6.26 (dt, J=16 Hz, 6.8 Hz, 1H), 6.70 (d, J=15.6 Hz, 1H), 7.18~7.46 (m, 3H)

Preparation Example 7

Synthesis of 1-(2,6-dichlorophenyl)-3-methyl-trans-1-butene

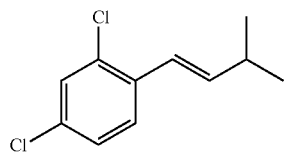

The substantially same method as described in Preparation Example 5 was conducted, except that 2,6-dimethylheptan-4-one was used instead of 3-pentanone, to obtain the title compound (0.23 g, yield 10~40%).

$^1$H NMR (400 MHz, CDCl$_3$) δ1.15 (d, J=6.8 Hz, 6H), 2.53~2.58 (m, 1H), 6.19 (dd, J=16.4 Hz, 6.8 Hz, 1H), 6.31 (d, J=16.4 Hz, 1H), 7.18~7.46 (m, 3H)

Preparation Example 8

Synthesis of 1-(2,4-dichlorophenyl)-trans-1-hexene

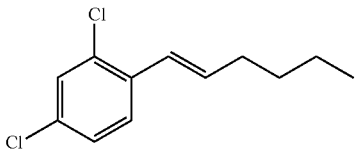

The substantially same method as described in Preparation Example 5 was conducted, except that 6-undecanone was used instead of 3-pentanone, to obtain the title compound (3.2 g, yield 40~80%).

$^1$H NMR (400 MHz, CDCl$_3$) δ0.96 (t, J=7.2 Hz, 3H), 1.38~1.52 (m, 4H), 2.25~2.31 (m, 2H), 6.22 (dt, J=15.6 Hz, 6.8 Hz, 1H), 6.70 (d, J=15.6 Hz, 1H), 7.18~7.46 (m, 3H)

Preparation Example 9

Synthesis of 1-(2,6-dichlorophenyl)-trans-1-propene

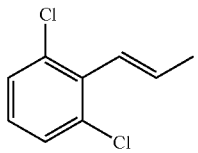

The substantially same method as described in Preparation Example 1 was conducted, except that 2,6-dichlorobenzenaldehyde was used instead of 2-chlorobenzenaldehyde, to obtain the title compound (0.4 g, yield 10~40%).

$^1$H NMR (400 MHz, CDCl$_3$) δ1.98 (d, J=8 Hz, 3H), 6.23~6.31 (m, 1H), 6.40 (d, J=16 Hz, 1H), 7.05~7.32 (m, 3H)

Preparation Example 10

Synthesis of 1-(2,6-dichlorophenyl)-trans-1-butene

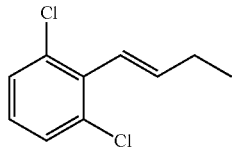

The substantially same method as described in Preparation Example 9 was conducted, except that 3-heptanone was used instead of 3-pentanone, to obtain the title compound (1.2 g, yield 10~40%).

$^1$H NMR (400 MHz, CDCl$_3$) δ1.17 (t, J=7.6 Hz, 3H), 2.30~2.37 (m, 2H), 6.29 (dt, J=16.4 Hz, 6 Hz, 1H), 6.37 (d, J=16.4 Hz, 1H), 7.05~7.32 (m, 3H)

Preparation Example 11

Synthesis of 1-(2,6-dichlorophenyl)-3-methyl-trans-1-butene

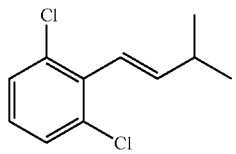

The substantially same method as described in Preparation Example 9 was conducted, except that 2,6-dimethylheptan-4-one was used instead of 3-pentanone, to obtain the title compound (0.23 g, yield 10~40%).

$^1$H NMR (400 MHz, CDCl$_3$) δ1.15 (d, J=6.8 Hz, 6H), 2.53~2.58 (m, 1H), 6.19 (dd, J=16.4 Hz, 6.8 Hz, 1H), 6.31 (d, J=16.4 Hz, 1H), 7.05~7.32 (m, 3H)

Preparation Example 12

Synthesis of 1-(2,6-dichlorophenyl)-trans-1-hexene

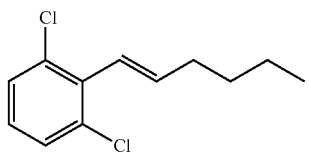

The substantially same method as described in Preparation Example 9 was conducted, except that 6-undecanone was used instead of 3-pentanone, to obtain the title compound (0.2 g, yield 10~40%).

$^1$H NMR (400 MHz, CDCl$_3$) δ0.99 (t, J=7.2 Hz, 3H), 1.14~1.59 (m, 4H), 2.30~2.36 (m, 2H), 6.24 (dt, J=16 Hz, 6.6 Hz, 1H), 6.38 (d, J=16.4 Hz, 1H), 7.05~7.33 (m, 3H)

Preparation Example 13

Synthesis of 1-(2,3-dichlorophenyl)-trans-1-propene

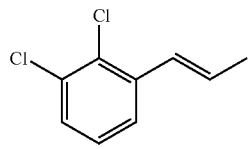

The substantially same method as described in Preparation Example 1 was conducted, except that 2,3-dichlorobenzenaldehyde was used instead of 2-chlorobenzenaldehyde, to obtain the title compound (0.2 g, yield 10~40%).

$^1$H NMR (400 MHz, CDCl$_3$) δ1.94 (d, J=4.8 Hz, 3H), 6.24 (m, 1H), 6.78 (d, J=14 Hz, 1H), 7.11~7.51 (m, 3H)

Preparation Example 14

Synthesis of 1-(2-chlorophenyl)-(S,S)-1,2-propanediol

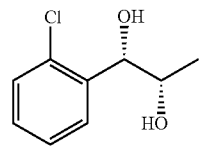

1-(2-chlorophenyl)-trans-1-propene (1.5 g, Preparation Example 1) was dissolved in 30 mL of the mixture of t-BuOH/H$_2$O (1:1 (V/V)). At 0° C., AD-mix-α (Aldrich, U.S.A.) (13.7 g) and methane sulfone amide (CH$_3$SO$_2$NH$_2$, 0.76 g, 0.0080 mol) were added thereto and stirred for overnight. When the reaction was completed, the obtained product was washed with an aqueous solution of sodium sulfite (Na$_2$SO$_3$) and ethylacetate (EA). Then, the organic layer was dehydrated with anhydrous magnesium sulfate (MgSO$_4$), filtrated, and concentrated under reduced pressure. The concentrated residue was purified by a silica gel column chromatography to produce the title compound (1.65 g, yield 90%).

$^1$H NMR (400 MHz, CDCl$_3$) δ1.20 (d, J=6.4 Hz, 3H), 2.48 (d, J=4.0 Hz 1H), 2.92 (d, J=4.4 Hz, 1H), 3.93~3.97 (m, 1H), 4.97 (t, J=4.8 Hz, 1H), 7.22~7.51 (m, 4H)

$^{13}$CNMR (100 MHz, CDCl$_3$) δ18.8, 71.5, 74.4, 127.1, 128.1, 128.9, 129.5, 132.6, 138.9

Preparation Example 15

Synthesis of 1-(2-chlorophenyl)-(R,R)-1,2-propanediol

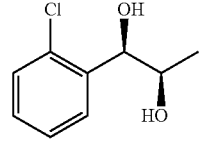

1-(2-chlorophenyl)-trans-1-propene (2.5 g, Preparation Example 1) was dissolved in 50 mL of the mixture of t-BuOH/H$_2$O (1:1 (V/V)). At 0° C., AD-mix-α (Aldrich, U.S.A.) (23.5 g) and methane sulfone amide (CH$_3$SO$_2$NH$_2$, 1.27 g, 0.013 mol) were added thereto and stirred for overnight. When the reaction was completed, the obtained product was washed with an aqueous solution of sodium sulfite (Na$_2$SO$_3$) and ethylacetate (EA). Then, the organic layer was dehydrated with anhydrous magnesium sulfate (MgSO$_4$), filtrated, and concentrated under reduced pressure. The concentrated residue was purified by a silica gel column chromatography to produce the title compound (2.96 g, yield 90%).

$^1$H NMR (400 MHz, CDCl$_3$) δ1.20 (d, J=6.4 Hz, 3H), 2.48 (d, J=4.0 Hz, 1H), 2.92 (d, J=4.4 Hz, 1H), 3.93~3.97 (m, 1H), 4.97 (t, J=4.8 Hz, 1H), 7.22~7.51 (m, 4H)

Preparation Example 16

Synthesis of the mixture of 1-(2-chlorophenyl)-(S,S)-1,2-propanediol and 1-(2-chlorophenyl)-(R,R)-1,2-propanediol

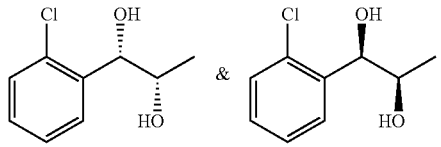

1-(2-chlorophenyl)-trans-1-propene (6.53 g, Preparation Example 1) was dissolved in 45 mL of the mixture of acetone/t-BuOH/H$_2$O (5:1:1 V/V). At the room temperature, N-methylmorpholine-N-oxide (7.51 g) and OsO$_4$ (0.54 g) were added thereto and stirred for 2-3 hours. When the reaction was completed, the obtained product was washed with water and methylenechloride (MC). Then, the organic layer was dehydrated with anhydrous magnesium sulfate (MgSO$_4$), filtrated, and concentrated under reduced pressure. The concentrated residue was purified by a silica gel column chromatography to produce the title compound (6.42 g, yield 80%).

$^1$H NMR (400 MHz, CDCl$_3$) δ1.20 (d, J=6.4 Hz, 3H), 2.48 (d, J=4.0 Hz, 1H), 2.92 (d, J=4.4 Hz, 1H), 3.93~3.97 (m, 1H), 4.97 (t, J=4.8 Hz, 1H), 7.22~7.51 (m, 4H)

Preparation Example 17

Synthesis of 1-(2-chlorophenyl)-(S,S)-1,2-butanediol

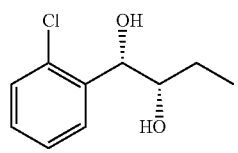

The substantially same method as described in Preparation Example 14 was conducted, except that 1-(2-chlorophenyl)-trans-1-butene (Preparation Example 2) was used instead of 1-(2-chlorophenyl)-trans-1-propene (Preparation Example 1), to obtain the title compound (0.36 g, yield 95%).

$^1$H NMR (400 MHz, CDCl$_3$) δ1.01 (t, J=7.4 Hz, 3H), 1.52~1.65 (m, 2H), 2.01 (d, J=4.4 Hz, 1H), 2.74 (d, J=5.2 Hz, 1H), 3.69~3.75 (m, 1H), 5.05 (t, J=5.0 Hz, 1H), 7.23~7.54 (m, 4H)

Preparation Example 18

Synthesis of 1-(2-chlorophenyl)-(R,R)-1,2-butanediol

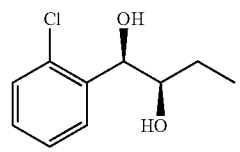

The substantially same method as described in Preparation Example 15 was conducted, except that 1-(2-chlorophenyl)-trans-1-butene (Preparation Example 2) was used instead of 1-(2-chlorophenyl)-trans-1-propene (Preparation Example 1), to obtain the title compound (0.84 g, yield 60~95%).

$^1$H NMR (400 MHz, CDCl$_3$) δ1.01 (t, J=7.4 Hz, 3H), 1.52~1.65 (m, 2H), 2.01 (d, J=4.4 Hz, 1H), 2.74 (d, J=5.2 Hz, 1H), 3.69~3.75 (m, 1H), 5.05 (t, J=5.0 Hz, 1H), 7.23~7.54 (m, 4H)

Preparation Example 19

Synthesis of the mixture of 1-(2-chlorophenyl)-(S,S)-1,2-butanediol and 1-(2-chlorophenyl)-(R,R)-1,2-butanediol

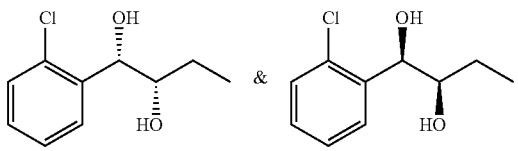

The substantially same method as described in Preparation Example 16 was conducted, except that 1-(2-chlorophenyl)-trans-1-butene (Preparation Example 2) was used instead of 1-(2-chlorophenyl)-trans-1-propene (Preparation Example 1), to obtain the title compound (5.1 g, yield 60~90%).

$^1$H NMR (400 MHz, CDCl$_3$) δ1.01 (t, J=7.4 Hz, 3H), 1.52~1.65 (m, 2H), 2.01 (d, J=4.4 Hz, 1H), 2.74 (d, J=5.2 Hz, 1H), 3.69~3.75 (m, 1H), 5.05 (t, J=5.0 Hz, 1H), 7.23~7.54 (m, 4H)

Preparation Example 20

Synthesis of 1-(2-chlorophenyl)-3-methyl-(S,S)-1,2-butanediol

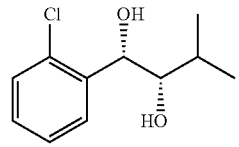

The substantially same method as described in Preparation Example 14 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (0.96 g, yield 60~90%).

$^1$H NMR (400 MHz, CDCl$_3$) δ1.07 (1, J=7.2 Hz, 6H), 1.83~1.89 (m, 1H), 1.92 (d, J=5.6 Hz, 1H), 2.69 (d, J=6.4 Hz, 1H), 3.53~3.56 (m, 1H), 5.22~5.25 (m, 1H), 7.23~7.55 (m, 4H)

Preparation Example 21

Synthesis of 1-(2-chlorophenyl)-3-methyl-(R,R)-1,2-butanediol

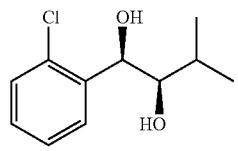

The substantially same method as described in Preparation Example 15 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (4.2 g, yield 60~90%).

$^1$H NMR (400 MHz, CDCl$_3$) δ1.07 (t, J=7.2 Hz, 6H), 1.82~1.90 (m, 1H), 1.93 (d, J=5.6 Hz, 1H), 2.79 (d, J=6 Hz, 1H), 3.53~3.57 (m, 1H), 5.23~5.25 (m, 1H), 7.23~7.54 (m, 4H)

Preparation Example 22

Synthesis of the mixture of 1-(2-chlorophenyl)-3-methyl-(S,S)-1,2-butanediol and 1-(2-chlorophenyl)-3-methyl-(R,R)-1,2-butanediol

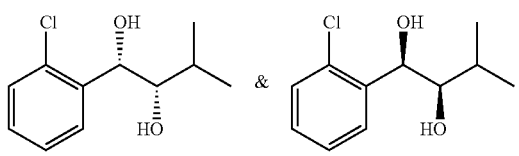

The substantially same method as described in Preparation Example 16 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (0.8 g, yield 60~90%).

$^1$H NMR (400 MHz, CDCl$_3$) δ1.07 (1, J=7.2 Hz, 6H), 1.83~1.90 (m, 1H), 1.92 (d, J=5.6 Hz, 1H), 2.69 (d, J=6.4 Hz, 1H), 3.53~3.56 (m, 1H), 5.22~5.25 (m, 1H), 7.23~7.55 (m, 4H)

Preparation Example 23

Synthesis of 1-(2-chlorophenyl)-(S,S)-1,2-hexanediol

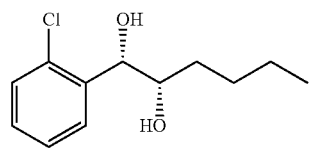

The substantially same method as described in Preparation Example 14 was conducted, except that 1-(2-chlorophenyl)-trans-1-hexene (Preparation Example 4) was used instead of 1-(2-chlorophenyl)-trans-1-propene (Preparation Example 1), to obtain the title compound (0.37 g, yield 90%).

$^1$H NMR (400 MHz, CDCl$_3$) δ0.90 (t, J=7.2 Hz, 3H), 1.35~1.65 (m, 6H), 2.08 (d, J=4.4 Hz, 1H), 2.71 (d, J=5.2 Hz, 1H), 3.78~3.83 (m, 1H), 5.04 (t, J=5.0 Hz, 1H), 7.23~7.53 (m, 4H)

Preparation Example 24

Synthesis of 1-(2-chlorophenyl)-(R,R)-1,2-hexanediol

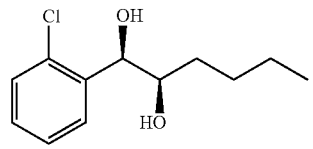

The substantially same method as described in Preparation Example 15 was conducted, except that 1-(2-chlorophenyl)-trans-1-hexene (Preparation Example 4) was used instead of 1-(2-chlorophenyl)-trans-1-propene (Preparation Example 1), to obtain the title compound (4.2 g, yield 60~90%).

$^1$H NMR (400 MHz, CDCl$_3$) δ0.91 (t, J=6.6 Hz, 3H), 1.35~1.65 (m, 6H), 2.08 (d, J=4.8 Hz, 1H), 2.70 (d, J=5.2 Hz, 1H), 3.80~3.83 (m, 1H), 5.05 (t, J=5.0 Hz, 1H), 7.24~7.56 (m, 4H)

Preparation Example 25

Synthesis of the mixture of 1-(2-chlorophenyl)-(S,S)-1,2-hexanediol and 1-(2-chlorophenyl)-(R,R)-1,2-hexanediol

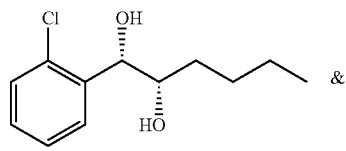

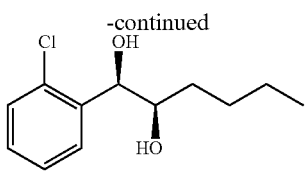

The substantially same method as described in Preparation Example 16 was conducted, except that 1-(2-chlorophenyl)-trans-1-hexene (Preparation Example 4) was used instead of 1-(2-chlorophenyl)-trans-1-propene (Preparation Example 1), to obtain the title compound (7.9 g, yield 60~90%).

$^1$H NMR (400 MHz, CDCl$_3$) δ0.90 (t, J=7.2 Hz, 3H), 1.26~1.55 (m, 6H), 2.08 (d, J=4.4 Hz, 1H), 2.71 (d, J=5.6 Hz, 1H), 3.78~3.84 (m, 1H), 5.04 (t, J=3.2 Hz, 1H), 7.24~7.55 (m, 4H)

Preparation Example 26

Synthesis of 1-(2,4-dichlorophenyl)-(S,S)-1,2-propanediol

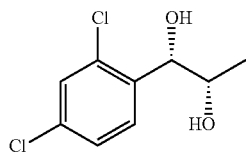

The substantially same method as described in Preparation Example 14 was conducted, except that 1-(2,4-ichlorophenyl)-trans-1-propene (Preparation Example 5) was used instead of 1-(2-chlorophenyl)-trans-1-propene (Preparation Example 1), to obtain the title compound (0.33 g, yield 60~95%).

$^1$H NMR (400 MHz, CDCl$_3$) δ1.22 (d, J=6.4 Hz, 3H), 2.10 (d, J=4.4 Hz, 1H), 2.71 (d, J=4.8 Hz, 1H), 3.90~3.95 (m, 1H), 4.94 (t, J=5.0 Hz, 1H), 7.31 (dd, J=2.0 Hz, J=8.0 Hz, 1H), 7.40 (d, J=2.0 Hz, 1H), 7.49 (d, J=8.4 Hz, 1H)

Preparation Example 27

Synthesis of 1-(2,4-dichlorophenyl)-(R,R)-1,2-propanediol

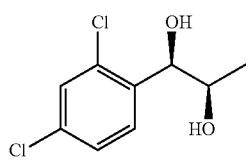

The substantially same method as described in Preparation Example 15 was conducted, except that 1-(2,4-ichlorophenyl)-trans-1-propene (Preparation Example 5) was used instead of 1-(2-chlorophenyl)-trans-1-propene (Preparation Example 1), to obtain the title compound (0.45 g, yield 60~95%).

$^1$H NMR (400 MHz, CDCl$_3$) δ1.22 (d, J=6.4 Hz, 3H), 2.10 (d, J=4.4 Hz, 1H), 2.71 (d, J=4.8 Hz, 1H), 3.90~3.95 (m, 1H), 4.94 (t, J=5.0 Hz, 1H), 7.31~7.49 (m, 3H)

Preparation Example 28

Synthesis of the mixture of 1-(2,4-dichlorophenyl)-(S,S)-1,2-propanediol and 1-(2,4-dichlorophenyl)-(R,R)-1,2-propanediol

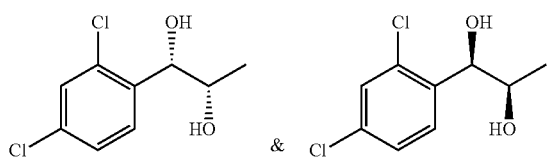

The substantially same method as described in Preparation Example 16 was conducted, except that 1-(2,4-ichlorophenyl)-trans-1-propene (Preparation Example 5) was used instead of 1-(2-chlorophenyl)-trans-1-propene (Preparation Example 1), to obtain the title compound (0.45 g, yield 60~95%).

$^1$H NMR (400 MHz, CDCl$_3$) δ1.22 (d, J=6.4 Hz, 3H), 2.10 (d, J=4.4 Hz, 1H), 2.71 (d, J=4.8 Hz, 1H), 3.90~3.95 (m, 1H), 4.94 (t, J=5.0 Hz, 1H), 7.31~7.49 (m, 3H)

Preparation Example 29

Synthesis of 1-(2,4-dichlorophenyl)-(S,S)-1,2-butanediol

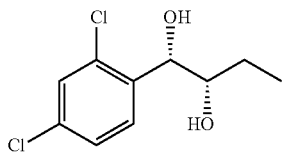

The substantially same method as described in Preparation Example 14 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.32 g, yield 90%).

$^1$H NMR (400 MHz, CDCl$_3$) δ1.02 (t, J=7.4 Hz, 3H), 1.54~1.61 (m, 2H), 2.07 (d, J=4.8 Hz, 1H), 2.74 (d, J=4.8 Hz, 1H), 3.65~3.68 (m, 1H), 5.01 (t, J=5.0 Hz, 1H), 7.31~7.49 (m, 3H)

Preparation Example 30

Synthesis of 1-(2,4-dichlorophenyl)-(R,R)-1,2-butanediol

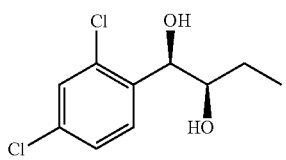

The substantially same method as described in Preparation Example 15 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.43 g, yield 60~90%).

¹H NMR (400 MHz, CDCl₃) δ1.02 (t, J=7.4 Hz, 3H), 1.54~1.61 (m, 2H), 2.07 (d, J=4.8 Hz, 1H), 2.74 (d, J=4.8 Hz, 1H), 3.65~3.68 (m, 1H), 5.01 (t, J=5.0 Hz, 1H), 7.31~7.49 (m, 3H)

Preparation Example 31

Synthesis of the mixture of 1-(2,4-dichlorophenyl)-(S,S)-1,2-butanediol and 1-(2,4-dichlorophenyl)-(R,R)-1,2-butanediol

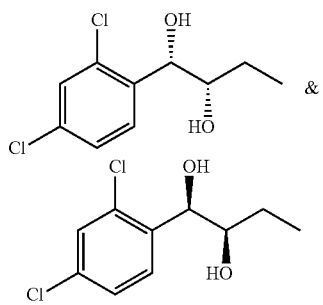

The substantially same method as described in Preparation Example 16 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.33 g, yield 60~90%).

¹H NMR (400 MHz, CDCl₃) δ1.02 (t, J=7.4 Hz, 3H), 1.54~1.61 (m, 2H), 2.07 (d, J=4.8 Hz, 1H), 2.74 (d, J=4.8 Hz, 1H), 3.65~3.68 (m, 1H), 5.01 (t, J=5.0 Hz, 1H), 77.31~7.49 (m, 3H)

Preparation Example 32

Synthesis of 1-(2,4-dichlorophenyl)-3-methyl-(S,S)-1,2-butanediol

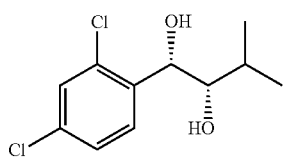

The substantially same method as described in Preparation Example 14 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.25 g, yield 60~95%).

¹H NMR (400 MHz, CDCl₃) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 33

Synthesis of 1-(2,4-dichlorophenyl)-3-methyl-(R,R)-1,2-butanediol

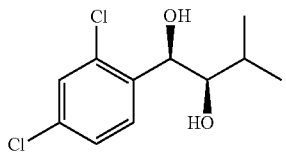

The substantially same method as described in Preparation Example 15 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.36 g, yield 60~95%).

¹H NMR (400 MHz, CDCl₃) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 34

Synthesis of the mixture of 1-(2,4-dichlorophenyl)-3-methyl-(S,S)-1,2-butanediol and 1-(2,4-dichlorophenyl)-3-methyl-(R,R)-1,2-butanediol

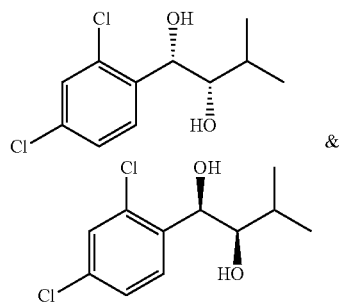

The substantially same method as described in Preparation Example 16 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.26 g, yield 60~95%).

¹H NMR (400 MHz, CDCl₃) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 35

Synthesis of 1-(2,4-dichlorophenyl)-(S,S)-1,2-hexanediol

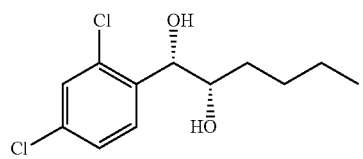 [SMILES: CCCC[C@H](O)[C@@H](O)c1ccc(Cl)cc1Cl]

The substantially same method as described in Preparation Example 14 was conducted, except that 1-(2,4-dichlorophenyl)-trans-1-propene (Preparation Example 8) was used instead of 1-(2-chlorophenyl)-trans-1-propene (Preparation Example 1), to obtain the title compound (1.1 g, yield 60~90%).

¹H NMR (400 MHz, CDCl₃) δ0.89~0.93 (m, 3H), 1.30~1.39 (m, 2H), 1.49~1.52 (m, 2H), 1.56~1.62 (m, 2H), 2.05 (d, J=5.2 Hz, 1H), 2.74 (d, J=5.2 Hz, 1H), 3.72~3.77 (m, 1H), 4.98 (t, J=4.8 Hz, 1H), 7.28~7.50 (m, 3H)

Preparation Example 36

Synthesis of 1-(2,4-dichlorophenyl)-(R,R)-1,2-hexanediol

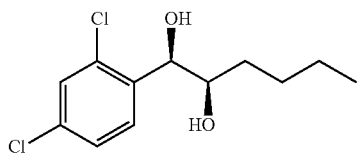 [SMILES: CCCC[C@@H](O)[C@H](O)c1ccc(Cl)cc1Cl]

The substantially same method as described in Preparation Example 15 was conducted, except that 1-(2,4-dichlorophenyl)-trans-1-propene (Preparation Example 8) was used instead of 1-(2-chlorophenyl)-trans-1-propene (Preparation Example 1), to obtain the title compound (1.2 g, yield 60~95%).

¹H NMR (400 MHz, CDCl₃) δ0.89~0.93 (m, 3H), 1.30~1.39 (m, 2H), 1.49~1.52 (m, 2H), 1.56~1.62 (m, 2H), 2.05 (d, J=5.2 Hz, 1H), 2.74 (d, J=5.2 Hz, 1H), 3.72~3.77 (m, 1H), 4.98 (t, J=4.8 Hz, 1H), 7.28~7.50 (m, 3H)

Preparation Example 37

Synthesis of the mixture of 1-(2,4-dichlorophenyl)-(S,S)-1,2-hexanediol and 1-(2,4-dichlorophenyl)-(R,R)-1,2-hexanediol

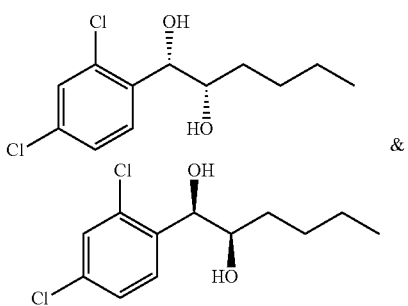

The substantially same method as described in Preparation Example 16 was conducted, except that 1-(2,4-dichlorophenyl)-trans-1-propene (Preparation Example 8) was used instead of 1-(2-chlorophenyl)-trans-1-propene (Preparation Example 1), to obtain the title compound (0.67 g, yield 60~95%).

¹H NMR (400 MHz, CDCl₃) δ0.89~0.93 (m, 3H), 1.30~1.39 (m, 2H), 1.49~1.52 (m, 2H), 1.56~1.62 (m, 2H), 2.05 (d, J=5.2 Hz, 1H), 2.74 (d, J=5.2 Hz, 1H), 3.72~3.77 (m, 1H), 4.98 (t, J=4.8 Hz, 1H), 7.28~7.50 (m, 3H)

Preparation Example 38

Synthesis of 1-(2,6-dichlorophenyl)-(S,S)-1,2-propanediol

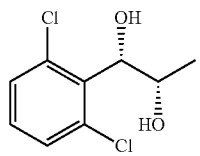

The substantially same method as described in Preparation Example 14 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.9 g, yield 60~90%).

¹H NMR (400 MHz, CDCl₃) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~7.36 (m, 3H)

Preparation Example 39

Synthesis of 1-(2,6-dichlorophenyl)-(R,R)-1,2-propanediol

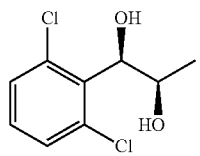

The substantially same method as described in Preparation Example 15 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.84 g, yield 60~90%).

¹H NMR (400 MHz, CDCl₃) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~7.36 (m, 3H)

Preparation Example 40

Synthesis of the mixture of 1-(2,6-dichlorophenyl)-(S,S)-1,2-propanediol and 1-(2,6-dichlorophenyl)-(R,R)-1,2-propanediol

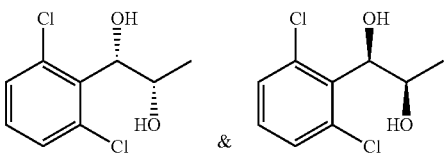

The substantially same method as described in Preparation Example 16 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.91 g, yield 60~90%).

¹H NMR (400 MHz, CDCl₃) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~7.36 (m, 3H)

Preparation Example 41

Synthesis of 1-(2,6-dichlorophenyl)-(S,S)-1,2-butanediol

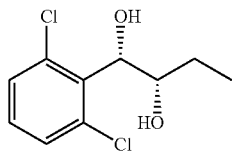

The substantially same method as described in Preparation Example 14 was conducted, except that 1-(2,6-dichlorophenyl)-trans-1-butene (Preparation Example 10) was used instead of 1-(2-chlorophenyl)-trans-1-propene (Preparation Example 1), to obtain the title compound (1.23 g, yield 60~95%).

¹H NMR (400 MHz, CDCl₃) δ0.97 (t, J=7.6 Hz, 3H), 1.26~1.53 (m, 2H), 2.64 (dd, J=0.8 Hz, J=4.0 Hz, 1H), 3.14 (d, J=8.4 Hz, 1H), 4.22~4.26 (m, 1H), 5.26 (t, J=8.4 Hz, 1H), 7.17~7.35 (m, 3H)

Preparation Example 42

Synthesis of 1-(2,6-dichlorophenyl)-(R,R)-1,2-butanediol

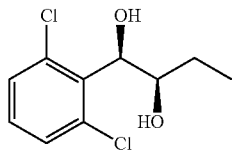

The substantially same method as described in Preparation Example 15 was conducted, except that 1-(2,6-dichlorophenyl)-trans-1-butene (Preparation Example 10) was used instead of 1-(2-chlorophenyl)-trans-1-propene (Preparation Example 1), to obtain the title compound (0.96 g, yield 60~95%).

¹H NMR (400 MHz, CDCl₃) δ0.97 (t, J=7.6 Hz, 3H), 1.26~1.53 (m, 2H), 2.64 (dd, J=0.8 Hz, J=4.0 Hz, 1H), 3.14 (d, J=8.4 Hz, 1H), 4.22~4.26 (m, 1H), 5.26 (t, J=8.4 Hz, 1H), 7.17~7.35 (m, 3H)

Preparation Example 43

Synthesis of the mixture of 1-(2,6-dichlorophenyl)-(S,S)-1,2-butanediol and 1-(2,6-dichlorophenyl)-(R,R)-1,2-butanediol

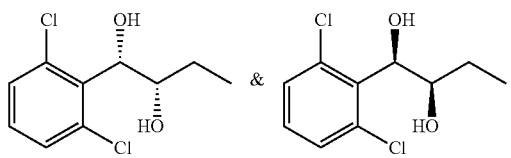

The substantially same method as described in Preparation Example 16 was conducted, except that 1-(2,6-dichlorophenyl)-trans-1-butene (Preparation Example 10) was used instead of 1-(2-chlorophenyl)-trans-1-propene (Preparation Example 1), to obtain the title compound (0.86 g, yield 60~95%).

¹H NMR (400 MHz, CDCl₃) δ0.97 (t, J=7.6 Hz, 3H), 1.26~1.53 (m, 2H), 2.64 (dd, J=0.8 Hz, J=4.0 Hz, 1H), 3.14 (d, J=8.4 Hz, 1H), 4.22~4.26 (m, 1H), 5.26 (t, J=8.4 Hz, 1H), 7.17~7.35 (m, 3H)

Preparation Example 44

Synthesis of 1-(2,6-dichlorophenyl)-3-methyl-(S,S)-1,2-butanediol

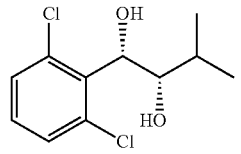

The substantially same method as described in Preparation Example 14 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.25 g, yield 60~95%).

¹H NMR (400 MHz, CDCl₃) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 45

Synthesis of 1-(2,6-dichlorophenyl)-3-methyl-(R,R)-1,2-butanediol

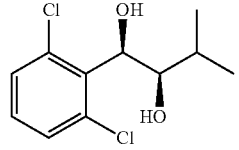

The substantially same method as described in Preparation Example 15 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.37 g, yield 60~95%).

¹H NMR (400 MHz, CDCl₃) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 46

Synthesis of the mixture of 1-(2,6-dichlorophenyl)-3-methyl-(S,S)-1,2-butanediol and 1-(2,6-dichlorophenyl)-3-methyl-(R,R)-1,2-butanediol

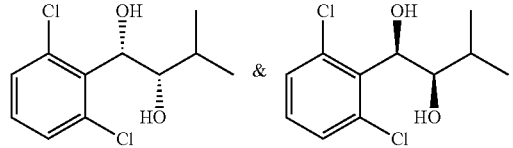

The substantially same method as described in Preparation Example 16 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.47 g, yield 60~95%).

$^1$H NMR (400 MHz, CDCl$_3$) δ1.00 (d, J=6.8 Hz, 6H), 1.60~1.65 (m, 1H), 2.35 (d, J=4.0 Hz, 1H), 3.12 (d, J=8.4 Hz, 1H), 4.13~4.18 (m, 1H), 5.36 (t, J=7.6 Hz, 1H), 7.17~7.35 (m, 3H)

Preparation Example 47

Synthesis of 1-(2,6-dichlorophenyl)-(S,S)-1,2-hexanediol

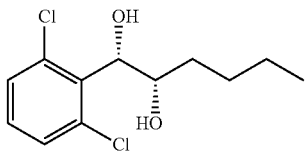 [SMILES: CCCC[C@H](O)[C@@H](O)c1c(Cl)cccc1Cl]

The substantially same method as described in Preparation Example 14 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.36 g, yield 60~90%).

$^1$H NMR (400 MHz, CDCl$_3$) δ0.85 (1, J=6.8 Hz, 3H), 1.20~1.31 (m, 4H), 1.45~1.53 (m, 2H), 2.61~2.62 (m, 1H), 3.12 (d, J=8.4 Hz, 1H), 4.28~4.33 (m, 1H), 5.25 (t, J=8.4 Hz, 1H), 7.18~7.35 (m, 3H)

Preparation Example 48

Synthesis of 1-(2,6-dichlorophenyl)-(R,R)-1,2-hexanediol

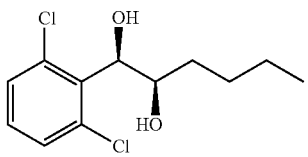 [SMILES: CCCC[C@@H](O)[C@H](O)c1c(Cl)cccc1Cl]

The substantially same method as described in Preparation Example 15 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.58 g, yield 60~90%).

$^1$H NMR (400 MHz, CDCl$_3$) δ0.85 (1, J=6.8 Hz, 3H), 1.20~1.31 (m, 4H), 1.45~1.53 (m, 2H), 2.61~2.62 (m, 1H), 3.12 (d, J=8.4 Hz, 1H), 4.28~4.33 (m, 1H), 5.25 (t, J=8.4 Hz, 1H), 7.18~7.35 (m, 3H)

Preparation Example 49

Synthesis of the mixture of 1-(2,6-dichlorophenyl)-(S,S)-1,2-hexanediol and 1-(2,6-dichlorophenyl)-(R,R)-1,2-hexanediol

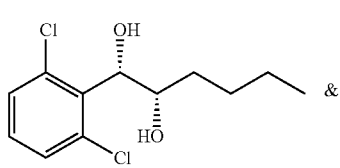

-continued

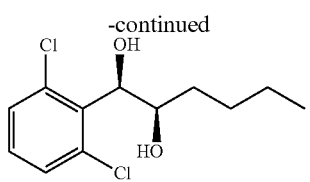

The substantially same method as described in Preparation Example 16 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.62 g, yield 60~90%).

$^1$H NMR (400 MHz, CDCl$_3$) δ0.85 (1, J=6.8 Hz, 3H), 1.20~1.31 (m, 4H), 1.45~1.53 (m, 2H), 2.61~2.62 (m, 1H), 3.12 (d, J=8.4 Hz, 1H), 4.28~4.33 (m, 1H), 5.25 (t, J=8.4 Hz, 1H), 7.18~7.35 (m, 3H)

Preparation Example 50

Synthesis of methyl 2-(2-chlorophenyl)-(R)-2-hydroxyacetate

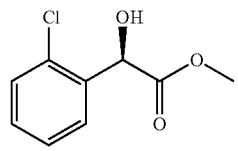

15 g of (R)-2-chloromandelic acid was mixed with methanol (CH$_3$OH, 150 ml) and phosphorus chloride oxide (POCl$_3$, 0.76 ml) in a flask by stirring using a magnetic stirrer at the room temperature for 6 hours. When the reaction was completed, the obtained product was washed with an aqueous solution of sodium sulfite (Na$_2$SO$_3$) and ethylacetate (EA). Then, the organic layer was dehydrated with anhydrous magnesium sulfate (MgSO$_4$), filtrated, and concentrated under reduced pressure. The concentrated residue was purified by a silica gel column chromatography to produce the title compound (15.64 g, yield 95%).

$^1$H NMR (400 MHz, CDCl$_3$) δ 3.59 (d, J=5.2, 1H), 3.79 (t, J=6.0, 3H), 5.59 (d, J=5.2, 1H), 7.28~7.43 (m, 4H)

Preparation Example 51

Synthesis of 2-(2-chlorophenyl)-(R)-2-hydroxy-N-methoxy-N-methylacetamide

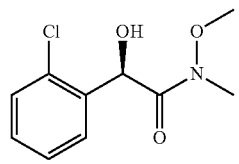

N,O-dimethylhydroxylamine hydrochloride (N,O-dimethylhydroxylamine.HCl, 15.2 g) was dissolved in dichloromethane (DCM, 150 ml), and cooled to 0° C. using an ice-bath. Then, 77.7 ml of 2.0M trimethylaluminium in hexane was slowly added thereto in drop-wise manner for 30 minutes. Thereafter, the ice-bath was removed, and the obtained product was stirred at the room temperature for 2 hours. Methyl-2-(2-chlorophenyl)-(R)-2-hydroxyacetate (15.64 g) dissolved in dichloromethane (DCM, 150 ml) was added in drop-wise manner thereto at the room temperature for 30 minutes, and subjected to reflux for 12 hours. When the reaction was completed, the obtained product was cooled to 0° C., and washed by a slow drop-wise addition of hydrochloric acid (HCl, 200 ml). The obtained organic layer was washed with distilled water and brine, dehydrated with anhydrous magnesium sulfate (MgSO$_4$), filtrated, and concentrated under reduced pressure. The concentrated residue was purified by a silica gel column chromatography to produce the title compound (14.68 g, yield 82%).

$^1$H NMR (400 MHz, CDCl$_3$) δ3.23 (s, 3H), 3.28 (s, 3H), 4.33 (d, J=6.0 Hz, 1H), 5.81 (d, J=5.6 Hz, 1H), 7.23~7.42 (m, 4H)

Preparation Example 52

Synthesis of 2-(2-chlorophenyl)-N-methoxy-(R)-2-(methoxymethoxy)-N-methylacetamide

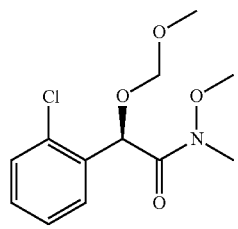 [SMILES: COCO[C@@H](C(=O)N(C)OC)c1ccccc1Cl]

2-(2-chlorophenyl)-(R)-2-hydroxy-N-methoxy-N-methylacetamide (14.68 g) obtained in Preparation Example 51 was dissolved in dichloromethane (DCM, 140 ml), and cooled to 0° C. Diisopropylethylamine (55.67 ml) was slowly added thereto in drop-wise manner, and stirred for 10 minutes. Chloro methyl methyl ether (25.25 ml) was slowly added thereto in drop-wise manner for 30 minutes. After 30 minutes, the ice-bath was removed and the obtained product was stirred for 30 at room temperature. When the reaction was completed, the obtained product was cooled to 0° C. And then, to the obtained product, 1M sodium hydroxide solution (1M NaOH, 20 ml) was added in drop-wise manner, and dichloromethane (DMC) was injected. Then the obtained product was washed with water. The obtained organic layer was dehydrated with anhydrous magnesium sulfate (MgSO$_4$), filtrated, and concentrated under reduced pressure. The concentrated residue was purified by a silica gel column chromatography to produce the title compound (15.57 g, yield 89%).

$^1$H NMR (400 MHz, CDCl$_3$) δ3.19 (s, 3H), 3.42 (s, 3H), 3.47 (s, 3H), 4.75 (d, J=6.8, 1H), 4.81 (d, J=6.8, 1H), 6.07 (s, 1H), 7.27~7.58 (m, 4H)

Preparation Example 53

Synthesis of 1-(2-Chlorophenyl)-(R)-1-(methoxymethoxy)propane-2-on

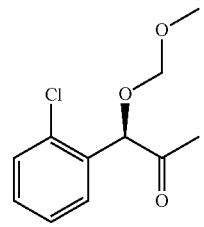

2-(2-chlorophenyl)-N-methoxy-(R)-2-(methoxymethoxy)-N-methylacetamide (15.57 g) obtained in Preparation Example 52 was dissolved in tetrahydrofuran (THF, 150 ml), and cooled to 0° C. 3.0M methyl magnesium bromide (MeMgBr) solution in ether was added thereto in drop-wise manner for 30 minutes, and the obtained product was stirred for 1 hour at 0° C. When the reaction was completed, diethylether (100 ml) was added thereto. The obtained product was washed with 10% (w/v) potassium hydrogen sulfate (KHSO$_4$, 100 ml) and then, washed again with brine. The obtained organic layer was dehydrated with anhydrous magnesium sulfate (MgSO$_4$), filtrated, and concentrated under reduced pressure. The concentrated residue was purified by a silica gel column chromatography to produce the title compound (11.83 g, yield 90%).

$^1$H NMR (400 MHz, CDCl$_3$) δ2.18 (s, 3H), 3.39 (s, 3H), 4.65 (d, J=6.8, 1H), 4.74 (d, J=6.8, 1H), 5.63 (s, 1H), 7.30~7.45 (m, 4H)

Preparation Example 54

Synthesis of 1-(2-chlorophenyl)-(R)-1-(methoxymethoxy)-(S)-2-propanol

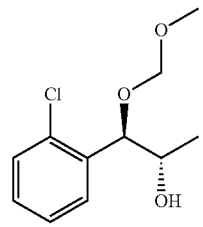

1-(2-chlorophenyl)-(R)-1-(methoxymethoxy)propane-2-on (11.83 g) obtained in Preparation Example 53 was dissolved in toluene (110 ml), and cooled to −40° C. Sodium bis(2-methoxyethoxy)aluminumhydride solution (15.7 ml) in toluene was slowly added thereto for 30 minutes, and then, the obtained product was stirred for 1 hour. When the reaction was completed, the obtained product was washed by slow drop-wise addition of sodium potassium tartrate (100 ml). The obtained organic layer was dehydrated with anhydrous magnesium sulfate (MgSO$_4$), filtrated, and concentrated under reduced pressure. The concentrated residue was purified by a silica gel column chromatography to produce the title compound (10.38 g, yield 87%).

$^1$H NMR (400 MHz, CDCl$_3$) δ1.13 (d, J=6.4, 3H), 2.33 (d, J=7.2, 1H), 3.44 (s, 3H), 4.10~4.18 (m, 1H), 4.61 (d, J=6.4, 1H), 4.69 (d, J=6.8, 1H), 5.14 (d, J=3.6, 1H), 7.22~7.55 (m, 4H)

Preparation Example 55

Synthesis of 1-(2-chlorophenyl)-(R,S)-1,2-propanediol

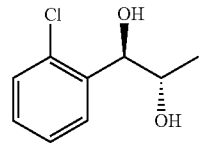

1-(2-chlorophenyl)-(R)-1-(methoxymethoxy)-(S)-2-propanol (10.38 g) obtained in Preparation Example 54 was dissolved in methanol (CH$_3$OH, 100 ml), and then, cooled to 0° C. 8M hydrochloric acid (HCl, 56.2 ml) was slowly added in drop-wise manner to the obtained product, and then, the obtained product was warmed to the room temperature, and stirred for 15 hours. When the reaction was completed, the obtained product was cooled to 0° C. 5N sodium hydroxide (NaOH, 30 ml) was slowly added thereto, and the obtained product was subjected to vacuum concentration. The obtained product was diluted with ethylacetate. The obtained organic layer was washed with distilled water, dehydrated with anhydrous magnesium sulfate (MgSO₄), filtrated, and concentrated under reduced pressure. The concentrated residue was purified by a silica gel column chromatography to produce the title compound (7.05 g, yield 60~90%).

¹H NMR (400 MHz, CDCl₃) δ1.07 (d, J=6.8, 3H), 2.01 (d, J=5.6, 1H), 2.61 (s, 1H), 4.21~4.27 (m, 1H), 5.24 (d, J=3.6, 1H), 7.22~7.64 (m, 4H)

Preparation Example 56

Synthesis of
1-(2-chlorophenyl)-(S,R)-1,2-propanediol

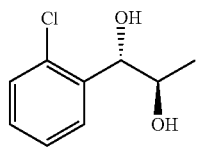

The substantially same method as described in Preparation Example 5055 was conducted, except that (S)-2-chloromandelic acid was used instead of (R)-2-chloromandelic acid, to obtain the title compound (5.04 g, yield 84%).

¹H NMR (400 MHz, CDCl₃) δ1.07 (d, J=6.8, 3H), 2.00 (d, J=5.6, 1H), 2.54 (d, J=3.6, 1H), 4.22~4.26 (m, 1H), 5.25 (t, J=3.2, 1H), 7.22~7.65 (m, 4H)

Preparation Example 57

Synthesis of
1-(2,3-dichlorophenyl)-(S,S)-1,2-propanediol

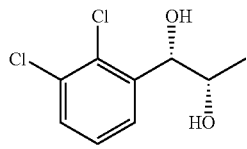

The substantially same method as described in Preparation Example 14 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.9 g, yield 60~90%).

¹H NMR (400 MHz, CDCl₃) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18 (m, 3H)

Preparation Example 58

Synthesis of
1-(2,3-dichlorophenyl)-(R,R)-1,2-propanediol

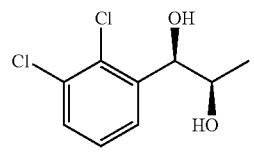

The substantially same method as described in Preparation Example 15 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.84 g, yield 60~90%).

¹H NMR (400 MHz, CDCl₃) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18 (m, 3H)

Preparation Example 59

Synthesis of the mixture of 1-(2,3-dichlorophenyl)-(S,S)-1,2-propanediol and 1-(2,3-dichlorophenyl)-(R,R)-1,2-propanediol

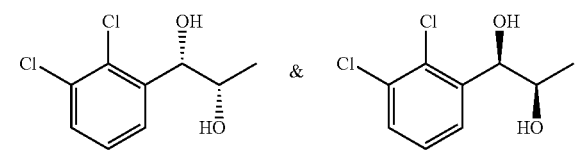

The substantially same method as described in Preparation Example 16 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.91 g, yield 60~90%).

¹H NMR (400 MHz, CDCl₃) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (1, J=8.8 Hz, 1H), 7.18 (m, 3H)

Preparation Example 60

Synthesis of 1-(2-fluorophenyl)-trans-1-propene

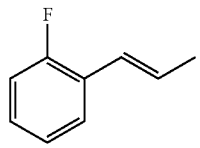

The substantially same method as described in Preparation Example 1 was conducted, except that 2-fluorobenzenaldehyde was used instead of 2-chlorobenzenealdehyde, to obtain the title compound (6.67 g, yield 61%).

¹H NMR (400 MHz, CDCl₃) δ1.94 (d, J=6.8 Hz, 3H), 6.30~6.38 (m, 1H), 6.57 (d, J=16 Hz, 1H), 7.00~7.41 (m, 4H)

Preparation Example 61

Synthesis of 1-(2-fluorophenyl)-(S,S)-1,2-propanediol

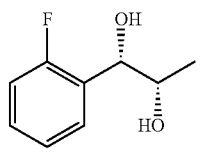

The substantially same method as described in Preparation Example 14 was conducted, except that 1-(2-fluorophenyl)-trans-1-propene (Preparation Example 60) was used instead of 1-(2-chlorophenyl)-trans-1-propene (Preparation Example 1), to obtain the title compound (6.46 g, yield 78%).
¹H NMR (400 MHz, CDCl₃) δ1.15 (d, J=6.4 Hz, 3H), 2.43 (d, J=3.6 Hz, 1H), 2.69 (d, J=4.8 Hz, 1H), 3.90~3.98 (m, 1H), 4.78 (dd, J=4.4, 7.2 Hz, 1H), 7.04~7.50 (m, 4H)

Preparation Example 62

Synthesis of 1-(2-fluorophenyl)-(R,R)-1,2-propanediol

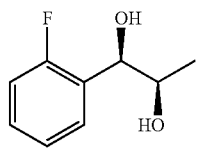

The substantially same method as described in Preparation Example 15 was conducted, except that 1-(2-fluorophenyl)-trans-1-propene (Preparation Example 60) was used instead of 1-(2-chlorophenyl)-trans-1-propene (Preparation Example 1), to obtain the title compound (3.29 g, yield 79%).
¹H NMR (400 MHz, CDCl₃) δ1.15 (d, J=6.4 Hz, 3H), 2.43 (d, J=3.6 Hz, 1H), 2.69 (d, J=4.8 Hz, 1H), 3.90~3.98 (m, 1H), 4.78 (dd, J=4.4, 7.2 Hz, 1H), 7.04~7.50 (m, 4H)

Preparation Example 63

Synthesis of 2-iodobenzenealdehyde

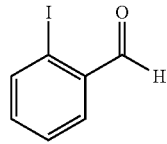

In a flask, 2-iodobenzyl alcohol (4 g, 17.09 mmol) was dissolved in dichloromethane (MC, 85 ml), and then, manganese oxide (MnO₂, 14.86 g, 170.92 mmol) was added thereto. The obtained reaction product was stirred under the reflux condition. When the reaction was completed, the obtained reaction product was cooled to the room temperature, and then, filtrated and concentrated using celite, to obtain the title compound (3.6 g, yield 91%).
¹H NMR (400 MHz, CDCl₃) δ7.30~7.99 (m, 4H), 10.10 (s, 1H)

Preparation Example 64

Synthesis of 1-(2-iodophenyl)-trans-1-propene

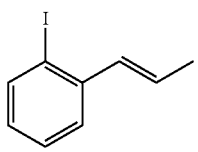

The substantially same method as described in Preparation Example 1 was conducted, except that 2-iodobenzenealdehyde (Preparation Example 63) was used instead of 2-chlorobenzenealdehyde, to obtain the title compound (3.4 g, yield 65%).
¹H NMR (400 MHz, CDCl₃) δ1.95 (dd, J=6.8 Hz, 1.6 Hz, 3H), 6.09~6.18 (m, 1H), 6.60 (dd, J=15.66 Hz, 1.8 Hz, 1H), 6.89~7.84 (m, 4H)

Preparation Example 65

Synthesis of 1-(2-iodophenyl)-trans-1-butene

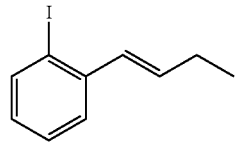

The substantially same method as described in Preparation Example 64 was conducted, except that 3-heptanone was used instead of 3-pentanone, to obtain the title compound (8.5 g, yield 75%).
¹H NMR (400 MHz, CDCl₃) δ1.46 (t, J=7.6 Hz, 3H), 2.26~2.34 (m, 2H), 6.17 (dt, J=15.6 Hz, 6.6 Hz 1H), 6.57 (d, J=15.6 Hz, 1H), 6.89~7.85 (m, 4H)

Preparation Example 66

Synthesis of 1-(2-iodophenyl)-(S,S)-1,2-propanediol

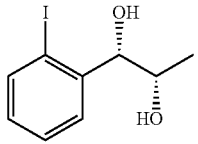

The substantially same method as described in Preparation Example 14 was conducted, except that 1-(2-iodophenyl)-trans-1-propene (Preparation Example 64) was used instead of 1-(2-chlorophenyl)-trans-1-propene (Preparation Example 1), to obtain the title compound (3.4 g, yield 88%).

$^1$H NMR (400 MHz, CDCl$_3$) δ1.27 (d, J=6.4 Hz, 3H), 2.26 (br s, 1H), 2.74 (br s, 1H), 3.99 (t, J=6.0 Hz, 1H), 4.81 (d, J=4.0 Hz, 1H), 7.01~7.87 (m, 4H)

Preparation Example 67

Synthesis of 1-(2-iodorophenyl)-(R,R)-1,2-propanediol

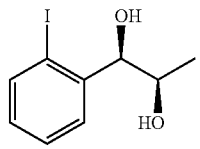

The substantially same method as described in Preparation Example 15 was conducted was conducted, except that 1-(2-iodophenyl)-trans-1-propene (Preparation Example 64) was used instead of 1-(2-chlorophenyl)-trans-1-propene (Preparation Example 1), to obtain the title compound (7.4 g, yield 84%).

$^1$H NMR (400 MHz, CDCl$_3$) δ1.26 (d, J=6.4 Hz, 3H), 2.35 (br s, 1H), 2.85 (br d, J=4.0 Hz, 1H), 3.98 (t, J=6.2 Hz, 1H), 4.80 (dd, J=5.0, 4.4 Hz, 1H), 7.00~7.87 (m, 4H)

Preparation Example 68

Synthesis of 1-(2-iodophenyl)-(S,S)-1,2-butanediol

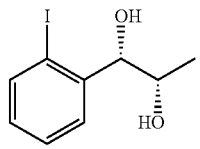

The substantially same method as described in Preparation Example 14 was conducted was conducted, except that 1-(2-iodophenyl)-trans-1-butene (Preparation Example 65) was used instead of 1-(2-chlorophenyl)-trans-1-propene (Preparation Example 1), to obtain the title compound (9.5 g, yield 84%).

$^1$H NMR (400 MHz, CDCl$_3$) δ1.04 (t, J=7.6 Hz, 3H), 1.60~1.71 (m, 2H), 2.07 (br s, 1H), 2.74 (br s, 1H), 3.71~3.76 (m, 1H), 4.87 (d, J=4.8 Hz, 1H), 7.01~7.87 (m, 4H)

Preparation Example 69

Synthesis of 1-(2-iodophenyl)-(R,R)-1,2-butanediol

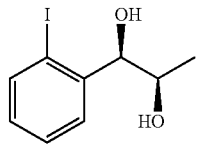

The substantially same method as described in Preparation Example 15 was conducted was conducted, except that 1-(2-iodophenyl)-trans-1-butene (Preparation Example 65) was used instead of 1-(2-chlorophenyl)-trans-1-propene (Preparation Example 1), to obtain the title compound (1.9 g, yield 70~90%).

$^1$H NMR (400 MHz, CDCl$_3$) δ1.01 (1, J=7.4 Hz, 3H), 1.52~1.65 (m, 2H), 2.01 (d, J=4.4 Hz, 1H), 2.74 (d, J=5.2 Hz, 1H), 3.69~3.75 (m, 1H), 5.05 (t, J=5.0 Hz, 1H), 7.03~7.84 (m, 4H)

Preparation Example 70

Synthesis of 1-(2-iodophenyl)-3-methyl-trans-1-butene

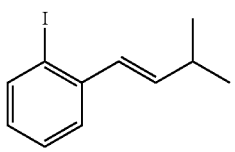

The substantially same method as described in Preparation Example 3 was conducted, except that 2-iodobenzenaldehyde was used instead of 2-chlorobenzenaldehyde, to obtain the title compound (0.37 g, yield 10~40%).

$^1$H NMR (400 MHz, CDCl$_3$) δ1.14 (d, J=6.8 Hz, 6H), 2.25~2.57 (m, 1H), 6.20 (dd, J=16 Hz, 7.2 Hz, 1H), 7.64 (d, J=16 Hz, 1H), 7.04~7.82 (m, 4H)

Preparation Example 71

Synthesis of 1-(2-iodophenyl)-trans-1-hexene

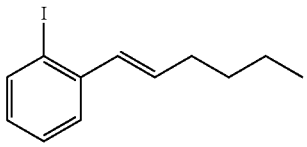

The substantially same method as described in Preparation Example 4 was conducted, except that 2-iodobenzenaldehyde was used instead of 2-chlorobenzenaldehyde, to obtain the title compound (1.21 g, yield 10~40%).

$^1$H NMR (400 MHz, CDCl$_3$) δ0.96 (t, J=7.2 Hz, 3H), 1.33~1.56 (m, 4H), 2.26~2.32 (m, 4H), 6.24 (dt, J=15.6 Hz, 7 Hz, 1H), 6.78 (d, J=16 Hz, 1H), 7.12~7.51 (m, 4H)

Preparation Example 72

Synthesis of 1-(2-fluorophenyl)-trans-1-butene

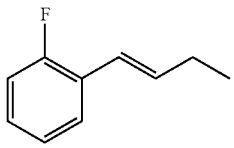

The substantially same method as described in Preparation Example 2 was conducted, except that 2-fluorobenzenaldehyde was used instead of 2-chlorobenzenaldehyde, to obtain the title compound (0.72 g, yield 10~40%).

$^1$H NMR (400 MHz, CDCl$_3$) δ1.14 (d, J=7.6 Hz, 3H), 2.29~2.33 (m, 2H), 6.28 (dt, J=16 Hz, 6.4 Hz, 1H), 6.78 (d, J=15.6 Hz, 1H), 7.15~7.55 (m, 4H)

Preparation Example 73

Synthesis of 1-(2-fluorophenyl)-3-methyl-trans-1-butene

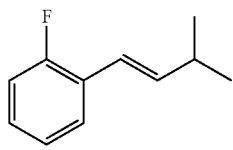

The substantially same method as described in Preparation Example 3 was conducted, except that 2-fluorobenzenaldehyde was used instead of 2-chlorobenzenaldehyde, to obtain the title compound (1.31 g, yield 10~40%).

$^1$H NMR (400 MHz, CDCl$_3$) δ1.14 (d, J=6.8 Hz, 6H), 2.25~2.57 (m, 1H), 6.20 (dd, J=16 Hz, 7.2 Hz, 1H), 7.64 (d, J=16 Hz, 1H), 7.11~7.55 (m, 4H)

Preparation Example 74

Synthesis of 1-(2-fluorophenyl)-trans-1-hexene

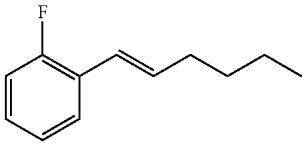

The substantially same method as described in Preparation Example 4 was conducted, except that 2-fluorobenzenaldehyde was used instead of 2-chlorobenzenaldehyde, to obtain the title compound (1.02 g, yield 10~40%).

$^1$H NMR (400 MHz, CDCl$_3$) δ0.96 (t, J=7.2 Hz, 3H), 1.33~1.56 (m, 4H), 2.26~2.32 (m, 4H), 6.24 (dt, J=15.6 Hz, 7 Hz, 1H), 6.78 (d, J=16 Hz, 1H), 7.14~7.52 (m, 4H)

Preparation Example 75

Synthesis of 1-(3-iodophenyl)-trans-1-propene

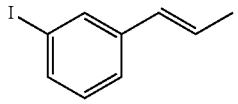

The substantially same method as described in Preparation Example 64 was conducted, except that 3-iodobenzenaldehyde was used instead of 2-iodobenzenaldehyde, to obtain the title compound (1.22 g, yield 10~40%).

$^1$H NMR (400 MHz, CDCl$_3$) δ1.95 (dd, J=6.8 Hz, 1.6 Hz, 3H), 6.09~6.18 (m, 1H), 6.60 (dd, J=15.66 Hz, 1.8 Hz, 1H), 6.87~7.80 (m, 4H)

Preparation Example 76

Synthesis of 1-(3-iodophenyl)-trans-1-butene

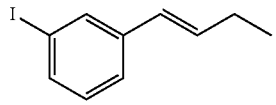

The substantially same method as described in Preparation Example 65 was conducted, except that 3-iodobenzenaldehyde was used instead of 2-iodobenzenaldehyde, to obtain the title compound (1.12 g, yield 10~40%).

$^1$H NMR (400 MHz, CDCl$_3$) δ1.46 (t, J=7.6 Hz, 3H), 2.26~2.34 (m, 2H), 6.17 (dt, J=15.6 Hz, 6.6 Hz 1H), 6.57 (d, J=15.6 Hz, 1H), 6.86~7.81 (m, 4H)

Preparation Example 77

Synthesis of 1-(3-iodophenyl)-3-methyl-trans-1-butene

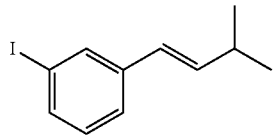

The substantially same method as described in Preparation Example 70 was conducted, except that 3-iodobenzenaldehyde was used instead of 2-iodobenzenaldehyde, to obtain the title compound (0.62 g, yield 10~40%).

$^1$H NMR (400 MHz, CDCl$_3$) δ1.14 (d, J=6.8 Hz, 6H), 2.25~2.57 (m, 1H), 6.20 (dd, J=16 Hz, 7.2 Hz, 1H), 7.64 (d, J=16 Hz, 1H), 6.88~7.64 (m, 4H)

Preparation Example 78

Synthesis of 1-(3-iodophenyl)-trans-1-hexene

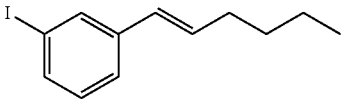

The substantially same method as described in Preparation Example 71 was conducted, except that 3-iodobenzenaldehyde was used instead of 2-iodobenzenaldehyde, to obtain the title compound (0.42 g, yield 10~40%).

$^1$H NMR (400 MHz, CDCl$_3$) δ0.96 (t, J=7.2 Hz, 3H), 1.33~1.56 (m, 4H), 2.26~2.32 (m, 4H), 6.24 (dt, J=15.6 Hz, 7 Hz, 1H), 6.78 (d, J=16 Hz, 1H), 6.88~7.59 (m, 4H)

Preparation Example 79

Synthesis of 1-(4-fluorophenyl)-trans-1-propene

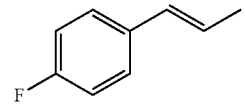

The substantially same method as described in Preparation Example 60 was conducted, except that 4-fluorobenzenaldehyde was used instead of 2-fluorobenzenaldehyde, to obtain the title compound (0.29 g, yield 10~40%).

¹H NMR (400 MHz, CDCl$_3$) δ1.94 (d, J=6.8 Hz, 3H), 6.30~6.38 (m, 1H), 6.57 (d, J=16 Hz, 1H), 6.85~7.04 (m, 4H)

Preparation Example 80

Synthesis of 1-(4-fluorophenyl)-trans-1-butene

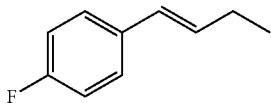

The substantially same method as described in Preparation Example 72 was conducted, except that 4-fluorobenzenaldehyde was used instead of 2-fluorobenzenaldehyde, to obtain the title compound (1.03 g, yield 10~40%).

¹H NMR (400 MHz, CDCl$_3$) δ1.14 (d, J=7.6 Hz, 3H), 2.29~2.33 (m, 2H), 6.28 (dt, J=16 Hz, 6.4 Hz, 1H), 6.78 (d, J=15.6 Hz, 1H), 6.88. 15~7.05 (m, 4H)

Preparation Example 81

Synthesis of 1-(4-fluorophenyl)-3-methyl-trans-1-butene

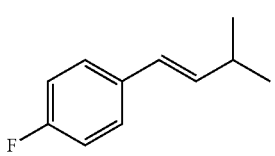

The substantially same method as described in Preparation Example 73 was conducted, except that 4-fluorobenzenaldehyde was used instead of 2-fluorobenzenaldehyde, to obtain the title compound (1.41 g, yield 10~40%)

¹H NMR (400 MHz, CDCl$_3$) δ1.14 (d, J=6.8 Hz, 6H), 2.25~2.57 (m, 1H), 6.20 (dd, J=16 Hz, 7.2 Hz, 1H), 7.64 (d, J=16 Hz, 1H), 6.83~7.09 (m, 4H)

Preparation Example 82

Synthesis of 1-(4-fluorophenyl)-trans-1-hexene

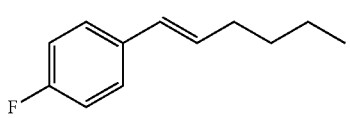

The substantially same method as described in Preparation Example 74 was conducted, except that 4-fluorobenzenaldehyde was used instead of 2-fluorobenzenaldehyde, to obtain the title compound (0.43 g, yield 10~40%)

¹H NMR (400 MHz, CDCl$_3$) δ0.96 (t, J=7.2 Hz, 3H), 1.33~1.56 (m, 4H), 2.26~2.32 (m, 4H), 6.24 (dt, J=15.6 Hz, 7 Hz, 1H), 6.78 (d, J=16 Hz, 1H), 6.84~7.07 (m, 4H)

Preparation Example 83

Synthesis of 1-(2-iodophenyl)-3-methyl-(S,S)-1,2-butanediol

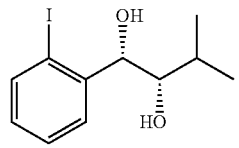

The substantially same method as described in Preparation Example 14 was conducted, except that 1-(2-iodophenyl)-3-methyl-trans-1-butene (Preparation Example 70) was used instead of 1-(2-chlorophenyl)-trans-1-propene (Preparation Example 1), to obtain the title compound (0.52 g, yield 60~90%).

¹H NMR (400 MHz, CDCl$_3$) δ1.07 (t, J=7.2 Hz, 6H), 1.83~1.89 (m, 1H), 1.92 (d, J=5.6 Hz, 1H), 2.69 (d, J=6.4 Hz, 1H), 3.53~3.56 (m, 1H), 5.22~5.25 (m, 1H), 7.04~7.85 (m, 4H)

Preparation Example 84

Synthesis of 1-(2-iodophenyl)-3-methyl-(R,R)-1,2-butanediol

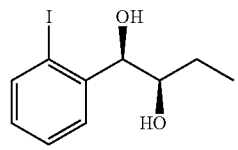

The substantially same method as described in Preparation Example 15 was conducted, except that 1-(2-iodophenyl)-trans-1-butene (Preparation Example 65) was used instead of 1-(2-chlorophenyl)-trans-1-propene (Preparation Example 1), to obtain the title compound (0.52 g, yield 60~90%)

¹H NMR (400 MHz, CDCl$_3$) δ1.04 (t, J=7.6 Hz, 3H), 1.60~1.71 (m, 2H), 2.07 (br s, 1H), 2.74 (br s, 1H), 3.71~3.76 (m, 1H), 4.87 (d, J=4.8 Hz, 1H), 7.01~7.87 (m, 4H)

Preparation Example 85

Synthesis of 1-(2-iodophenyl)-(S,S)-1,2-hexanediol

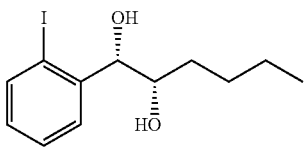

The substantially same method as described in Preparation Example 14 was conducted, except that 1-(2-iodophenyl)-trans-1-hexene (Preparation Example 71) was used instead of 1-(2-chlorophenyl)-trans-1-propene (Preparation Example 1), to obtain the title compound (1.21 g, yield 60~90%)

¹H NMR (400 MHz, CDCl₃) δ0.90 (t, J=7.2 Hz, 3H), 1.35~1.65 (m, 6H), 2.08 (d, J=4.4 Hz, 1H), 2.71 (d, J=5.2 Hz, 1H), 3.78~3.83 (m, 1H), 5.04 (t, J=5.0 Hz, 1H), 7.02~7.79 (m, 4H)

Preparation Example 86

Synthesis of 1-(2-iodophenyl)-(R,R)-1,2-hexanediol

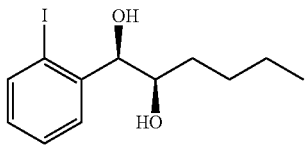

The substantially same method as described in Preparation Example 15 was conducted, except that 1-(2-iodophenyl)-trans-1-hexene (Preparation Example 71) was used instead of 1-(2-chlorophenyl)-trans-1-propene (Preparation Example 1), to obtain the title compound (0.74 g, yield 60~90%)

¹H NMR (400 MHz, CDCl₃) δ0.90 (t, J=7.2 Hz, 3H), 1.35~1.65 (m, 6H), 2.08 (d, J=4.4 Hz, 1H), 2.71 (d, J=5.2 Hz, 1H), 3.78~3.83 (m, 1H), 5.04 (t, J=5.0 Hz, 1H), 7.02~7.79 (m, 4H)

Preparation Example 87

Synthesis of 1-(3-iodophenyl)-(S,S)-1,2-propanediol

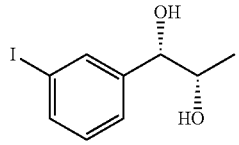

The substantially same method as described in Preparation Example 66 was conducted, except that 1-(3-iodophenyl)-trans-1-propene (Preparation Example 75) was used instead of 1-(2-iodophenyl)-trans-1-propene (Preparation Example 64), to obtain the title compound (2.03 g, yield 60~90%).

¹H NMR (400 MHz, CDCl₃) δ1.27 (d, J=6.4 Hz, 3H), 2.26 (br s, 1H), 2.74 (br s, 1H), 3.99 (t, J=6.0 Hz, 1H), 4.81 (d, J=4.0 Hz, 1H), 6.98~7.50 (m, 4H)

Preparation Example 88

Synthesis of 1-(3-iodophenyl)-(R,R)-1,2-propanediol

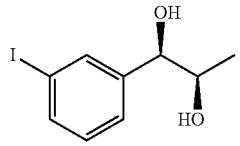

The substantially same method as described in Preparation Example 67 was conducted, except that 1-(3-iodophenyl)-trans-1-propene (Preparation Example 75) was used instead of 1-(2-iodophenyl)-trans-1-propene (Preparation Example 64), to obtain the title compound (1.12 g, yield 60~90%).

¹H NMR (400 MHz, CDCl₃) δ1.27 (d, J=6.4 Hz, 3H), 2.26 (br s, 1H), 2.74 (br s, 1H), 3.99 (t, J=6.0 Hz, 1H), 4.81 (d, J=4.0 Hz, 1H), 6.98~7.50 (m, 4H)

Preparation Example 89

Synthesis of 1-(3-iodophenyl)-(S,S)-1,2-butanediol

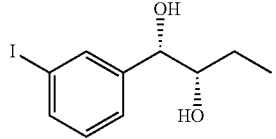

The substantially same method as described in Preparation Example 68 was conducted, except that 1-(3-iodophenyl)-trans-1-butene (Preparation Example 76) was used instead of 1-(2-iodophenyl)-trans-1-propene (Preparation Example 64), to obtain the title compound (2.03 g, yield 60~90%).

¹H NMR (400 MHz, CDCl₃) δ1.04 (t, J=7.6 Hz, 3H), 1.60~1.71 (m, 2H), 2.07 (br s, 1H), 2.74 (br s, 1H), 3.71~3.76 (m, 1H), 4.87 (d, J=4.8 Hz, 1H), 6.99~7.52 (m, 4H)

Preparation Example 90

Synthesis of 1-(3-iodophenyl)-(R,R)-1,2-butanediol

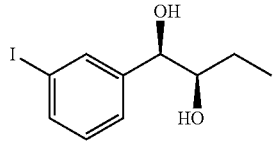

The substantially same method as described in Preparation Example 84 was conducted, except that 1-(3-iodophenyl)-trans-1-butene (Preparation Example 76) was used instead of 1-(2-iodophenyl)-trans-1-propene (Preparation Example 64), to obtain the title compound (1.18 g, yield 60~90%).

¹H NMR (400 MHz, CDCl₃) δ1.04 (t, J=7.6 Hz, 3H), 1.60~1.71 (m, 2H), 2.07 (br s, 1H), 2.74 (br s, 1H), 3.71~3.76 (m, 1H), 4.87 (d, J=4.8 Hz, 1H), 6.99~7.52 (m, 4H)

Preparation Example 91

Synthesis of 1-(3-iodophenyl)-3-methyl-(S,S)-1,2-butanediol

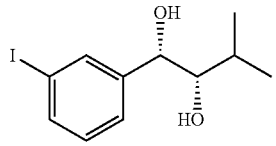

The substantially same method as described in Preparation Example 83 was conducted, except that 1-(3-iodophenyl)-3-methyl-trans-1-butene (Preparation Example 77) was used instead of 1-(2-iodophenyl)-3-methyl-trans-1-butene (Preparation Example 70), to obtain the title compound (0.51 g, yield 60~90%).

$^1$H NMR (400 MHz, CDCl$_3$) δ1.07 (1, J=7.2 Hz, 6H), 1.83~1.89 (m, 1H), 1.92 (d, J=5.6 Hz, 1H), 2.69 (d, J=6.4 Hz, 1H), 3.53~3.56 (m, 1H), 5.22~5.25 (m, 1H), 6.92~7.50 (m, 4H)

Preparation Example 92

Synthesis of 1-(3-iodophenyl)-3-methyl-(R,R)-1,2-butanediol

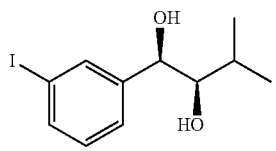

The substantially same method as described in Preparation Example 90 was conducted, except that 1-(3-iodophenyl)-3-methyl-trans-1-butene (Preparation Example 77) was used instead of 1-(3-iodophenyl)-trans-1-butene (Preparation Example 76), to obtain the title compound (1.10 g, yield 60~90%).

$^1$H NMR (400 MHz, CDCl$_3$) δ1.07 (t, J=7.2 Hz, 6H), 1.83~1.89 (m, 1H), 1.92 (d, J=5.6 Hz, 1H), 2.69 (d, J=6.4 Hz, 1H), 3.53~3.56 (m, 1H), 5.22~5.25 (m, 1H), 6.92~7.50 (m, 4H)

Preparation Example 93

Synthesis of 1-(3-iodophenyl)-(S,S)-1,2-hexanediol

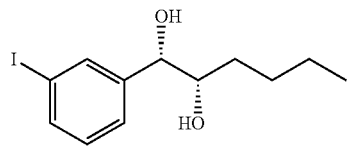

The substantially same method as described in Preparation Example 85 was conducted, except that 1-(3-iodophenyl)-trans-1-hexene (Preparation Example 78) was used instead of 1-(2-iodophenyl)-trans-1-hexene (Preparation Example 71), to obtain the title compound (0.95 g, yield 60~90%)

$^1$H NMR (400 MHz, CDCl$_3$) δ0.90 (t, J=7.2 Hz, 3H), 1.35~1.65 (m, 6H), 2.08 (d, J=4.4 Hz, 1H), 2.71 (d, J=5.2 Hz, 1H), 3.78~3.83 (m, 1H), 5.04 (t, J=5.0 Hz, 1H), 6.95~7.49 (m, 4H)

Preparation Example 94

Synthesis of 1-(3-iodophenyl)-(R,R)-1,2-hexanediol

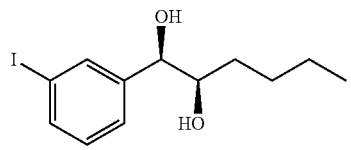

The substantially same method as described in Preparation Example 86 was conducted, except that 1-(3-iodophenyl)-trans-1-hexene (Preparation Example 78) was used instead of 1-(2-iodophenyl)-trans-1-hexene (Preparation Example 71), to obtain the title compound (0.41 g, yield 60~90%)

$^1$H NMR (400 MHz, CDCl$_3$) δ0.90 (t, J=7.2 Hz, 3H), 1.35~1.65 (m, 6H), 2.08 (d, J=4.4 Hz, 1H), 2.71 (d, J=5.2 Hz, 1H), 3.78~3.83 (m, 1H), 5.04 (t, J=5.0 Hz, 1H), 6.95~7.49 (m, 4H)

Preparation Example 95

Synthesis of 1-(4-fluorophenyl)-(S,S)-1,2-propanediol

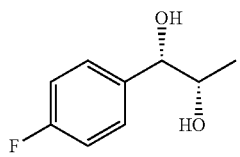

The substantially same method as described in Preparation Example 87 was conducted, except that 1-(4-fluorophenyl)-trans-1-propene (Preparation Example 79) was used instead of 1-(3-iodophenyl)-trans-1-propene (Preparation Example 75), to obtain the title compound (2.01 g, yield 60~90%).

$^1$H NMR (400 MHz, CDCl$_3$) δ1.15 (d, J=6.4 Hz, 3H), 2.43 (d, J=3.6 Hz, 1H), 2.69 (d, J=4.8 Hz, 1H), 3.90~3.98 (m, 1H), 4.78 (dd, J=4.4, 7.2 Hz, 1H), 6.85~7.04 (m, 4H)

Preparation Example 96

Synthesis of 1-(3-fluorophenyl)-(R,R)-1,2-propanediol

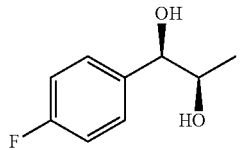

The substantially same method as described in Preparation Example 88 was conducted, except that 1-(4-fluorophenyl)-trans-1-propene (Preparation Example 79) was used instead of 1-(3-iodophenyl)-trans-1-propene (Preparation Example 75), to obtain the title compound (1.27 g, yield 60~90%).

$^1$H NMR (400 MHz, CDCl$_3$) δ1.15 (d, J=6.4 Hz, 3H), 2.43 (d, J=3.6 Hz, 1H), 2.69 (d, J=4.8 Hz, 1H), 3.90~3.98 (m, 1H), 4.78 (dd, J=4.4, 7.2 Hz, 1H), 6.85~7.04 (m, 4H)

Preparation Example 97

Synthesis of 1-(4-fluorophenyl)-(S,S)-1,2-butanediol

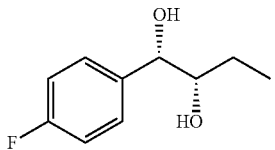

The substantially same method as described in Preparation Example 89 was conducted, except that 1-(4-fluorophenyl)-trans-1-butene (Preparation Example 80) was used instead of 1-(3-iodophenyl)-trans-1-butene (Preparation Example 76), to obtain the title compound (0.43 g, yield 60~90%).

$^1$H NMR (400 MHz, CDCl$_3$) δ1.04 (t, J=7.6 Hz, 3H), 1.60~1.71 (m, 2H), 2.07 (br s, 1H), 2.74 (br s, 1H), 3.71~3.76 (m, 1H), 4.87 (d, J=4.8 Hz, 1H), 6.88~7.05 (m, 4H)

Preparation Example 98

Synthesis of 1-(3-fluorophenyl)-(R,R)-1,2-butanediol

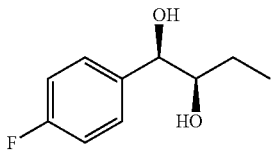

The substantially same method as described in Preparation Example 90 was conducted, except that 1-(4-fluorophenyl)-trans-1-butene (Preparation Example 80) was used instead of 1-(3-iodophenyl)-trans-1-butene (Preparation Example 76), to obtain the title compound (1.13 g, yield 60~90%).

$^1$H NMR (400 MHz, CDCl$_3$) δ1.04 (t, J=7.6 Hz, 3H), 1.60~1.71 (m, 2H), 2.07 (br s, 1H), 2.74 (br s, 1H), 3.71~3.76 (m, 1H), 4.87 (d, J=4.8 Hz, 1H), 6.88~7.05 (m, 4H)

Preparation Example 99

Synthesis of 1-(4-fluorophenyl)-3-methyl-(S,S)-1,2-butanediol

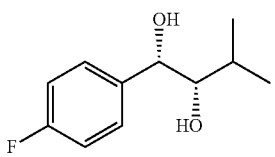

The substantially same method as described in Preparation Example 91 was conducted, except that 1-(4-fluorophenyl)-3-methyl-trans-1-butene (Preparation Example 81) was used instead of 1-(3-iodophenyl)-3-methyl-trans-1-butene (Preparation Example 77), to obtain the title compound (0.71 g, yield 60~90%).

$^1$H NMR (400 MHz, CDCl$_3$) δ1.07 (t, J=7.2 Hz, 6H), 1.83~1.89 (m, 1H), 1.92 (d, J=5.6 Hz, 1H), 2.69 (d, J=6.4 Hz, 1H), 3.53~3.56 (m, 1H), 5.22~5.25 (m, 1H), 6.87~7.02 (m, 4H)

Preparation Example 100

Synthesis of 1-(3-fluorophenyl)-3-methyl-(R,R)-1,2-butanediol

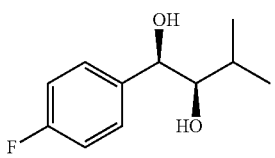

The substantially same method as described in Preparation Example 92 was conducted, except that 1-(4-fluorophenyl)-3-methyl-trans-1-butene (Preparation Example 81) was used instead of 1-(3-iodophenyl)-3-methyl-trans-1-butene (Preparation Example 77), to obtain the title compound (1.21 g, yield 60~90%).

$^1$H NMR (400 MHz, CDCl$_3$) δ1.07 (t, J=7.2 Hz, 6H), 1.83~1.89 (m, 1H), 1.92 (d, J=5.6 Hz, 1H), 2.69 (d, J=6.4 Hz, 1H), 3.53~3.56 (m, 1H), 5.22~5.25 (m, 1H), 6.87~7.02 (m, 4H)

Preparation Example 101

Synthesis of 1-(4-fluorophenyl)-(S,S)-1,2-hexanediol

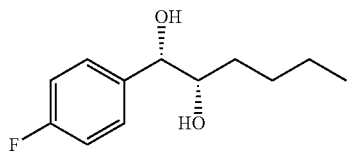

The substantially same method as described in Preparation Example 93 was conducted, except that 1-(4-fluorophenyl)-trans-1-hexene (Preparation Example 82) was used instead of 1-(3-iodophenyl)-trans-1-hexene (Preparation Example 78), to obtain the title compound (1.13 g, yield 60~90%)

$^1$H NMR (400 MHz, CDCl$_3$) δ0.90 (t, J=7.2 Hz, 3H), 1.35~1.65 (m, 6H), 2.08 (d, J=4.4 Hz, 1H), 2.71 (d, J=5.2 Hz, 1H), 3.78~3.83 (m, 1H), 5.04 (t, J=5.0 Hz, 1H), 6.88~7.09 (m, 4H)

Preparation Example 102

Synthesis of 1-(3-fluorophenyl)-(R,R)-1,2-hexanediol

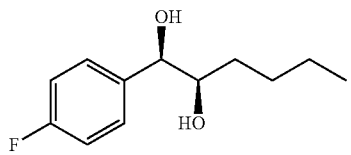

The substantially same method as described in Preparation Example 94 was conducted, except that 1-(4-fluorophenyl)-trans-1-hexene (Preparation Example 82) was used instead of 1-(3-iodophenyl)-trans-1-hexene (Preparation Example 78), to obtain the title compound (1.42 g, yield 60~90%)

$^1$H NMR (400 MHz, CDCl$_3$) δ0.90 (1, J=7.2 Hz, 3H), 1.35~1.65 (m, 6H), 2.08 (d, J=4.4 Hz, 1H), 2.71 (d, J=5.2 Hz, 1H), 3.78~3.83 (m, 1H), 5.04 (t, J=5.0 Hz, 1H), 6.88~7.09 (m, 4H)

Preparation Example 103

Synthesis of 1-(2-chlorophenyl)-(S)-1-hydroxypropyl-(S)-2-carbamate

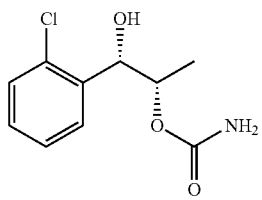

1-(2-chlorophenyl)-(S,S)-1,2-propanediol (2.33 g) obtained in Preparation Example 14, tetrahydrofuran (THF, 12 ml), and carbonyldiimidazole (CDI, 3.04 g) were put into a flask and stirred at the room temperature. After approximately 3 hours, ammonia solution (NH₄OH, 4 ml) was added thereto. When the reaction was completed, the obtained product was washed with 1M HCl solution and ethylacetate (EA). The separated organic layer was dehydrated with anhydrous magnesium sulfate (MgSO₄), filtrated, and concentrated under reduced pressure. The concentrated residue was purified by a silica gel column chromatography, to obtain the title compound (1.40 g, yield 49%).

M.P. 83~84 t $^1$H NMR (400 MHz, CDCl$_3$) δ1.24 (d, J=6.4 Hz, 3H), 2.91 (d, J=4.8 Hz, 1H), 4.68 (br s, 2H), 5.06~5.09 (m, 1H), 5.18~5.21 (m, 1H), 7.23~7.55 (m, 4H)

$^{13}$C NMR (100 MHz, CDCl$_3$) δ16.4, 73.1, 75.0, 127.0, 128.4, 129.1, 129.5, 132.7, 138.0, 156.6

Preparation Example 104

Synthesis of 1-(2-chlorophenyl)-(R)-1-hydroxypropyl-(R)-2-carbamate

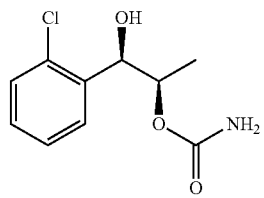

The substantially same method as described in Preparation Example 10303 was conducted, except that 1-(2-chlorophenyl)-(R,R)-1,2-propanediol obtained in Preparation Example 15 was used instead of 1-(2-chlorophenyl)-(S,S)-1,2-propanediol, to obtain the title compound (1.74 g, yield 50%).

M.P. 85~86° C.

$^1$H NMR (400 MHz, CDCl$_3$) δ1.24 (d, J=6.4 Hz, 3H), 2.98 (d, J=4.0 Hz, 1H), 4.73 (br s, 2H), 5.04~5.10 (m, 1H), 5.18~5.20 (m, 1H), 7.24~7.55 (m, 4H)

Preparation Example 105

Synthesis of 1-(2-chlorophenyl)-1-hydroxypropyl-2-carbamate

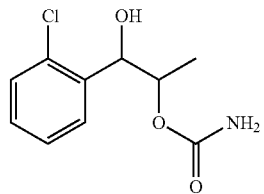

The substantially same method as described in Preparation Example 103 was conducted, except that the mixture of 1-(2-chlorophenyl)-(S,S)-1,2-propanediol and 1-(2-chlorophenyl)-(R,R)-1,2-propanediol obtained in Preparation Example 16 was used instead of 1-(2-chlorophenyl)-(S,S)-1,2-propanediol, to obtain the title compound (0.41 g, yield 38%).

1H NMR (400 MHz, CDCl$_3$) δ1.14 (d, J=6.8 Hz, 3H), 3.34 (d, J=3.2 Hz, 1H), 5.06 (brs, 2H), 5.09~5.15 (m, 1H), 5.31 (br t, J=2.4 Hz, 1H), 7.18~7.59 (m, 4H)

Preparation Example 106

Synthesis of 1-(2-chlorophenyl)-(R)-1-hydroxypropyl-(S)-2-carbamate

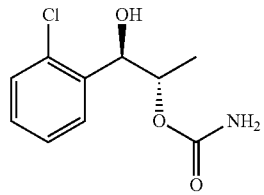

The substantially same method as described in Preparation Example 103 was conducted, except that 1-(2-chlorophenyl)-(R,S)-1,2-propanediol obtained in Preparation Example 55 was used instead of 1-(2-chlorophenyl)-(S,S)-1,2-propanediol, to obtain the title compound (1.7 g, yield 50%).

$^1$H NMR (400 MHz, CDCl3) δ1.20 (d, J=6.8, 3H), 2.68 (s, 1H), 4.67 (s, 2H), 5.16~5.22 (m, 1H), 5.36 (t, J=3.2, 1H), 7.23~7.61 (m, 4H)

Preparation Example 107

Synthesis of 1-(2-chlorophenyl)-(S)-1-hydroxypropyl-(R)-2-carbamate

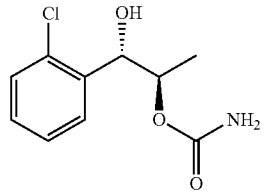

The substantially same method as described in Preparation Example 103 was conducted, except that 1-(2-chlorophenyl)-(S,R)-1,2-propanediol obtained in Preparation Example 56 was used instead of 1-(2-chlorophenyl)-(S,S)-1,2-propanediol, to obtain the title compound (1.74 g, yield 50%).

$^1$H NMR (400 MHz, CDCl3) δ1.20 (d, J=6.4, 3H), 2.83 (d, J=3.6, 1H), 4.78 (s, 2H), 5.15~5.21 (m, 1H), 5.36 (t, J=3.2, 1H), 7.23~7.63 (m, 4H)

Preparation Example 108

Synthesis of 1-(2-chlorophenyl)-(S)-1-hydroxybutyl-(S)-2-carbamate

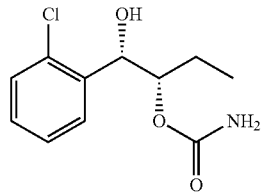 [SMILES: CC[C@H](OC(N)=O)[C@@H](O)c1ccccc1Cl]

The substantially same method as described in Preparation Example 103 was conducted, except that 1-(2-chlorophenyl)-(S,S)-1,2-butanediol obtained in Preparation Example 17 was used instead of 1-(2-chlorophenyl)-(S,S)-1,2-propanediol, to obtain the title compound (1.0 g, yield 45%).

$^1$H NMR (400 MHz, CDCl$_3$) δ0.96 (t, J=7.4 Hz, 3H), 1.57~1.73 (m, 2H), 3.01 (d, J=5.6 Hz, 1H), 4.74 (br s, 2H), 4.95 (dt, J=7.2, 8.8 Hz, 1H), 5.23 (t, J=5.6 Hz, 1H), 7.22~7.54 (m, 4H)

Preparation Example 109

Synthesis of 1-(2-chlorophenyl)-(R)-1-hydroxbtyl-(R)-2-carbamate

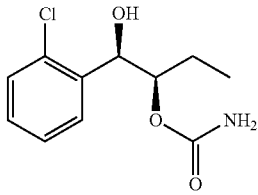 [SMILES: CC[C@@H](OC(N)=O)[C@H](O)c1ccccc1Cl]

The substantially same method as described in Preparation Example 103 was conducted, except that 1-(2-chlorophenyl)-(R,R)-1,2-butanediol obtained in Preparation Example 18 was used instead of 1-(2-chlorophenyl)-(S,S)-1,2-propanediol, to obtain the title compound (1.5 g, yield 25%).

$^1$H NMR (400 MHz, CDCl$_3$) δ 0.94 (t, J=7.4 Hz, 3H), 1.53~1.73 (m, 2H), 2.92 (s, 1H), 4.78 (br s, 2H), 4.91~4.96 (m, 1H), 5.22 (d, J=5.5 Hz, 1H), 7.20~7.54 (m, 4H)

Preparation Example 110

Synthesis of 1-(2-chlorophenyl)-1-hydroxybutyl-2-carbamate(8)

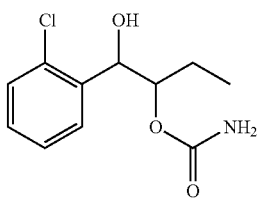 [SMILES: CCC(OC(N)=O)C(O)c1ccccc1Cl]

The substantially same method as described in Preparation Example 103 was conducted, except that 1-(2-chlorophenyl)-1,2-butanediol obtained in Preparation Example 19 was used instead of 1-(2-chlorophenyl)-(S,S)-1,2-propanediol, to obtain the title compound (1.8 g, yield 30%).

$^1$H NMR (400 MHz, CDCl$_3$) δ 0.97 (t, J=7 Hz, 3H), 1.58~1.74 (m, 2H), 2.94 (d, J=6 Hz, 1H), 4.69 (br s, 2H), 4.94~4.99 (m, 1H), 5.24 (t, J=6 Hz, 1H), 7.23~7.56 (m, 4H)

Preparation Example 111

Synthesis of 1-(2-chlorophenyl)-(S)-1-hydroxy-3-methyl-butyl-(S)-2-carbamate

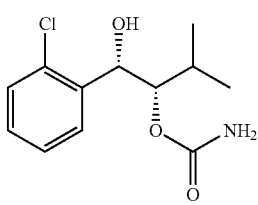

The substantially same method as described in Preparation Example 103 was conducted, except that 1-(2-chlorophenyl)-3-methyl-(S,S)-1,2-butanediol obtained in Preparation Example 20 was used instead of 1-(2-chlorophenyl)-(S,S)-1,2-propanediol, to obtain the title compound (0.72 g, yield 48%).

$^1$H NMR (400 MHz, CDCl$_3$) δ1.01 (d, J=6.4 Hz, 3H), 1.09 (d, J=6.8 Hz, 3H), 2.06 (m, 1H), 2.75 (d, J=6.8 Hz, 1H), 4.58 (br s, 2H), 4.85~4.88 (m, 1H), 5.34~5.37 (m, 1H), 7.22~7.33 (m, 2H), 7.35~7.37 (m, 1H), 7.51~7.53 (m, 1H)

Preparation Example 112

Synthesis of 1-(2-chlorophenyl)-(R)-1-hydroxy-3-methyl-butyl-(R)-2-carbamate

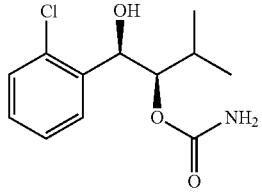 [SMILES: CC(C)[C@@H](OC(N)=O)[C@H](O)c1ccccc1Cl]

The substantially same method as described in Preparation Example 103 was conducted, except that 1-(2-chlorophenyl)-3-methyl-(R,R)-1,2-butanediol obtained in Preparation Example 21 was used instead of 1-(2-chlorophenyl)-(S,S)-1,2-propanediol, to obtain the title compound (0.56 g, yield 43%).

$^1$H NMR (400 MHz, CDCl$_3$) δ1.01 (d, J=6.8 Hz, 3H), 1.09 (d, J=6.8 Hz, 3H), 2.06 (m, 1H), 2.73 (d, J=6.8 Hz, 1H), 4.57 (br s, 2H), 4.85~4.88 (m, 1H), 5.34~5.37 (m, 1H), 7.24~7.30 (m, 2H), 7.35~7.37 (m, 1H), 7.51~7.53 (m, 1H)

Preparation Example 113

Synthesis of 1-(2-chlorophenyl)-1-hydroxy-3-methyl-butyl-2-carbamate

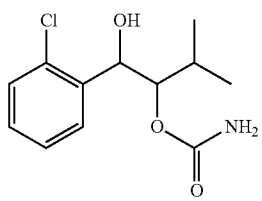 [SMILES: CC(C)C(OC(N)=O)C(O)c1ccccc1Cl]

The substantially same method as described in Preparation Example 103 was conducted, except that 1-(2-chlorophenyl)-3-methyl-1,2-butanediol obtained in Preparation Example 22 was used instead of 1-(2-chlorophenyl)-(S,S)-1,2-propanediol, to obtain the title compound (1.5 g, yield 23%).

$^1$H NMR (400 MHz, CDCl$_3$) δ1.00 (d, J=6.4 Hz, 3H), 1.09 (d, J=6.4 Hz, 3H), 2.08 (m, 1H), 2.76 (d, J=6.0 Hz, 1H), 4.59 (br s, 2H), 4.87 (dd, J=7.2 Hz, 4.4 Hz, 1H), 5.36 (t, J=4.6 Hz, 1H), 7.23~7.54 (m, 4H)

Preparation Example 114

Synthesis of 1-(2-chlorophenyl)-(S)-1-hydroxyhexyl-(S)-2-carbamate

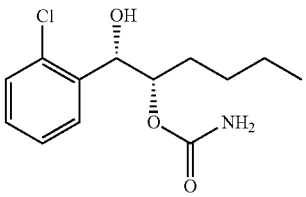

The substantially same method as described in Preparation Example 103 was conducted, except that 1-(2-chlorophenyl)-(S,S)-1,2-hexanediol obtained in Preparation Example 23 was used instead of 1-(2-chlorophenyl)-(S,S)-1,2-propanediol, to obtain the title compound (0.24 g, yield 49%).

$^1$H NMR (400 MHz, CDCl$_3$) δ 0.88 (t, J=7 Hz, 3H), 1.33~1.42 (m, 4H), 1.53~1.71 (m, 2H), 2.89 (d, J=5.6 Hz, 1H) 4.64 (br s, 2H), 5.04 (dt, J=5.0, 9.0 Hz, 1H), 5.20 (t, J=5.6 Hz, 1H), 7.23~7.55 (m, 4H)

Preparation Example 115

Synthesis of 1-(2-chlorophenyl)-(R)-1-hydroxyhexyl-(R)-2-carbamate

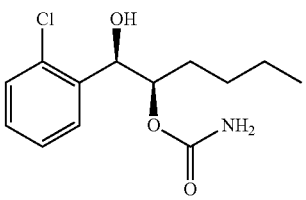 [SMILES: CCCC[C@@H](OC(N)=O)[C@H](O)c1ccccc1Cl]

The substantially same method as described in Preparation Example 103 was conducted, except that 1-(2-chlorophenyl)-(R,R)-1,2-hexanediol obtained in Preparation Example 24 was used instead of 1-(2-chlorophenyl)-(S,S)-1,2-propanediol, to obtain the title compound (2.2 g, yield 44%).

$^1$H NMR (400 MHz, CDCl$_3$) δ 0.89 (dd, J=5 Hz, 3H), 1.28~1.43 (m, 4H), 1.52~1.58 (m, 1H), 1.65~1.72 (m, 1H), 2.90 (d, J=6 Hz, 1H), 4.64 (br s, 2H), 5.01~5.06 (m, 1H), 5.22 (t, J=6 Hz, 1H), 7.22~7.56 (m, 4H)

Preparation Example 116

Synthesis of 1-(2-chlorophenyl)-1-hydroxyhexyl-2-carbamate

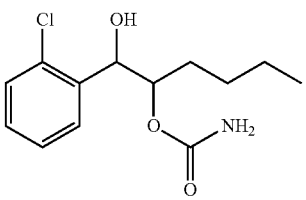 [SMILES: CCCCC(OC(N)=O)C(O)c1ccccc1Cl]

The substantially same method as described in Preparation Example 103 was conducted, except that 1-(2-chlorophenyl)-1,2-hexanediol obtained in Preparation Example 25 was used instead of 1-(2-chlorophenyl)-(S,S)-1,2-propanediol, to obtain the title compound (1.6 g, yield 34%).

$^1$H NMR (400 MHz, CDCl$_3$) δ 0.88 (dd, J=5 Hz, 3H), 1.31~1.43 (m, 4H), 1.63~1.70 (m, 1H), 1.52~1.60 (m, 1H), 3.06 (d, J=6 Hz, 1H), 4.75 (br s, 2H), 5.00~5.05 (m, 1H), 5.21 (t, J=6 Hz, 1H), 7.22~7.55 (m, 4H)

Preparation Example 117

Synthesis of 1-(2-chlorophenyl)-(S)-1-hydroxypropyl-(S)-2-methylcarbamate

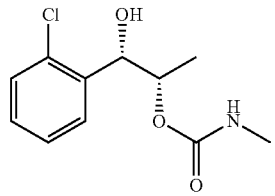

The substantially same method as described in Preparation Example 103 was conducted, except that methylamine was used instead of ammonia solution (NH$_4$OH), to obtain the title compound (1.6 g, yield 51%).

$^1$H NMR (400 MHz, CDCl$_3$) δ 1.03~1.25 (m, 3H), 2.76 (s, 3H), 3.34 (s, 1H), 4.80 (br s 1H), 5.04 (t, J=12.5 Hz, 1H), 5.14 (s, 1H), 7.20~7.53 (m, 4H)

Preparation Example 118

Synthesis of 1-(2-chlorophenyl)-(S)-1-hydroxypropyl-(S)-2-propylcarbamate

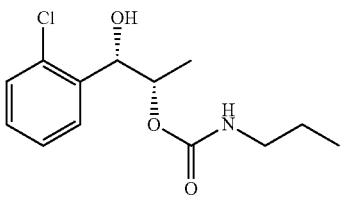

The substantially same method as described in Preparation Example 103 was conducted, except that propylamine was used instead of ammonia solution (NH$_4$OH), to obtain the title compound (0.79 g, yield 25%).

$^1$H NMR (400 MHz, CDCl$_3$) δ 0.90 (t, J=6.8 Hz, 3H), 1.20 (d, J=5.96 Hz, 3H), 1.49 (dd, J=14.2 Hz, 2H), 3.11 (d, J=6.28 Hz, 2H), 3.34 (s, 1H), 4.84 (br s, 1H), 5.05 (t, J=5.88 Hz, 1H), 5.14 (s, 1H), 7.22~7.53 (m, 4H)

Preparation Example 119

Synthesis of 1-(2-chlorophenyl)-(S)-1-hydroxypropyl-(R)-2-isopropylcarbamate

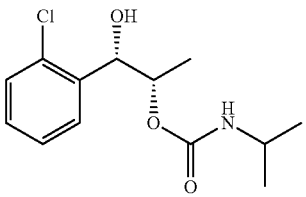 [SMILES: CC(C)NC(=O)O[C@@H](C)[C@@H](O)c1ccccc1Cl]

The substantially same method as described in Preparation Example 103 was conducted, except that isopropylamine was used instead of ammonia solution (NH$_4$OH), to obtain the title compound (1.5 g, yield 41%).

$^1$H NMR (400 MHz, CDCl$_3$) δ1.14 (dd, J=6.5 Hz, 6H), 1.19 (d, J=6.4 Hz, 3H), 3.21 (s, 1H), 3.73~3.82 (m, 1H), 4.59 (br s, 1H), 5.01~5.07 (m, 1H), 5.14 (t, J=5.8 Hz, 1H), 7.20~7.53 (m, 4H)

Preparation Example 120

Synthesis of 1-(2-chlorophenyl)-(S)-1-hydroxypropyl-(R)-2-cyclopropylcarbamate

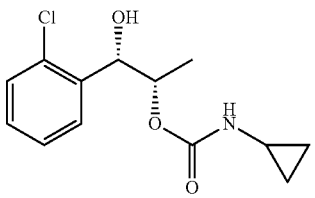 [SMILES: C[C@H](OC(=O)NC1CC1)[C@@H](O)c1ccccc1Cl]

The substantially same method as described in Preparation Example 103 was conducted, except that cyclopropylamine was used instead of ammonia solution (NH$_4$OH), to obtain the title compound (2.2 g, yield 43%).

$^1$H NMR (400 MHz, CDCl$_3$) δ0.50~0.56 (m, 2H), 0.74 (d, J=7.21 Hz, 2H), 1.25 (s, 3H), 2.56~2.61 (m, 1H), 3.72 (s, 1H), 4.98 (br s, 1H), 5.05~5.11 (m, 1H), 7.16 (s, 1H), 7.23~7.54 (m, 4H)

Preparation Example 121

Synthesis of 1-(2-chlorophenyl)-(S)-1-hydroxypropyl-(R)-2-cyclohexyl carbamate

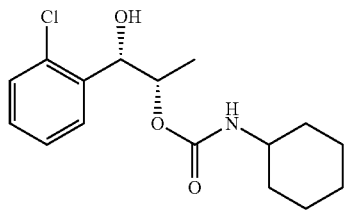 [SMILES: C[C@H](OC(=O)NC1CCCCC1)[C@@H](O)c1ccccc1Cl]

The substantially same method as described in Preparation Example 103 was conducted, except that cyclohexylamine was used instead of ammonia solution (NH$_4$OH), to obtain the title compound (1.1 g, yield 26%).

$^1$H NMR (400 MHz, CDCl$_3$) δ1.06~1.40 (m, 7H), 1.56~1.61 (m, 2H), 1.69~1.71 (m, 2H), 1.87~1.94 (m, 2H), 3.19 (d, J=4.32 Hz, 1H), 3.45 (s, 1H), 4.64 (br s 1H), 5.02~5.07 (m, 1H), 5.14 (t, J=6.08 Hz, 1H) 7.20~7.53 (m, 4H)

Preparation Example 122

Synthesis of 1-(2-chlorophenyl)-(S)-1-hydroxypropyl-(S)-2-benzyl carbamate

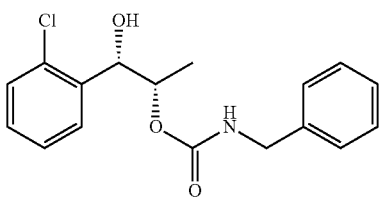

The substantially same method as described in Preparation Example 103 was conducted, except that benzylamine was used instead of ammonia solution (NH$_4$OH), to obtain the title compound (1.2 g, yield 18%).

$^1$H NMR (400 MHz, CDCl$_3$) δ 1.27 (d, J=10 Hz, 3H), 3.12 (d, J=5 Hz, 1H), 4.37 (d, J=6 Hz, 2H), 5.12~5.19 (m, 3H), 7.15~7.56 (m, 9H)

Preparation Example 123

Synthesis of 1-(2-chlorophenyl)-(S)-1-hydroxypropyl-(S)-2-bicyclo[2,2,1]heptanescarbamate

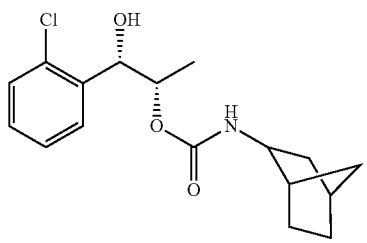 [SMILES: C[C@H](OC(=O)NC1CC2CCC1C2)[C@@H](O)c1ccccc1Cl]

The substantially same method as described in Preparation Example 103 was conducted, except that 2-aminonorbornane was used instead of ammonia solution (NH$_4$OH), to obtain the title compound (1.7 g, yield 32%).

$^1$H NMR (400 MHz, CDCl$_3$) δ1.08~1.35 (m, 9H), 1.65 (br s, 1H), 1.75~1.71 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.22~7.55 (m, 4H)

Preparation Example 124

Synthesis of 1-(2-chlorophenyl)-(R)-1-hydroxypropyl-(R)-2-methylcarbamate

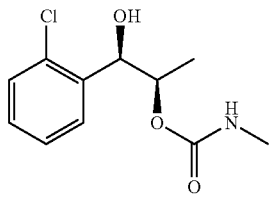 [SMILES: CNC(=O)O[C@H](C)[C@H](O)c1ccccc1Cl]

The substantially same method as described in Example 2 was conducted, except that methylamine was used instead of ammonia solution (NH₄OH), to obtain the title compound (3.36 g, yield 60%).

¹H NMR (400 MHz, CDCl₃) δ 1.20 (d, J=6.8 Hz, 3H), 2.80 (d, J=4.8 Hz, 3H), 3.20 (d, J=4.4 Hz, 1H), 4.75 (br s, 1H), 5.03~5.09 (m, 1H), 5.14~5.17 (m, 1H), 7.22~7.55 (m, 4H)

Preparation Example 125

Synthesis of 1-(2-chlorophenyl)-(R)-1-hydroxypropyl-(R)-2-propylcarbamate

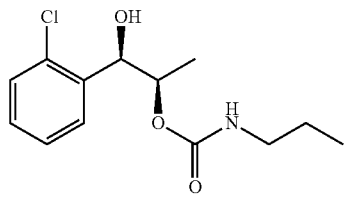 [SMILES: CCCNC(=O)O[C@H](C)[C@H](O)c1ccccc1Cl]

The substantially same method as described in Preparation Example 104 was conducted, except that propylamine was used instead of ammonia solution (NH₄OH), to obtain the title compound (3.1 g, yield 53%).

¹H NMR (400 MHz, CDCl₃) δ0.92 (t, J=7.6 Hz, 3H), 1.21 (d, J=6.4 Hz, 3H), 1.51 (m, 2H), 3.09~3.14 (m, 2H), 3.28 (d, J=4.4 Hz, 1H), 4.82 (br s, 1H), 5.03~5.09 (m, 1H), 5.14~5.17 (m, 1H), 7.22~7.55 (m, 4H)

Preparation Example 126

Synthesis 1-(2-chlorophenyl)-(R)-1-hydroxypropyl-(R)-2-isopropylcarbamate

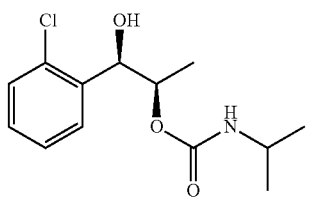 [SMILES: CC(C)NC(=O)O[C@H](C)[C@H](O)c1ccccc1Cl]

The substantially same method as described in Preparation Example 104 was conducted, except that isopropylamine was used instead of ammonia solution (NH₄OH), to obtain the title compound (0.16 g, yield 27%).

¹H NMR (400 MHz, CDCl₃) δ0.88~1.16 (m, 6H), 1.19~1.26 (m, 3H), 3.34 (s, 1H), 3.71~3.78 (m, 1H), 4.62 (br s, 1H), 5.03 (t, J=5.8 Hz, 1H), 5.13 (d, J=4.9 Hz, 1H), 7.20~7.53 (m, 4H)

Preparation Example 127

Synthesis of 1-(2-chlorophenyl)-(R)-1-hydroxypropyl-(R)-2-cyclopropylcarbamate

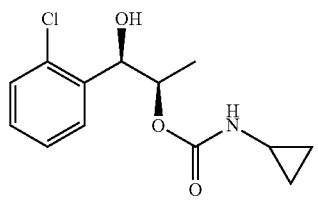 [SMILES: C[C@@H](OC(=O)NC1CC1)[C@H](O)c1ccccc1Cl]

The substantially same method as described in Preparation Example 104 was conducted, except that cyclopropylamine was used instead of ammonia solution (NH₄OH), to obtain the title compound (3.7 g, yield 60%).

¹H NMR (400 MHz, CDCl₃) δ0.49~0.54 (m, 2H), 0.74 (d, J=7.2 Hz, 2H), 1.22 (s, 3H), 2.55~2.60 (m, 1H), 3.16 (s, 1H), 5.00 (s, 1H), 5.04~5.11 (m, 1H), 5.16 (s, 1H), 7.23~7.54 (m, 4H)

Preparation Example 128

Synthesis of 1-(2-chlorophenyl)-(R)-1-hydroxypropyl-(R)-2-cyclohexyl carbamate

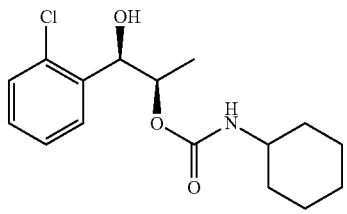 [SMILES: C[C@@H](OC(=O)NC1CCCCC1)[C@H](O)c1ccccc1Cl]

The substantially same method as described in Preparation Example 104 was conducted, except that cyclohexylamine was used instead of ammonia solution (NH₄OH), to obtain the title compound (1.9 g, yield 28%).

¹H NMR (400 MHz, CDCl₃) δ1.05~1.38 (m, 8H), 1.58~1.70 (m, 3H), 1.85~1.95 (m, 2H), 3.39~3.47 (m, 1H), 3.56 (s, 1H), 4.79 (br s, 1H), 5.01~5.07 (m, 1H), 5.14 (t, J=5.2 Hz, 1H), 7.20~7.54 (m, 4H)

Preparation Example 129

Synthesis of 1-(2-chlorophenyl)-(R)-1-hydroxypropyl-(R)-2-benzylcarbamate

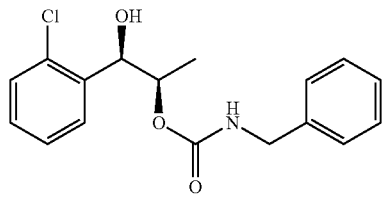 [SMILES: C[C@@H](OC(=O)NCc1ccccc1)[C@H](O)c1ccccc1Cl]

The substantially same method as described in Preparation Example 104 was conducted, except that benzylamine was used instead of ammonia solution (NH₄OH), to obtain the title compound (0.52 g, yield 19%).

¹H NMR (400 MHz, CDCl₃) δ1.25 (d, J=6 Hz, 3H), 1.64 (s, 1H), 3.13 (d, J=4.4 Hz, 1H), 4.37 (d, J=5.6 Hz, 2H), 5.12~5.19 (m, 2H), 7.23~7.55 (m, 9H)

Preparation Example 130

Synthesis of 1-(2-chlorophenyl)-(R)-1-hydroxypropyl-(R)-2-bicyclo[2,2,1]heptanecarbamate

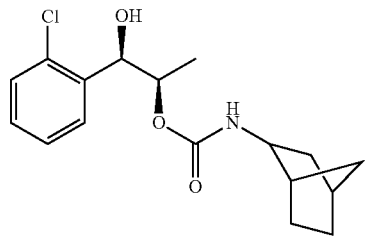 [SMILES: C[C@@H](OC(=O)NC1CC2CCC1C2)[C@H](O)c1ccccc1Cl]

The substantially same method as described in Preparation Example 104 was conducted, except that 2-aminonorbornane was used instead of ammonia solution (NH₄OH), to obtain the title compound (1.7 g, yield 20~50%).

¹H NMR (400 MHz, CDCl₃) δ1.08~1.35 (m, 9H), 1.65 (br s, 1H), 1.75~1.71 (m, 1H), 2.14~2.24 (m, 1H), 2.27~2.30 (m, 1H), 3.23=3.29 (m, 1H), 3.47~3.52 (m, 1H), 4.67 (br s, 1H), 5.01~5.09 (m, 1H), 5.12~5.18 (m, 1H), 7.22~7.55 (m, 4H)

Preparation Example 131

Synthesis of 1-(2-chlorophenyl)-1-hydroxypropyl-2-methylcarbamate

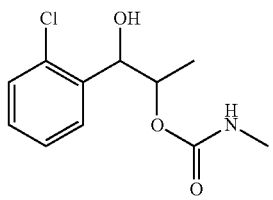 [SMILES: CNC(=O)OC(C)C(O)c1ccccc1Cl]

The substantially same method as described in Preparation Example 105 was conducted, except that methylamine was used instead of ammonia solution (NH₄OH), to obtain the title compound (2.6 g, yield 45%).

¹H NMR (400 MHz, CDCl₃) δ 1.21 (d, J=6 Hz, 3H), 2.81 (d, J=5 Hz, 3H), 3.14 (d, J=4 Hz, 1H), 4.72 (br s, 1H), 5.07 (dd, J=6 Hz, 1H), 5.16 (t, J=6 Hz, 1H), 7.22~7.56 (m, 4H)

Preparation Example 132

Synthesis of 1-(2-chlorophenyl)-1-hydroxypropyl-2-propylcarbamate

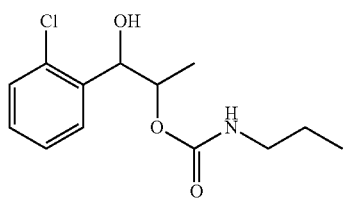 [SMILES: CCCNC(=O)OC(C)C(O)c1ccccc1Cl]

The substantially same method as described in Preparation Example 105 was conducted, except that propylamine was used instead of ammonia solution (NH₄OH), to obtain the title compound (1.0 g, yield 17%).

¹H NMR (400 MHz, CDCl₃) δ 0.92 (t, J=7 Hz, 3H), 1.21 (d, J=6 Hz, 3H), 1.53 (dd, J=7 Hz, 2H), 3.13 (dd, J=7 Hz, 2H), 3.28 (d, 1H), 4.82 (S, 1H), 5.06 (dd, J=7 Hz, 1H), 5.16 (t, J=5 Hz, 1H), 7.21~7.56 (m, 4H)

Preparation Example 133

Synthesis of 1-(2-chlorophenyl)-1-hydroxypropyl-2-isopropylcarbamate

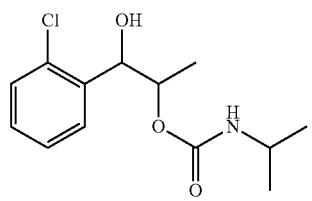 [SMILES: CC(C)NC(=O)OC(C)C(O)c1ccccc1Cl]

The substantially same method as described in Preparation Example 105 was conducted, except that isopropylamine was used instead of ammonia solution (NH₄OH), to obtain the title compound (0.54 g, yield 16%).

¹H NMR (400 MHz, CDCl₃) δ 1.16 (dd, J=6 Hz, 6H), 1.21 (d, J=6 Hz, 3H), 3.23 (d, J=6 Hz, 1H), 3.75~3.84 (m, 1H), 4.61 (br s, 1H), 5.06 (t, J=6 Hz, 1H), 5.16 (t, J=6 Hz, 1H), 7.22~7.56 (m, 4H)

Preparation Example 134

Synthesis of 1-(2-chlorophenyl)-1-hydroxypropyl-2-cyclopropylcarbamate

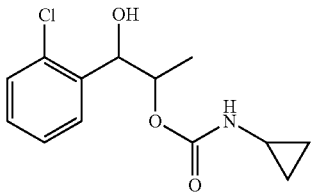 [SMILES: CC(OC(=O)NC1CC1)C(O)c1ccccc1Cl]

The substantially same method as described in Preparation Example 105 was conducted, except that cyclopropylamine was used instead of ammonia solution (NH₄OH), to obtain the title compound (1.0 g, yield 17%).

¹H NMR (400 MHz, CDCl₃) δ 0.50 (t, J=6 Hz, 2H), 0.77 (t, J=3 Hz, 2H), 1.12 (d, J=7 Hz, 3H), 2.53~2.59 (m, 1H), 3.22 (d, J=4 Hz, 1H), 5.08 (dd, J=6 Hz, 1H), 5.15 (S, 1H), 7.22~7.55 (m, 4H)

Preparation Example 135

Synthesis of 1-(2-chlorophenyl)-1-hydroxypropyl-2-cyclohexylcarbamate

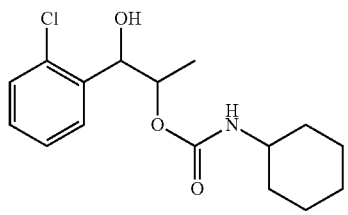 [SMILES: CC(OC(=O)NC1CCCCC1)C(O)c1ccccc1Cl]

The substantially same method as described in Preparation Example 105 was conducted, except that cyclohexylamine was used instead of ammonia solution (NH₄OH), to obtain the title compound (2.2 g, yield 33%).

¹H NMR (400 MHz, CDCl₃) δ 1.07~1.17 (m, 3H), 1.21 (d, J=6 Hz, 3H), 1.29~1.42 (m, 3H), 1.72 (dd, J=6 Hz, 2H), 1.92 (dd, J=6 Hz, 2H), 3.26 (d, J=4 Hz, 1H), 3.46 (t, J=4 Hz, 1H), 4.68 (d, J=6 Hz, 1H), 5.07 (dd, J=6 Hz, 1H), 5.16 (t, J=6 Hz, 1H), 7.22~7.55 (m, 4H)

Preparation Example 136

Synthesis of 1-(2-chlorophenyl)-1-hydroxypropyl-2-benzylcarbamate

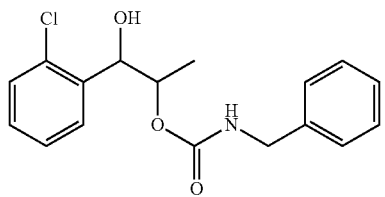 [SMILES: CC(OC(=O)NCc1ccccc1)C(O)c1ccccc1Cl]

The substantially same method as described in Preparation Example 105 was conducted, except that benzylamine was used instead of ammonia solution (NH₄OH), to obtain the title compound (1.3 g, yield 19%).

¹H NMR (400 MHz, CDCl₃) δ 1.25 (d, J=6 Hz, 3H), 3.16 (d, J=4 Hz, 1H), 4.36 (d, J=6 Hz, 2H), 5.14 (dd, J=6 Hz, 3H), 7.23~7.56 (m, 9H), yield: 19% (1.3 g)

Preparation Example 137

Synthesis of 1-(2-chlorophenyl)-1-hydroxypropyl-2-bicyclo[2,2,1]heptanecarbamate

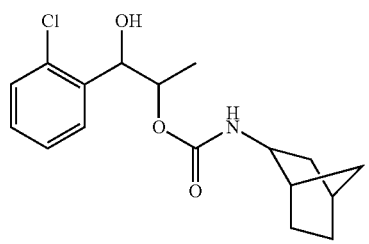 [SMILES: CC(OC(=O)NC1CC2CCC1C2)C(O)c1ccccc1Cl]

The substantially same method as described in Preparation Example 105 was conducted, except that 2-aminonorbornane was used instead of ammonia solution (NH₄OH), to obtain the title compound (1.7 g, yield 20~50%).

¹H NMR (400 MHz, CDCl₃) δ1.08~1.35 (m, 9H), 1.65 (br s, 1H), 1.75~1.71 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.22~7.55 (m, 4H)

Preparation Example 138

Synthesis of 1-(2,4-dichlorophenyl)-(S)-1-hydroxypropyl-(S)-2-carbamate

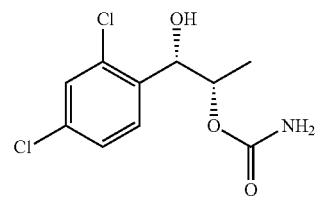 [SMILES: C[C@H](OC(N)=O)[C@@H](O)c1ccc(Cl)cc1Cl]

The substantially same method as described in Preparation Example 103 was conducted, except that 1-(2,4-dichlorophenyl)-(S,S)-1,2-propanediol obtained in Preparation Example 26 was used instead of 1-(2-chlorophenyl)-(S,S)-1,2-propanediol, to obtain the title compound (0.14 g, yield 34%).

¹H NMR (400 MHz, CDCl₃) δ1.22 (d, J=6.4 Hz, 3H), 4.16 (br t, 1H) 4.96 (br t, 3H), 5.07 (t, J=4.8 Hz, 1H), 7.23~7.52 (m, 3H)

Preparation Example 139

Synthesis of 1-(2,6-dichlorophenyl)-(S)-1-hydroxypropyl-(S)-2-carbamate

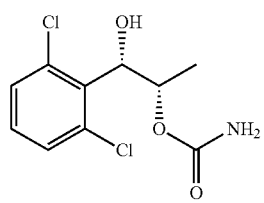

The substantially same method as described in Preparation Example 103 was conducted, except that 1-(2,6-dichlorophenyl)-(S,S)-1,2-propanediol obtained in Preparation Example 38 was used instead of 1-(2-chlorophenyl)-(S,S)-1,2-propanediol, to obtain the title compound (0.22 g, yield 49%).

¹H NMR (400 MHz, CDCl₃) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Preparation Example 140

Synthesis of 1-(2,3-dichlorophenyl)-(S)-1-hydroxy-propyl-(S)-2-carbamate

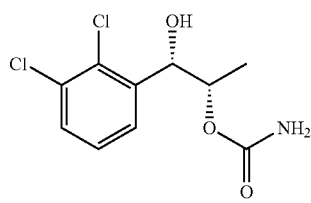 [SMILES: C[C@H](OC(N)=O)[C@@H](O)c1cccc(Cl)c1Cl]

The substantially same method as described in Preparation Example 103 was conducted, except that 1-(2,3-dichlorophenyl)-(S,S)-1,2-propanediol obtained in Preparation Example 57 was used instead of 1-(2-chlorophenyl)-(S,S)-1,2-propanediol, to obtain the title compound (0.21 g, yield 20~60%).
$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Preparation Example 141

Synthesis of 1-(2,4-dichlorophenyl)-(S)-1-hydroxy-butyl-(S)-2-carbamate

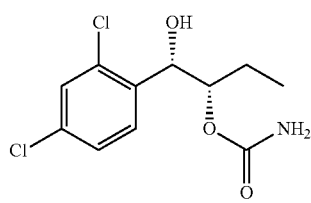 [SMILES: CC[C@H](OC(N)=O)[C@@H](O)c1ccc(Cl)cc1Cl]

The substantially same method as described in Preparation Example 103 was conducted, except that 1-(2,4-dichlorophenyl)-(S,S)-1,2-butanediol obtained in Preparation Example 29 was used instead of 1-(2-chlorophenyl)-(S,S)-1,2-propanediol, to obtain the title compound (0.23 g, yield 52%).
$^1$H NMR (400 MHz, CDCl$_3$) δ0.96 (t, J=7.4 Hz, 3H), 1.58~1.74 (m, 2H), 2.98 (d, J=5.6 Hz, 1H) 4.68 (br s, 2H), 5.59 (dt, J=5.2, 8.8 Hz, 1H), 5.19 (t, J=5.4 Hz, 1H), 7.30~7.50 (m, 3H)

Preparation Example 142

Synthesis of 1-(2,6-dichlorophenyl)-(S)-1-hydroxy-butyl-(S)-2-carbamate

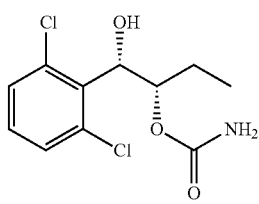 [SMILES: CC[C@H](OC(N)=O)[C@@H](O)c1c(Cl)cccc1Cl]

The substantially same method as described in Preparation Example 103 was conducted, except that 1-(2,6-dichlorophenyl)-(S,S)-1,2-butanediol obtained in Preparation Example 41 was used instead of 1-(2-chlorophenyl)-(S,S)-1,2-propanediol, to obtain the title compound (0.49 g, yield 34%).

$^1$H NMR (400 MHz, CDCl$_3$) δ0.92 (t, J=7.4 Hz, 3H), 1.30~1.38 (m, 1H), 1.57~1.64 (m, 1H), 3.74 (d, J=9.2 Hz, 1H), 4.80 (br s, 2H), 5.40~5.50 (m, 2H), 7.17~7.34 (m, 3H)

Preparation Example 143

Synthesis of 1-(2,4-dichlorophenyl)-(S)-1-hydroxy-3-methyl-butyl-(S)-2-carbamate

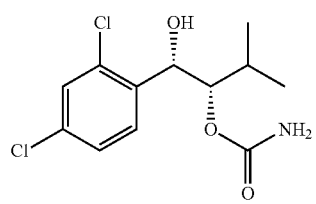

The substantially same method as described in Preparation Example 103 was conducted, except that 1-(2,4-dichlorophenyl)-3-methyl-(S,S)-1,2-butanediol obtained in Preparation Example 32 was used instead of 1-(2-chlorophenyl)-(S,S)-1,2-propanediol, to obtain the title compound (0.13 g, yield 20~60%).
$^1$H NMR (400 MHz, CDCl$_3$) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.30~7.50 (m, 3H)

Preparation Example 144

Synthesis of 1-(2,6-dichlorophenyl)-(S)-1-hydroxy-3-methyl-butyl-(S)-2-carbamate

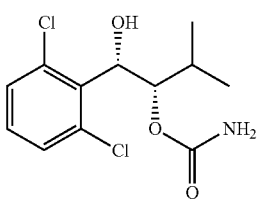 [SMILES: CC(C)[C@H](OC(N)=O)[C@@H](O)c1c(Cl)cccc1Cl]

The substantially same method as described in Preparation Example 103 was conducted, except that 1-(2,6-dichlorophenyl)-3-methyl-(S,S)-1,2-butanediol obtained in Preparation Example 44 was used instead of 1-(2-chlorophenyl)-(S,S)-1,2-propanediol, to obtain the title compound (0.12 g, yield 20%).
$^1$H NMR (400 MHz, CDCl$_3$) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.16~7.33 (m, 3H)

Preparation Example 145

Synthesis of 1-(2,4-dichlorophenyl)-(S)-1-hydroxy-hexyl-(S)-2-carbamate

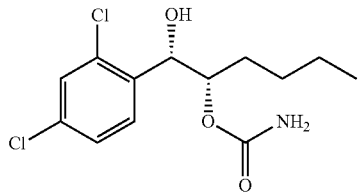

The substantially same method as described in Preparation Example 103 was conducted, except that 1-(2,4-dichlorophenyl)-(S,S)-1,2-hexanediol obtained in Preparation Example 35 was used instead of 1-(2-chlorophenyl)-(S,S)-1,2-propanediol, to obtain the title compound (0.94 g, yield 81%).

$^1$H NMR (400 MHz, CDCl$_3$) δ0.89 (1, J=3.6 Hz, 3H), 1.28~1.42 (m, 4H), 1.52~1.59 (m, 1H), 1.64~1.71 (m, 1H), 2.98 (d, J=5.6 Hz, 1H), 4.67 (br s, 2H), 4.96~5.00 (m, 1H), 5.17 (t, J=5.6 Hz, 1H), 7.30~7.49 (m 3H)

Preparation Example 146

Synthesis of 1-(2,6-dichlorophenyl)-(S)-1-hydroxy-hexyl-(S)-2-carbamate

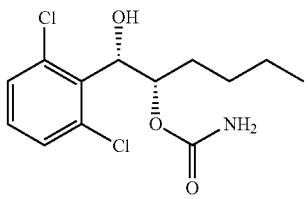 [SMILES: CCCC[C@H](OC(N)=O)[C@@H](O)c1c(Cl)cccc1Cl]

The substantially same method as described in Preparation Example 103 was conducted, except that 1-(2,6-dichlorophenyl)-(S,S)-1,2-hexanediol obtained in Preparation Example 47 was used instead of 1-(2-chlorophenyl)-(S,S)-1,2-propanediol, to obtain the title compound (0.15 g, yield 31%).

$^1$H NMR (400 MHz, CDCl$_3$) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 7.17~7.35 (m, 3H)

Preparation Example 147

Synthesis of 1-(2,4-dichlorophenyl)-(R)-1-hydroxy-propyl-(R)-2-carbamate

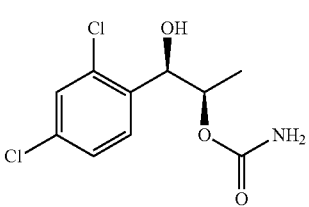 [SMILES: C[C@@H](OC(N)=O)[C@H](O)c1ccc(Cl)cc1Cl]

The substantially same method as described in Preparation Example 103 was conducted, except that 1-(2,4-dichlorophenyl)-(R,R)-1,2-propanediol obtained in Preparation Example 27 was used instead of 1-(2-chlorophenyl)-(S,S)-1,2-propanediol, to obtain the title compound (0.14 g, yield 20~60%).

$^1$H NMR (400 MHz, CDCl$_3$) δ1.22 (d, J=6.4 Hz, 3H), 4.16 (br t, 1H) 4.96 (br t, 3H), 5.07 (t, J=4.8 Hz, 1H), 7.23~7.52 (m, 3H)

Preparation Example 148

Synthesis of 1-(2,6-dichlorophenyl)-(R)-1-hydroxy-propyl-(R)-2-carbamate

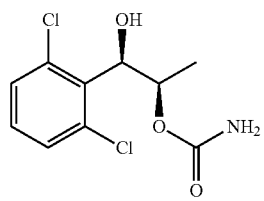

The substantially same method as described in Preparation Example 103 was conducted, except that 1-(2,6-dichlorophenyl)-(R,R)-1,2-propanediol obtained in Preparation Example 39 was used instead of 1-(2-chlorophenyl)-(S,S)-1,2-propanediol, to obtain the title compound (0.21 g, yield 20~60%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Preparation Example 149

Synthesis of 1-(2,3-dichlorophenyl)-(R)-1-hydroxy-propyl-(R)-2-carbamate

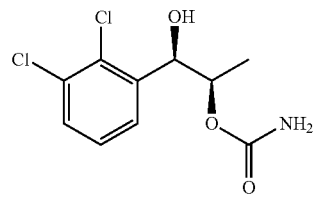 [SMILES: C[C@@H](OC(N)=O)[C@H](O)c1cccc(Cl)c1Cl]

The substantially same method as described in Preparation Example 103 was conducted, except that 1-(2,3-dichlorophenyl)-(R,R)-1,2-propanediol obtained in Preparation Example 58 was used instead of 1-(2-chlorophenyl)-(S,S)-1,2-propanediol, to obtain the title compound (0.08 g, yield 20~60%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Preparation Example 150

Synthesis of 1-(2,4-dichlorophenyl)-(R)-1-hydroxy-butyl-(R)-2-carbamate

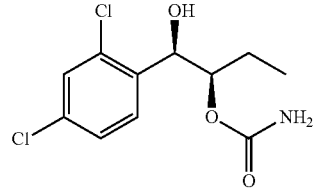 [SMILES: CC[C@@H](OC(N)=O)[C@H](O)c1ccc(Cl)cc1Cl]

The substantially same method as described in Preparation Example 103 was conducted, except that 1-(2,4-dichlorophenyl)-(R,R)-1,2-butanediol obtained in Preparation Example 30 was used instead of 1-(2-chlorophenyl)-(S,S)-1,2-propanediol, to obtain the title compound (0.23 g, yield 20~60%).

¹H NMR (400 MHz, CDCl₃) δ0.96 (1, J=7.4 Hz, 3H), 1.58~1.74 (m, 2H), 2.98 (d, J=5.6 Hz, 1H) 4.68 (br s, 2H), 5.59 (dt, J=5.2, 8.8 Hz, 1H), 5.19 (t, J=5.4 Hz, 1H), 7.30~7.50 (m, 3H)

Preparation Example 151

Synthesis of 1-(2,6-dichlorophenyl)-(R)-1-hydroxy-butyl-(R)-2-carbamate

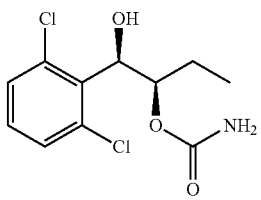 [SMILES: CC[C@@H](OC(N)=O)[C@H](O)c1c(Cl)cccc1Cl]

The substantially same method as described in Preparation Example 103 was conducted, except that 1-(2,6-dichlorophenyl)-(R,R)-1,2-butanediol obtained in Preparation Example 42 was used instead of 1-(2-chlorophenyl)-(S,S)-1,2-propanediol, to obtain the title compound (0.49 g, yield 20~60%).

¹H NMR (400 MHz, CDCl₃) δ0.92 (t, J=7.4 Hz, 3H), 1.30~1.38 (m, 1H), 1.57~1.64 (m, 1H), 3.74 (d, J=9.2 Hz, 1H), 4.80 (br s, 2H), 5.40~5.50 (m, 2H), 7.17~7.34 (m, 3H)

Preparation Example 152

Synthesis of 1-(2,4-dichlorophenyl)-(R)-1-hydroxy-3-methyl-butyl-(R)-2-carbamate

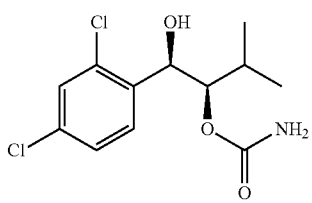 [SMILES: CC(C)[C@@H](OC(N)=O)[C@H](O)c1ccc(Cl)cc1Cl]

The substantially same method as described in Preparation Example 103 was conducted, except that 1-(2,4-dichlorophenyl)-3-methyl-(R,R)-1,2-butanediol obtained in Preparation Example 33 was used instead of 1-(2-chlorophenyl)-(S,S)-1,2-propanediol, to obtain the title compound (0.23 g, yield 20~60%).

¹H NMR (400 MHz, CDCl₃) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.30~7.50 (m, 3H)

Preparation Example 153

Synthesis of 1-(2,6-dichlorophenyl)-(R)-1-hydroxy-3-methyl-butyl-(R)-2-carbamate

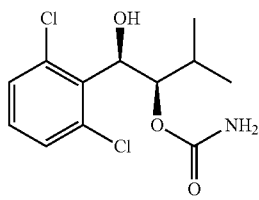 [SMILES: CC(C)[C@@H](OC(N)=O)[C@H](O)c1c(Cl)cccc1Cl]

The substantially same method as described in Preparation Example 103 was conducted, except that 1-(2,6-dichlorophenyl)-3-methyl-(R,R)-1,2-butanediol obtained in Preparation Example 45 was used instead of 1-(2-chlorophenyl)-(S,S)-1,2-propanediol, to obtain the title compound (0.14 g, yield 20~60%).

¹H NMR (400 MHz, CDCl₃) δ1.00 (1, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.16~7.33 (m, 3H)

Preparation Example 154

Synthesis of 1-(2,4-dichlorophenyl)-(R)-1-hydroxy-hexyl-(R)-2-carbamate

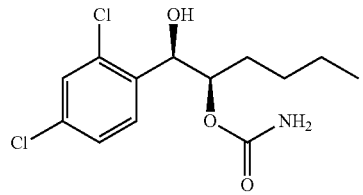 [SMILES: CCCC[C@@H](OC(N)=O)[C@H](O)c1ccc(Cl)cc1Cl]

The substantially same method as described in Preparation Example 103 was conducted, except that 1-(2,4-dichlorophenyl)-(R,R)-1,2-hexanediol obtained in Preparation Example 36 was used instead of 1-(2-chlorophenyl)-(S,S)-1,2-propanediol, to obtain the title compound (0.84 g, yield 20~60%).

¹H NMR (400 MHz, CDCl₃) δ0.89 (t, J=3.6 Hz, 3H), 1.28~1.42 (m, 4H), 1.52~1.59 (m, 1H), 1.64~1.71 (m, 1H), 2.98 (d, J=5.6 Hz, 1H), 4.67 (br s, 2H), 4.96~5.00 (m, 1H), 5.17 (t, J=5.6 Hz, 1H), 7.30~7.49 (m, 3H)

Preparation Example 155

Synthesis of 1-(2,6-dichlorophenyl)-(R)-1-hydroxy-hexyl-(R)-2-carbamate

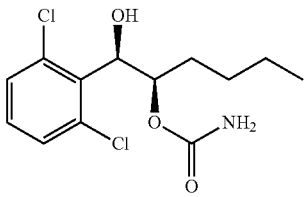 [SMILES: CCCC[C@@H](OC(N)=O)[C@H](O)c1c(Cl)cccc1Cl]

The substantially same method as described in Preparation Example 103 was conducted, except that 1-(2,6-dichlorophenyl)-(R,R)-1,2-hexanediol obtained in Preparation Example 48 was used instead of 1-(2-chlorophenyl)-(S,S)-1,2-propanediol, to obtain the title compound (0.15 g, yield 20~60%).

$^1$H NMR (400 MHz, CDCl$_3$) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 7.17~7.35 (m, 3H)

Preparation Example 156

Synthesis of 1-(2,4-dichlorophenyl)-1-hydroxypropyl-2-carbamate

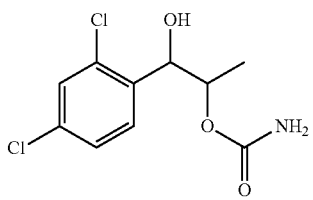 [SMILES: CC(OC(N)=O)C(O)c1ccc(Cl)cc1Cl]

The substantially same method as described in Preparation Example 103 was conducted, except that 1-(2,4-dichlorophenyl)-1,2-propanediol obtained in Preparation Example 28 was used instead of 1-(2-chlorophenyl)-(S,S)-1,2-propanediol, to obtain the title compound (0.14 g, yield 20~60%).

$^1$H NMR (400 MHz, CDCl$_3$) δ1.22 (d, J=6.4 Hz, 3H), 4.16 (br t, 1H) 4.96 (br t, 3H), 5.07 (t, J=4.8 Hz, 1H), 7.23~7.52 (m, 3H)

Preparation Example 157

Synthesis of 1-(2,6-dichlorophenyl)-1-hydroxypropyl-2-carbamate

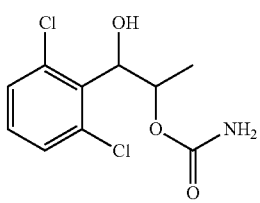 [SMILES: CC(OC(N)=O)C(O)c1c(Cl)cccc1Cl]

The substantially same method as described in Preparation Example 103 was conducted, except that 1-(2,6-dichlorophenyl)-1,2-propanediol obtained in Preparation Example 40 was used instead of 1-(2-chlorophenyl)-(S,S)-1,2-propanediol, to obtain the title compound (0.19 g, yield 20~60%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H)

Preparation Example 158

Synthesis of 1-(2,3-dichlorophenyl)-1-hydroxypropyl-2-carbamate

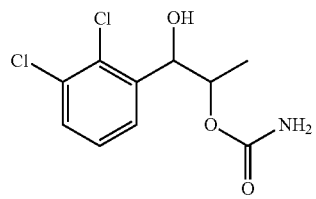 [SMILES: CC(OC(N)=O)C(O)c1cccc(Cl)c1Cl]

The substantially same method as described in Preparation Example 103 was conducted, except that 1-(2,3-dichlorophenyl)-1,2-propanediol obtained in Preparation Example 59 was used instead of 1-(2-chlorophenyl)-(S,S)-1,2-propanediol, to obtain the title compound (0.21 g, yield 20~60%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Preparation Example 159

Synthesis of 1-(2,4-dichlorophenyl)-1-hydroxybutyl-2-carbamate

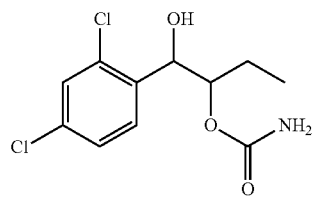 [SMILES: CCC(OC(N)=O)C(O)c1ccc(Cl)cc1Cl]

The substantially same method as described in Preparation Example 103 was conducted, except that 1-(2,4-dichlorophenyl)-1,2-butanediol obtained in Preparation Example 31 was used instead of 1-(2-chlorophenyl)-(S,S)-1,2-propanediol, to obtain the title compound (0.23 g, yield 20~60%).

$^1$H NMR (400 MHz, CDCl$_3$) δ0.96 (t, J=7.4 Hz, 3H), 1.58~1.74 (m, 2H), 2.98 (d, J=5.6 Hz, 1H) 4.68 (br s, 2H), 5.59 (dt, J=5.2, 8.8 Hz, 1H), 5.19 (t, J=5.4 Hz, 1H), 7.30~7.50 (m, 3H)

Preparation Example 160

Synthesis of 1-(2,6-dichlorophenyl)-1-hydroxybutyl-2-carbamate

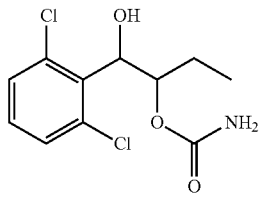 [SMILES: CCC(OC(N)=O)C(O)c1c(Cl)cccc1Cl]

The substantially same method as described in Preparation Example 103 was conducted, except that 1-(2,6-dichlorophenyl)-1,2-butanediol obtained in Preparation Example 43 was used instead of 1-(2-chlorophenyl)-(S,S)-1,2-propanediol, to obtain the title compound (0.49 g, yield 20~60%).

¹H NMR (400 MHz, CDCl₃) δ0.92 (t, J=7.4 Hz, 3H), 1.30~1.38 (m, 1H), 1.57~1.64 (m, 1H), 3.74 (d, J=9.2 Hz, 1H), 4.80 (br s, 2H), 5.40~5.50 (m, 2H), 7.17~7.34 (m, 3H)

Preparation Example 161

Synthesis of 1-(2,4-dichlorophenyl)-1-hydroxy-3-methyl-butyl-2-carbamate

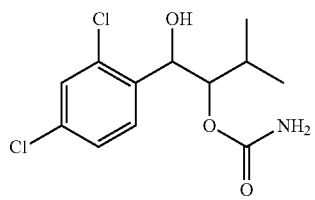 [SMILES: CC(C)C(OC(N)=O)C(O)c1ccc(Cl)cc1Cl]

The substantially same method as described in Preparation Example 103 was conducted, except that 1-(2,4-dichlorophenyl)-3-methyl-1,2-butanediol obtained in Preparation Example 34 was used instead of 1-(2-chlorophenyl)-(S,S)-1,2-propanediol, to obtain the title compound (0.13 g, yield 20~60%).

¹H NMR (400 MHz, CDCl₃) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.30~7.50 (m, 3H)

Preparation Example 162

Synthesis of 1-(2,6-dichlorophenyl)-1-hydroxy-3-methyl-butyl-2-carbamate

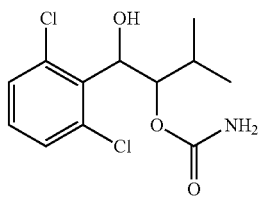 [SMILES: CC(C)C(OC(N)=O)C(O)c1c(Cl)cccc1Cl]

The substantially same method as described in Preparation Example 103 was conducted, except that 1-(2,6-dichlorophenyl)-3-methyl-1,2-butanediol obtained in Preparation Example 46 was used instead of 1-(2-chlorophenyl)-(S,S)-1,2-propanediol, to obtain the title compound (0.13 g, yield 20~60%).

¹H NMR (400 MHz, CDCl₃) δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 7.16~7.33 (m, 3H)

Preparation Example 163

Synthesis of 1-(2,4-dichlorophenyl)-1-hydroxyhexyl-2-carbamate

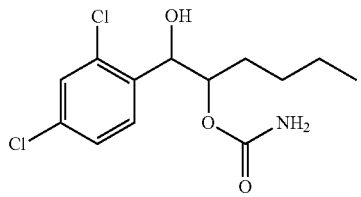 [SMILES: CCCCC(OC(N)=O)C(O)c1ccc(Cl)cc1Cl]

The substantially same method as described in Preparation Example 103 was conducted, except that 1-(2,4-dichlorophenyl)-1,2-hexanediol obtained in Preparation Example 37 was used instead of 1-(2-chlorophenyl)-(S,S)-1,2-propanediol, to obtain the title compound (0.94 g, yield 20~60%).

¹H NMR (400 MHz, CDCl₃) δ0.89 (1, J=3.6 Hz, 3H), 1.28~1.42 (m, 4H), 1.52~1.59 (m, 1H), 1.64~1.71 (m, 1H), 2.98 (d, J=5.6 Hz, 1H), 4.67 (br s, 2H), 4.96~5.00 (m, 1H), 5.17 (t, J=5.6 Hz, 1H), 7.30~7.49 (m, 3H)

Preparation Example 164

Synthesis of 1-(2,6-dichlorophenyl)-1-hydroxyhexyl-2-carbamate

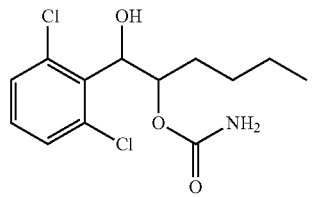 [SMILES: CCCCC(OC(N)=O)C(O)c1c(Cl)cccc1Cl]

The substantially same method as described in Preparation Example 103 was conducted, except that 1-(2,6-dichlorophenyl)-1,2-hexanediol obtained in Preparation Example 49 was used instead of 1-(2-chlorophenyl)-(S,S)-1,2-propanediol, to obtain the title compound (0.15 g, yield 20~60%).

¹H NMR (400 MHz, CDCl₃) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 7.17~7.35 (m, 3H)

Preparation Example 165

Synthesis of 1-(2-fluorophenyl)-(S)-1-hydroxypropyl-(S)-2-carbamate

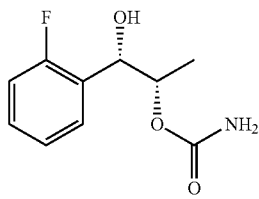

The substantially same method as described in Preparation Example 103 was conducted, except that 1-(2-fluorophenyl)-(S,S)-1,2-propanediol (12.23 g) obtained in Preparation Example 61 was used instead of 1-(2-chlorophenyl)-(S,S)-1,2-propanediol, to obtain the title compound (6.11 g, yield 40%).

$^1$H NMR (400 MHz, CDCl$_3$) δ1.19 (d, J=5.2 Hz, 3H), 2.93 (d, J=4.4 Hz, 1H), 4.71 (br s, 2H), 4.99~5.06 (m, H), 7.04~7.48 (m, 4H)

Preparation Example 166

Synthesis of 1-(2-fluorophenyl)-(R)-1-hydroxypropyl-(R)-2-carbamate

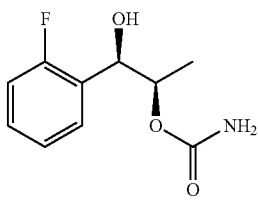

The substantially same method as described in Preparation Example 103 was conducted, except that 1-(2-fluorophenyl)-(R,R)-1,2-propanediol (6.26 g) obtained in Preparation Example 62 was used instead of 1-(2-chlorophenyl)-(S,S)-1,2-propanediol, to obtain the title compound (3.13 g, yield 40%).

$^1$H NMR (400 MHz, CDCl$_3$) δ1.19 (d, J=5.2 Hz, 3H), 2.93 (d, J=4.4 Hz, 1H), 4.71 (br s, 2H), 4.99~5.06 (m, H), 7.04~7.48 (m, 4H)

Preparation Example 167

Synthesis of 1-(2-iodophenyl)-(S)-1-hydroxypropyl-(S)-2-carbamate

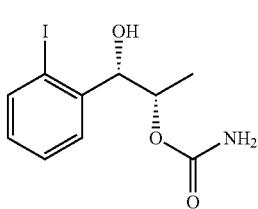

The substantially same method as described in Preparation Example 103 was conducted, except that 1-(2-iodophenyl)-(S,S)-1,2-propanediol obtained in Preparation Example 66 was used instead of 1-(2-chlorophenyl)-(S,S)-1,2-propanediol, to obtain the title compound (2.2 g, yield 30~60%).

$^1$H NMR (400 MHz, CDCl$_3$) δ1.27 (d, J=6.4 Hz, 3H), 3.09 (br s, 1H), 4.83 (br s, 2H), 5.00~5.10 (m, 2H), 7.00~7.76 (m, 4H)

Preparation Example 168

Synthesis of 1-(2-iodophenyl)-(R)-1-hydroxypropyl-(R)-2-carbamate

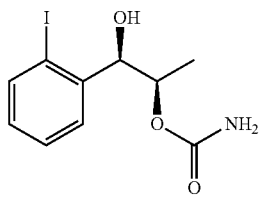

The substantially same method as described in Preparation Example 103 was conducted, except that 1-(2-iodophenyl)-(R,R)-1,2-propanediol obtained in Preparation Example 67 was used instead of 1-(2-chlorophenyl)-(S,S)-1,2-propanediol, to obtain the title compound (3.13 g, yield 30~60%).

$^1$H NMR (400 MHz, CDCl$_3$) δ1.27 (d, J=6.4 Hz, 3H), 2.95 (d, J=3.6 Hz, 1H), 4.73 (br s, 2H), 5.01~5.11 (m, 2H), 7.01~7.86 (m, 4H)

Preparation Example 169

Synthesis of 1-(2-iodophenyl)-(S)-1-hydroxybutyl-(S)-2-carbamate

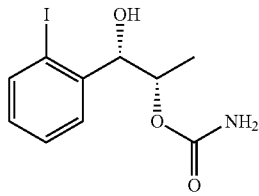

The substantially same method as described in Preparation Example 103 was conducted, except that 1-(2-iodophenyl)-(S,S)-1,2-butanediol obtained in Preparation Example 68 was used instead of 1-(2-chlorophenyl)-(S,S)-1,2-propanediol, to obtain the title compound (3.6 g, yield 30~60%).

$^1$H NMR (400 MHz, CDCl$_3$) δ1.27 (d, J=6.4 Hz, 3H), 3.09 (br s, 1H), 4.83 (br s, 2H), 5.00~5.10 (m, 2H), 7.00~7.76 (m, 4H)

Preparation Example 170

Synthesis of 1-(2-chlorophenyl)-(S)-2-hydroxypropyl-(S)-1-carbamate

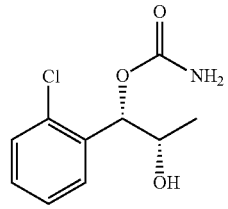

A regioisomer of monocarbamate was separated and purified by conducting the silica gel column chromatography as described in Preparation Example 103, to obtain the title compound (0.34 g, yield 10%).

$^1$H NMR (400 MHz, CDCl$_3$) δ1.24 (d, J=6.8 Hz, 3H), 2.13 (d, J=4.4 Hz, 1H), 4.12~4.16 (m, 1H), 4.85 (br s, 2H), 5.98 (d, J=5.6 Hz, 1H), 7.24~7.43 (m, 4H)

Preparation Example 171

Synthesis of 1-(2-chlorophenyl)-(R)-2-hydroxypropyl-(R)-1-carbamate

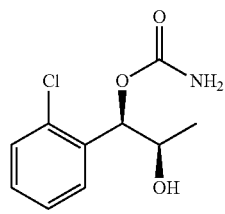

A regioisomer of monocarbamate was separated and purified by conducting the silica gel column chromatography as described in Preparation Example 104, to obtain the title compound (0.77 g, yield 16%).

$^1$H NMR (400 MHz, CDCl$_3$) δ1.24 (d, J=6.4 Hz, 3H), 2.04 (d, J=4.8 Hz, 1H), 4.11~4.18 (m, 1H), 4.74 (br s, 2H), 6.00 (d, J=5.6 Hz, 1H), 7.24~7.43 (m, 4H)

Preparation Example 172

Synthesis of 1-(2-chlorophenyl)-2-hydroxypropyl-1-carbamate

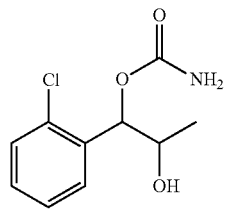

A regioisomer of monocarbamate was separated and purified by conducting the silica gel column chromatography as described in Preparation Example 105, to obtain the title compound (0.16 g, yield 10~30%).

$^1$H NMR (400 MHz, CDCl$_3$) δ1.24 (d, J=6.4 Hz, 3H), 2.04 (d, J=4.8 Hz, 1H), 4.11~4.18 (m, 1H), 4.74 (br s, 2H), 6.00 (d, J=5.6 Hz, 1H), 7.24~7.43 (m, 4H)

Preparation Example 173

Synthesis of 1-(2-chlorophenyl)-(S)-2-hydroxypropyl-(S)-1-methylcarbamate

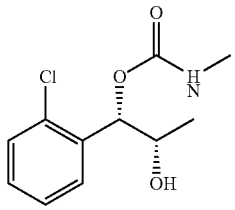 [SMILES: CNC(=O)O[C@@H](c1ccccc1Cl)[C@H](C)O]

A regioisomer of monocarbamate was separated and purified by conducting the silica gel column chromatography as described in Preparation Example 117, to obtain the title compound (0.70 g, yield 10~30%).

$^1$H NMR (400 MHz, CDCl$_3$) δ1.21 (d, J=6.4 Hz, 3H), 2.80 (d, J=4.8 Hz, 3H), 3.12 (s, 1H), 4.09~4.16 (m, 1H), 4.86 (br s, 1H), 5.99 (d, J=6.0 Hz, 1H), 7.23~7.40 (m, 4H)

Preparation Example 174

Synthesis of 1-(2-chlorophenyl)-(R)-2-hydroxypropyl-(R)-1-methylcarbamate

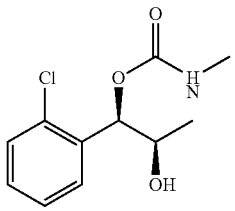 [SMILES: CNC(=O)O[C@H](c1ccccc1Cl)[C@@H](C)O]

A regioisomer of monocarbamate was separated and purified by conducting the silica gel column chromatography as described in Preparation Example 124, to obtain the title compound (0.69 g, yield 10~30%).

$^1$H NMR (400 MHz, CDCl$_3$) δ1.21 (d, J=6.4 Hz, 3H), 2.80 (d, J=4.8 Hz, 3H), 3.12 (s, 1H), 4.09~4.16 (m, 1H), 4.86 (br s, 1H), 5.99 (d, J=6.0 Hz, 1H), 7.23~7.40 (m, 4H)

Preparation Example 175

Synthesis of 1-(2-chlorophenyl)-2-hydroxypropyl-1-methylcarbamate

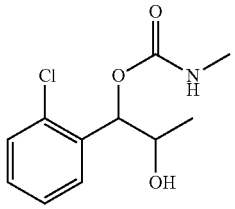 [SMILES: CNC(=O)OC(c1ccccc1Cl)C(C)O]

A regioisomer of monocarbamate was separated and purified by conducting the silica gel column chromatography as described in Preparation Example 131, to obtain the title compound (0.73 g, yield 10%).

$^1$H NMR (400 MHz, CDCl$_3$) δ 1.22 (d, J=6 Hz, 3H), 2.15 (d, J=4 Hz, 1H), 2.81 (d, J=5 Hz, 3H), 4.12 (dd, J=6 Hz, 1H), 4.83 (br s, 1H), 6.00 (d, J=6 Hz, 1H), 7.23~7.41 (m, 4H)

Preparation Example 176

Synthesis of 1-(2-chlorophenyl)-(S)-2-hydroxypropyl-(S)-1-propylcarbamate

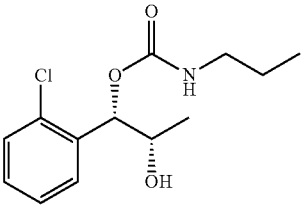 [SMILES: CCCNC(=O)O[C@@H](c1ccccc1Cl)[C@H](C)O]

A regioisomer of monocarbamate was separated and purified by conducting the silica gel column chromatography as described in Preparation Example 118, to obtain the title compound (0.15 g, yield 10~30%).

$^1$H NMR (400 MHz, CDCl$_3$) δ 0.91 (t, J=7 Hz, 3H), 1.22 (d, J=6 Hz, 3H), 1.52 (dd, J=7 Hz; 2H), 2.23 (d, J=4 Hz, 1H), 3.09~3.21 (m, 2H), 4.09~4.17 (m, 1H), 4.93 (s, 1H), 5.99 (d, J=6 Hz, 1H), 7.23~7.47 (m, 4H)

Preparation Example 177

Synthesis of 1-(2-chlorophenyl)-(R)-2-hydroxypropyl-(R)-1-propylcarbamate

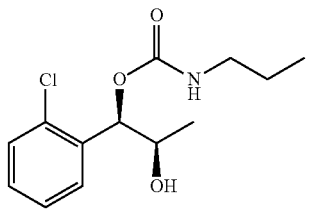 [SMILES: CCCNC(=O)O[C@H](c1ccccc1Cl)[C@@H](C)O]

A regioisomer of monocarbamate was separated and purified by conducting the silica gel column chromatography as described in Preparation Example 125, to obtain the title compound (0.04 g, yield 10~30%).

$^1$H NMR (400 MHz, CDCl$_3$) δ 0.91 (t, J=7 Hz, 3H), 1.22 (d, J=6 Hz, 3H), 1.52 (dd, J=7 Hz, 2H), 2.23 (d, J=4 Hz, 1H), 3.09~3.21 (m, 2H), 4.09~4.17 (m, 1H), 4.93 (s, 1H), 5.99 (d, J=6 Hz, 1H), 7.23~7.47 (m, 4H)

Preparation Example 178

Synthesis of 1-(2-chlorophenyl)-2-hydroxypropyl-1-propylcarbamate

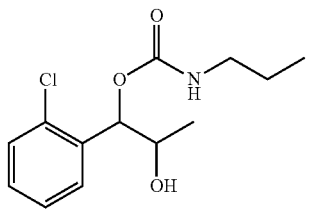

A regioisomer of monocarbamate was separated and purified by conducting the silica gel column chromatography as described in Preparation Example 132, to obtain the title compound (0.15 g, yield 10%).

$^1$H NMR (400 MHz, CDCl$_3$) δ 0.91 (t, J=7 Hz, 3H), 1.22 (d, J=6 Hz, 3H), 1.52 (dd, J=7 Hz, 2H), 2.23 (d, J=4 Hz, 1H), 3.09~3.21 (m, 2H), 4.09~4.17 (m, 1H), 4.93 (s, 1H), 5.99 (d, J=6 Hz, 1H), 7.23~7.47 (m, 4H)

Preparation Example 179

Synthesis of 1-(2-chlorophenyl)-(S)-2-hydroxypropyl-(S)-1-isopropylcarbamate

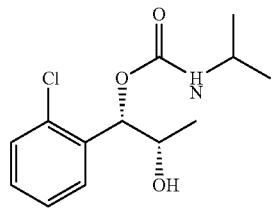 [SMILES: CC(C)NC(=O)O[C@@H](c1ccccc1Cl)[C@H](C)O]

A regioisomer of monocarbamate was separated and purified by conducting the silica gel column chromatography as described in Preparation Example 119, to obtain the title compound (0.42 g, yield 28%).

$^1$H NMR (400 MHz, CDCl$_3$) δ1.10 (d, J=6.0 Hz, 3H), 1.15~1.19 (m, 6H), 2.41 (s, 1H), 3.76~4.08 (m, 1H), 4.34 (s, 1H), 4.83 (br s 1H), 5.95 (d, J=5.3 Hz, 1H), 7.19~7.39 (m, 4H)

Preparation Example 180

Synthesis of 1-(2-chlorophenyl)-(R)-2-hydroxypropyl-(R)-1-isopropylcarbamate

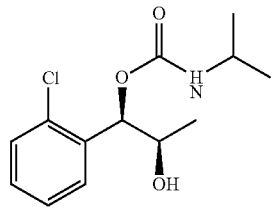 [SMILES: CC(C)NC(=O)O[C@H](c1ccccc1Cl)[C@@H](C)O]

A regioisomer of monocarbamate was separated and purified by conducting the silica gel column chromatography as described in Preparation Example 126, to obtain the title compound (0.5 g, yield 10%).

$^1$H NMR (400 MHz, CDCl$_3$) δ1.13 (d, J=6 Hz, 3H), 1.20 (dd, J=9.2 Hz, 6H), 2.23 (s, 1H), 3.77~3.82 (m, 1H), 4.10 (s, 1H), 4.76 (br s, 1H), 5.98 (d, J=5.6 Hz, 1H), 7.23~7.41 (m, 4H)

Preparation Example 181

Synthesis of 1-(2-chlorophenyl)-2-hydroxypropyl-1-isopropylcarbamate

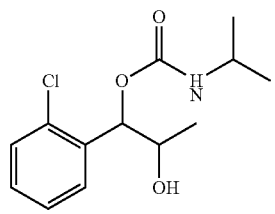 [SMILES: CC(C)NC(=O)OC(c1ccccc1Cl)C(C)O]

A regioisomer of monocarbamate was separated and purified by conducting the silica gel column chromatography as described in Preparation Example 133, to obtain the title compound (0.09 g, yield 40%).

$^1$H NMR (400 MHz, CDCl$_3$) δ 1.14 (d, J=6 Hz, 3H), 1.21 (dd, J=6 Hz, 6H), 2.16 (d, J=5 Hz, 1H), 3.81 (t, J=6 Hz, 1H), 4.11 (d, J=5 Hz, 1H), 4.73 (br s, 1H), 5.98 (d, J=5 Hz, 1H), 7.24~741 (m, 4H)

Preparation Example 182

Synthesis of 1-(2-chlorophenyl)-(S)-2-hydroxypropyl-(S)-1-cyclopropylcarbamate

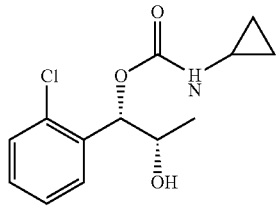 [SMILES: C[C@H](O)[C@@H](OC(=O)NC1CC1)c1ccccc1Cl]

A regioisomer of monocarbamate was separated and purified by conducting the silica gel column chromatography as described in Preparation Example 120, to obtain the title compound (0.53 g, yield 10~30%).

$^1$H NMR (400 MHz, CDCl$_3$) δ0.53~0.60 (m, 2H), 0.74 (s, 2H), 1.21 (d, J=6.0 Hz, 3H), 2.19 (s, 1H), 2.59 (s, 1H), 4.11~4.15 (m, 1H), 5.13 (br s, 1H), 5.99 (d, J=5.20 Hz, 1H), 7.23~7.40 (m, 4H)

Preparation Example 183

Synthesis of 1-(2-chlorophenyl)-(R)-2-hydroxypropyl-(R)-1-cyclopropylcarbamate

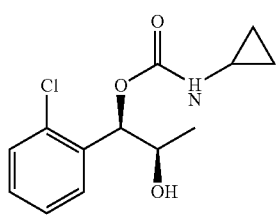 [SMILES: C[C@@H](O)[C@H](OC(=O)NC1CC1)c1ccccc1Cl]

A regioisomer of monocarbamate was separated and purified by conducting the silica gel column chromatography as described in Preparation Example 127, to obtain the title compound (0.58 g, yield 10%).

$^1$H NMR (400 MHz, CDCl$_3$) δ0.53~0.60 (m, 2H), 0.74 (s, 2H), 1.21 (d, J=6.0 Hz, 3H), 2.19 (s, 1H), 2.59 (s, 1H), 4.11~4.15 (m, 1H), 5.13 (br s, 1H), 5.99 (d, J=5.20 Hz, 1H), 7.23~7.40 (m, 4H)

Preparation Example 184

Synthesis of 1-(2-chlorophenyl)-2-hydroxypropyl-1-cyclopropylcarbamate

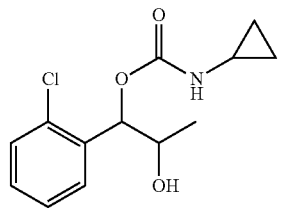 [SMILES: CC(O)C(OC(=O)NC1CC1)c1ccccc1Cl]

A regioisomer of monocarbamate was separated and purified by conducting the silica gel column chromatography as described in Preparation Example 134, to obtain the title compound (0.38 g, yield 14%).

$^1$H NMR (400 MHz, CDCl$_3$) δ 0.71 (s, 2H), 1.19 (d, J=6 Hz, 3H), 2.45 (S, 1H), 2.57 (S, 1H), 4.08~4.12 (m, 1H), 5.26 (s, 1H), 5.97 (d, J=4 Hz, 1H), 7.22~7.54 (m, 4H)

Preparation Example 185

Synthesis of 1-(2-chlorophenyl)-(S)-2-hydroxypropyl-(S)-1-cyclohexylcarbamate

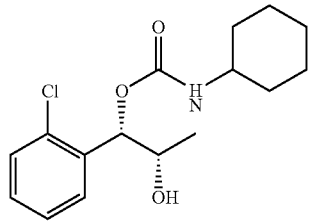 [SMILES: C[C@H](O)[C@@H](OC(=O)NC1CCCCC1)c1ccccc1Cl]

A regioisomer of monocarbamate was separated and purified by conducting the silica gel column chromatography as described in Preparation Example 121, to obtain the title compound (0.24 g, yield 10~30%).

$^1$H NMR (400 MHz, CDCl$_3$) δ1.10~1.39 (m, 7H), 1.61 (s, 3H), 1.71~1.74 (m, 2H), 1.87 (d, J=11.2 Hz, 1H), 2.48 (d, J=10.8 Hz, 1H), 3.46 (t, J=4 Hz, 1H), 4.10~4.11 (m, 1H), 4.80 (br s 1H), 5.97 (d, J=5.6 Hz, 1H), 7.23~7.41 (m, 4H)

Preparation Example 186

Synthesis of 1-(2-chlorophenyl)-(R)-2-hydroxypropyl-(R)-1-cyclohexylcarbamate

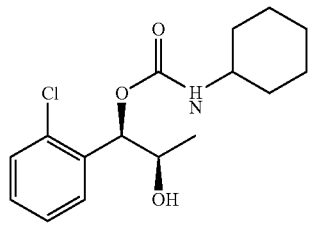 [SMILES: C[C@@H](O)[C@H](OC(=O)NC1CCCCC1)c1ccccc1Cl]

A regioisomer of monocarbamate was separated and purified by conducting the silica gel column chromatography as described in Preparation Example 128, to obtain the title compound (0.35 g, yield 10%).

$^1$H NMR (400 MHz, CDCl$_3$) δ1.10~1.39 (m, 7H), 1.61 (s, 3H), 1.71~1.74 (m, 2H), 1.87 (d, J=11.2 Hz, 1H), 2.48 (d, J=10.8 Hz, 1H), 3.46 (t, J=4 Hz, 1H), 4.10~4.11 (m, 1H), 4.80 (br s 1H), 5.97 (d, J=5.6 Hz, 1H), 7.23~7.41 (m, 4H)

Preparation Example 187

Synthesis of 1-(2-chlorophenyl)-2-hydroxypropyl-1-cyclohexylcarbamate

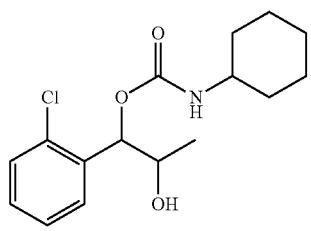 [SMILES: CC(O)C(OC(=O)NC1CCCCC1)c1ccccc1Cl]

A regioisomer of monocarbamate was separated and purified by conducting the silica gel column chromatography as described in Preparation Example 135, to obtain the title compound (0.26 g, yield 10%).

$^1$H NMR (400 MHz, CDCl$_3$) δ 1.12~1.19 (m, 3H), 1.22 (d, J=6 Hz, 3H), 1.27~1.37 (m, 1H), 1.71 (t, J=6 Hz, 2H), 1.86~1.88 (m, 1H), 1.97~2.00 (m, 1H), 2.18 (d, J=4 Hz, 1H), 3.47 (S, 1H), 4.12 (t, J=6 Hz, 1H), 4.78 (S, 1H), 5.97 (d, J=6 Hz, 1H), 7.23~7.40 (m, 4H)

Preparation Example 188

Synthesis of 1-(2-chlorophenyl)-(S)-2-hydroxypropyl-(S)-1-benzylcarbamate

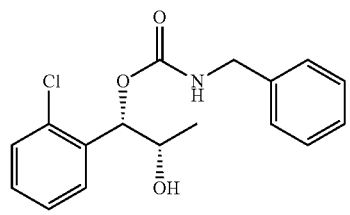

A regioisomer of monocarbamate was separated and purified by conducting the silica gel column chromatography as described in Preparation Example 122, to obtain the title compound (0.19 g, yield 10~30%).

$^1$H NMR (400 MHz, CDCl$_3$) δ 1.23 (d, J=6 Hz, 3H), 2.16 (d, J=4 Hz, 1H), 4.12 (t, J=6 Hz, 1H), 4.31~4.44 (m, 2H), 5.22 (br S, 1H), 6.04 (d, J=6 Hz, 1H), 7.27~7.42 (m, 9H)

Preparation Example 189

Synthesis of 1-(2-chlorophenyl)-(R)-2-hydroxypropyl-(R)-1-benzylcarbamate

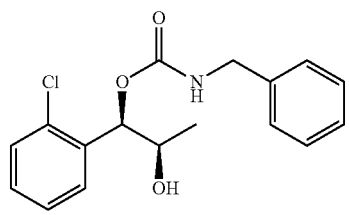 [SMILES: C[C@@H](O)[C@H](OC(=O)NCc1ccccc1)c1ccccc1Cl]

A regioisomer of monocarbamate was separated and purified by conducting the silica gel column chromatography as described in Preparation Example 129, to obtain the title compound (0.07 g, yield 10~30%).

$^1$H NMR (400 MHz, CDCl$_3$) δ 1.23 (d, J=6 Hz, 3H), 2.16 (d, J=4 Hz, 1H), 4.12 (t, J=6 Hz, 1H), 4.31~4.44 (m, 2H), 5.22 (br S, 1H), 6.04 (d, J=6 Hz, 1H), 7.27~7.42 (m, 9H)

Preparation Example 190

Synthesis of 1-(2-chlorophenyl)-2-hydroxypropyl-1-benzylcarbamate

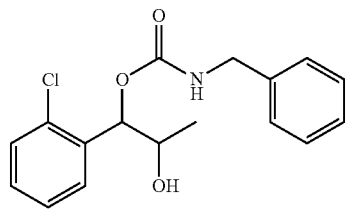 [SMILES: CC(O)C(OC(=O)NCc1ccccc1)c1ccccc1Cl]

A regioisomer of monocarbamate was separated and purified by conducting the silica gel column chromatography as described in Preparation Example 136, to obtain the title compound (0.21 g, yield 14%).

$^1$H NMR (400 MHz, CDCl$_3$) δ 1.23 (d, J=6 Hz, 3H), 2.16 (d, J=4 Hz, 1H), 4.12 (t, J=6 Hz, 1H), 4.31~4.44 (m, 2H), 5.22 (br S, 1H), 6.04 (d, J=6 Hz, 1H), 7.27~7.42 (m, 9H)

Preparation Example 191

Synthesis of 1-(2,4-dichlorophenyl)-(S)-2-hydroxypropyl-(S)-1-carbamate

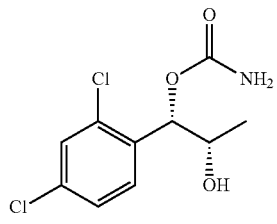

A regioisomer of monocarbamate was separated and purified by conducting the silica gel column chromatography as described in Preparation Example 138, to obtain the title compound (0.05 g, yield 10~30%).

¹H NMR (400 MHz, CDCl₃) δ1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.30 (d, J=8.4 Hz, 1H), 7.39 (d, J=2.0 Hz, 2H), 7.50 (dd, J=8.4 Hz, 2.0 Hz, 1H)

Preparation Example 192

Synthesis of 1-(2,6-dichlorophenyl)-(S)-2-hydroxy-propyl-(S)-1-carbamate

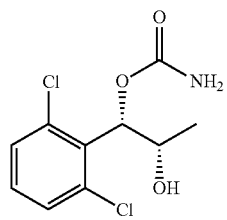 [SMILES: C[C@H](O)[C@@H](OC(N)=O)c1c(Cl)cccc1Cl]

A regioisomer of monocarbamate was separated and purified by conducting the silica gel column chromatography as described in Preparation Example 139, to obtain the title compound (0.07 g, yield 24%).
¹H NMR (400 MHz, CDCl₃) δ1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.25~7.40 (m, 3H)

Preparation Example 193

Synthesis of 1-(2,3-dichlorophenyl)-(S)-2-hydroxy-propyl-(S)-1-carbamate

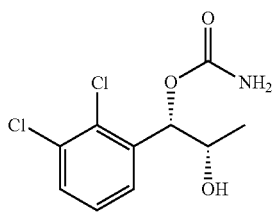 [SMILES: C[C@H](O)[C@@H](OC(N)=O)c1cccc(Cl)c1Cl]

A regioisomer of monocarbamate was separated and purified by conducting the silica gel column chromatography as described in Preparation Example 140, to obtain the title compound (0.08 g, yield 10~30%).
¹H NMR (400 MHz, CDCl₃) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H), Preparation Example 194

Synthesis of 1-(2,4-dichlorophenyl)-(S)-2-hydroxy-butyl-(S)-1-carbamate

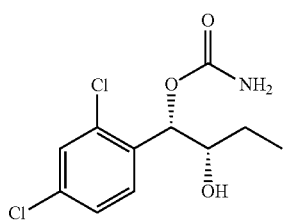 [SMILES: CC[C@H](O)[C@@H](OC(N)=O)c1ccc(Cl)cc1Cl]

A regioisomer of monocarbamate was separated and purified by conducting the silica gel column chromatography as described in Preparation Example 141, to obtain the title compound (0.07 g, yield 10~30%).
¹H NMR (400 MHz, CDCl₃) δ0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.30~7.50 (m, 3H)

Preparation Example 195

Synthesis of 1-(2,6-dichlorophenyl)-(S)-2-hydroxy-butyl-(S)-1-carbamate

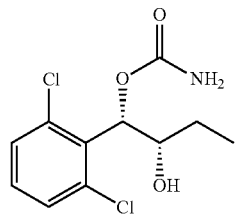 [SMILES: CC[C@H](O)[C@@H](OC(N)=O)c1c(Cl)cccc1Cl]

A regioisomer of monocarbamate was separated and purified by conducting the silica gel column chromatography as described in Preparation Example 142, to obtain the title compound (0.11 g, yield 29%).
¹H NMR (400 MHz, CDCl₃) δ0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.25~7.40 (m, 3H)

Preparation Example 196

Synthesis of 1-(2,4-dichlorophenyl)-(S)-2-hydroxy-3-methyl-butyl-(S)-1-carbamate

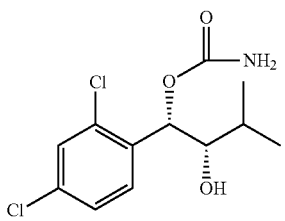 [SMILES: CC(C)[C@H](O)[C@@H](OC(N)=O)c1ccc(Cl)cc1Cl]

A regioisomer of monocarbamate was separated and purified by conducting the silica gel column chromatography as described in Preparation Example 143, to obtain the title compound (0.01 g, yield 10~30%).
¹H NMR (400 MHz, CDCl₃) δ1.00 (1, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.30~7.50 (m, 3H)

Preparation Example 197

Synthesis of 1-(2,6-dichlorophenyl)-(S)-2-hydroxy-3-methyl-butyl-(S)-1-carbamate

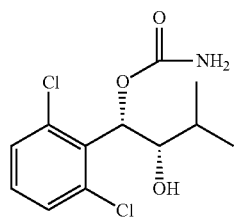 [SMILES: CC(C)[C@H](O)[C@@H](OC(N)=O)c1c(Cl)cccc1Cl]

A regioisomer of monocarbamate was separated and purified by conducting the silica gel column chromatography as described in Preparation Example 144, to obtain the title compound (0.03 g, yield 10~30%).

$^1$H NMR (400 MHz, CDCl$_3$) δ1.00 (t, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.25~7.40 (m, 3H)

Preparation Example 198

Synthesis of 1-(2,4-dichlorophenyl)-(S)-2-hydroxy-hexyl-(S)-1-carbamate

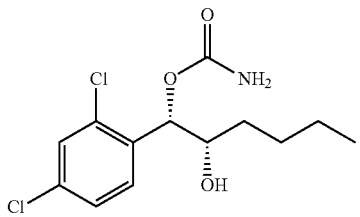 [SMILES: CCCC[C@H](O)[C@@H](OC(N)=O)c1ccc(Cl)cc1Cl]

A regioisomer of monocarbamate was separated and purified by conducting the silica gel column chromatography as described in Preparation Example 145, to obtain the title compound (0.21 g, yield 10~30%).

$^1$H NMR (400 MHz, CDCl$_3$) δ0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.30~7.50 (m, 3H)

Preparation Example 199

Synthesis of 1-(2,6-dichlorophenyl)-(S)-2-hydroxy-hexyl-(S)-1-carbamate

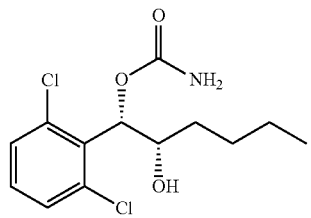

A regioisomer of monocarbamate was separated and purified by conducting the silica gel column chromatography as described in Preparation Example 146, to obtain the title compound (0.06 g, yield 29%).

$^1$H NMR (400 MHz, CDCl$_3$) δ0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.16~7.34 (m, 3H)

Preparation Example 200

Synthesis of 1-(2,4-dichlorophenyl)-(R)-2-hydroxy-propyl-(R)-1-carbamate

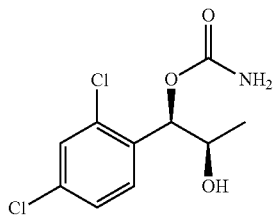 [SMILES: C[C@@H](O)[C@H](OC(N)=O)c1ccc(Cl)cc1Cl]

A regioisomer of monocarbamate was separated and purified by conducting the silica gel column chromatography as described in Preparation Example 147, to obtain the title compound (0.04 g, yield 10~30%).

$^1$H NMR (400 MHz, CDCl$_3$) δ1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.30~7.50 (m, 3H)

Preparation Example 201

Synthesis of 1-(2,6-dichlorophenyl)-(R)-2-hydroxy-propyl-(R)-1-carbamate

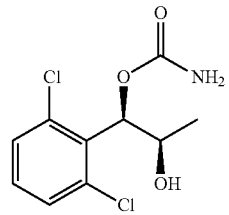 [SMILES: C[C@@H](O)[C@H](OC(N)=O)c1c(Cl)cccc1Cl]

A regioisomer of monocarbamate was separated and purified by conducting the silica gel column chromatography as described in Preparation Example 148, to obtain the title compound (0.09 g, yield 10~30%).

$^1$H NMR (400 MHz, CDCl$_3$) δ1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.25~7.40 (m, 3H)

Preparation Example 202

Synthesis of 1-(2,3-dichlorophenyl)-(R)-2-hydroxy-propyl-(R)-1-carbamate

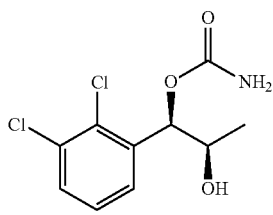 [SMILES: C[C@@H](O)[C@H](OC(N)=O)c1cccc(Cl)c1Cl]

A regioisomer of monocarbamate was separated and purified by conducting the silica gel column chromatography as described in Preparation Example 149, to obtain the title compound (0.25 g, yield 10~30%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Preparation Example 203

Synthesis of 1-(2,4-dichlorophenyl)-(R)-2-hydroxy-butyl-(R)-1-carbamate

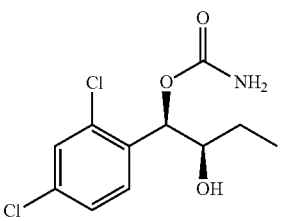 [SMILES: CC[C@@H](O)[C@H](OC(N)=O)c1ccc(Cl)cc1Cl]

A regioisomer of monocarbamate was separated and purified by conducting the silica gel column chromatography as described in Preparation Example 150, to obtain the title compound (0.08 g, yield 10~30%).

$^1$H NMR (400 MHz, CDCl$_3$) δ0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.30~7.50 (m, 3H)

Preparation Example 204

Synthesis of 1-(2,6-dichlorophenyl)-(R)-2-hydroxy-butyl-(R)-1-carbamate

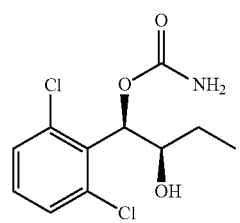 [SMILES: CC[C@@H](O)[C@H](OC(N)=O)c1c(Cl)cccc1Cl]

A regioisomer of monocarbamate was separated and purified by conducting the silica gel column chromatography as described in Preparation Example 151, to obtain the title compound (0.09 g, yield 10~30%). $^1$H NMR (400 MHz, CDCl$_3$) δ0.77 (t, J=7.4 Hz, 3H), 0.92~1.01 (m, 1H), 1.18~1.28 (m, 1H), 4.0~64.13 (m, 1H), 4.96 (d, J=6.0 Hz, 1H), 5.91 (d, J=8.8 Hz, 1H), 6.4 (br s, 2H), 7.25~7.40 (m, 3H)

Preparation Example 205

Synthesis of 1-(2,4-dichlorophenyl)-(R)-2-hydroxy-3-methyl-butyl-(R)-1-carbamate

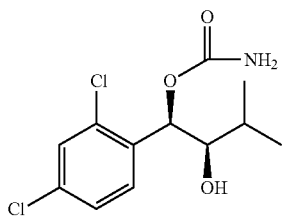 [SMILES: CC(C)[C@@H](O)[C@H](OC(N)=O)c1ccc(Cl)cc1Cl]

A regioisomer of monocarbamate was separated and purified by conducting the silica gel column chromatography as described in Preparation Example 152, to obtain the title compound (0.01 g, yield 10~30%).

$^1$H NMR (400 MHz, CDCl$_3$) δ1.00 (1, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.30~7.50 (m, 3H)

Preparation Example 206

Synthesis of 1-(2,6-dichlorophenyl)-(R)-2-hydroxy-3-methyl-butyl-(R)-1-carbamate

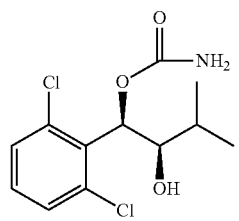 [SMILES: CC(C)[C@@H](O)[C@H](OC(N)=O)c1c(Cl)cccc1Cl]

A regioisomer of monocarbamate was separated and purified by conducting the silica gel column chromatography as described in Preparation Example 153, to obtain the title compound (0.01 g, yield 10~30%).

$^1$H NMR (400 MHz, CDCl$_3$) δ1.00 (t, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.25~7.40 (m, 3H)

Preparation Example 207

Synthesis of 1-(2,4-dichlorophenyl)-(R)-2-hydroxy-hexyl-(R)-1-carbamate

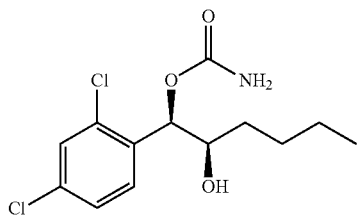 [SMILES: CCCC[C@@H](O)[C@H](OC(N)=O)c1ccc(Cl)cc1Cl]

A regioisomer of monocarbamate was separated and purified by conducting the silica gel column chromatography as described in Preparation Example 154, to obtain the title compound (0.21 g, yield 10~30%).

$^1$H NMR (400 MHz, CDCl$_3$) δ0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.30~7.50 (m, 3H)

Preparation Example 208

Synthesis of 1-(2,6-dichlorophenyl)-(R)-2-hydroxy-hexyl-(R)-1-carbamate

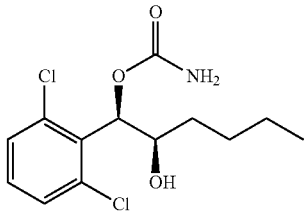 [SMILES: CCCC[C@@H](O)[C@H](OC(N)=O)c1c(Cl)cccc1Cl]

A regioisomer of monocarbamate was separated and purified by conducting the silica gel column chromatography as described in Preparation Example 155, to obtain the title compound (0.12 g, yield 10~30%).

$^1$H NMR (400 MHz, CDCl$_3$) δ0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.16~7.34 (m, 3H)

Preparation Example 209

Synthesis of 1-(2,4-dichlorophenyl)-2-hydroxypropyl-1-carbamate

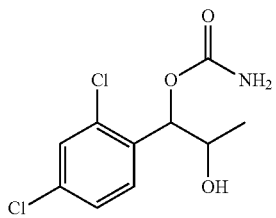

A regioisomer of monocarbamate was separated and purified by conducting the silica gel column chromatography as described in Preparation Example 156, to obtain the title compound (0.05 g, yield 10~30%).

$^1$H NMR (400 MHz, CDCl$_3$) δ1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.30~7.50 (m, 3H)

Preparation Example 210

Synthesis of 1-(2,6-dichlorophenyl)-2-hydroxypropyl-1-carbamate

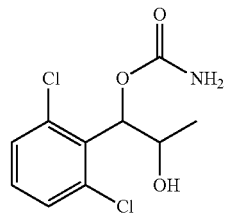 [SMILES: CC(O)C(OC(N)=O)c1c(Cl)cccc1Cl]

A regioisomer of monocarbamate was separated and purified by conducting the silica gel column chromatography as described in Preparation Example 157, to obtain the title compound (0.06 g, yield 10~30%).

$^1$H NMR (400 MHz, CDCl$_3$) δ1.13 (d, J=6.8 Hz, 3H), 2.49 (d, J=4.0 Hz, 1H), 4.66~4.74 (m, 1H), 4.76 (br s, 2H), 6.20 (d, J=8.8 Hz, 1H), 7.25~7.40 (m, 3H)

Preparation Example 211

Synthesis of 1-(2,3-dichlorophenyl)-(R)-2-hydroxy-propyl-(R)-1-carbamate

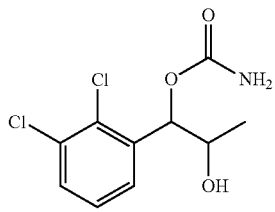 [SMILES: CC(O)C(OC(N)=O)c1cccc(Cl)c1Cl]

A regioisomer of monocarbamate was separated and purified by conducting the silica gel column chromatography as described in Preparation Example 158, to obtain the title compound (0.02 g, yield 10~30%).

$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Preparation Example 212

Synthesis of 1-(2,4-dichlorophenyl)-2-hydroxybutyl-1-carbamate

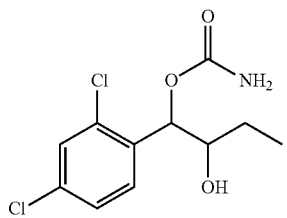 [SMILES: CCC(O)C(OC(N)=O)c1ccc(Cl)cc1Cl]

A regioisomer of monocarbamate was separated and purified by conducting the silica gel column chromatography as described in Preparation Example 159, to obtain the title compound (0.07 g, yield 10~30%).

$^1$H NMR (400 MHz, CDCl$_3$) δ0.77 (1, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz; 1H), 6.4 (br s, 2H), 7.30~7.50 (m, 3H)

Preparation Example 213

Synthesis of 1-(2,6-dichlorophenyl)-2-hydroxybutyl-1-carbamate

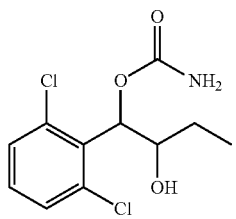 [SMILES: CCC(O)C(OC(N)=O)c1c(Cl)cccc1Cl]

A regioisomer of monocarbamate was separated and purified by conducting the silica gel column chromatography as described in Preparation Example 160, to obtain the title compound (0.10 g, yield 10~30%).

$^1$H NMR (400 MHz, CDCl$_3$) δ0.77 (t, J=7.4 Hz, 3H), 0.92~1.01 (m, 1H), 1.18~1.28 (m, 1H), 4.06~4.13 (m, 1H), 4.96 (d, J=6.0 Hz, 1H), 5.91 (d, J=8.8 Hz, 1H), 6.4 (br s, 2H), 7.25~7.40 (m, 3H)

Preparation Example 214

Synthesis of 1-(2,4-dichlorophenyl)-2-hydroxy-3-methyl-butyl-1-carbamate

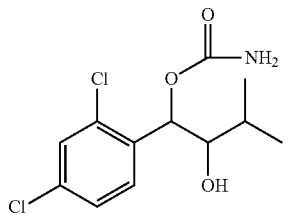 [SMILES: CC(C)C(O)C(OC(N)=O)c1ccc(Cl)cc1Cl]

A regioisomer of monocarbamate was separated and purified by conducting the silica gel column chromatography as described in Preparation Example 161, to obtain the title compound (0.04 g, yield 10~30%).

$^1$H NMR (400 MHz, CDCl$_3$) δ1.00 (t, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.30~7.50 (m, 3H)

Preparation Example 215

Synthesis of 1-(2,6-dichlorophenyl)-2-hydroxy-3-methyl-butyl-1-carbamate

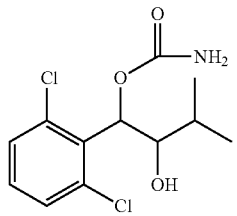 [SMILES: CC(C)C(O)C(OC(N)=O)c1c(Cl)cccc1Cl]

A regioisomer of monocarbamate was separated and purified by conducting the silica gel column chromatography as described in Preparation Example 162, to obtain the title compound (0.01 g, yield 10~30%).

$^1$H NMR (400 MHz, CDCl$_3$) δ1.00 (t, J=7.2 Hz, 6H), 1.73~1.79 (m, 1H), 3.67~3.69 (m, 1H), 4.96 (d, J=6.0 Hz, 1H), 5.91 (d, J=8.8 Hz, 1H), 6.42 (br s, 2H), 7.25~7.40 (m, 3H)

Preparation Example 216

Synthesis of 1-(2,4-dichlorophenyl)-2-hydroxyhexyl-1-carbamate

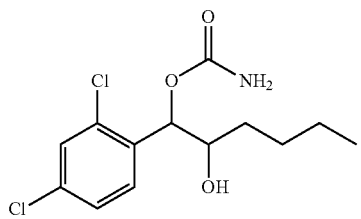 [SMILES: CCCCC(O)C(OC(N)=O)c1ccc(Cl)cc1Cl]

A regioisomer of monocarbamate was separated and purified by conducting the silica gel column chromatography as described in Preparation Example 163, to obtain the title compound (0.21 g, yield 10~30%).

$^1$H NMR (400 MHz, CDCl$_3$) δ0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.30~7.50 (m, 3H)

Preparation Example 217

Synthesis of 1-(2,6-dichlorophenyl)-2-hydroxyhexyl-1-carbamate

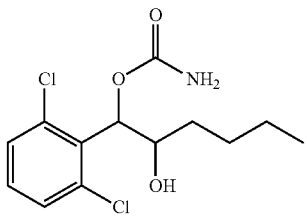 [SMILES: CCCCC(O)C(OC(N)=O)c1c(Cl)cccc1Cl]

A regioisomer of monocarbamate was separated and purified by conducting the silica gel column chromatography as described in Preparation Example 164, to obtain the title compound (0.12 g, yield 10~30%).

$^1$H NMR (400 MHz, CDCl$_3$) δ0.85 (t, J=7.2 Hz, 3H), 1.18~1.33 (m, 4H), 1.48~1.55 (m, 2H), 2.35 (d, J=4.4 Hz, 1H), 4.45~4.50 (m, 1H), 4.76 (br s, 2H), 6.21 (d, J=8.4 Hz, 1H), 7.16~7.34 (m, 3H)

Preparation Example 218

Synthesis of 1-(2-iodophenyl)-(S)-1-hydroxy-3-methyl-butyl-(S)-2-carbamate

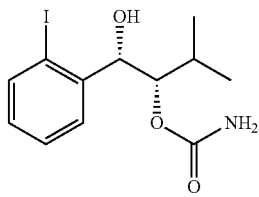 [SMILES: CC(C)[C@H](OC(N)=O)[C@@H](O)c1ccccc1I]

The substantially same method as described in Example 169 was conducted, except that 1-(2-iodophenyl)-3-methyl-(S,S)-1,2-butanediol (Preparation example 83) was used instead of 1-(2-iodophenyl)-(S,S)-1,2-butanediol (Preparation Example 68), to obtain the title compound (1.92 g, yield 20~50%).

$^1$H NMR (400 MHz, CDCl$_3$) δ0.97 (d, J=6.4 Hz, 6H), 2.36~2.52 (m, 1H), 3.34 (s, 1H), 4.80 (br s 2H), 5.04 (t, J=12.5 Hz, 1H), 5.14 (s, 1H), 7.01~7.63 (m, 4H)

Preparation Example 219

Synthesis of 1-(2-iodophenyl)-(S)-1-hydroxyhexyl-(S)-2-carbamate

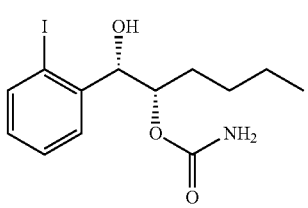 [SMILES: CCCC[C@H](OC(N)=O)[C@@H](O)c1ccccc1I]

The substantially same method as described in Preparation Example 103 was conducted, except that 1-(2-iodophenyl)-(S,S)-1,2-hexanediol obtained in Preparation Example 85 was used instead of 1-(2-chlorophenyl)-(S,S)-1,2-propanediol, to obtain the title compound (1.68 g, yield 30~60%).

$^1$H NMR (400 MHz, CDCl$_3$) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 6.96~7.57 (m, 4H)

Preparation Example 220

Synthesis of 1-(2-iodophenyl)-(S)-1-hydroxypropyl-(S)-2-methylcarbamate

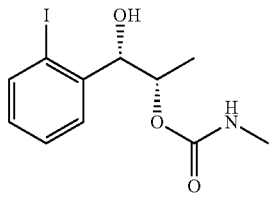

The substantially same method as described in Example 117 was conducted, except that 1-(2-iodophenyl)-(S,S)-1,2-propandiol (Preparation example 66) was used instead of 1-(2-chlorophenyl)-(S,S)-1,2-propanediol (Preparation example 14), to obtain the title compound (1.01 g, yield 20~50%).

$^1$H NMR (400 MHz, CDCl$_3$) δ1.03~1.25 (m, 3H), 2.76 (s, 3H), 3.34 (s, 1H), 4.80 (br s 1H), 5.04 (t, J=12.5 Hz, 1H), 5.14 (s, 1H), 7.01~7.63 (m, 4H)

Preparation Example 221

Synthesis of 1-(2-iodophenyl)-(S)-1-hydroxypropyl-(S)-2-propylcarbamate

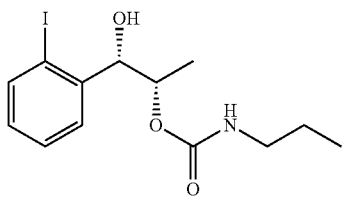 [SMILES: CCCNC(=O)O[C@@H](C)[C@@H](O)c1ccccc1I]

The substantially same method as described in Example 118 was conducted, except that 1-(2-iodophenyl)-(S,S)-1,2-propandiol (Preparation example 66) was used instead of 1-(2-chlorophenyl)-(S,S)-1,2-propanediol (Preparation example 14), to obtain the title compound (0.72 g, yield 20~50%).

$^1$H NMR (400 MHz, CDCl$_3$) δ0.90 (t, J=6.8 Hz, 3H), 1.20 (d, J=5.96 Hz, 3H), 1.49 (dd, J=14.2 Hz, 2H), 3.11 (d, J=6.28 Hz, 2H), 3.34 (s, 1H), 4.84 (br s, 1H), 5.05 (t, J=5.88 Hz, 1H), 5.14 (s, 1H), 7.02~7.63 (m, 4H)

Preparation Example 222

Synthesis of 1-(2-iodophenyl)-(S)-1-hydroxypropyl-(S)-2-isopropylcarbamate

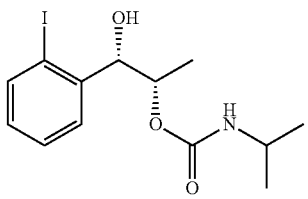 [SMILES: CC(C)NC(=O)O[C@@H](C)[C@@H](O)c1ccccc1I]

The substantially same method as described in Example 119 was conducted, except that 1-(2-iodophenyl)-(S,S)-1,2-propandiol (Preparation example 66) was used instead of 1-(2-chlorophenyl)-(S,S)-1,2-propandiol (Preparation example 14), to obtain the title compound (1.08 g, yield 20~50%).

$^1$H NMR (400 MHz, CDCl$_3$) δ1.14 (dd, J=6.5 Hz, 6H), 1.19 (d, J=6.4 Hz, 3H), 3.21 (s, 1H), 3.73~3.82 (m, 1H), 4.59 (br s, 1H), 5.01~5.07 (m, 1H), 5.14 (t, J=5.8 Hz, 1H), 7.01~7.65 (m, 4H)

Preparation Example 223

Synthesis of 1-(2-iodophenyl)-(S)-1-hydroxypropyl-(S)-2-cyclopropylcarbamate

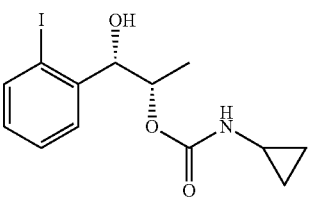 [SMILES: C[C@H](OC(=O)NC1CC1)[C@@H](O)c1ccccc1I]

The substantially same method as described in Example 120 was conducted, except that 1-(2-iodophenyl)-(S,S)-1,2-propandiol (Preparation example 66) was used instead of 1-(2-chlorophenyl)-(S,S)-1,2-propandiol (Preparation example 14), to obtain the title compound (1.02 g, yield 20~50%).

$^1$H NMR (400 MHz, CDCl$_3$) δ0.50~0.56 (m, 2H), 0.74 (d, J=7.21 Hz, 2H), 1.25 (s, 3H), 2.56~2.61 (m, 1H), 3.72 (s, 1H), 4.98 (br s, 1H), 5.05~5.11 (m, 1H), 7.16 (s, 1H), 7.03~7.64 (m, 4H)

Preparation Example 224

Synthesis of 1-(2-iodophenyl)-(S)-1-hydroxypropyl-(S)-2-cyclohexyl carbamate

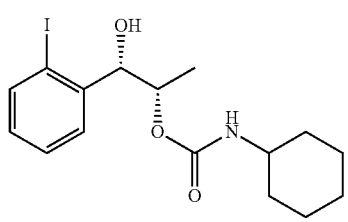 [SMILES: C[C@H](OC(=O)NC1CCCCC1)[C@@H](O)c1ccccc1I]

The substantially same method as described in Example 121 was conducted, except that 1-(2-iodophenyl)-(S,S)-1,2-propandiol (Preparation example 66) was used instead of 1-(2-chlorophenyl)-(S,S)-1,2-propandiol (Preparation example 14), to obtain the title compound (1.84 g, yield 20~50%).

$^1$H NMR (400 MHz, CDCl$_3$) δ1.06~1.40 (m, 7H), 1.56~1.61 (m, 2H), 1.69~1.71 (m, 2H), 1.87~1.94 (m, 2H), 3.19 (d, J=4.32 Hz, 1H), 3.45 (s, 1H), 4.64 (br s 1H), 5.02~5.07 (m, 1H), 5.14 (t, J=6.08 Hz, 1H) 7.02~7.63 (m, 4H)

Preparation Example 225

Synthesis of 1-(2-iodophenyl)-(S)-1-hydroxypropyl-(S)-2-benzyl carbamate

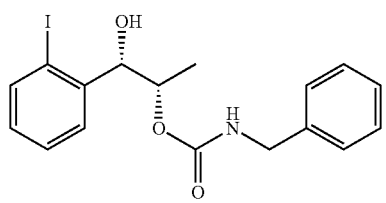 [SMILES: C[C@H](OC(=O)NCc1ccccc1)[C@@H](O)c1ccccc1I]

The substantially same method as described in Example 122 was conducted, except that 1-(2-iodophenyl)-(S,S)-1,2-propandiol (Preparation example 66) was used instead of 1-(2-chlorophenyl)-(S,S)-1,2-propandiol (Preparation example 14), to obtain the title compound (0.72 g, yield 20~50%).

$^1$H NMR (400 MHz, CDCl$_3$) δ 1.27 (d, J=10 Hz, 3H), 3.12 (d, J=5 Hz, 1H), 4.37 (d, J=6 Hz, 2H), 5.12~5.19 (m, 3H), 7.05~7.66 (m, 9H)

Preparation Example 226

Synthesis of 1-(2-chlorophenyl)-(S)-1-hydroxypropyl-(S)-2-bicyclo[2,2,1]heptanescarbamate

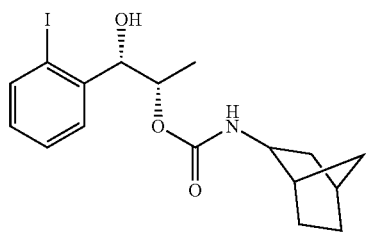 [SMILES: C[C@H](OC(=O)NC1CC2CCC1C2)[C@@H](O)c1ccccc1I]

The substantially same method as described in Example 123 was conducted, except that 1-(2-iodophenyl)-(S,S)-1,2-propandiol (Preparation example 66) was used instead of 1-(2-chlorophenyl)-(S,S)-1,2-propandiol (Preparation example 14), to obtain the title compound (0.82 g, yield 20~50%).

$^1$H NMR (400 MHz, CDCl$_3$) δ1.08~1.35 (m, 9H), 1.65 (br s, 1H), 1.75~1.71 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.02~7.65 (m, 4H)

Preparation Example 227

Synthesis of 1-(2-fluorophenyl)-(S)-1-hydroxypropyl-(S)-2-methylcarbamate

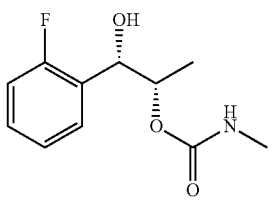 [SMILES: CNC(=O)O[C@@H](C)[C@@H](O)c1ccccc1F]

The substantially same method as described in Example 220 was conducted, except that 1-(2-fluorophenyl)-(S,S)-1,2-propandiol (Preparation example 61) was used instead of 1-(2-iodophenyl)-(S,S)-1,2-propandiol (Preparation example 66), to obtain the title compound (1.19 g, yield 20~50%).

$^1$H NMR (400 MHz, CDCl$_3$) δ1.03~1.25 (m, 314), 2.76 (s, 3H), 3.34 (s, 1H), 4.80 (br s 1H), 5.04 (1, J=12.5 Hz, 1H), 5.14 (s, 1H), 6.90~7.50 (m, 4H)

Preparation Example 228

Synthesis of 1-(2-fluorophenyl)-(S)-1-hydroxypropyl-(S)-2-propylcarbamate

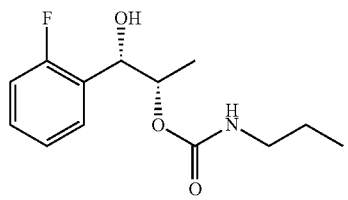

The substantially same method as described in Example 221 was conducted, except that 1-(2-fluorophenyl)-(S,S)-1,2-propandiol (Preparation example 61) was used instead of 1-(2-iodophenyl)-(S,S)-1,2-propandiol (Preparation example 66), to obtain the title compound (0.86 g, yield 20~50%).

$^1$H NMR (400 MHz, CDCl$_3$) δ0.90 (1, J=6.8 Hz, 3H), 1.20 (d, J=5.96 Hz, 3H), 1.49 (dd, J=14.2 Hz, 2H), 3.11 (d, J=6.28 Hz, 2H), 3.34 (s, 1H), 4.84 (br s, 1H), 5.05 (t, J=5.88 Hz, 1H), 5.14 (s, 1H), 6.99~7.53 (m, 4H)

Preparation Example 229

Synthesis of 1-(2-fluorophenyl)-(S)-1-hydroxypropyl-(S)-2-isopropylcarbamate

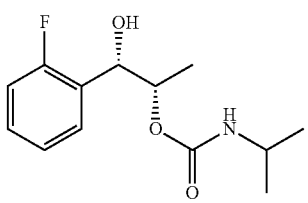

The substantially same method as described in Example 222 was conducted, except that 1-(2-fluorophenyl)-(S,S)-1,2-propandiol (Preparation example 61) was used instead of 1-(2-iodophenyl)-(S,S)-1,2-propandiol (Preparation example 66), to obtain the title compound (0.48 g, yield 20~50%).

$^1$H NMR (400 MHz, CDCl$_3$) δ1.14 (dd, J=6.5 Hz, 6H), 1.19 (d, J=6.4 Hz, 3H), 3.21 (s, 1H), 3.73~3.82 (m, 1H), 4.59 (br s, 1H), 5.01~5.07 (m, 1H), 5.14 (t, J=5.8 Hz, 1H), 7.01~7.62 (m, 4H)

Preparation Example 230

Synthesis of 1-(2-fluorophenyl)-(S)-1-hydroxypropyl-(S)-2-cyclopropylcarbamate

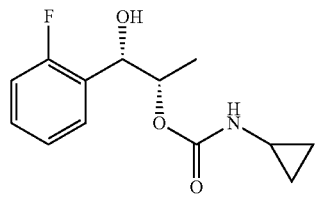 [SMILES: C[C@H](OC(=O)NC1CC1)[C@@H](O)c1ccccc1F]

The substantially same method as described in Example 223 was conducted, except that 1-(2-fluorophenyl)-(S,S)-1,2-propandiol (Preparation example 61) was used instead of 1-(2-iodophenyl)-(S,S)-1,2-propandiol (Preparation example 66), to obtain the title compound (0.39 g, yield 20~50%)

$^1$H NMR (400 MHz, CDCl$_3$) δ0.50~0.56 (m, 2H), 0.74 (d, J=7.21 Hz, 2H), 1.25 (s, 3H), 2.56~2.61 (m, 1H), 3.72 (s, 1H), 4.98 (br s, 1H), 5.05~5.11 (m, 1H), 7.16 (s, 1H), 7.01~7.65 (m, 4H)

Preparation Example 231

Synthesis of 1-(2-fluorophenyl)-(S)-1-hydroxypropyl-(S)-2-cyclohexyl carbamate

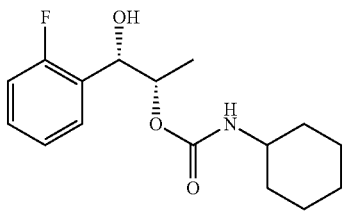

The substantially same method as described in Example 225 was conducted, except that 1-(2-fluorophenyl)-(S,S)-1,2-propandiol (Preparation example 61) was used instead of 1-(2-iodophenyl)-(S,S)-1,2-propandiol (Preparation example 66), to obtain the title compound (0.54 g, yield 20~50%)

$^1$H NMR (400 MHz, CDCl$_3$) δ1.06~1.40 (m, 7H), 1.56~1.61 (m, 2H), 1.69~1.71 (m, 2H), 1.87~1.94 (m, 2H), 3.19 (d, J=4.32 Hz, 1H), 3.45 (s, 1H), 4.64 (br s 1H), 5.02~5.07 (m, 1H), 5.14 (t, J=6.08 Hz, 1H) 7.00~7.65 (m, 4H)

Preparation Example 232

Synthesis of 1-(2-fluorophenyl)-(S)-1-hydroxypropyl-(S)-2-benzyl carbamate

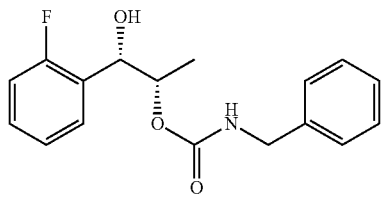

The substantially same method as described in Example 226 was conducted, except that 1-(2-fluorophenyl)-(S,S)-1,2-propandiol (Preparation example 61) was used instead of 1-(2-iodophenyl)-(S,S)-1,2-propandiol (Preparation example 66), to obtain the title compound (0.39 g, yield 20~50%)

$^1$H NMR (400 MHz, CDCl$_3$) δ 1.27 (d, J=10 Hz, 3H), 3.12 (d, J=5 Hz, 1H), 4.37 (d, J=6 Hz, 2H), 5.12~5.19 (m, 3H), 7.01~7.67 (m, 9H)

Preparation Example 233

Synthesis of 1-(2-fluorophenyl)-(S)-1-hydroxypropyl-(S)-2-bicyclo[2,2,1]heptanescarbamate

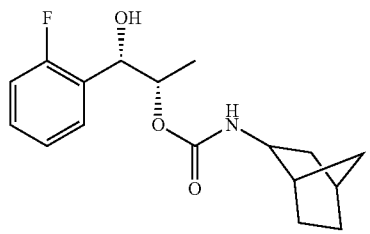

The substantially same method as described in Example 227 was conducted, except that 1-(2-fluorophenyl)-(S,S)-1,2-propandiol (Preparation example 61) was used instead of 1-(2-iodophenyl)-(S,S)-1,2-propandiol (Preparation example 66), to obtain the title compound (0.57 g, yield 20~50%)

$^1$H NMR (400 MHz, CDCl$_3$) δ1.08~1.35 (m, 9H), 1.65 (br s, 1H), 1.75~1.71 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.01~7.66 (m, 4H)

Preparation Example 234

Synthesis of 1-(2-iodophenyl)-(S)-1-hydroxybutyl-(S)-2-methylcarbamate

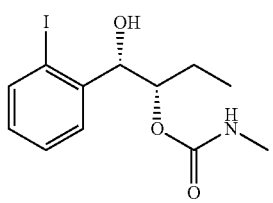 [SMILES: CC[C@H](OC(=O)NC)[C@@H](O)c1ccccc1I]

The substantially same method as described in Example 117 was conducted, except that 1-(2-iodophenyl)-(S,S)-1,2-butanediol (Preparation example 68) was used instead of 1-(2-iodophenyl)-(S,S)-1,2-propandiol (Preparation example 66), to obtain the title compound (1.81 g, yield 20~50%).

$^1$H NMR (400 MHz, CDCl$_3$) δ0.97 (d, J=6.4 Hz, 3H), 1.56 (m, 2H), 2.76 (s, 3H), 3.34 (s, 1H), 4.80 (br s 1H), 5.04 (t, J=12.5 Hz, 1H), 5.14 (s, 1H), 7.01~7.63 (m, 4H)

Preparation Example 235

Synthesis of 1-(2-iodophenyl)-(S)-1-hydroxybutyl-(S)-2-propylcarbamate

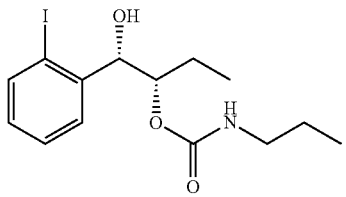 [SMILES: CCCNC(=O)O[C@@H](CC)[C@@H](O)c1ccccc1I]

The substantially same method as described in Example 118 was conducted, except that 1-(2-iodophenyl)-(S,S)-1,2-butanediol (Preparation example 68) was used instead of 1-(2-iodophenyl)-(S,S)-1,2-propandiol (Preparation example 66), to obtain the title compound (0.92 g, yield 20~50%).

$^1$H NMR (400 MHz, CDCl$_3$) δ0.90 (t, J=6.8 Hz, 3H), 1.20 (d, J=5.96 Hz, 3H), 1.49 (dd, J=14.2 Hz, 2H), 1.57 (m, 2H), 3.11 (d, J=6.28 Hz, 2H), 3.34 (s, 1H), 4.84 (br s, 1H), 5.05 (t, J=5.88 Hz, 1H), 5.14 (s, 1H), 7.02~7.63 (m, 4H)

Preparation Example 236

Synthesis of 1-(2-iodophenyl)-(S)-1-hydroxybutyl-(S)-2-isopropylcarbamate

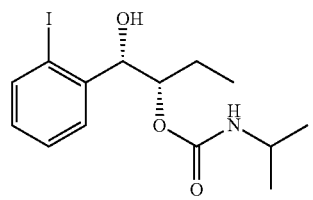 [SMILES: CC[C@H](OC(=O)NC(C)C)[C@@H](O)c1ccccc1I]

The substantially same method as described in Example 119 was conducted, except that 1-(2-iodophenyl)-(S,S)-1,2-butanediol (Preparation example 68) was used instead of 1-(2-chlorophenyl)-(S,S)-1,2-propandiol (Preparation example 14), to obtain the title compound (1.28 g, yield 20~50%).

$^1$H NMR (400 MHz, CDCl$_3$) δ0.96 (t, J=6.8 Hz, 3H), 1.14 (dd, J=6.5 Hz, 6H), 1.57 (m, 2H), 3.21 (s, 1H), 3.73~3.82 (m, 1H), 4.59 (br s, 1H), 5.01~5.07 (m, 1H), 5.14 (t, J=5.8 Hz, 1H), 7.01~7.65 (m, 4H)

Preparation Example 237

Synthesis of 1-(2-iodophenyl)-(S)-1-hydroxybutyl-(S)-2-cyclopropylcarbamate

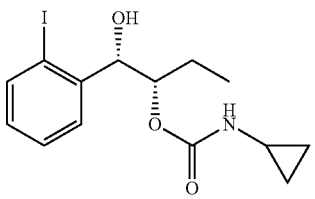 [SMILES: CC[C@H](OC(=O)NC1CC1)[C@@H](O)c1ccccc1I]

The substantially same method as described in Example 120 was conducted, except that 1-(2-iodophenyl)-(S,S)-1,2-butanediol (Preparation example 68) was used instead of 1-(2-chlorophenyl)-(S,S)-1,2-propandiol (Preparation example 14), to obtain the title compound (1.51 g, yield 20~50%).

$^1$H NMR (400 MHz, CDCl$_3$) δ0.50~0.56 (m, 2H), 0.74 (d, J=7.21 Hz, 2H), 0.96 (t, J=6.8 Hz, 3H), 1.25 (m, 2H), 2.56~2.61 (m, 1H), 3.72 (s, 1H), 4.98 (br s, 1H), 5.05~5.11 (m, 1H), 7.16 (s, 1H), 6.96~7.57 (m, 4H)

Preparation Example 238

Synthesis of 1-(2-iodophenyl)-(S)-1-hydroxybutyl-(S)-2-cyclohexyl carbamate

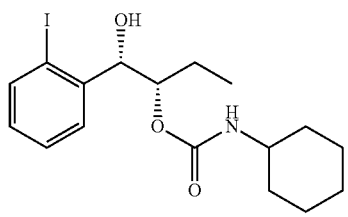 [SMILES: CC[C@H](OC(=O)NC1CCCCC1)[C@@H](O)c1ccccc1I]

The substantially same method as described in Example 121 was conducted, except that 1-(2-iodophenyl)-(S,S)-1,2-butanediol (Preparation example 68) was used instead of 1-(2-chlorophenyl)-(S,S)-1,2-propandiol (Preparation example 14), to obtain the title compound (1.92 g, yield 20~50%).

$^1$H NMR (400 MHz, CDCl$_3$) δ0.96 (t, J=6.8 Hz, 3H), 1.06~1.40 (m, 7H), 1.56~1.61 (m, 2H), 1.69~1.71 (m, 2H), 1.87~1.94 (m, 2H), 3.19 (d, J=4.32 Hz, 1H), 3.45 (s, 1H), 4.64 (br s 1H), 5.02~5.07 (m, 1H), 5.14 (t, J=6.08 Hz, 1H) 7.02~7.63 (m, 4H)

Preparation Example 239

Synthesis of 1-(2-iodophenyl)-(S)-1-hydroxybutyl-(S)-2-benzyl carbamate

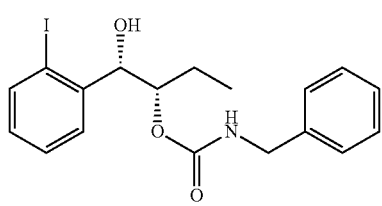 [SMILES: CC[C@H](OC(=O)NCc1ccccc1)[C@@H](O)c1ccccc1I]

The substantially same method as described in Example 122 was conducted, except that 1-(2-iodophenyl)-(S,S)-1,2-butanediol (Preparation example 68) was used instead of 1-(2-chlorophenyl)-(S,S)-1,2-propandiol (Preparation example 14), to obtain the title compound (1.52 g, yield 20~50%).

$^1$H NMR (400 MHz, CDCl$_3$) δ 0.96 (t, J=6.8 Hz, 3H), 1.55~1.62 (m, 2H), 3.12 (d, J=5 Hz, 1H), 4.37 (d, J=6 Hz, 2H), 5.12~5.19 (m, 3H), 7.05~7.66 (m, 9H)

Preparation Example 240

Synthesis of 1-(2-chlorophenyl)-(S)-1-hydroxybutyl-(S)-2-bicyclo[2,2,1]heptanescarbamate

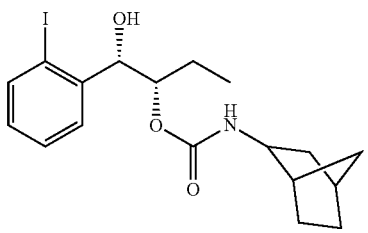 [SMILES: CC[C@H](OC(=O)NC1CC2CCC1C2)[C@@H](O)c1ccccc1I]

The substantially same method as described in Example 123 was conducted, except that 1-(2-iodophenyl)-(S,S)-1,2-butanediol (Preparation example 68) was used instead of 1-(2-chlorophenyl)-(S,S)-1,2-propandiol (Preparation example 14), to obtain the title compound (1.08 g, yield 20~50%).

$^1$H NMR (400 MHz, CDCl$_3$) δ0.96 (t, J=6.8 Hz, 3H), 1.08~1.35 (m, 6H), 1.55~1.62 (m, 2H), 1.65 (br s, 1H), 1.75~1.71 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.02~7.65 (m, 4H)

Preparation Example 241

Synthesis of 1-(2-iodophenyl)-(S)-1-hydroxy-3-methyl-butyl-(S)-2-methylcarbamate

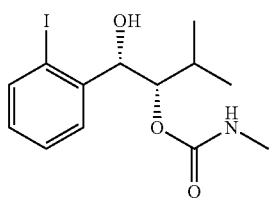 [SMILES: CNC(=O)O[C@@H](C(C)C)[C@@H](O)c1ccccc1I]

The substantially same method as described in Example 117 was conducted, except that 1-(2-iodophenyl)-3-methyl-(S,S)-1,2-butanediol (Preparation example 83) was used instead of 1-(2-iodophenyl)-(S,S)-1,2-propandiol (Preparation example 66), to obtain the title compound (1.92 g, yield 20~50%).

$^1$H NMR (400 MHz, CDCl$_3$) δ0.97 (d, J=6.4 Hz, 6H), 2.36~2.52 (m, 1H), 2.76 (s, 3H), 3.34 (s, 1H), 4.80 (br s 1H), 5.04 (t, J=12.5 Hz, 1H), 5.14 (s, 1H), 7.01~7.63 (m, 4H)

Preparation Example 242

Synthesis of 1-(2-iodophenyl)-(S)-1-hydroxy-3-methyl-butyl-(S)-2-propylcarbamate

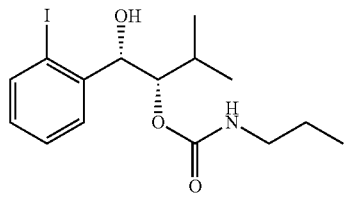 [SMILES: CCCNC(=O)O[C@@H](C(C)C)[C@@H](O)c1ccccc1I]

The substantially same method as described in Example 118 was conducted, except that 1-(2-iodophenyl)-3-methyl-(S,S)-1,2-butanediol (Preparation example 83) was used instead of 1-(2-iodophenyl)-(S,S)-1,2-propandiol (Preparation example 66), to obtain the title compound (1.82 g, yield 20~50%).

$^1$H NMR (400 MHz, CDCl$_3$) δ0.96 (1, J=6.8 Hz, 3H), 1.10 (d, J=6.4 Hz, 6H), 1.49 (dd, J=14.2 Hz, 2H), 2.38~2.42 (m, 1H), 3.11 (d, J=6.28 Hz, 2H), 3.34 (s, 1H), 4.84 (br s, 1H), 5.05 (t, J=5.88 Hz, 1H), 5.14 (s, 1H), 7.02~7.63 (m, 4H)

Preparation Example 243

Synthesis of 1-(2-iodophenyl)-(S)-1-hydroxy-3-methyl-butyl-(S)-2-isopropylcarbamate

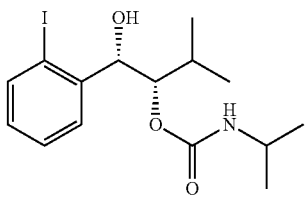 [SMILES: CC(C)NC(=O)O[C@@H](C(C)C)[C@@H](O)c1ccccc1I]

The substantially same method as described in Example 119 was conducted, except that 1-(2-iodophenyl)-3-methyl-(S,S)-1,2-butanediol (Preparation example 83) was used instead of 1-(2-chlorophenyl)-(S,S)-1,2-propandiol (Preparation example 14), to obtain the title compound (1.77 g, yield 20~50%).

$^1$H NMR (400 MHz, CDCl$_3$) δ1.01 (d, J=6.8 Hz, 6H), 1.14 (d, J=6.5 Hz, 6H), 2.39~2.47 (m, 1H), 3.90~3.98 (m, 1H), 3.73~3.82 (m, 1H), 4.59 (br s, 1H), 5.01~5.07 (m, 1H), 5.14 (t, J=5.8 Hz, 1H), 7.01~7.65 (m, 4H)

Preparation Example 244

Synthesis of 1-(2-iodophenyl)-(S)-1-hydroxy-3-methyl-butyl-(S)-2-cyclopropylcarbamate

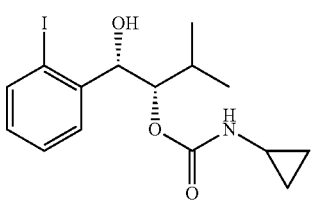 [SMILES: CC(C)[C@H](OC(=O)NC1CC1)[C@@H](O)c1ccccc1I]

The substantially same method as described in Example 120 was conducted, except that 1-(2-iodophenyl)-3-methyl-(S,S)-1,2-butanediol (Preparation example 83) was used instead of 1-(2-chlorophenyl)-(S,S)-1,2-propandiol (Preparation example 14), to obtain the title compound (1.81 g, yield 20~50%).

$^1$H NMR (400 MHz, CDCl$_3$) δ0.50~0.56 (m, 2H), 0.74 (d, J=7.21 Hz, 2H), 1.01 (d, J=6.8 Hz, 6H), 2.38~2.44 (m, 1H), 2.56~2.61 (m, 1H), 3.72 (s, 1H), 4.98 (br s, 1H), 5.05~5.11 (m, 1H), 7.16 (s, 1H), 6.96~7.57 (m, 4H)

Preparation Example 245

Synthesis of 1-(2-iodophenyl)-(S)-1-hydroxy-3-methyl-butyl-(S)-2-cyclohexyl carbamate

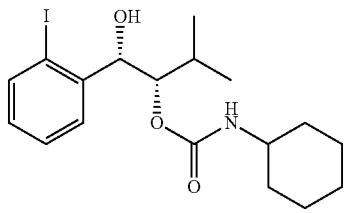 [SMILES: CC(C)[C@H](OC(=O)NC1CCCCC1)[C@@H](O)c1ccccc1I]

The substantially same method as described in Example 121 was conducted, except that 1-(2-iodophenyl)-3-methyl-(S,S)-1,2-butanediol (Preparation example 83) was used instead of 1-(2-chlorophenyl)-(S,S)-1,2-propandiol (Preparation example 14), to obtain the title compound (1.29 g, yield 20~50%).

$^1$H NMR (400 MHz, CDCl$_3$) δ1.01 (d, J=6.8 Hz, 6H), 1.11~1.21 (m, 4H), 1.47~1.49 (m, 4H), 1.69~1.71 (m, 2H), 2.38~2.44 (m, 1H), 3.19 (d, J=4.32 Hz, 1H), 3.45 (s, 1H), 4.64 (br s 1H), 5.02~5.07 (m, 1H), 5.14 (t, J=6.08 Hz, 1H) 7.02~7.63 (m, 4H)

Preparation Example 246

Synthesis of 1-(2-iodophenyl)-(S)-1-hydroxy-3-methyl-butyl-(S)-2-benzyl carbamate

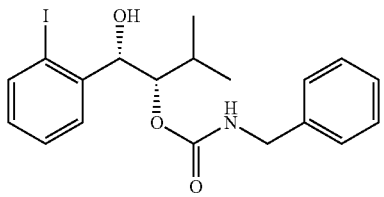 [SMILES: CC(C)[C@H](OC(=O)NCc1ccccc1)[C@@H](O)c1ccccc1I]

The substantially same method as described in Example 122 was conducted, except that 1-(2-iodophenyl)-(S,S)-1,2-butanediol (Preparation example 68) was used instead of 1-(2-chlorophenyl)-(S,S)-1,2-propandiol (Preparation example 14), to obtain the title compound (1.91 g, yield 20~50%).

$^1$H NMR (400 MHz, CDCl$_3$) δ 1.10 (d, J=6.8 Hz, 3H), 2.42 (m, 1H), 3.12 (d, J=5 Hz, 1H), 4.37 (d, J=6 Hz, 2H), 5.12~5.19 (m, 3H), 7.05~7.66 (m, 9H)

Preparation Example 247

Synthesis of 1-(2-chlorophenyl)-(S)-1-hydroxy-3-methyl-butyl-(S)-2-bicyclo[2,2,1]heptanescarbamate

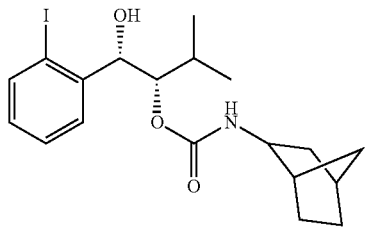 [SMILES: CC(C)[C@H](OC(=O)NC1CC2CCC1C2)[C@@H](O)c1ccccc1I]

The substantially same method as described in Example 123 was conducted, except that 1-(2-iodophenyl)-(S,S)-1,2-butanediol (Preparation example 68) was used instead of 1-(2-chlorophenyl)-(S,S)-1,2-propandiol (Preparation example 14), to obtain the title compound (1.68 g, yield 20~50%).

$^1$H NMR (400 MHz, CDCl$_3$) δ1.01 (d, J=6.8 Hz, 6H), 1.08~1.35 (m, 6H), 1.55~1.62 (m, 2H), 1.65 (br s, 1H), 1.75~1.71 (m, 1H), 2.14~2.24 (m, 1H), 2.42 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.02~7.65 (m, 4H)

Preparation Example 248

Synthesis of 1-(2-iodophenyl)-(S)-1-hydroxyhexyl-(S)-2-methylcarbamate

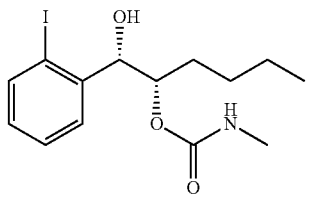 [SMILES: CCCC[C@H](OC(=O)NC)[C@@H](O)c1ccccc1I]

The substantially same method as described in Example 117 was conducted, except that 1-(2-iodophenyl)-(S,S)-1,2-hexanediol (Preparation example 85) was used instead of 1-(2-iodophenyl)-(S,S)-1,2-propandiol (Preparation example 66), to obtain the title compound (1.58 g, yield 20~50%).

$^1$H NMR (400 MHz, CDCl$_3$) δ0.97 (t, J=6.4 Hz, 3H), 1.29~1.33 (m, 4H), 1.53 (m, 2H), 2.76 (s, 3H), 3.34 (s, 1H), 4.80 (br s 1H), 5.04 (t, J=12.5 Hz, 1H), 5.14 (s, 1H), 7.01~7.63 (m, 4H)

Preparation Example 249

Synthesis of 1-(2-iodophenyl)-(S)-1-hydroxyhexyl-(S)-2-propylcarbamate

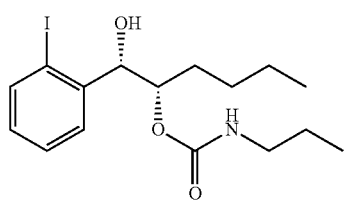 [SMILES: CCCC[C@H](OC(=O)NCCC)[C@@H](O)c1ccccc1I]

The substantially same method as described in Example 118 was conducted, except that 1-(2-iodophenyl)-(S,S)-1,2-hexanediol (Preparation example 85) was used instead of 1-(2-iodophenyl)-(S,S)-1,2-propandiol (Preparation example 66), to obtain the title compound (1.38 g, yield 20~50%).

$^1$H NMR (400 MHz, CDCl$_3$) δ0.96 (t, J=6.8 Hz, 3H), 0.97 (t, J=6.4 Hz, 3H), 1.29~1.33 (m, 4H), 1.53 (m, 2H), 1.55~1.60 (m, 2H), 2.96 (t, J=6.0, 2H), 3.34 (s, 1H), 4.84 (br s, 1H), 5.05 (t, J=5.88 Hz, 1H), 5.14 (s, 1H), 7.02~7.63 (m, 4H)

Preparation Example 250

Synthesis of 1-(2-iodophenyl)-(S)-1-hydroxyhexyl-(S)-2-isopropylcarbamate

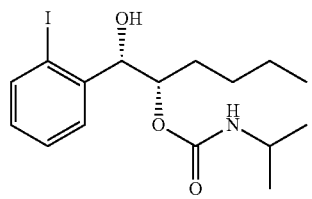 [SMILES: CCCC[C@H](OC(=O)NC(C)C)[C@@H](O)c1ccccc1I]

The substantially same method as described in Example 119 was conducted, except that 1-(2-iodophenyl)-(S,S)-1,2-hexanediol (Preparation example 85) was used instead of 1-(2-chlorophenyl)-(S,S)-1,2-propandiol (Preparation example 14), to obtain the title compound (1.73 g, yield 20~50%).

$^1$H NMR (400 MHz, CDCl$_3$) δ0.97 (t, J=6.4 Hz, 3H), 1.14 (d, J=6.5 Hz, 6H), 1.29~1.33 (m, 4H), 1.53 (m, 2H), 3.90~3.98 (m, 1H), 3.73~3.82 (m, 1H), 4.59 (br s, 1H), 5.01~5.07 (m, 1H), 5.14 (t, J=5.8 Hz, 1H), 7.01~7.65 (m, 4H)

Preparation Example 251

Synthesis of 1-(2-iodophenyl)-(S)-1-hydroxyhexyl-(S)-2-cyclopropylcarbamate

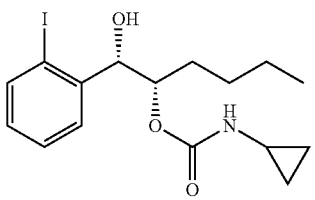 [SMILES: CCCC[C@H](OC(=O)NC1CC1)[C@@H](O)c1ccccc1I]

The substantially same method as described in Example 120 was conducted, except that 1-(2-iodophenyl)-(S,S)-1,2-hexanediol (Preparation example 85) was used instead of 1-(2-chlorophenyl)-(S,S)-1,2-propandiol (Preparation example 14), to obtain the title compound (1.81 g, yield 20~50%).

$^1$H NMR (400 MHz, CDCl$_3$) δ0.50~0.56 (m, 2H), 0.74 (d, J=7.21 Hz, 2H), 0.97 (t, J=6.4 Hz, 3H), 1.29~1.33 (m, 4H), 1.53 (m, 2H), 2.38~2.44 (m, 1H), 3.72 (s, 1H), 4.98 (br s, 1H), 5.05~5.11 (m, 1H), 7.16 (s, 1H), 6.96~7.57 (m, 4H)

Preparation Example 252

Synthesis of 1-(2-iodophenyl)-(S)-1-hydroxyhexyl-(S)-2-cyclohexyl carbamate

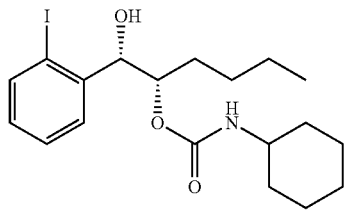 [SMILES: CCCC[C@H](OC(=O)NC1CCCCC1)[C@@H](O)c1ccccc1I]

The substantially same method as described in Example 121 was conducted, except that 1-(2-iodophenyl)-(S,S)-1,2-hexanediol (Preparation example 85) was used instead of 1-(2-chlorophenyl)-(S,S)-1,2-propandiol (Preparation example 14), to obtain the title compound (1.79 g, yield 20~50%).

$^1$H NMR (400 MHz, CDCl$_3$) δ0.97 (1, J=6.4 Hz, 3H), 1.11~1.21 (m, 4H), 1.29~1.33 (m, 4H), 1.47~1.49 (m, 4H), 1.53 (m, 2H), 1.69~1.71 (m, 2H), 3.19 (d, J=4.32 Hz, 1H), 3.45 (s, 1H), 4.64 (br s 1H), 5.02~5.07 (m, 1H), 5.14 (t, J=6.08 Hz, 1H) 7.02~7.63 (m, 4H)

Preparation Example 253

Synthesis of 1-(2-iodophenyl)-(S)-1-hydroxyhexyl-(S)-2-benzyl carbamate

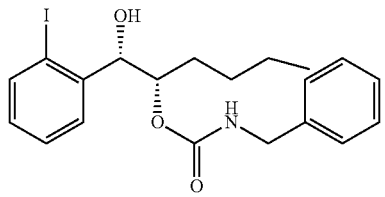 [SMILES: CCCC[C@H](OC(=O)NCc1ccccc1)[C@@H](O)c1ccccc1I]

The substantially same method as described in Example 122 was conducted, except that 1-(2-iodophenyl)-(S,S)-1,2-hexanediol (Preparation example 85) was used instead of 1-(2-chlorophenyl)-(S,S)-1,2-propandiol (Preparation example 14), to obtain the title compound (1.51 g, yield 20~50%).

$^1$H NMR (400 MHz, CDCl$_3$) δ0.97 (t, J=6.4 Hz, 3H), 1.29~1.33 (m, 4H), 1.53 (m, 2H), 3.12 (d, J=5 Hz, 1H), 4.37 (d, J=6 Hz, 2H), 5.12~5.19 (m, 3H), 7.05~7.66 (m, 9H)

Preparation Example 254

Synthesis of 1-(2-chlorophenyl)-(S)-1-hydroxyhexyl-(S)-2-bicyclo[2,2,1]heptanescarbamate

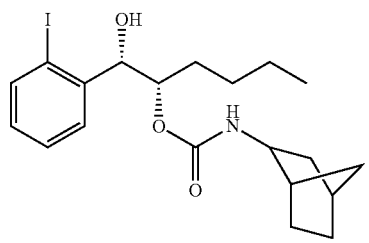 [SMILES: CCCC[C@H](OC(=O)NC1CC2CCC1C2)[C@@H](O)c1ccccc1I]

The substantially same method as described in Example 123 was conducted, except that 1-(2-iodophenyl)-(S,S)-1,2-butanediol (Preparation example 68) was used instead of 1-(2-chlorophenyl)-(S,S)-1,2-propandiol (Preparation example 14), to obtain the title compound (1.68 g, yield 20~50%).

$^1$H NMR (400 MHz, CDCl$_3$) δ0.97 (t, J=6.4 Hz, 3H), 1.08~1.35 (m, 6H), 1.29~1.33 (m, 4H), 1.53 (m, 2H), 1.55~1.62 (m, 2H), 1.65 (br s, 1H), 1.75~1.71 (m, 1H), 2.14~2.24 (m, 1H), 2.27~2.30 (m, 1H), 3.23~3.29 (m, 1H), 3.47~3.52 (m, 1H), 4.67 (br s, 1H), 5.01~5.09 (m, 1H), 5.12~5.18 (m, 1H), 7.02~7.65 (m, 4H)

Preparation Example 255

Synthesis of 1-(3-iodophenyl)-(S)-1-hydroxypropyl-(S)-2-carbamate

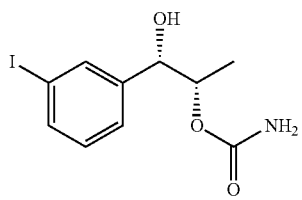

The substantially same method as described in Preparation Example 103 was conducted, except that 1-(3-iodophenyl)-(S,S)-1,2-butanediol obtained in Preparation Example 87 was used instead of 1-(2-chlorophenyl)-(S,S)-1,2-propanediol, to obtain the title compound (2.04 g, yield 30~60%).

$^1$H NMR (400 MHz, CDCl$_3$) δ0.96 (t. J=7.4 Hz, 3H), 1.53~1.73 (m, 2H), 3.09 (br s, 1H), 4.83 (br s, 2H), 5.00~5.10 (m, 2H), 6.96~7.57 (m, 4H)

Preparation Example 256

Synthesis of 1-(3-iodophenyl)-(S)-1-hydroxybutyl-(S)-2-carbamate

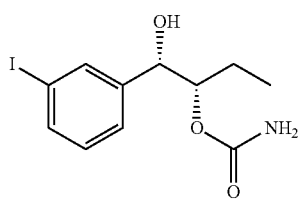 [SMILES: CC[C@H](OC(N)=O)[C@@H](O)c1cccc(I)c1]

The substantially same method as described in Preparation Example 103 was conducted, except that 1-(3-iodophenyl)-(S,S)-1,2-butanediol obtained in Preparation Example 89 was used instead of 1-(2-chlorophenyl)-(S,S)-1,2-propanediol, to obtain the title compound (1.49 g, yield 30~60%).

$^1$H NMR (400 MHz, CDCl$_3$) δ0.96 (t. J=7.4 Hz, 3H), 1.53~1.73 (m, 2H), 3.09 (br s, 1H), 4.83 (br s, 2H), 5.00~5.10 (m, 2H), 6.92~7.51 (m, 4H)

Preparation Example 257

Synthesis of 1-(3-iodophenyl)-(S)-1-hydroxy-3-methyl-butyl-(S)-2-carbamate

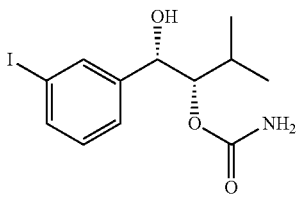 [SMILES: CC(C)[C@H](OC(N)=O)[C@@H](O)c1cccc(I)c1]

The substantially same method as described in Preparation Example 103 was conducted, except that 1-(3-iodophenyl)-3-methyl-(S,S)-1,2-butanediol obtained in Preparation Example 91 was used instead of 1-(2-chlorophenyl)-(S,S)-1,2-propanediol, to obtain the title compound (1.82 g, yield 30~60%).

$^1$H NMR (400 MHz, CDCl$_3$) δ 61.00 (1, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 6.97~7.53 (m, 4H)

Preparation Example 258

Synthesis of 1-(3-iodophenyl)-(S)-1-hydroxyhexyl-(S)-2-carbamate

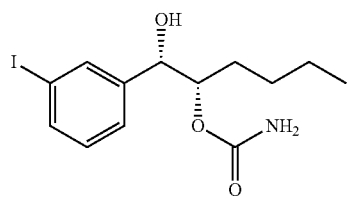 [SMILES: CCCC[C@H](OC(N)=O)[C@@H](O)c1cccc(I)c1]

The substantially same method as described in Preparation Example 103 was conducted, except that 1-(3-iodophenyl)-(S,S)-1,2-hexanediol obtained in Preparation Example 93 was used instead of 1-(2-chlorophenyl)-(S,S)-1,2-propanediol, to obtain the title compound (1.92 g, yield 30~60%).

$^1$H NMR (400 MHz, CDCl$_3$) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 7.01~7.55 (m, 4H)

Preparation Example 259

Synthesis of 1-(4-fluorophenyl)-(S)-1-hydroxypropyl-(S)-2-carbamate

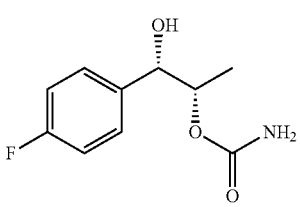

The substantially same method as described in Preparation Example 103 was conducted, except that 1-(4-fluorophenyl)-(S,S)-1,2-propanediol obtained in Preparation Example 95 was used instead of 1-(2-chlorophenyl)-(S,S)-1,2-propanediol, to obtain the title compound (1.61 g, yield 30~60%).

$^1$H NMR (400 MHz, CDCl$_3$) δ1.27 (d, J=6.4 Hz, 3H), 3.09 (br s, 1H), 4.83 (br s, 2H), 5.00~5.10 (m, 2H), 6.89~7.05 (m, 4H)

Preparation Example 260

Synthesis of 1-(4-fluorophenyl)-(S)-1-hydroxybutyl-(S)-2-carbamate

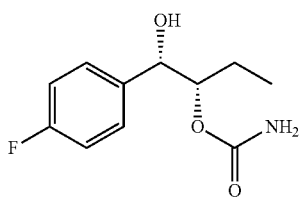 [SMILES: CC[C@H](OC(N)=O)[C@@H](O)c1ccc(F)cc1]

The substantially same method as described in Preparation Example 103 was conducted, except that 1-(4-fluorophenyl)-(S,S)-1,2-butanediol obtained in Preparation Example 97 was used instead of 1-(2-chlorophenyl)-(S,S)-1,2-propanediol, to obtain the title compound (1.55 g, yield 30~60%).

$^1$H NMR (400 MHz, CDCl$_3$) δ0.96 (t. J=7.4 Hz, 3H), 1.53~1.73 (m, 2H), 3.09 (br s, 1H), 4.83 (br s, 2H), 5.00~5.10 (m, 2H), 6.92~7.09 (m, 4H)

Preparation Example 261

Synthesis of 1-(4-fluorophenyl)-(S)-1-hydroxy-3-methyl-butyl-(S)-2-carbamate

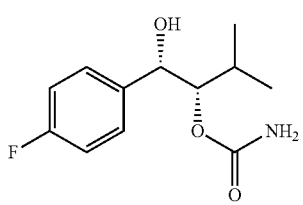 [SMILES: CC(C)[C@H](OC(N)=O)[C@@H](O)c1ccc(F)cc1]

The substantially same method as described in Preparation Example 103 was conducted, except that 1-(4-fluorophenyl)-3-methyl-(S,S)-1,2-butanediol obtained in Preparation Example 99 was used instead of 1-(2-chlorophenyl)-(S,S)-1,2-propanediol, to obtain the title compound (1.97 g, yield 30~60%).

$^1$H NMR (400 MHz, CDCl$_3$) δ 61.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 6.94~7.03 (m, 4H)

Preparation Example 262

Synthesis of 1-(4-fluorophenyl)-(S)-1-hydroxy-hexyyl-(S)-2-carbamate

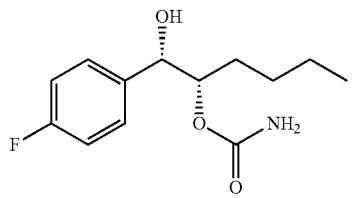 [SMILES: CCCC[C@H](OC(N)=O)[C@@H](O)c1ccc(F)cc1]

The substantially same method as described in Preparation Example 103 was conducted, except that 1-(4-fluorophenyl)-(S,S)-1,2-hexanediol obtained in Preparation Example 101 was used instead of 1-(2-chlorophenyl)-(S,S)-1,2-propanediol, to obtain the title compound (1.86 g, yield 30~60%).

$^1$H NMR (400 MHz, CDCl$_3$) δ0.84 (1, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 6.95~7.17 (m, 4H)

Preparation Example 263

Synthesis of 1-(2-iodophenyl)-(R)-1-hydroxybutyl-(R)-2-carbamate

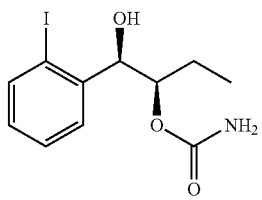 [SMILES: CC[C@@H](OC(N)=O)[C@H](O)c1ccccc1I]

The substantially same method as described in Preparation Example 103 was conducted, except that 1-(2-iodophenyl)-(R,R)-1,2-butanediol obtained in Preparation Example 69 was used instead of 1-(2-chlorophenyl)-(S,S)-1,2-propanediol, to obtain the title compound (1.98 g, yield 30~60%).

$^1$H NMR (400 MHz, CDCl$_3$) δ1.27 (d, J=6.4 Hz, 3H), 3.09 (br s, 1H), 4.83 (br s, 2H), 5.00~5.10 (m, 2H), 7.00~7.76 (m, 4H)

Preparation Example 264

Synthesis of 1-(2-iodophenyl)-(R)-1-hydroxy-3-methyl-butyl-(R)-2-carbamate

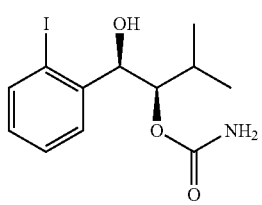 [SMILES: CC(C)[C@@H](OC(N)=O)[C@H](O)c1ccccc1I]

The substantially same method as described in Example 169 was conducted, except that 1-(2-iodophenyl)-3-methyl-(R,R)-1,2-butanediol (Preparation example 84) was used instead of 1-(2-iodophenyl)-(S,S)-1,2-butanediol (Preparation Example 68), to obtain the title compound (1.88 g, yield 20~50%).

$^1$H NMR (400 MHz, CDCl$_3$) δ0.97 (d, J=6.4 Hz, 6H), 2.36~2.52 (m, 1H), 3.34 (s, 1H), 4.80 (br s 2H), 5.04 (t, J=12.5 Hz, 1H), 5.14 (s, 1H), 7.01~7.63 (m, 4H)

Preparation Example 265

Synthesis of 1-(2-iodophenyl)-(R)-1-hydroxyhexyl-(R)-2-carbamate

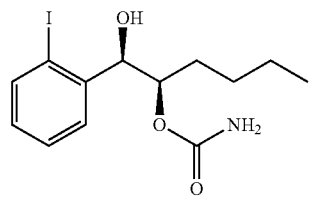 [SMILES: CCCC[C@@H](OC(N)=O)[C@H](O)c1ccccc1I]

The substantially same method as described in Preparation Example 103 was conducted, except that 1-(2-iodophenyl)-(R,R)-1,2-hexanediol obtained in Preparation Example 86 was used instead of 1-(2-chlorophenyl)-(S,S)-1,2-propanediol, to obtain the title compound (1.68 g, yield 30~60%).

$^1$H NMR (400 MHz, CDCl$_3$) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 6.99~7.55 (m, 4H)

Preparation Example 266

Synthesis of 1-(4-fluorophenyl)-(R)-1-hydroxypropyl-(R)-2-carbamate

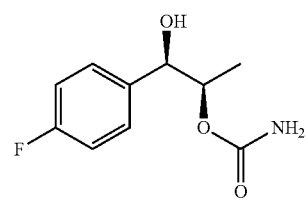

The substantially same method as described in Preparation Example 103 was conducted, except that 1-(4-fluorophenyl)-(R,R)-1,2-propanediol obtained in Preparation Example 96 was used instead of 1-(2-chlorophenyl)-(S,S)-1,2-propanediol, to obtain the title compound (1.49 g, yield 30~60%).

$^1$H NMR (400 MHz, CDCl$_3$) δ1.27 (d, J=6.4 Hz, 3H), 3.09 (br s, 1H), 4.83 (br s, 2H), 5.00~5.10 (m, 2H), 7.00~7.22 (m, 4H)

Preparation Example 267

Synthesis of 1-(4-fluorophenyl)-(R)-1-hydroxybutyl-(R)-2-carbamate

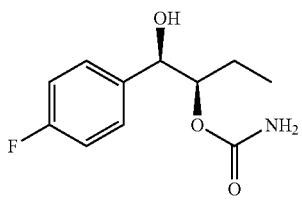 [SMILES: CC[C@@H](OC(N)=O)[C@H](O)c1ccc(F)cc1]

The substantially same method as described in Preparation Example 103 was conducted, except that 1-(4-fluorophenyl)-(R,R)-1,2-butanediol obtained in Preparation Example 98 was used instead of 1-(2-chlorophenyl)-(S,S)-1,2-propanediol, to obtain the title compound (2.25 g, yield 30~60%).

$^1$H NMR (400 MHz, CDCl$_3$) δ0.96 (t. J=7.4 Hz, 3H), 1.53~1.73 (m, 2H), 3.09 (br s, 1H), 4.83 (br s, 2H), 5.00~5.10 (m, 2H), 6.92~7.20 (m, 4H)

Preparation Example 268

Synthesis of 1-(4-fluorophenyl)-(R)-1-hydroxy-3-methyl-butyl-(R)-2-carbamate

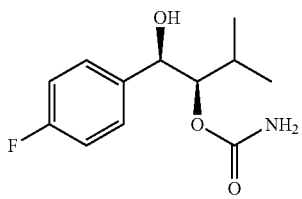 [SMILES: CC(C)[C@@H](OC(N)=O)[C@H](O)c1ccc(F)cc1]

The substantially same method as described in Preparation Example 103 was conducted, except that 1-(4-fluorophenyl)-3-methyl-(R,R)-1,2-butanediol obtained in Preparation Example 100 was used instead of 1-(2-chlorophenyl)-(S,S)-1,2-propanediol, to obtain the title compound (1.74 g, yield 30~60%).

$^1$H NMR (400 MHz, CDCl$_3$) δ 61.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 6.92~7.20 (m, 4H)

Preparation Example 269

Synthesis of 1-(4-fluorophenyl)-(R)-1-hydroxy-hexyyl-(R)-2-carbamate

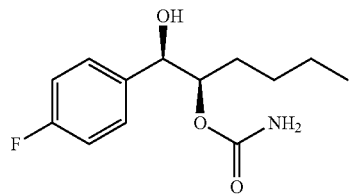 [SMILES: CCCC[C@@H](OC(N)=O)[C@H](O)c1ccc(F)cc1]

The substantially same method as described in Preparation Example 103 was conducted, except that 1-(4-fluorophenyl)-(R,R)-1,2-hexanediol obtained in Preparation Example 102 was used instead of 1-(2-chlorophenyl)-(S,S)-1,2-propanediol, to obtain the title compound (1.59 g, yield 30~60%).

$^1$H NMR (400 MHz, CDCl$_3$) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 6.95~7.21 (m, 4H)

Preparation Example 270

Synthesis of 1-(3-iodophenyl)-(R)-1-hydroxypropyl-(R)-2-carbamate

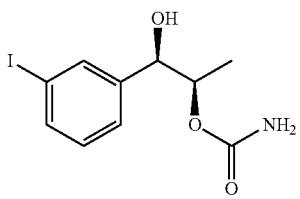

The substantially same method as described in Preparation Example 103 was conducted, except that 1-(3-iodophenyl)-(R,R)-1,2-butanediol obtained in Preparation Example 88 was used instead of 1-(2-chlorophenyl)-(S,S)-1,2-propanediol, to obtain the title compound (1.54 g, yield 30~60%).

$^1$H NMR (400 MHz, CDCl$_3$) δ0.96 (t. J=7.4 Hz, 3H), 1.53~1.73 (m, 2H), 3.09 (br s, 1H), 4.83 (br s, 2H), 5.00~5.10 (m, 2H), 6.96~7.57 (m, 4H)

Preparation Example 271

Synthesis of 1-(3-iodophenyl)-(R)-1-hydroxybutyl-(R)-2-carbamate

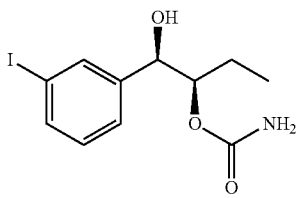 [SMILES: CC[C@@H](OC(N)=O)[C@H](O)c1cccc(I)c1]

The substantially same method as described in Preparation Example 103 was conducted, except that 1-(3-iodophenyl)-(R,R)-1,2-butanediol obtained in Preparation Example 90 was used instead of 1-(2-chlorophenyl)-(S,S)-1,2-propanediol, to obtain the title compound (1.44 g, yield 30~60%).

$^1$H NMR (400 MHz, CDCl$_3$) δ0.96 (t. J=7.4 Hz, 3H), 1.53~1.73 (m, 2H), 3.09 (br s, 1H), 4.83 (br s, 2H), 5.00~5.10 (m, 2H), 6.92~7.51 (m, 4H)

Preparation Example 272

Synthesis of 1-(3-iodophenyl)-(R)-1-hydroxy-3-methyl-butyl-(R)-2-carbamate

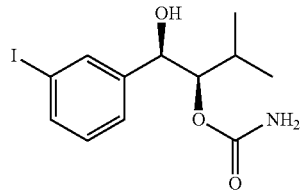 [SMILES: CC(C)[C@@H](OC(N)=O)[C@H](O)c1cccc(I)c1]

The substantially same method as described in Preparation Example 103 was conducted, except that 1-(3-iodophenyl)-3-methyl-(R,R)-1,2-butanediol obtained in Preparation Example 92 was used instead of 1-(2-chlorophenyl)-(S,S)-1,2-propanediol, to obtain the title compound (1.65 g, yield 30~60%).
$^1$H NMR (400 MHz, CDCl$_3$) δ δ1.00 (t, J=7.2 Hz, 6H), 1.73~1.79 (m, 1H), 3.67~3.69 (m, 1H), 4.85 (br s, 2H), 5.40~5.43 (m, 1H), 5.49~5.54 (m, 1H), 6.97~7.53 (m, 4H)

Preparation Example 273

Synthesis of 1-(3-iodophenyl)-(R)-1-hydroxy-hexyyl-(R)-2-carbamate

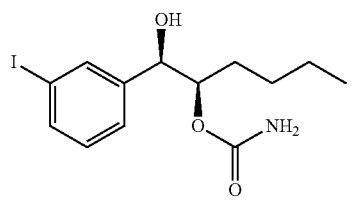 [SMILES: CCCC[C@@H](OC(N)=O)[C@H](O)c1cccc(I)c1]

The substantially same method as described in Preparation Example 103 was conducted, except that 1-(3-iodophenyl)-(R,R)-1,2-hexanediol obtained in Preparation Example 94 was used instead of 1-(2-chlorophenyl)-(S,S)-1,2-propanediol, to obtain the title compound (1.71 g, yield 30~60%).
$^1$H NMR (400 MHz, CDCl$_3$) δ0.84 (t, J=7.0 Hz, 3H), 1.20~1.35 (m, 4H), 1.36~1.41 (m, 1H), 1.59~1.63 (m, 1H), 3.71 (d, J=10.0 Hz, 1H), 4.74 (br s, 2H), 5.40~5.44 (m, 1H), 5.52~5.57 (m, 1H), 7.01~7.55 (m, 4H)

Preparation Example 274

Synthesis of 1-(2,6-difluorophenyl)-trans-1-propene

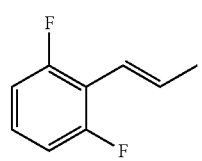

The substantially same method as described in Preparation Example 1 was conducted, except that 2,6-difluorobenzenaldehyde was used instead of 2-chlorobenzenaldehyde, to obtain the title compound (3.4 g, yield 52%).
$^1$H NMR (400 MHz, CDCl$_3$) δ1.95 (dd, J=6.8 Hz, 1.6 Hz, 3H), 6.24 (m, 1H), 6.72 (d, J=15.6 Hz, 1H), 7.18~7.44 (m, 3H)

Preparation Example 275

Synthesis of 1-(2,6-difluorophenyl)-(S,S)-1,2-propanediol

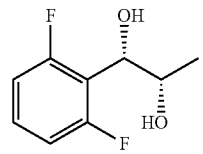

The substantially same method as described in Preparation Example 14 was conducted, except that 1-(2,6-difluorophenyl)-trans-1-propene (Preparation Example 275) was used instead of 1-(2-chlorophenyl)-trans-1-propene (Preparation Example 1), to obtain the title compound (1.5 g, yield 60~90%).
$^1$H NMR (400 MHz, CDCl$_3$) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.18~7.36 (m, 3H)

Preparation Example 276

Synthesis of 1-(2,6-difluorophenyl)-(S)-1-hydroxy-propyl-(S)-2-carbamate

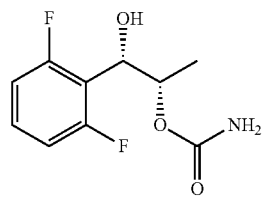 [SMILES: C[C@H](OC(N)=O)[C@@H](O)c1c(F)cccc1F]

The substantially same method as described in Preparation Example 103 was conducted, except that 1-(2,6-difluorophenyl)-1,2-propanediol (Preparation Example 275) was used instead of 1-(2-chlorophenyl)-(S,S)-1,2-propanediol, to obtain the title compound (2.4 g, yield 20~60%).
$^1$H NMR (400 MHz, CDCl$_3$) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H),

Preparation Example 277

Synthesis of 1-(2,5-dichlorophenyl)-trans-1-propene

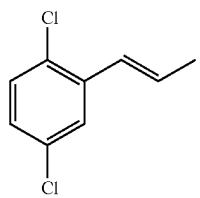

The substantially same method as described in Preparation Example 1 was conducted, except that 2,5-dichlorobenzenaldehyde was used instead of 2-chlorobenzenaldehyde, to obtain the title compound (3.1 g, yield 52%).

¹H NMR (400 MHz, CDCl₃) δ1.95 (dd, J=6.8 Hz, 1.6 Hz, 3H), 6.24 (m, 1H), 6.72 (d, J=15.6 Hz, 1H), 7.09~7.25 (m, 3H)

Preparation Example 278

Synthesis of 1-(2,5-dichlorophenyl)-(S,S)-1,2-propanediol

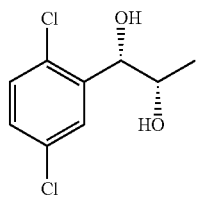

The substantially same method as described in Preparation Example 14 was conducted, except that 1-(2,5-dichlorophenyl)-trans-1-propene (Preparation Example 277) was used instead of 1-(2-chlorophenyl)-trans-1-propene (Preparation Example 1), to obtain the title compound (1.9 g, yield 60~90%).

¹H NMR (400 MHz, CDCl₃) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.14~7.26 (m, 3H)

Preparation Example 279

Synthesis of 1-(2,5-dichlorophenyl)-1-hydroxypropyl-2-carbamate

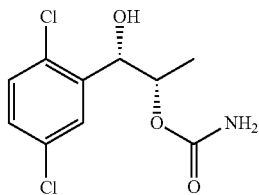 [SMILES: C[C@H](OC(N)=O)[C@@H](O)c1cc(Cl)ccc1Cl]

The substantially same method as described in Preparation Example 103 was conducted, except that 1-(2,5-dichlorophenyl)-1,2-propanediol (Preparation Example 278) was used instead of 1-(2-chlorophenyl)-(S,S)-1,2-propanediol, to obtain the title compound (2.29 g, yield 20~60%).

¹H NMR (400 MHz, CDCl₃) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.18~7.22 (m, 3H)

Preparation Example 280

Synthesis of 1-(2,5-dichlorophenyl)-(R,R)-1,2-propanediol

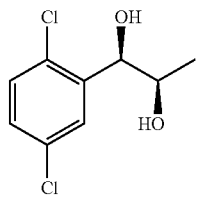

The substantially same method as described in Preparation Example 15 was conducted, except that 1-(2,5-dichlorophenyl)-trans-1-propene (Preparation Example 277) was used instead of 1-(2-chlorophenyl)-trans-1-propene (Preparation Example 1), to obtain the title compound (2.3 g, yield 60~90%).

¹H NMR (400 MHz, CDCl₃) δ1.10 (d, J=6.4 Hz, 3H), 2.72 (d, J=2.4 Hz, 1H), 3.10 (d, J=8.4 Hz, 1H), 4.47~4.54 (m, 1H), 5.24 (t, J=8.8 Hz, 1H), 7.14~7.26 (m, 3H)

Preparation Example 281

Synthesis of 1-(2,5-dichlorophenyl)-(R)-1-hydroxypropyl-(R)-2-carbamate

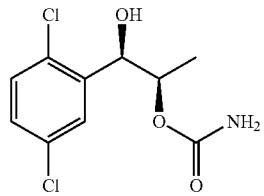 [SMILES: C[C@@H](OC(N)=O)[C@H](O)c1cc(Cl)ccc1Cl]

The substantially same method as described in Preparation Example 103 was conducted, except that 1-(2,5-dichlorophenyl)-1,2-propanediol (Preparation Example 278) was used instead of 1-(2-chlorophenyl)-(S,S)-1,2-propanediol, to obtain the title compound (2.25 g, yield 20~60%).

¹H NMR (400 MHz, CDCl₃) δ1.15 (d, J=6.4 Hz, 3H), 3.66 (d, J=9.2 Hz, 1H), 4.73 (br s, 2H), 5.43 (t, J=9.0 Hz, 1H), 5.62~5.69 (m, 1H), 7.13~7.25 (m, 3H)

Preparation Example 282

Synthesis of 1-(2-chlorophenyl)-1-(S)-1,2-ethanediol

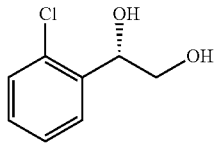 [SMILES: OC[C@@H](O)c1ccccc1Cl]

The substantially same method as described in Preparation Example 14 was conducted, except that 2-chlorostyrene (Aldrich No. 160679) was used instead of 1-(2-chlorophenyl)-trans-1-propene (Preparation Example 1), to obtain the title compound (2.29 g, yield 60~90%).

¹H NMR (400 MHz, CDCl₃) δ 2.72 (d, J=2.4 Hz, 1H), 3.10 (d, J=8.4 Hz, 1H), 4.47~4.54 (m, 1H), 4.91 (t, J=8.8 Hz, 1H), 7.09~7.26 (m, 4H)

Preparation Example 283

Synthesis of 1-(2-chlorophenyl)-(S)-1-hydroxyethyl-2-carbamate

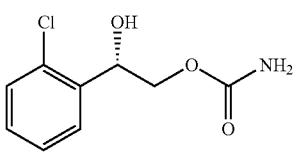

The substantially same method as described in Preparation Example 103 was conducted, except that 1-(2-chlorophenyl)-1-(S)-1,2-ethanediol (Preparation Example 282)

was used instead of 1-(2-chlorophenyl)-(S,S)-1,2-propanediol, to obtain the title compound (1.92 g, yield 20~60%).

$^1$H NMR (400 MHz, CDCl$_3$) δ 1.72 (br s, 1H), 4.26 (dd, J=12.0, 7.8 Hz, 1H), 4.39 (dd, J=12.0, 2.7 Hz, 1H), 4.41 (dd, J=7.8, 2.7 Hz, 1H), 4.77 (br 2H), 7.26~7.68 (m, 4H)

Preparation Example 284

Synthesis of 2-iodostyrene

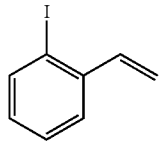

The substantially same method as described in Preparation Example 64 was conducted, except that 2-propanone was used instead of 3-pentanone, to obtain the title compound (2.1 g, yield 20~40%).

$^1$H NMR (400 MHz, CDCl$_3$) δ5.34 (dd, J=10.8, 0.8 Hz, 1H), 5.65 (dd, J=17.2, 0.8 Hz, 1H), 6.89~7.92 (m, 5H)

Preparation Example 285

Synthesis of 1-(2-iodophenyl)-1-(S)-1,2-ethanediol

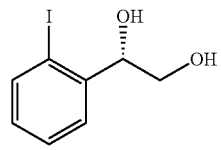 [SMILES: OC[C@@H](O)c1ccccc1I]

The substantially same method as described in Preparation Example 14 was conducted, except that 2-iodostyrene (Preparation Example 284) was used instead of 1-(2-chlorophenyl)-trans-1-propene (Preparation Example 1), to obtain the title compound (2.52 g, yield 60~90%).

$^1$H NMR (400 MHz, CDCl$_3$) δ 2.07~2.13 (m, 1H), 3.52~3.58 (m, 1H), 3.89~3.94 (m, 1H), 5.04~5.08 (m, 1H), 7.01~7.85 (m, 4H)

Preparation Example 286

Synthesis of 1-(2-iodophenyl)-(S)-1-hydroxyethyl-2-carbamate

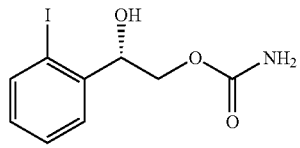 [SMILES: NC(=O)OC[C@@H](O)c1ccccc1I]

The substantially same method as described in Preparation Example 103 was conducted, except that 1-(2-chlorophenyl)-1-(S)-1,2-ethanediol (Preparation Example 282) was used instead of 1-(2-chlorophenyl)-(S,S)-1,2-propanediol, to obtain the title compound (1.92 g, yield 20~60%).

$^1$H NMR (400 MHz, CDCl$_3$) δ 1.72 (br s, 1H), 4.26 (dd, J=12.0, 7.8 Hz, 1H), 4.39 (dd, J=12.0, 2.7 Hz, 1H), 4.41 (dd, J=7.8, 2.7 Hz, 1H), 4.77 (br 2H), 7.06~7.29 (m, 4H)

Preparation Example 287

Synthesis of 2-fluorostyrene

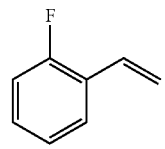

The substantially same method as described in Preparation Example 284 was conducted, except that 2-fluorobenzaldehyde (Aldrich No. F4807) was used instead of 2-iodobenzaldehyde (Preparation Example 63) to obtain the title compound (1.82 g, yield 20~40%).

$^1$H NMR (400 MHz, CDCl$_3$) δ5.34 (dd, J=10.8, 0.8 Hz, 1H), 5.65 (dd, J=17.2, 0.8 Hz, 1H), 6.92~7.89 (m, 5H)

Preparation Example 285

Synthesis of 1-(2-fluorophenyl)-1-(S)-1,2-ethanediol

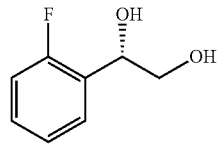 [SMILES: OC[C@@H](O)c1ccccc1F]

The substantially same method as described in Preparation Example 14 was conducted, except that 2-fluorostyrene (Preparation Example 287) was used instead of 1-(2-chlorophenyl)-trans-1-propene (Preparation Example 1), to obtain the title compound (2.32 g, yield 60~90%).

$^1$H NMR (400 MHz, CDCl$_3$) δ 2.07~2.13 (m, 1H), 3.52~3.58 (m, 1H), 3.89~3.94 (m, 1H), 5.04~5.08 (m, 1H), 6.90~7.17 (m, 4H)

Preparation Example 286

Synthesis of 1-(2-fluorophenyl)-(S)-1-hydroxyethyl-2-carbamate

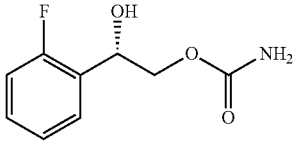 [SMILES: NC(=O)OC[C@@H](O)c1ccccc1F]

The substantially same method as described in Preparation Example 103 was conducted, except that 1-(2-fluorophenyl)-1-(S)-1,2-ethanediol (Preparation Example 285) was used instead of 1-(2-chlorophenyl)-(S,S)-1,2-propanediol, to obtain the title compound (1.59 g, yield 20~60%).

¹H NMR (400 MHz, CDCl₃) δ 1.72 (br s, 1H), 4.26 (dd, J=12.0, 7.8 Hz, 1H), 4.39 (dd, J=12.0, 2.7 Hz, 1H), 4.41 (dd, J=7.8, 2.7 Hz, 1H), 4.77 (br 2H), 7.01~7.27 (m, 4H)

Preparation Example 287

Synthesis of 1-(2-chloro-6-fluorophenyl)-trans-1-propene

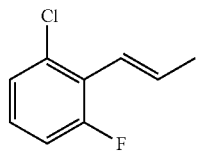

The substantially same method as described in Preparation Example 1 was conducted, except that 2-chloro-6-fluorobenzaldehyde was used instead of 2-chlorobenzaldehyde, to obtain the title compound (2.7 g, yield 40~80%).
¹H NMR (400 MHz, CDCl₃) δ 1.65 (d, J=7.2, 3H), 6.03~6.11 (m, 1H), 6.24 (d, J=11.2, 1H), 6.97~7.23 (m, 3H)

Preparation Example 288

Synthesis of 1-(2-chloro-6-fluorophenyl)-(S,S)-1,2-propanediol

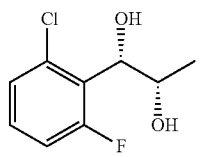

The substantially same method as described in Preparation Example 14 was conducted, except that 1-(2-chloro-6-fluorophenyl)-trans-1-propene (Preparation Example 287) was used instead of 1-(2-chlorophenyl)-trans-1-propene (Preparation Example 1), to obtain the title compound (1.6 g, yield 70~90%).
¹H NMR (400 MHz, CDCl₃) δ 1.13 (d, J=5.6, 3H), 2.78 (s, 1H), 2.92 (s, 1H), 4.17 (s, 1H), 5.01 (s, 1H) 6.03~6.11 (m, 1H), 6.24 (d, J=11.2, 1H), 6.97~7.23 (m, 3H)

Preparation Example 289

Synthesis of 1-(2-chloro-6-fluorophenyl)-(R,R)-1,2-propanediol

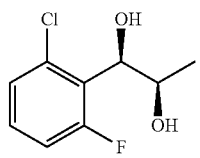

The substantially same method as described in Preparation Example 15 was conducted, except that 1-(2-chloro-6-fluorophenyl)-trans-1-propene (Preparation Example 287) was used instead of 1-(2-chlorophenyl)-trans-1-propene (Preparation Example 1), to obtain the title compound (1.9 g, yield 70~90%).

Preparation Example 290

Synthesis of 1-(2-chloro-6-fluorophenyl)-(S)-1-hydroxypropyl-(S)-2-carbamate

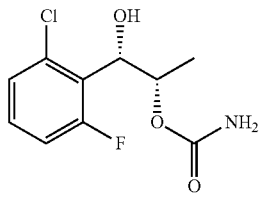 [SMILES: C[C@H](OC(N)=O)[C@@H](O)c1c(F)cccc1Cl]

The substantially same method as described in Preparation Example 103 was conducted, except that 1-(2-chloro-6-fluorophenyl)-(S,S)-1,2-propanediol (Preparation Example 288) was used instead of 1-(2-chlorophenyl)-(S,S)-1,2-propanediol (Preparation Example 14), to obtain the title compound (0.8 g, yield 30~60%).
¹H NMR (400 MHz, DMSO) δ 0.99 (d, J=6.4, 3H), 5.06 (d, J=8.8, 1H), 5.14~5.18 (m, 1H), 5.70 (s, 1H), 6.46 (brs, 2H), 7.19~7.40 (m, 3H)

Preparation Example 291

Synthesis of 1-(2-chloro-6-fluorophenyl)-(R)-1-hydroxypropyl-(R)-2-carbamate

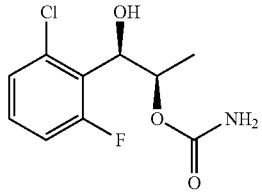 [SMILES: C[C@@H](OC(N)=O)[C@H](O)c1c(F)cccc1Cl]

The substantially same method as described in Preparation Example 103 was conducted, except that 1-(2-chloro-6-fluorophenyl)-(R,R)-1,2-propanediol (Preparation Example 289) was used instead of 1-(2-chlorophenyl)-(S,S)-1,2-propanediol (Preparation Example 14), to obtain the title compound (0.6 g, yield 30~60%).

Preparation Example 292

Synthesis of 1-(2-fluorophenyl)-(S)-2-hydroxypropyl-(S)-1-carbamate

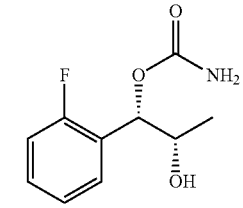

A regioisomer of monocarbamate was separated and purified by conducting the silica gel column chromatography as described in Preparation Example 165, to obtain the title compound (0.25 g, yield 10~30%).

$^1$H NMR (400 MHz, CDCl$_3$) δ1.12 (d, J=6.8, 3H), 2.46 (d, J=4.0, 1H), 4.61~4.70 (m, 1H), 4.74 (br s, 2H), 6.19 (d, J=8.8, 1H), 7.28~7.49 (m, 4H).

Preparation Example 293

Synthesis of 1-(2-iodophenyl)-(S)-2-hydroxypropyl-(S)-1-carbamate

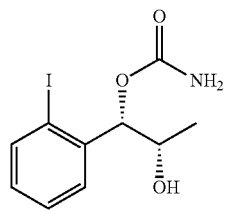

A regioisomer of monocarbamate was separated and purified by conducting the silica gel column chromatography as described in Preparation Example 167, to obtain the title compound (0.1.7 g, yield 10~30%).

$^1$H NMR (400 MHz, CDCl$_3$) δ1.15 (d, J=6.8, 3H), 2.47 (d, J=4.0, 1H), 4.76~4.82 (m, 1H), 4.76 (br s, 2H), 6.23 (d, J=8.8, 1H), 7.31~7.52 (m, 4H).

$^1$H NMR (400 MHz, CDCl$_3$) δ1.28 (d, J=8.4, 3H), 2.10 (d, J=5.2, 1H), 4.12~4.16 (m, 1H), 4.84 (brs, 2H), 5.79 (s, J=5.2, 1H), 7.0~7.39 (m, 3H), 7.87 (d, J=8.4, 1H)

Example Scheme I

Synthesis of 1-(n-halophenyl)-1-methoxymethoxyalkyl-2-alkylcarbamate (Examples 1 to 123, 271 to 274, 276 to 278 and 282, 284)

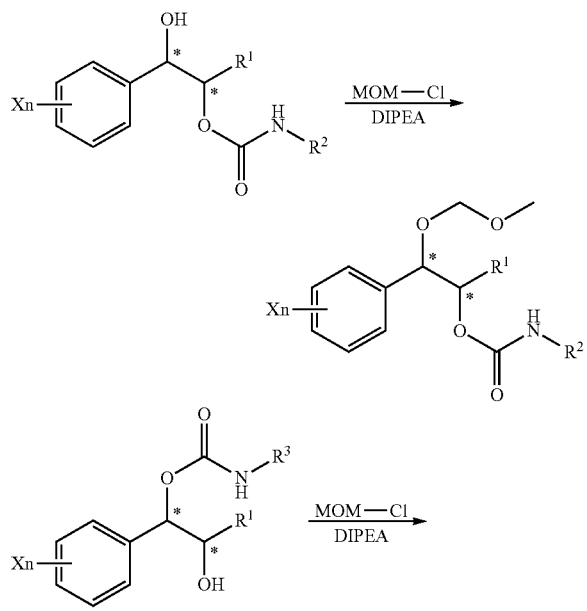

To a stirred solution of 1-(n-halophenyl)-1-hydorxyalkyl-2-alkylcarbamate in MC (Methylenechloloride) was added DIPEA (Diisopropylethylamine) at 0° C. under N$_2$ condition. The mixture was added MOM-Cl (MOMchloride) at 0° C. then slowly warm to R.T. When the reaction was completed, the obtained product was washed with H$_2$O and MC. The separated organic layer was dehydrated with anhydrous MgSO$_4$(Magnesium sulfate), filtrated, and concentrated under reduced pressure. The concentrated residue was purified by a silicagel aolumn chromatography, to obtain title compound (Yield 40~60%)

Example Scheme II

Synthesis of 1-(n-halophenyl)-1-methoxyalkyl-2-alkylcarbamate (Examples 124 to 246, 275, 279 to 281 and 283, 285)

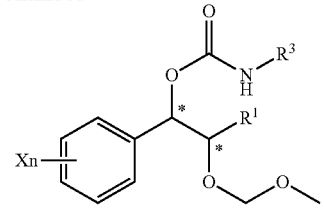

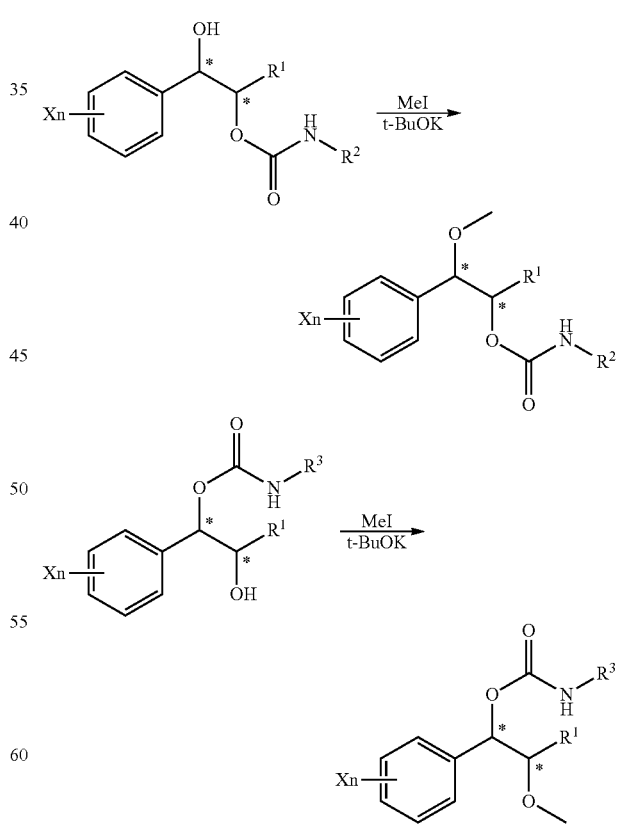

1-(n-halophenyl)-1-hydorxyalkyl-2-alkylcarbamate, THF (Tetrahydrofuran), MeI (Methyliodide) and t-BuOH (Potassium tert-butoxide) were put into a flask and stirred at the 0°

C. When the reaction was completed, the obtained product was washed with 1M HCl solution and EA (Ethylacetate). The separated organic layer was dehydrated with anhydrous MgSO4 (Magnesium sulfate), filtrated, and concentrated under reduced pressure. The concentrated residue was purified by a silicagel column chromatography, to obtain title compound (Yield 204~0%)

Example Scheme III

Synthesis of 1-(n-halophenyl)-1-carbamoyloxyalkyl-2-alkylcarbamate (Examples 247 to 270 and 286 to 295)

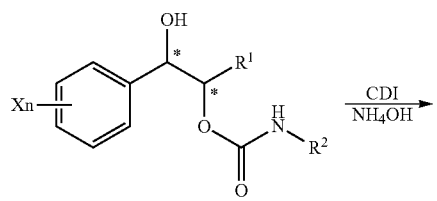

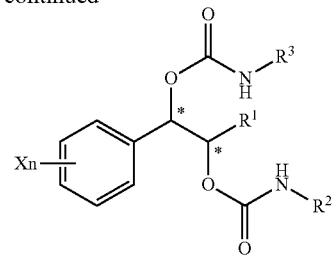

1-(n-halophenyl)-1-hydroxypropyl-1-carbamate, tetrahydrofuran (THF), and carbonyldiimidazole (CDI) were put into a flask and stirred at the room temperature. After approximately 3 hours, ammonia solution (NH4OH) was added thereto. When the reaction was completed, the obtained product was washed with 1M HCl solution and ethylacetate (EA). The separated organic layer was dehydrated with anhydrous MgSO4(Magnesium sulfate), filtrated, and concentrated under reduced pressure. The concentrated residue was purified by a silica gel column chromatography, to obtain the title compound (yield 75~95%).

According to the above described methods, the compounds as defined in following Tables 1 and 2 were prepared.

TABLE 1

Carbamate derivetives (B is not a carbamoyl derivative)

| Example | X | Position | A | B | $R^1$ | $R^2$ | Chiral-1 | Chiral-2 |
|---|---|---|---|---|---|---|---|---|
| 1 | Cl | 2 | Carbamoyl | MOM | Me | H | S | S |
| 2 | Cl | 2 | Carbamoyl | MOM | Me | Me | S | S |
| 3 | Cl | 2 | Carbamoyl | MOM | Me | Propyl | S | S |
| 4 | Cl | 2 | Carbamoyl | MOM | Me | Isopropyl | S | S |
| 5 | Cl | 2 | Carbamoyl | MOM | Me | Cyclopropyl | S | S |
| 6 | Cl | 2 | Carbamoyl | MOM | Me | Cyclohexyl | S | S |
| 7 | Cl | 2 | Carbamoyl | MOM | Me | Benzyl | S | S |
| 8 | Cl | 2 | Carbamoyl | MOM | Me | Bicycloheptyl | S | S |
| 9 | Cl | 2 | Carbamoyl | MOM | Et | H | S | S |
| 10 | Cl | 2 | Carbamoyl | MOM | Isopropyl | H | S | S |
| 11 | Cl | 2 | Carbamoyl | MOM | Butyl | H | S | S |
| 12 | F | 2 | Carbamoyl | MOM | Me | H | S | S |
| 13 | F | 2 | Carbamoyl | MOM | Me | Me | S | S |
| 14 | F | 2 | Carbamoyl | MOM | Me | Propyl | S | S |
| 15 | F | 2 | Carbamoyl | MOM | Me | Isopropyl | S | S |
| 16 | F | 2 | Carbamoyl | MOM | Me | Cyclopropyl | S | S |
| 17 | F | 2 | Carbamoyl | MOM | Me | Cyclohexyl | S | S |
| 18 | F | 2 | Carbamoyl | MOM | Me | Benzyl | S | S |
| 19 | F | 2 | Carbamoyl | MOM | Me | Bicycloheptyl | S | S |
| 20 | I | 2 | Carbamoyl | MOM | Me | H | S | S |
| 21 | I | 2 | Carbamoyl | MOM | Me | Me | S | S |
| 22 | I | 2 | Carbamoyl | MOM | Me | Propyl | S | S |
| 23 | I | 2 | Carbamoyl | MOM | Me | Isopropyl | S | S |
| 24 | I | 2 | Carbamoyl | MOM | Me | Cyclopropyl | S | S |
| 25 | I | 2 | Carbamoyl | MOM | Me | Cyclohexyl | S | S |
| 26 | I | 2 | Carbamoyl | MOM | Me | Benzyl | S | S |
| 27 | I | 2 | Carbamoyl | MOM | Me | Bicycloheptyl | S | S |
| 28 | I | 2 | Carbamoyl | MOM | Et | H | S | S |
| 29 | I | 2 | Carbamoyl | MOM | Et | Me | S | S |
| 30 | I | 2 | Carbamoyl | MOM | Et | Propyl | S | S |
| 31 | I | 2 | Carbamoyl | MOM | Et | Isopropyl | S | S |
| 32 | I | 2 | Carbamoyl | MOM | Et | Cyclopropyl | S | S |
| 33 | I | 2 | Carbamoyl | MOM | Et | Cyclohexyl | S | S |
| 34 | I | 2 | Carbamoyl | MOM | Et | Benzyl | S | S |
| 35 | I | 2 | Carbamoyl | MOM | Et | Bicycloheptyl | S | S |
| 36 | I | 2 | Carbamoyl | MOM | Isopropyl | H | S | S |
| 37 | I | 2 | Carbamoyl | MOM | Isopropyl | Me | S | S |
| 38 | I | 2 | Carbamoyl | MOM | Isopropyl | Propyl | S | S |
| 39 | I | 2 | Carbamoyl | MOM | Isopropyl | Isopropyl | S | S |
| 40 | I | 2 | Carbamoyl | MOM | Isopropyl | Cyclopropyl | S | S |
| 41 | I | 2 | Carbamoyl | MOM | Isopropyl | Cyclohexyl | S | S |
| 42 | I | 2 | Carbamoyl | MOM | Isopropyl | Benzyl | S | S |

TABLE 1-continued

Carbamate derivetives (B is not a carbamoyl derivative)

| Example | X | Position | A | B | R$^1$ | R$^2$ | Chiral-1 | Chiral-2 |
|---|---|---|---|---|---|---|---|---|
| 43 | I | 2 | Carbamoyl | MOM | Isopropyl | Bicycloheptyl | S | S |
| 44 | I | 2 | Carbamoyl | MOM | Butyl | H | S | S |
| 45 | I | 2 | Carbamoyl | MOM | Butyl | Me | S | S |
| 46 | I | 2 | Carbamoyl | MOM | Butyl | Propyl | S | S |
| 47 | I | 2 | Carbamoyl | MOM | Butyl | Isopropyl | S | S |
| 48 | I | 2 | Carbamoyl | MOM | Butyl | Cuclopropyl | S | S |
| 49 | I | 2 | Carbamoyl | MOM | Butyl | Cyclohexyl | S | S |
| 50 | I | 2 | Carbamoyl | MOM | Butyl | Benzyl | S | S |
| 51 | I | 2 | Carbamoyl | MOM | Butyl | Bicycloheptyl | S | S |
| 52 | I | 3 | Carbamoyl | MOM | Me | H | S | S |
| 53 | I | 3 | Carbamoyl | MOM | Et | H | S | S |
| 54 | I | 3 | Carbamoyl | MOM | Isopropyl | H | S | S |
| 55 | I | 3 | Carbamoyl | MOM | Butyl | H | S | S |
| 56 | F | 4 | Carbamoyl | MOM | Me | H | S | S |
| 57 | F | 4 | Carbamoyl | MOM | Et | H | S | S |
| 58 | F | 4 | Carbamoyl | MOM | Isopropyl | H | S | S |
| 59 | F | 4 | Carbamoyl | MOM | Butyl | H | S | S |
| 60 | Cl | 2, 4 | Carbamoyl | MOM | Me | H | S | S |
| 61 | Cl | 2, 4 | Carbamoyl | MOM | Et | H | S | S |
| 62 | Cl | 2, 4 | Carbamoyl | MOM | Isopropyl | H | S | S |
| 63 | Cl | 2, 4 | Carbamoyl | MOM | Butyl | H | S | S |
| 64 | Cl | 2, 6 | Carbamoyl | MOM | Me | H | S | S |
| 65 | Cl | 2, 6 | Carbamoyl | MOM | Et | H | S | S |
| 66 | Cl | 2, 6 | Carbamoyl | MOM | Isopropyl | H | S | S |
| 67 | Cl | 2, 6 | Carbamoyl | MOM | Butyl | H | S | S |
| 68 | Cl | 2, 3 | Carbamoyl | MOM | Me | H | S | S |
| 69 | Cl | 2 | Carbamoyl | MOM | Me | H | R | R |
| 70 | Cl | 2 | Carbamoyl | MOM | Me | H | rac | rac |
| 71 | Cl | 2 | Carbamoyl | MOM | Me | H | R | S |
| 72 | Cl | 2 | Carbamoyl | MOM | Me | H | S | R |
| 73 | Cl | 2 | Carbamoyl | MOM | Et | H | R | R |
| 74 | Cl | 2 | Carbamoyl | MOM | Et | H | rac | rac |
| 75 | Cl | 2 | Carbamoyl | MOM | Isopropyl | H | R | R |
| 76 | Cl | 2 | Carbamoyl | MOM | Isopropyl | H | rac | rac |
| 77 | Cl | 2 | Carbamoyl | MOM | Butyl | H | R | R |
| 78 | Cl | 2 | Carbamoyl | MOM | Butyl | H | rac | rac |
| 79 | Cl | 2 | Carbamoyl | MOM | Me | Me | R | R |
| 80 | Cl | 2 | Carbamoyl | MOM | Me | Propyl | R | R |
| 81 | Cl | 2 | Carbamoyl | MOM | Me | Isopropyl | R | R |
| 82 | Cl | 2 | Carbamoyl | MOM | Me | Cyclopropyl | R | R |
| 83 | Cl | 2 | Carbamoyl | MOM | Me | Cyclohexyl | R | R |
| 84 | Cl | 2 | Carbamoyl | MOM | Me | Benzyl | R | R |
| 85 | Cl | 2 | Carbamoyl | MOM | Me | Bicycloheptyl | R | R |
| 86 | F | 2 | Carbamoyl | MOM | Me | H | R | R |
| 87 | F | 4 | Carbamoyl | MOM | Me | H | R | R |
| 88 | F | 4 | Carbamoyl | MOM | Et | H | R | R |
| 89 | F | 4 | Carbamoyl | MOM | Isopropyl | H | R | R |
| 90 | F | 4 | Carbamoyl | MOM | Butyl | H | R | R |
| 91 | I | 2 | Carbamoyl | MOM | Me | H | R | R |
| 92 | I | 2 | Carbamoyl | MOM | Et | H | R | R |
| 93 | I | 2 | Carbamoyl | MOM | Isopropyl | H | R | R |
| 94 | I | 2 | Carbamoyl | MOM | Butyl | H | R | R |
| 95 | I | 3 | Carbamoyl | MOM | Me | H | R | R |
| 96 | I | 3 | Carbamoyl | MOM | Et | H | R | R |
| 97 | I | 3 | Carbamoyl | MOM | Isopropyl | H | R | R |
| 98 | I | 3 | Carbamoyl | MOM | Butyl | H | R | R |
| 99 | Cl | 2 | Carbamoyl | MOM | Me | Me | rac | rac |
| 100 | Cl | 2 | Carbamoyl | MOM | Me | Propyl | rac | rac |
| 101 | Cl | 2 | Carbamoyl | MOM | Me | Isopropyl | rac | rac |
| 102 | Cl | 2 | Carbamoyl | MOM | Me | Cyclopropyl | rac | rac |
| 103 | Cl | 2 | Carbamoyl | MOM | Me | Cyclohexyl | rac | rac |
| 104 | Cl | 2 | Carbamoyl | MOM | Me | Benzyl | rac | rac |
| 105 | Cl | 2 | Carbamoyl | MOM | Me | Bicycloheptyl | rac | rac |
| 106 | Cl | 2, 4 | Carbamoyl | MOM | Me | H | R | R |
| 107 | Cl | 2, 6 | Carbamoyl | MOM | Me | H | R | R |
| 108 | Cl | 2, 3 | Carbamoyl | MOM | Me | H | R | R |
| 109 | Cl | 2, 4 | Carbamoyl | MOM | Et | H | R | R |
| 110 | Cl | 2, 6 | Carbamoyl | MOM | Et | H | R | R |
| 111 | Cl | 2, 4 | Carbamoyl | MOM | Isopropyl | H | R | R |
| 112 | Cl | 2, 6 | Carbamoyl | MOM | Isopropyl | H | R | R |
| 113 | Cl | 2, 4 | Carbamoyl | MOM | Butyl | H | R | R |
| 114 | Cl | 2, 6 | Carbamoyl | MOM | Butyl | H | R | R |
| 115 | Cl | 2, 4 | Carbamoyl | MOM | Me | H | rac | rac |
| 116 | Cl | 2, 6 | Carbamoyl | MOM | Me | H | rac | rac |
| 117 | Cl | 2, 3 | Carbamoyl | MOM | Me | H | rac | rac |
| 118 | Cl | 2, 4 | Carbamoyl | MOM | Et | H | rac | rac |

TABLE 1-continued

Carbamate derivetives (B is not a carbamoyl derivative)

| Example | X | Position | A | B | R¹ | R² | Chiral-1 | Chiral-2 |
|---|---|---|---|---|---|---|---|---|
| 119 | Cl | 2, 6 | Carbamoyl | MOM | Et | H | rac | rac |
| 120 | Cl | 2, 4 | Carbamoyl | MOM | Isopropyl | H | rac | rac |
| 121 | Cl | 2, 6 | Carbamoyl | MOM | Isopropyl | H | rac | rac |
| 122 | Cl | 2, 4 | Carbamoyl | MOM | Butyl | H | rac | rac |
| 123 | Cl | 2, 6 | Carbamoyl | MOM | Butyl | H | rac | rac |
| 124 | Cl | 2 | Carbamoyl | Methyl | Me | H | S | S |
| 125 | Cl | 2 | Carbamoyl | Methyl | Me | Me | S | S |
| 126 | Cl | 2 | Carbamoyl | Methyl | Me | Propyl | S | S |
| 127 | Cl | 2 | Carbamoyl | Methyl | Me | Isopropyl | S | S |
| 128 | Cl | 2 | Carbamoyl | Methyl | Me | Cuclopropyl | S | S |
| 129 | Cl | 2 | Carbamoyl | Methyl | Me | Cyclohexyl | S | S |
| 130 | Cl | 2 | Carbamoyl | Methyl | Me | Benzyl | S | S |
| 131 | Cl | 2 | Carbamoyl | Methyl | Me | Bicycloheptyl | S | S |
| 132 | Cl | 2 | Carbamoyl | Methyl | Et | H | S | S |
| 133 | Cl | 2 | Carbamoyl | Methyl | Isopropyl | H | S | S |
| 134 | Cl | 2 | Carbamoyl | Methyl | Butyl | H | S | S |
| 135 | F | 2 | Carbamoyl | Methyl | Me | H | S | S |
| 136 | F | 2 | Carbamoyl | Methyl | Me | Me | S | S |
| 137 | F | 2 | Carbamoyl | Methyl | Me | Propyl | S | S |
| 138 | F | 2 | Carbamoyl | Methyl | Me | Isopropyl | S | S |
| 139 | F | 2 | Carbamoyl | Methyl | Me | Cuclopropyl | S | S |
| 140 | F | 2 | Carbamoyl | Methyl | Me | Cyclohexyl | S | S |
| 141 | F | 2 | Carbamoyl | Methyl | Me | Benzyl | S | S |
| 142 | F | 2 | Carbamoyl | Methyl | Me | Bicycloheptyl | S | S |
| 143 | I | 2 | Carbamoyl | Methyl | Me | H | S | S |
| 144 | I | 2 | Carbamoyl | Methyl | Me | Me | S | S |
| 145 | I | 2 | Carbamoyl | Methyl | Me | Propyl | S | S |
| 146 | I | 2 | Carbamoyl | Methyl | Me | Isopropyl | S | S |
| 147 | I | 2 | Carbamoyl | Methyl | Me | Cuclopropyl | S | S |
| 148 | I | 2 | Carbamoyl | Methyl | Me | Cyclohexyl | S | S |
| 149 | I | 2 | Carbamoyl | Methyl | Me | Benzyl | S | S |
| 150 | I | 2 | Carbamoyl | Methyl | Me | Bicycloheptyl | S | S |
| 151 | I | 2 | Carbamoyl | Methyl | Et | H | S | S |
| 152 | I | 2 | Carbamoyl | Methyl | Et | Me | S | S |
| 153 | I | 2 | Carbamoyl | Methyl | Et | Propyl | S | S |
| 154 | I | 2 | Carbamoyl | Methyl | Et | Isopropyl | S | S |
| 155 | I | 2 | Carbamoyl | Methyl | Et | Cyclopropyl | S | S |
| 156 | I | 2 | Carbamoyl | Methyl | Et | Cyclohexyl | S | S |
| 157 | I | 2 | Carbamoyl | Methyl | Et | Benzyl | S | S |
| 158 | I | 2 | Carbamoyl | Methyl | Et | Bicycloheptyl | S | S |
| 159 | I | 2 | Carbamoyl | Methyl | Isopropyl | H | S | S |
| 160 | I | 2 | Carbamoyl | Methyl | Isopropyl | Me | S | S |
| 161 | I | 2 | Carbamoyl | Methyl | Isopropyl | Propyl | S | S |
| 162 | I | 2 | Carbamoyl | Methyl | Isopropyl | Isopropyl | S | S |
| 163 | I | 2 | Carbamoyl | Methyl | Isopropyl | Cyclopropyl | S | S |
| 164 | I | 2 | Carbamoyl | Methyl | Isopropyl | Cyclohexyl | S | S |
| 165 | I | 2 | Carbamoyl | Methyl | Isopropyl | Benzyl | S | S |
| 166 | I | 2 | Carbamoyl | Methyl | Isopropyl | Bicycloheptyl | S | S |
| 167 | I | 2 | Carbamoyl | Methyl | Butyl | H | S | S |
| 168 | I | 2 | Carbamoyl | Methyl | Butyl | Me | S | S |
| 169 | I | 2 | Carbamoyl | Methyl | Butyl | Propyl | S | S |
| 170 | I | 2 | Carbamoyl | Methyl | Butyl | Isopropyl | S | S |
| 171 | I | 2 | Carbamoyl | Methyl | Butyl | Cuclopropyl | S | S |
| 172 | I | 2 | Carbamoyl | Methyl | Butyl | Cyclohexyl | S | S |
| 173 | I | 2 | Carbamoyl | Methyl | Butyl | Benzyl | S | S |
| 174 | I | 2 | Carbamoyl | Methyl | Butyl | Bicycloheptyl | S | S |
| 175 | I | 3 | Carbamoyl | Methyl | Me | H | S | S |
| 176 | I | 3 | Carbamoyl | Methyl | Et | H | S | S |
| 177 | I | 3 | Carbamoyl | Methyl | Isopropyl | H | S | S |
| 178 | I | 3 | Carbamoyl | Methyl | Butyl | H | S | S |
| 179 | F | 4 | Carbamoyl | Methyl | Me | H | S | S |
| 180 | F | 4 | Carbamoyl | Methyl | Et | H | S | S |
| 181 | F | 4 | Carbamoyl | Methyl | Isopropyl | H | S | S |
| 182 | F | 4 | Carbamoyl | Methyl | Butyl | H | S | S |
| 183 | Cl | 2, 4 | Carbamoyl | Methyl | Me | H | S | S |
| 184 | Cl | 2, 4 | Carbamoyl | Methyl | Et | H | S | S |
| 185 | Cl | 2, 4 | Carbamoyl | Methyl | Isopropyl | H | S | S |
| 186 | Cl | 2, 4 | Carbamoyl | Methyl | Butyl | H | S | S |
| 187 | Cl | 2, 6 | Carbamoyl | Methyl | Me | H | S | S |
| 188 | Cl | 2, 6 | Carbamoyl | Methyl | Et | H | S | S |
| 189 | Cl | 2, 6 | Carbamoyl | Methyl | Isopropyl | H | S | S |
| 190 | Cl | 2, 6 | Carbamoyl | Methyl | Butyl | H | S | S |
| 191 | Cl | 2, 3 | Carbamoyl | Methyl | Me | H | S | S |
| 192 | Cl | 2 | Carbamoyl | Methyl | Me | H | R | R |
| 193 | Cl | 2 | Carbamoyl | Methyl | Me | H | rac | rac |
| 194 | Cl | 2 | Carbamoyl | Methyl | Me | H | R | S |

TABLE 1-continued

Carbamate derivetives (B is not a carbamoyl derivative)

| Example | X | Position | A | B | R¹ | R² | Chiral-1 | Chiral-2 |
|---|---|---|---|---|---|---|---|---|
| 195 | Cl | 2 | Carbamoyl | Methyl | Me | H | S | R |
| 196 | Cl | 2 | Carbamoyl | Methyl | Et | H | R | R |
| 197 | Cl | 2 | Carbamoyl | Methyl | Et | H | rac | rac |
| 198 | Cl | 2 | Carbamoyl | Methyl | Isopropyl | H | R | R |
| 199 | Cl | 2 | Carbamoyl | Methyl | Isopropyl | H | rac | rac |
| 200 | Cl | 2 | Carbamoyl | Methyl | Butyl | H | R | R |
| 201 | Cl | 2 | Carbamoyl | Methyl | Butyl | H | rac | rac |
| 202 | Cl | 2 | Carbamoyl | Methyl | Me | Me | R | R |
| 203 | Cl | 2 | Carbamoyl | Methyl | Me | Propyl | R | R |
| 204 | Cl | 2 | Carbamoyl | Methyl | Me | Isopropyl | R | R |
| 205 | Cl | 2 | Carbamoyl | Methyl | Me | Cyclopropyl | R | R |
| 206 | Cl | 2 | Carbamoyl | Methyl | Me | Cyclohexyl | R | R |
| 207 | Cl | 2 | Carbamoyl | Methyl | Me | Benzyl | R | R |
| 208 | Cl | 2 | Carbamoyl | Methyl | Me | Bicycloheptyl | R | R |
| 209 | F | 2 | Carbamoyl | Methyl | Me | H | R | R |
| 210 | F | 4 | Carbamoyl | Methyl | Me | H | R | R |
| 211 | F | 4 | Carbamoyl | Methyl | Et | H | R | R |
| 212 | F | 4 | Carbamoyl | Methyl | Isopropyl | H | R | R |
| 213 | F | 4 | Carbamoyl | Methyl | Butyl | H | R | R |
| 214 | I | 2 | Carbamoyl | Methyl | Me | H | R | R |
| 215 | I | 2 | Carbamoyl | Methyl | Et | H | R | R |
| 216 | I | 2 | Carbamoyl | Methyl | Isopropyl | H | R | R |
| 217 | I | 2 | Carbamoyl | Methyl | Butyl | H | R | R |
| 218 | I | 3 | Carbamoyl | Methyl | Me | H | R | R |
| 219 | I | 3 | Carbamoyl | Methyl | Et | H | R | R |
| 220 | I | 3 | Carbamoyl | Methyl | Isopropyl | H | R | R |
| 221 | I | 3 | Carbamoyl | Methyl | Butyl | H | R | R |
| 222 | Cl | 2 | Carbamoyl | Methyl | Me | Me | rac | rac |
| 223 | Cl | 2 | Carbamoyl | Methyl | Me | Propyl | rac | rac |
| 224 | Cl | 2 | Carbamoyl | Methyl | Me | Isopropyl | rac | rac |
| 225 | Cl | 2 | Carbamoyl | Methyl | Me | Cyclopropyl | rac | rac |
| 226 | Cl | 2 | Carbamoyl | Methyl | Me | Cyclohexyl | rac | rac |
| 227 | Cl | 2 | Carbamoyl | Methyl | Me | Benzyl | rac | rac |
| 228 | Cl | 2 | Carbamoyl | Methyl | Me | Bicycloheptyl | rac | rac |
| 229 | Cl | 2, 4 | Carbamoyl | Methyl | Me | H | R | R |
| 230 | Cl | 2, 6 | Carbamoyl | Methyl | Me | H | R | R |
| 231 | Cl | 2, 3 | Carbamoyl | Methyl | Me | H | R | R |
| 232 | Cl | 2, 4 | Carbamoyl | Methyl | Et | H | R | R |
| 233 | Cl | 2, 6 | Carbamoyl | Methyl | Et | H | R | R |
| 234 | Cl | 2, 4 | Carbamoyl | Methyl | Isopropyl | H | R | R |
| 235 | Cl | 2, 6 | Carbamoyl | Methyl | Isopropyl | H | R | R |
| 236 | Cl | 2, 4 | Carbamoyl | Methyl | Butyl | H | R | R |
| 237 | Cl | 2, 6 | Carbamoyl | Methyl | Butyl | H | R | R |
| 238 | Cl | 2, 4 | Carbamoyl | Methyl | Me | H | rac | rac |
| 239 | Cl | 2, 6 | Carbamoyl | Methyl | Me | H | rac | rac |
| 240 | Cl | 2, 3 | Carbamoyl | Methyl | Me | H | rac | rac |
| 241 | Cl | 2, 4 | Carbamoyl | Methyl | Et | H | rac | rac |
| 242 | Cl | 2, 6 | Carbamoyl | Methyl | Et | H | rac | rac |
| 243 | Cl | 2, 4 | Carbamoyl | Methyl | Isopropyl | H | rac | rac |
| 244 | Cl | 2, 6 | Carbamoyl | Methyl | Isopropyl | H | rac | rac |
| 245 | Cl | 2, 4 | Carbamoyl | Methyl | Butyl | H | rac | rac |
| 246 | Cl | 2, 6 | Carbamoyl | Methyl | Butyl | H | rac | rac |
| 271 | F | 2, 6 | Carbamoyl | MOM | Me | H | S | S |
| 272 | Cl | 2, 5 | Carbamoyl | MOM | Me | H | S | S |
| 273 | Cl | 2, 5 | Carbamoyl | MOM | Me | H | R | R |
| 276 | Cl | 2 | Carbamoyl | MOM | H | H | S | — |
| 277 | F | 2 | Carbamoyl | MOM | H | H | S | — |
| 278 | I | 2 | Carbamoyl | MOM | H | H | S | — |
| 279 | Cl | 2 | Carbamoyl | Methyl | H | H | S | — |
| 280 | F | 2 | Carbamoyl | Methyl | H | H | S | — |
| 281 | I | 2 | Carbamoyl | Methyl | H | H | S | — |

TABLE 2

Carbamate derivertives (B is a carbamoyl derivative)

| Example | X | Position | A | B | | R³ | R¹ | R² | Chiral-1 | Chiral-2 |
|---|---|---|---|---|---|---|---|---|---|---|
| 247 | Cl | 2 | Carbamoyl | Carbamoyl | | H | Me | H | S | S |
| 248 | Cl | 2 | Carbamoyl | Carbamoyl | | H | Me | Me | S | S |
| 249 | Cl | 2 | Carbamoyl | Carbamoyl | | H | Me | Propyl | S | S |

TABLE 2-continued

Carbamate derivertives (B is a carbamoyl derivative)

| Example | X | Position | A | B — | R³ | R¹ | R² | Chiral-1 | Chiral-2 |
|---|---|---|---|---|---|---|---|---|---|
| 250 | Cl | 2 | Carbamoyl | Carbamoyl | H | Me | H | R | R |
| 251 | Cl | 2 | Carbamoyl | Carbamoyl | H | Me | H | rac | rac |
| 252 | Cl | 2 | Carbamoyl | Carbamoyl | H | Et | H | S | S |
| 253 | Cl | 2 | Carbamoyl | Carbamoyl | H | Isopropyl | H | S | S |
| 254 | Cl | 2 | Carbamoyl | Carbamoyl | H | Butyl | H | S | S |
| 255 | F | 2 | Carbamoyl | Carbamoyl | H | Me | H | S | S |
| 256 | F | 2 | Carbamoyl | Carbamoyl | H | Et | H | S | S |
| 257 | F | 2 | Carbamoyl | Carbamoyl | H | Isopropyl | H | S | S |
| 258 | F | 2 | Carbamoyl | Carbamoyl | H | Butyl | H | S | S |
| 259 | I | 2 | Carbamoyl | Carbamoyl | H | Me | H | S | S |
| 260 | I | 2 | Carbamoyl | Carbamoyl | H | Et | H | S | S |
| 261 | I | 2 | Carbamoyl | Carbamoyl | H | Isopropyl | H | S | S |
| 262 | I | 2 | Carbamoyl | Carbamoyl | H | Butyl | H | S | S |
| 263 | Cl | 2, 4 | Carbamoyl | Carbamoyl | H | Me | H | S | S |
| 264 | Cl | 2, 4 | Carbamoyl | Carbamoyl | H | Et | H | S | S |
| 265 | Cl | 2, 4 | Carbamoyl | Carbamoyl | H | Isopropyl | H | S | S |
| 266 | Cl | 2, 4 | Carbamoyl | Carbamoyl | H | Butyl | H | S | S |
| 267 | Cl | 2, 6 | Carbamoyl | Carbamoyl | H | Me | H | S | S |
| 268 | Cl | 2, 6 | Carbamoyl | Carbamoyl | H | Et | H | S | S |
| 269 | Cl | 2, 6 | Carbamoyl | Carbamoyl | H | Isopropyl | H | S | S |
| 270 | Cl | 2, 6 | Carbamoyl | Carbamoyl | H | Butyl | H | S | S |
| 274 | Cl | 2 | MOM | Carbamoyl | H | Me | H | S | S |
| 275 | Cl | 2 | Methyl | Carbamoyl | H | Me | H | S | S |
| 282 | I | 2 | MOM | Carbamoyl | H | Me | H | S | S |
| 283 | I | 2 | Methyl | Carbamoyl | H | Me | H | S | S |
| 284 | F | 2 | MOM | Carbamoyl | H | Me | H | S | S |
| 285 | F | 2 | Methyl | Carbamoyl | H | Me | H | S | S |
| 286 | Cl, F | 2, 6 | Carbamoyl | Carbamoyl | H | Me | H | S | S |
| 287 | Cl, F | 2, 6 | Carbamoyl | Carbamoyl | H | Me | H | R | R |
| 288 | I | 2 | Carbamoyl | Carbamoyl | H | Me | H | R | R |
| 289 | F | 2 | Carbamoyl | Carbamoyl | H | Me | H | R | R |
| 290 | Cl | 2, 6 | Carbamoyl | Carbamoyl | H | Me | H | R | R |
| 291 | F | 2, 4 | Carbamoyl | Carbamoyl | H | Me | H | R | R |
| 292 | F | 2, 6 | Carbamoyl | Carbamoyl | H | Me | H | R | R |
| 293 | F | 2, 5 | Carbamoyl | Carbamoyl | H | Me | H | R | R |
| 294 | Cl | 2 | Carbamoyl | Carbamoyl | H | Me | H | S | R |
| 295 | Cl | 2 | Carbamoyl | Carbamoyl | H | Me | H | R | S |

Example 1

Synthesis of 1-(2-chlorophenyl)-(S)-1-methoxymethoxypropyl-(S)-2-carbamate

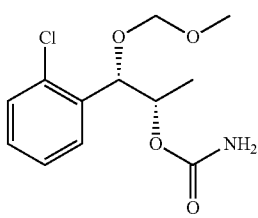 [SMILES: COCO[C@@H](c1ccccc1Cl)[C@H](C)OC(N)=O]

To a stirred solution of 1-(2-chlorophenyl)-1-hydorxyalkyl-2-carbamate (Preparation Example 103, 1.7 g) in MC (Methylenechloloride) was added DIPEA (Diisopropylethylamine, 5 eq, 5.1 ml) at 0° C. under $N_2$ condition. The mixture was added MOM-Cl (MOMchloride, 5 eq, 2.3 ml) at 0° C. then slowly warm to R.T. When the reaction was completed, the obtained product was washed with $H_2O$ and MC. The separated organic layer was dehydrated with anhydrous $MgSO_4$(Magnesium sulfate), filtrated, and concentrated under reduced pressure. The concentrated residue was purified by a silicagel aolumn chromatography, to obtain title compound.

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.26~7.70 (m, 4H)

According to the method described in Example 1, the following compounds of Examples 2 to 123 were prepared:

Example 2

Synthesis of 1-(2-chlorophenyl)-(S)-1-methoxymethoxypropyl-(S)-2-methylcarbamate

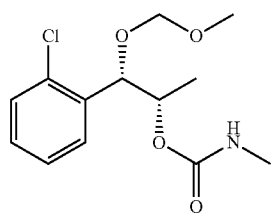 [SMILES: CNC(=O)O[C@@H](C)[C@@H](OCOC)c1ccccc1Cl]

The substantially same method as described in Example 1 was conducted, except that 1-(2-chlorophenyl)-(S)-1-hydroxypropyl-(S)-2-methylcarbamate (Preparation example 117) was used instead of 1-(2-chlorophenyl)-(S)-1-hydroxypropyl-(S)-2-carbamate (Preparation example 103), to obtain the title compound (0.86 g, yield 20~50%).

¹H NMR (400 MHz, CDCl₃) δ1.37 (d, J=6.8 Hz, 3H), 2.58 (s, 3H), 3.30 (s, 3H), 4.71 (d, J=6.8, 1H), 4.82~4.88 (m, 1H), 5.45 (s, 2H), 7.26~7.70 (m, 4H)

Example 3

Synthesis of 1-(2-chlorophenyl)-(S)-1-methoxymethoxypropyl-(S)-2-propylcarbamate

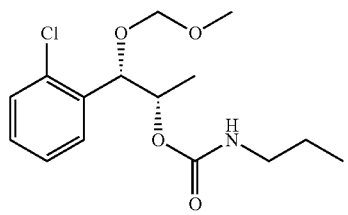 [SMILES: CCCNC(=O)O[C@@H](C)[C@@H](OCOC)c1ccccc1Cl]

¹H NMR (400 MHz, CDCl₃) δ0.90 (t, J=6.8 Hz, 3H), 1.37 (d, J=6.8 Hz, 3H), 1.60 (m, 2H), 3.18 (t, J=7.1 Hz, 2H), 3.30 (s, 3H), 4.71 (d, J=6.8, 1H), 4.82~4.88 (m, 1H), 5.45 (s, 2H), 7.26~7.70 (m, 4H)

Example 4

Synthesis of 1-(2-chlorophenyl)-(S)-1-methoxymethoxypropyl-(S)-2-isopropylcarbamate

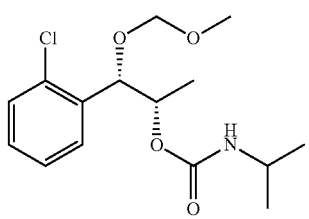

¹H NMR (400 MHz, CDCl₃) δ, 1.27 (d, J=6.8 Hz, 6H), 1.37 (d, J=6.8 Hz, 3H), 3.30 (s, 3H), 4.17 (m, 1H), 4.71 (d, J=6.8, 1H), 4.82~4.88 (m, 1H), 5.45 (s, 2H), 7.26~7.70 (m, 4H)

Example 5

Synthesis of 1-(2-chlorophenyl)-(S)-1-methoxymethoxypropyl-(S)-2-cyclopropylcarbamate

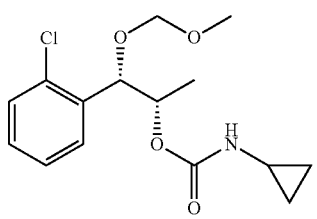

¹H NMR (400 MHz, CDCl₃) δ0.57 (m, 2H), 0.82 (m, 2H), 1.37 (d, J=6.8 Hz, 3H), 2.75 (m, 1H), 3.30 (s, 3H), 4.71 (d, J=6.8, 1H), 4.82~4.88 (m, 1H), 5.45 (s, 2H), 7.26~7.70 (m, 4H)

Example 6

Synthesis of 1-(2-chlorophenyl)-(S)-1-methoxymethoxypropyl-(S)-2-cyclohexylcarbamate

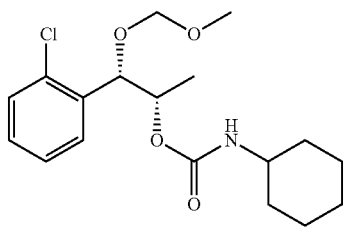

¹H NMR (400 MHz, CDCl₃) δ1.11~1.21 (m, 4H), 1.37 (d, J=6.8 Hz, 3H), 1.47~1.49 (m, 4H), 1.74 (m, 2H), 3.30 (s, 3H), 3.54 (m, 1H), 4.71 (d, J=6.8, 1H), 4.82~4.88 (m, 1H), 5.45 (s, 2H), 7.26~7.70 (m, 4H)

Example 7

Synthesis of 1-(2-chlorophenyl)-(S)-1-methoxymethoxypropyl-(S)-2-cyclohexylcarbamate

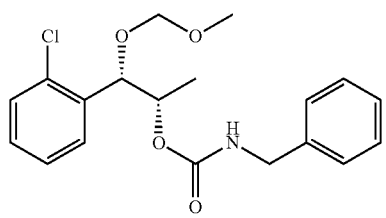 [SMILES: COCO[C@@H](c1ccccc1Cl)[C@H](C)OC(=O)NCc1ccccc1]

¹H NMR (400 MHz, CDCl₃) δ1.37 (d, J=6.8 Hz, 3H), 3.30 (s, 3H), 4.20 (m, 2H), 4.71 (d, J=6.8, 1H), 4.82~4.88 (m, 1H), 5.45 (s, 2H), 7.13~7.19 (m, 4H), 7.37~7.88 (m, 5H)

Example 8

Synthesis of 1-(2-chlorophenyl)-(S)-1-methoxymethoxypropyl-(S)-2-bicyclo[2,2,1]heptan-escarbamate

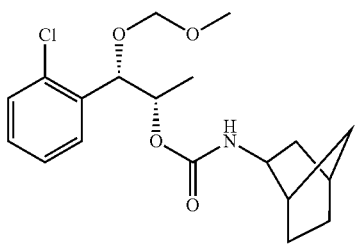 [SMILES: COCO[C@@H](c1ccccc1Cl)[C@H](C)OC(=O)NC1CC2CCC1C2]

¹H NMR (400 MHz, CDCl₃) δ1.33~1.58 (m, 9H), 1.75~1.88 (m, 2H), 2.06~2.13 (m, 2H), 3.30 (s, 3H), 3.53 (m, 1H), 4.71 (d, J=6.8, 1H), 4.82~4.88 (m, 1H), 5.45 (s, 2H), 7.13~7.19 (m, 4H), 7.37~7.88 (m, 5H)

Example 9

Synthesis of 1-(2-chlorophenyl)-(S)-1-methoxymethoxybutyl-(S)-2-carbamate

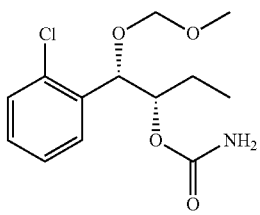

$^1$H NMR (400 MHz, CDCl$_3$) δ1.04 (t, J=7.6 Hz, 3H), 1.60~1.71 (m, 2H), 3.30 (s, 3H), 4.71 (d, J=6.8, 1H), 4.73 (br s, 2H), 4.82~4.88 (m, 1H), 5.45 (s, 2H), 7.26~7.70 (m, 4H)

Example 10

Synthesis of 1-(2-chlorophenyl)-(S)-1-methoxymethoxy-3-methyl-butyl-(S)-2-carbamate

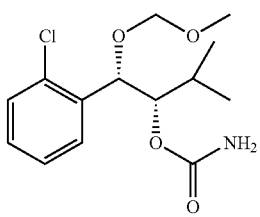 [SMILES: COCO[C@@H](c1ccccc1Cl)[C@@H](OC(N)=O)C(C)C]

$^1$H NMR (400 MHz, CDCl$_3$) δ1.07 (t, J=7.6 Hz, 6H), 1.83~1.89 (m, 1H), 3.30 (s, 3H), 4.71 (d, J=6.8, 1H), 4.73 (br s, 2H), 4.82~4.88 (m, 1H), 5.45 (s, 2H), 7.26~7.70 (m, 4H)

Example 11

Synthesis of 1-(2-chlorophenyl)-(S)-1-methoxymethoxyhexyl-(S)-2-carbamate

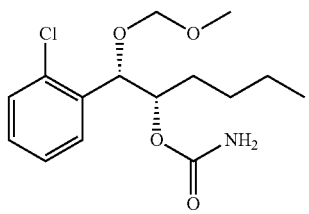 [SMILES: CCCC[C@H](OC(N)=O)[C@@H](OCOC)c1ccccc1Cl]

$^1$H NMR (400 MHz, CDCl$_3$) δ0.90 (1, J=7.6 Hz, 3H), 1.35~1.65 (m, 6H), 3.30 (s, 3H), 4.71 (d, J=6.8, 1H), 4.73 (br s, 2H), 4.82~4.88 (m, 1H), 5.45 (s, 2H), 7.26~7.70 (m, 4H)

Example 12

Synthesis of 1-(2-fluorophenyl)-(S)-1-methoxymethoxypropyl-(S)-2-carbamate

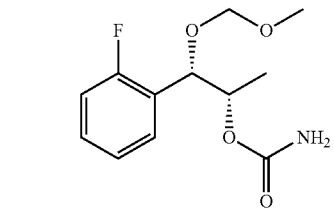 [SMILES: COCO[C@@H](c1ccccc1F)[C@H](C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.15~7.68 (m, 4H)

Example 13

Synthesis of 1-(2-fluorophenyl)-(S)-1-methoxymethoxypropyl-(S)-2-methylcarbamate

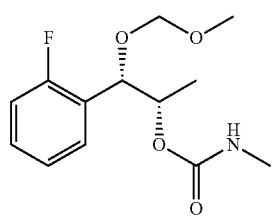 [SMILES: CNC(=O)O[C@@H](C)[C@@H](OCOC)c1ccccc1F]

$^1$H NMR (400 MHz, CDCl$_3$) δ1.37 (d, J=6.8 Hz, 3H), 2.58 (s, 3H), 3.30 (s, 3H), 4.71 (d, J=6.8, 1H), 4.82~4.88 (m, 1H), 5.45 (s, 2H), 7.15~7.68 (m, 4H)

Example 14

Synthesis of 1-(2-fluorophenyl)-(S)-1-methoxymethoxypropyl-(S)-2-propylcarbamate

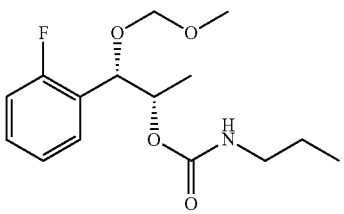 [SMILES: CCCNC(=O)O[C@@H](C)[C@@H](OCOC)c1ccccc1F]

$^1$H NMR (400 MHz, CDCl$_3$) δ0.90 (1, J=6.8 Hz, 3H), 1.37 (d, J=6.8 Hz, 3H), 1.60 (m, 2H), 3.18 (t, J=7.1 Hz, 2H), 3.30 (s, 3H), 4.71 (d, J=6.8, 1H), 4.82~4.88 (m, 1H), 5.45 (s, 2H), 7.15~7.68 (m, 4H)

Example 15

Synthesis of 1-(2-fluorophenyl)-(S)-1-methoxymethoxypropyl-(S)-2-isopropylcarbamate

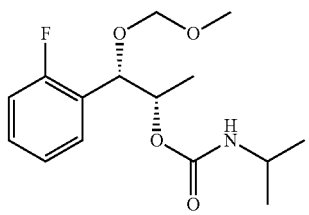 [SMILES: COCO[C@@H](c1ccccc1F)[C@H](C)OC(=O)NC(C)C]

¹H NMR (400 MHz, CDCl₃) δ, 1.27 (d, J=6.8 Hz, 6H), 1.37 (d, J=6.8 Hz, 3H), 3.30 (s, 3H), 4.17 (m, 1H), 4.71 (d, J=6.8, 1H), 4.82~4.88 (m, 1H), 5.45 (s, 2H), 7.15~7.69 (m, 4H)

Example 16

Synthesis of 1-(2-fluorophenyl)-(S)-1-methoxymethoxypropyl-(S)-2-cyclopropylcarbamate

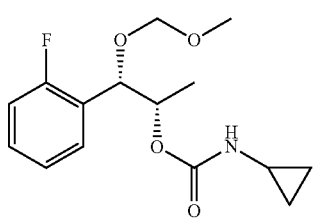 [SMILES: COCO[C@@H](c1ccccc1F)[C@H](C)OC(=O)NC1CC1]

¹H NMR (400 MHz, CDCl₃) δ0.57 (m, 2H), 0.82 (m, 2H), 1.37 (d, J=6.8 Hz, 3H), 2.75 (m, 1H), 3.30 (s, 3H), 4.71 (d, J=6.8, 1H), 4.82~4.88 (m, 1H), 5.45 (s, 2H), 7.16~7.70 (m, 4H)

Example 17

Synthesis of 1-(2-fluorophenyl)-(S)-1-methoxymethoxypropyl-(S)-2-cyclohexylcarbamate

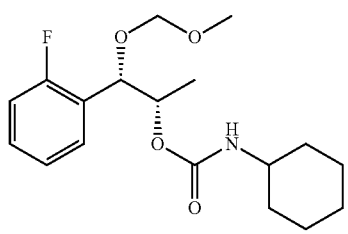 [SMILES: COCO[C@@H](c1ccccc1F)[C@H](C)OC(=O)NC1CCCCC1]

¹H NMR (400 MHz, CDCl₃) δ1.11~1.21 (m, 4H), 1.37 (d, J=6.8 Hz, 3H), 1.47~1.49 (m, 4H), 1.74 (m, 2H), 3.30 (s, 3H), 3.54 (m, 1H), 4.71 (d, J=6.8, 1H), 4.82~4.88 (m, 1H), 5.45 (s, 2H), 7.15~7.66 (m, 4H)

Example 18

Synthesis of 1-(2-fluorophenyl)-(S)-1-methoxymethoxypropyl-(5)-2-cyclohexylcarbamate

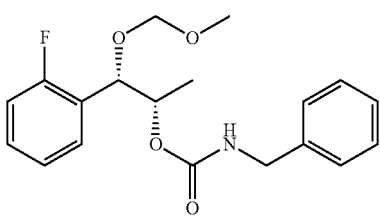

¹H NMR (400 MHz, CDCl₃) δ1.37 (d, J=6.8 Hz, 3H), 3.30 (s, 3H), 4.20 (m, 2H), 4.71 (d, J=6.8, 1H), 4.82~4.88 (m, 1H), 5.45 (s, 2H), 7.15~7.68 (m, 4H), 7.72~7.88 (m, 5H)

Example 19

Synthesis of 1-(2fluorophenyl)-(S)-1-methoxymethoxypropyl-(S)-2-bicyclo[2,2,1]heptan-escarbamate

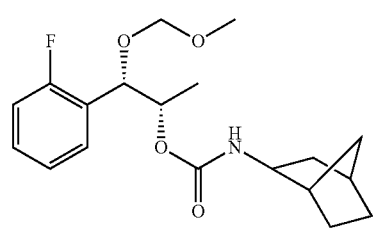

¹H NMR (400 MHz, CDCl₃) δ1.33~1.58 (m, 9H), 1.75~1.88 (m, 2H), 2.06~2.13 (m, 2H), 3.30 (s, 3H), 3.53 (m, 1H), 4.71 (d, J=6.8, 1H), 4.82~4.88 (m, 1H), 5.45 (s, 2H), 7.15~7.68 (m, 4H), 7.37~7.88 (m, 5H)

Example 20

Synthesis of 1-(2-iodophenyl)-(S)-1-methoxymethoxypropyl-(S)-2-carbamate

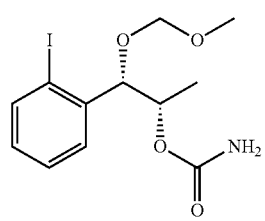 [SMILES: COCO[C@@H](c1ccccc1I)[C@H](C)OC(N)=O]

¹H NMR (400 MHz, CDCl₃) δ1.37 (d, J=6.8 Hz, 3H), 3.30 (s, 3H), 4.71 (d, J=6.8, 1H), 4.82~4.88 (m, 1H), 5.45 (s, 2H), 7.13~7.88 (m, 4H).

Example 21

Synthesis of 1-(2-iodophenyl)-(S)-1-methoxymethoxypropyl-(S)-2-methylcarbamate

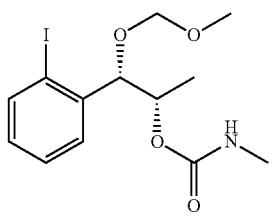

$^1$H NMR (400 MHz, CDCl$_3$) δ1.37 (d, J=6.8 Hz, 3H), 2.58 (s, 3H), 3.30 (s, 3H), 4.71 (d, J=6.8, 1H), 4.82~4.88 (m, 1H), 5.45 (s, 2H), 7.13~7.898 (m, 4H)

Example 22

Synthesis of 1-(2-iodophenyl)-(S)-1-methoxymethoxypropyl-(S)-2-propylcarbamate

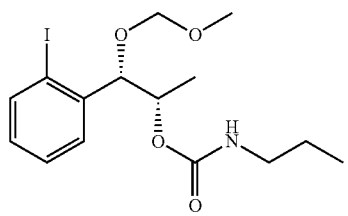 [SMILES: CCCNC(=O)O[C@@H](C)[C@@H](OCOC)c1ccccc1I]

$^1$H NMR (400 MHz, CDCl$_3$) δ0.90 (t, J=6.8 Hz, 3H), 1.37 (d, J=6.8 Hz, 3H), 1.60 (m, 2H), 3.18 (t, J=7.1 Hz, 2H), 3.30 (s, 3H), 4.71 (d, J=6.8, 1H), 4.82~4.88 (m, 1H), 5.45 (s, 2H), 7.14~7.87 (m, 4H)

Example 23

Synthesis of 1-(2-iodophenyl)-(S)-1-methoxymethoxypropyl-(S)-2-isopropylcarbamate

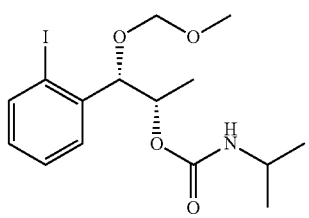

$^1$H NMR (400 MHz, CDCl$_3$) δ, 1.27 (d, J=6.8 Hz, 6H), 1.37 (d, J=6.8 Hz, 3H), 3.30 (s, 3H), 4.17 (m, 1H), 4.71 (d, J=6.8, 1H), 4.82~4.88 (m, 1H), 5.45 (s, 2H), 7.15~7.89 (m, 4H)

Example 24

Synthesis of 1-(2-iodophenyl)-(S)-1-methoxymethoxypropyl-(S)-2-cyclopropylcarbamate

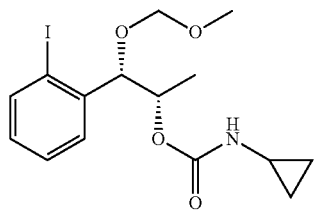 [SMILES: COCO[C@@H](c1ccccc1I)[C@H](C)OC(=O)NC1CC1]

$^1$H NMR (400 MHz, CDCl$_3$) δ0.57 (m, 2H), 0.82 (m, 2H), 1.37 (d, J=6.8 Hz, 3H), 2.75 (m, 1H), 3.30 (s, 3H), 4.71 (d, J=6.8, 1H), 4.82~4.88 (m, 1H), 5.45 (s, 2H), 7.16~7.87 (m, 4H)

Example 25

Synthesis of 1-(2-iodophenyl)-(S)-1-methoxymethoxypropyl-(S)-2-cyclohexylcarbamate

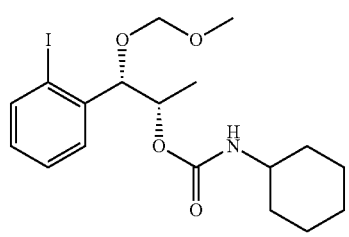 [SMILES: COCO[C@@H](c1ccccc1I)[C@H](C)OC(=O)NC1CCCCC1]

$^1$H NMR (400 MHz, CDCl$_3$) δ1.11~1.21 (m, 4H), 1.37 (d, J=6.8 Hz, 3H), 1.47~1.49 (m, 4H), 1.74 (m, 2H), 3.30 (s, 3H), 3.54 (m, 1H), 4.71 (d, J=6.8, 1H), 4.82~4.88 (m, 1H), 5.45 (s, 2H), 7.18~7.91 (m, 4H)

Example 26

Synthesis of 1-(2-iodophenyl)-(S)-1-methoxymethoxypropyl-(S)-2-cyclohexylcarbamate

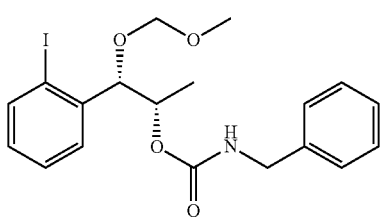

$^1$H NMR (400 MHz, CDCl$_3$) δ1.37 (d, J=6.8 Hz, 3H), 3.30 (s, 3H), 4.20 (m, 2H), 4.71 (d, J=6.8, 1H), 4.82~4.88 (m, 1H), 5.45 (s, 2H), 7.15~7.68 (m, 4H), 7.72~7.88 (m, 5H)

Example 27

Synthesis of 1-(2-iodophenyl)-(S)-1-methoxymethoxypropyl-(S)-2-bicyclo[2,2,1]heptanescarbamate

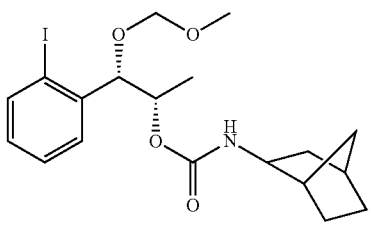 [SMILES: COCO[C@@H](c1ccccc1I)[C@H](C)OC(=O)NC1CC2CCC1C2]

¹H NMR (400 MHz, CDCl₃) δ1.33~1.58 (m, 9H), 1.75~1.88 (m, 2H), 2.06~2.13 (m, 2H), 3.30 (s, 3H), 3.53 (m, 1H), 4.71 (d, J=6.8, 1H), 4.82~4.88 (m, 1H), 5.45 (s, 2H), 7.15~7.68 (m, 4H), 7.37~7.88 (m, 5H)

Example 28

Synthesis of 1-(2-iodophenyl)-(S)-1-methoxymethoxybutyl-(S)-2-carbamate

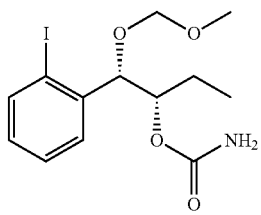

¹H NMR (400 MHz, CDCl₃) δ1.04 (1, J=7.6 Hz, 3H), 1.60~1.71 (m, 2H), 3.30 (s, 3H), 4.71 (d, J=6.8, 1H), 4.82~4.88 (m, 1H), 5.45 (s, 2H), 7.26~7.70 (m, 4H)

Example 29

Synthesis of 1-(2-iodophenyl)-(S)-1-methoxymethoxybutyl-(S)-2-methylcarbamate

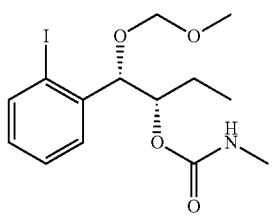 [SMILES: CC[C@H](OC(=O)NC)[C@@H](OCOC)c1ccccc1I]

¹H NMR (400 MHz, CDCl₃) δ1.04 (1, J=7.6 Hz, 3H), 1.60~1.71 (m, 2H), 2.58 (s, 3H), 3.30 (s, 3H), 4.71 (d, J=6.8, 1H), 4.82~4.88 (m, 1H), 5.45 (s, 2H), 7.13~7.88 (m, 4H)

Example 30

Synthesis of 1-(2-iodophenyl)-(S)-1-methoxymethoxybutyl-(S)-2-propylcarbamate

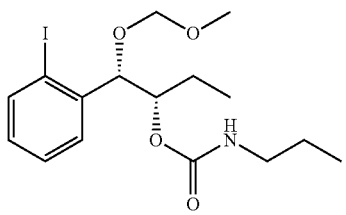 [SMILES: CCCNC(=O)O[C@@H](CC)[C@@H](OCOC)c1ccccc1I]

¹H NMR (400 MHz, CDCl₃) δ0.90 (t, J=6.8 Hz, 3H), 1.04 (t, J=7.6 Hz, 3H), 1.58~1.71 (m, 4H), 3.18 (t, J=7.1 Hz, 2H), 3.30 (s, 3H), 4.71 (d, J=6.8, 1H), 4.82~4.88 (m, 1H), 5.45 (s, 2H), 7.14~7.89 (m, 4H)

Example 31

Synthesis of 1-(2-iodophenyl)-(S)-1-methoxymethoxybutyl-(S)-2-isopropylcarbamate

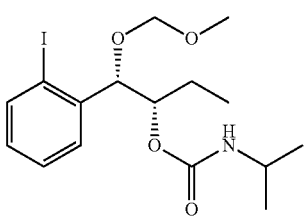 [SMILES: CC[C@H](OC(=O)NC(C)C)[C@@H](OCOC)c1ccccc1I]

¹H NMR (400 MHz, CDCl₃) δ1.04 (t, J=7.6 Hz, 3H), 1.27 (d, J=6.8 Hz, 6H), 1.60~1.71 (m, 2H), 3.30 (s, 3H), 4.17 (m, 1H), 4.71 (d, J=6.8, 1H), 4.82~4.88 (m, 1H), 5.45 (s, 2H), 7.15~7.90 (m, 4H)

Example 32

Synthesis of 1-(2-iodophenyl)-(S)-1-methoxymethoxybutyl-(S)-2-cyclopropylcarbamate

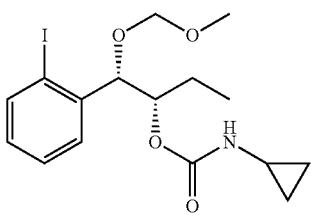 [SMILES: CC[C@H](OC(=O)NC1CC1)[C@@H](OCOC)c1ccccc1I]

¹H NMR (400 MHz, CDCl₃) δ0.57 (m, 2H), 0.82 (m, 2H), 1.04 (t, J=7.6 Hz, 3H), 1.60~1.71 (m, 2H), 2.75 (m, 1H), 3.30 (s, 3H), 4.71 (d, J=6.8, 1H), 4.82~4.88 (m, 1H), 5.45 (s, 2H), 7.16~7.90 (m, 4H)

Example 33

Synthesis of 1-(2-iodophenyl)-(S)-1-methoxymethoxybutyl-(S)-2-cyclohexylcarbamate

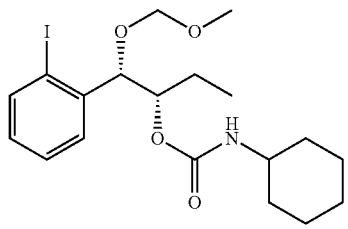 [SMILES: CC[C@H](OC(=O)NC1CCCCC1)[C@@H](OCOC)c1ccccc1I]

¹H NMR (400 MHz, CDCl₃) δ1.04 (t, J=7.6 Hz, 3H), 1.11~1.21 (m, 4H), 1.47~1.49 (m, 4H), 1.60~1.71 (m, 2H), 1.74 (m, 2H), 3.30 (s, 3H), 3.54 (m, 1H), 4.71 (d, J=6.8, 1H), 4.82~4.88 (m, 1H), 5.45 (s, 2H), 7.14~7.87 (m, 4H)

Example 34

Synthesis of 1-(2-iodophenyl)-(S)-1-methoxymethoxybutyl-(S)-2-cyclohexylcarbamate

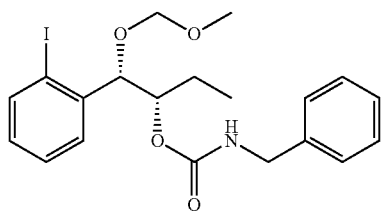 [SMILES: CC[C@H](OC(=O)NCc1ccccc1)[C@@H](OCOC)c1ccccc1I]

¹H NMR (400 MHz, CDCl₃) δ1.04 (t, J=7.6 Hz, 3H), 1.60~1.71 (m, 2H), 3.30 (s, 3H), 4.20 (m, 2H), 4.71 (d, J=6.8, 1H), 4.82~4.88 (m, 1H), 5.45 (s, 2H), 7.14~7.19 (m, 4H), 7.37~7.88 (m, 5H)

Example 35

Synthesis of 1-(2-iodophenyl)-(S)-1-methoxymethoxybutyl-(S)-2-bicyclo[2,2,1]heptanescarbamate

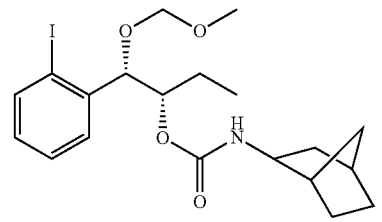 [SMILES: CC[C@H](OC(=O)NC1CC2CCC1C2)[C@@H](OCOC)c1ccccc1I]

¹H NMR (400 MHz, CDCl₃) δ1.04 (t, J=7.6 Hz, 3H), 1.33~1.58 (m, 6H), 1.60~1.71 (m, 2H), 1.75~1.88 (m, 2H), 2.06~2.13 (m, 2H), 3.30 (s, 3H), 3.53 (m, 1H), 4.71 (d, J=6.8, 1H), 4.82~4.88 (m, 1H), 5.45 (s, 2H), 7.15~7.19 (m, 4H), 7.37~7.88 (m, 5H)

Example 36

Synthesis of 1-(2-iodophenyl)-(S)-1-methoxymethoxy-3-methyl-butyl-(S)-2-carbamate

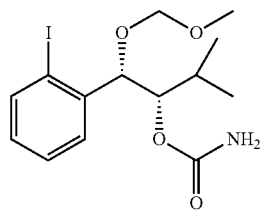 [SMILES: COCO[C@@H](c1ccccc1I)[C@@H](OC(N)=O)C(C)C]

¹H NMR (400 MHz, CDCl₃) δ1.07 (d, J=7.6 Hz, 3H), 1.83~1.89 (m, 1H), 3.30 (s, 3H), 4.71 (d, J=6.8, 1H), 4.82~4.88 (m, 1H), 5.45 (s, 2H), 7.26~7.70 (m, 4H)

Example 37

Synthesis of 1-(2-iodophenyl)-(S)-1-methoxymethoxy-3-methyl-butyl-(S)-2-methylcarbamate

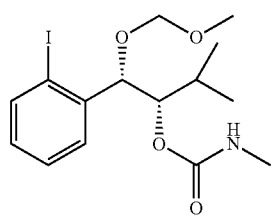 [SMILES: CNC(=O)O[C@@H](C(C)C)[C@@H](OCOC)c1ccccc1I]

¹H NMR (400 MHz, CDCl₃) δ1.04 (d, J=7.6 Hz, 6H), 1.60~1.71 (m, 1H), 2.58 (s, 3H), 3.30 (s, 3H), 4.71 (d, J=6.8, 1H), 4.82~4.88 (m, 1H), 5.45 (s, 2H), 7.13~7.88 (m, 4H)

Example 38

Synthesis of 1-(2-iodophenyl)-(S)-1-methoxymethoxy-3-methyl-butyl-(S)-2-propylcarbamate

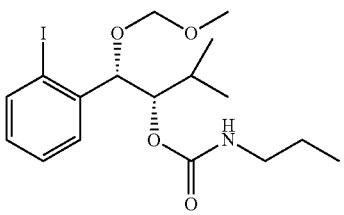 [SMILES: CCCNC(=O)O[C@@H](C(C)C)[C@@H](OCOC)c1ccccc1I]

¹H NMR (400 MHz, CDCl₃) δ0.90 (1, J=6.8 Hz, 3H), 1.04 (d, J=7.6 Hz, 6H), 1.58~1.71 (m, 5H), 3.18 (t, J=7.1 Hz, 2H), 3.30 (s, 3H), 4.71 (d, J=6.8, 1H), 4.82~4.88 (m, 1H), 5.45 (s, 2H), 7.14~7.89 (m, 4H)

Example 39

Synthesis of 1-(2-iodophenyl)-(S)-1-methoxymethoxy-3-methyl-butyl-(S)-2-isopropyl-carbamate

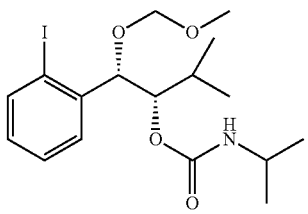 [SMILES: COCO[C@@H](c1ccccc1I)[C@@H](OC(=O)NC(C)C)C(C)C]

$^1$H NMR (400 MHz, CDCl$_3$) δ1.04 (t, J=7.6 Hz, 6H), 1.27 (d, J=6.8 Hz, 6H), 1.60~1.71 (m, 1H), 3.30 (s, 3H), 4.17 (m, 1H), 4.71 (d, J=6.8, 1H), 4.82~4.88 (m, 1H), 5.45 (s, 2H), 7.15~7.90 (m, 4H)

Example 40

Synthesis of 1-(2-iodophenyl)-(S)-1-methoxymethoxy-3-methyl-butyl-(S)-2-cyclopropyl-carbamate

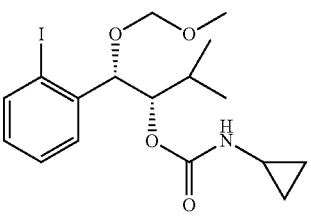 [SMILES: COCO[C@@H](c1ccccc1I)[C@@H](OC(=O)NC1CC1)C(C)C]

$^1$H NMR (400 MHz, CDCl$_3$) δ0.57 (m, 2H), 0.82 (m, 2H), 1.04 (d, J=7.6 Hz, 6H), 1.60~1.71 (m, 1H), 2.75 (m, 1H), 3.30 (s, 3H), 4.71 (d, J=6.8, 1H), 4.82~4.88 (m, 1H), 5.45 (s, 2H), 7.16~7.90 (m, 4H)

Example 41

Synthesis of 1-(2-iodophenyl)-(S)-1-methoxymethoxy-3-methyl-butyl-(S)-2-cyclohexyl-carbamate

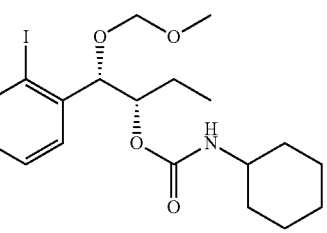

$^1$H NMR (400 MHz, CDCl$_3$) δ1.04 (d, J=7.6 Hz, 6H), 1.11~1.21 (m, 4H), 1.47~1.49 (m, 4H), 1.74 (m, 2H), 1.84~1.90 (m, 1H), 3.30 (s, 3H), 3.54 (m, 1H), 4.71 (d, J=6.8, 1H), 4.82~4.88 (m, 1H), 5.45 (s, 2H), 7.14~7.87 (m, 4H)

Example 42

Synthesis of 1-(2-iodophenyl)-(S)-1-methoxymethoxy-3-methyl-butyl-(S)-2-cyclohexyl-carbamate

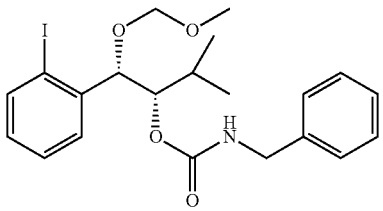 [SMILES: COCO[C@@H](c1ccccc1I)[C@@H](OC(=O)NCc1ccccc1)C(C)C]

$^1$H NMR (400 MHz, CDCl$_3$) δ1.04 (d, J=7.6 Hz, 6H), 1.87~1.90 (m, 1H), 3.30 (s, 3H), 4.20 (m, 2H), 4.71 (d, J=6.8, 1H), 4.82~4.88 (m, 1H), 5.45 (s, 2H), 7.14~7.19 (m, 4H), 7.37~7.88 (m, 5H)

Example 43

Synthesis of 1-(2-iodophenyl)-(S)-1-methoxymethoxy-3-methyl-butyl-(S)-2-bicyclo[2,2,1]heptanescarbamate

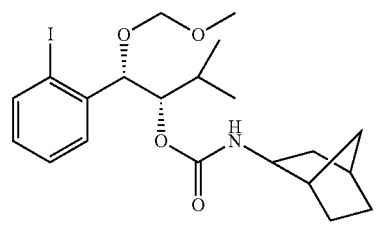 [SMILES: COCO[C@@H](c1ccccc1I)[C@@H](OC(=O)NC1CC2CCC1C2)C(C)C]

$^1$H NMR (400 MHz, CDCl$_3$) δ1.04 (d, J=7.6 Hz, 6H), 1.33~1.58 (m, 6H), 1.75~1.88 (m, 2H), 1.88~1.93 (m, 1H), 2.06~2.13 (m, 2H), 3.30 (s, 3H), 3.53 (m, 1H), 4.71 (d, J=6.8, 1H), 4.82~4.88 (m, 1H), 5.45 (s, 2H), 7.15~7.19 (m, 4H), 7.37~7.88 (m, 5H)

Example 44

Synthesis of 1-(2-iodophenyl)-(S)-1-methoxymethoxyhexyl-(S)-2-carbamate

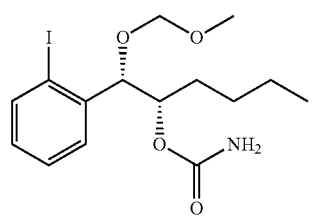

$^1$H NMR (400 MHz, CDCl$_3$) δ0.84 (t, J=7.0 Hz, 3H), 1.20~1.35 (m, 4H), 1.36~1.41 (m, 1H), 1.59~1.63 (m, 1H), 3.30 (s, 3H), 4.47 (br s, 2H), 4.71 (d, J=6.8, 1H), 4.82~4.88 (m, 1H), 5.45 (s, 2H), 7.26~7.70 (m, 4H)

Example 45

Synthesis of 1-(2-iodophenyl)-(S)-1-methoxymethoxyhexyl-(S)-2-methylcarbamate

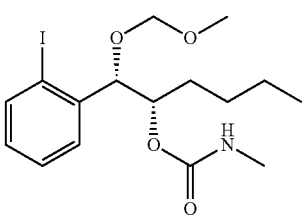 [SMILES: CCCC[C@H](OC(=O)NC)[C@@H](OCOC)c1ccccc1I]

¹H NMR (400 MHz, CDCl₃) δ0.89 (t, J=7.2 Hz, 3H), 1.20~1.35 (m, 4H), 1.36~1.41 (m, 1H), 1.59~1.63 (m, 1H), 2.58 (s, 3H), 3.30 (s, 3H), 4.71 (d, J=6.8, 1H), 4.82~4.88 (m, 1H), 5.45 (s, 2H), 7.13~7.88 (m, 4H)

Example 46

Synthesis of 1-(2-iodophenyl)-(S)-1-methoxymethoxyhexyl-(S)-2-propylcarbamate

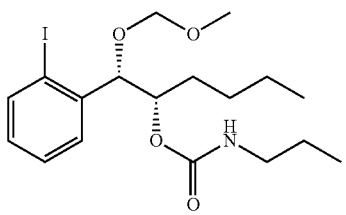 [SMILES: CCCC[C@H](OC(=O)NCCC)[C@@H](OCOC)c1ccccc1I]

¹H NMR (400 MHz, CDCl₃) δ0.87 (t, J=6.8 Hz, 3H), 0.90 (t, J=6.8 Hz, 3H), 1.21~1.35 (m, 4H), 1.36~1.40 (m, 1H), 1.58~1.62 (m, 1H), 3.18 (t, J=7.1 Hz, 2H), 3.30 (s, 3H), 4.71 (d, J=6.8, 1H), 4.82~4.88 (m, 1H), 5.45 (s, 2H), 7.14~7.89 (m, 4H)

Example 47

Synthesis of 1-(2-iodophenyl)-(S)-1-methoxymethoxyhexyl-(S)-2-isopropylcarbamate

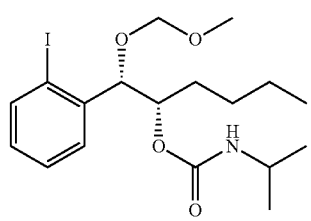 [SMILES: CCCC[C@H](OC(=O)NC(C)C)[C@@H](OCOC)c1ccccc1I]

¹H NMR (400 MHz, CDCl₃) δ0.84 (t, J=7.6 Hz, 3H), 1.22~1.35 (m, 4H), 1.27 (d, J=6.8 Hz, 6H), 136~1.40 (m, 1H), 1.58~1.62 (m, 1H), 3.30 (s, 3H), 4.17 (m, 1H), 4.71 (d, J=6.8, 1H), 4.82~4.88 (m, 1H), 5.45 (s, 2H), 7.15~7.90 (m, 4H)

Example 48

Synthesis of 1-(2-iodophenyl)-(S)-1-methoxymethoxyhexyl-(S)-2-cyclopropylcarbamate

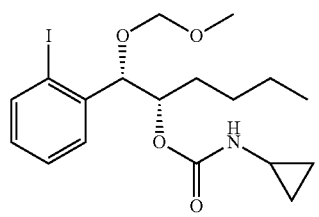 [SMILES: CCCC[C@H](OC(=O)NC1CC1)[C@@H](OCOC)c1ccccc1I]

¹H NMR (400 MHz, CDCl₃) δ0.57 (m, 2H), 0.82 (m, 2H), 0.88 (t, J=7.6 Hz, 3H), 1.22~1.35 (m, 4H), 1.36~1.40 (m, 1H), 1.58~1.62 (m, 1H), 2.75 (m, 1H), 3.30 (s, 3H), 4.71 (d, J=6.8, 1H), 4.82~4.88 (m, 1H), 5.45 (s, 2H), 7.16~7.90 (m, 4H)

Example 49

Synthesis of 1-(2-iodophenyl)-(S)-1-methoxymethoxyhexyl-(S)-2-cyclohexylcarbamate

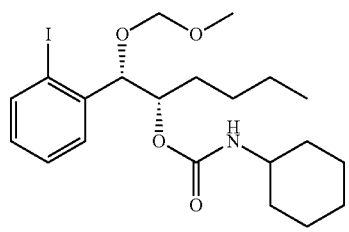 [SMILES: CCCC[C@H](OC(=O)NC1CCCCC1)[C@@H](OCOC)c1ccccc1I]

¹H NMR (400 MHz, CDCl₃) δ0.98 (t, J=7.6 Hz, 3H), 1.11~1.21 (m, 4H), 1.26~1.33 (m, 4H), 1.47~1.49 (m, 2H), 1.52~1.54 (m, 2H), 1.74 (m, 2H), 1.84~1.90 (m, 1H), 3.30 (s, 3H), 3.54 (m, 1H), 4.71 (d, J=6.8, 1H), 4.82~4.88 (m, 1H), 5.45 (s, 2H), 7.14~7.87 (m, 4H)

Example 50

Synthesis of 1-(2-iodophenyl)-(S)-1-methoxymethoxyhexyl-(S)-2-cyclohexylcarbamate

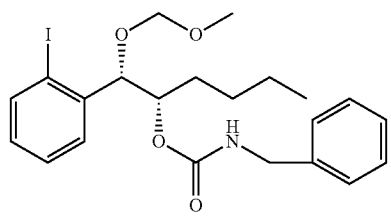 [SMILES: CCCC[C@H](OC(=O)NCc1ccccc1)[C@@H](OCOC)c1ccccc1I]

¹H NMR (400 MHz, CDCl₃) δ0.94 (t, J=7.6 Hz, 3H), 1.26~1.33 (m, 4H), 1.51~1.55 (m, 2H), 3.30 (s, 3H), 4.20

(m, 2H), 4.71 (d, J=6.8, 1H), 4.82~4.88 (m, 1H), 5.45 (s, 2H), 7.14~7.19 (m, 4H), 7.37~7.88 (m, 5H)

Example 51

Synthesis of 1-(2-iodophenyl)-(S)-1-methoxymethoxyhexyl-(S)-2-bicyclo[2,2,1]heptan-escarbamate

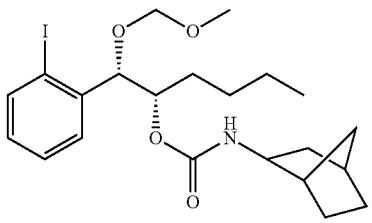 [SMILES: CCCC[C@H](OC(=O)NC1CC2CCC1C2)[C@@H](OCOC)c1ccccc1I]

$^1$H NMR (400 MHz, CDCl$_3$) δ0.97 (t, J=7.0 Hz, 3H), 1.25~1.32 (m, 4H), 1.33~1.58 (m, 8H), 1.60~1.71 (m, 2H), 1.75~1.88 (m, 2H), 2.06~2.13 (m, 2H), 3.30 (s, 3H), 3.53 (m, 1H), 4.71 (d, J=6.8, 1H), 4.82~4.88 (m, 1H), 5.45 (s, 2H), 7.15~7.19 (m, 4H), 7.37~7.88 (m, 5H)

Example 52

Synthesis of 1-(3-iodophenyl)-(S)-1-methoxymethoxypropyl-(S)-2-carbamate

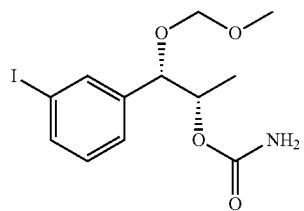 [SMILES: COCO[C@@H](c1cccc(I)c1)[C@H](C)OC(N)=O]

$^1$H NMR (400 MHz, CDCl$_3$) δ1.16 (d, J=6.4 Hz, 3H), 3.39 (s, 3H), 4.54~4.63 (m, 6H), 5.04~5.10 (m, 1H), 7.09~7.73 (m, 4H)

Example 53

Synthesis of 1-(3-iodophenyl)-(S)-1-methoxymethoxybutyl-(S)-2-carbamate

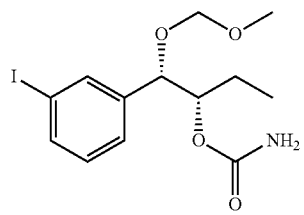 [SMILES: CC[C@H](OC(N)=O)[C@@H](OCOC)c1cccc(I)c1]

$^1$H NMR (400 MHz, CDCl$_3$) δ1.04 (t, J=7.6 Hz, 3H), 1.60~1.71 (m, 2H), 3.30 (s, 3H), 4.71 (d, J=6.8, 1H), 4.73 (br s, 2H), 4.82~4.88 (m, 1H), 5.45 (s, 2H), 6.96~7.57 (m, 4H)

Example 54

Synthesis of 1-(3-iodophenyl)-(S)-1-methoxymethoxy-3-methyl-butyl-(S)-2-carbamate

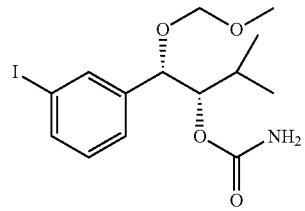 [SMILES: COCO[C@@H](c1cccc(I)c1)[C@@H](OC(N)=O)C(C)C]

$^1$H NMR (400 MHz, CDCl$_3$) δ1.07 (t, J=7.6 Hz, 6H), 1.83~1.89 (m, 1H), 3.30 (s, 3H), 4.71 (d, J=6.8, 1H), 4.73 (br s, 2H), 4.82~4.88 (m, 1H), 5.45 (s, 2H), 7.00~7.58 (m, 4H)

Example 55

Synthesis of 1-(3-iodophenyl)-(S)-1-methoxymethoxyhexyl-(S)-2-carbamate

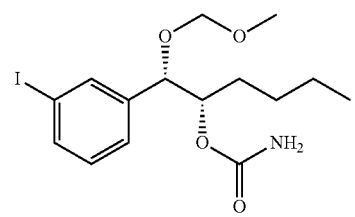 [SMILES: CCCC[C@H](OC(N)=O)[C@@H](OCOC)c1cccc(I)c1]

$^1$H NMR (400 MHz, CDCl$_3$) δ0.90 (t, J=7.6 Hz, 3H), 1.35~1.65 (m, 6H), 3.30 (s, 3H), 4.71 (d, J=6.8, 1H), 4.73 (br s, 2H), 4.82~4.88 (m, 1H), 5.45 (s, 2H), 7.01~7.59 (m, 4H)

Example 56

Synthesis of 1-(4-fluorophenyl)-(S)-1-methoxymethoxypropyl-(S)-2-carbamate

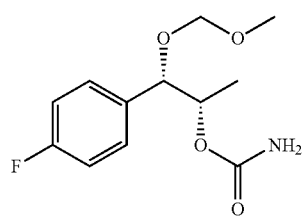 [SMILES: COCO[C@@H](c1ccc(F)cc1)[C@H](C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 6.96~7.17 (m, 4H)

Example 57

Synthesis of 1-(4-fluorophenyl)-(S)-1-methoxymethoxybutyl-(S)-2-carbamate

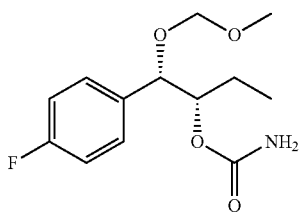 [SMILES: CC[C@H](OC(N)=O)[C@@H](OCOC)c1ccc(F)cc1]

$^1$H NMR (400 MHz, CDCl$_3$) δ1.04 (t, J=7.6 Hz, 3H), 1.60~1.71 (m, 2H), 3.30 (s, 3H), 4.71 (d, J=6.8 Hz, 1H), 4.73 (br s, 2H), 4.82~4.88 (m, 1H), 5.45 (s, 2H), 6.90~7.20 (m, 4H)

Example 58

Synthesis of 1-(4-fluorophenyl)-(S)-1-methoxymethoxy-3-methyl-butyl-(S)-2-carbamate

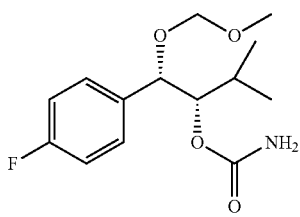 [SMILES: COCO[C@@H](c1ccc(F)cc1)[C@@H](OC(N)=O)C(C)C]

$^1$H NMR (400 MHz, CDCl$_3$) δ1.07 (1, J=7.6 Hz, 6H), 1.83~1.89 (m, 1H), 3.30 (s, 3H), 4.71 (d, J=6.8 Hz, 1H), 4.73 (br s, 2H), 4.82~4.88 (m, 1H), 5.45 (s, 2H), 6.92~7.17 (m, 4H)

Example 59

Synthesis of 1-(4-fluorophenyl)-(S)-1-methoxymethoxyhexyl-(S)-2-carbamate

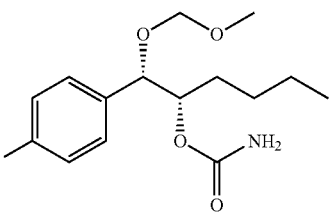

$^1$H NMR (400 MHz, CDCl$_3$) δ0.90 (t, J=7.6 Hz, 3H), 1.35~1.65 (m, 6H), 3.30 (s, 3H), 4.71 (d, J=6.8 Hz, 1H), 4.73 (br s, 2H), 4.82~4.88 (m, 1H), 5.45 (s, 2H), 6.96~7.19 (m, 4H)

Example 60

Synthesis of 1-(2,4-dichlorophenyl)-(S)-1-methoxymethoxypropyl-(S)-2-carbamate

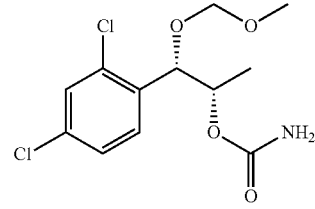 [SMILES: COCO[C@@H](c1ccc(Cl)cc1Cl)[C@H](C)OC(N)=O]

$^1$H NMR (400 MHz, CDCl$_3$) δ1.37 (d, J=6.8 Hz, 3H), 3.30 (s, 3H), 4.71 (d, J=6.8 Hz, 1H), 4.82~4.88 (m, 1H), 5.45 (s, 2H), 7.24~7.30 (m, 2H), 7.73 (d, J=1.5 Hz, 1H)

Example 61

Synthesis of 1-(2,4-dichlorophenyl)-(S)-1-methoxymethoxybutyl-(S)-2-carbamate

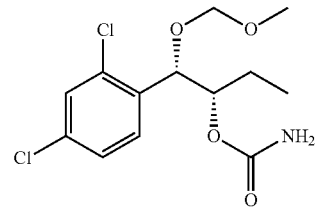 [SMILES: CC[C@H](OC(N)=O)[C@@H](OCOC)c1ccc(Cl)cc1Cl]

$^1$H NMR (400 MHz, CDCl$_3$) δ1.04 (t, J=7.6 Hz, 3H), 1.60~1.71 (m, 2H), 3.30 (s, 3H), 4.71 (d, J=6.8 Hz, 1H), 4.73 (br s, 2H), 4.82~4.88 (m, 1H), 5.45 (s, 2H), 7.24~7.30 (m, 2H), 7.73 (d, J=1.5 Hz, 1H)

Example 62

Synthesis of 1-(2,4-dichlorophenyl)-(S)-1-methoxymethoxy-3-methyl-butyl-(S)-2-carbamate

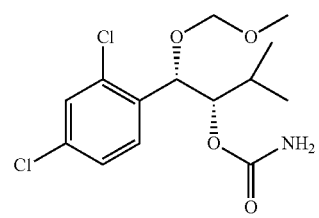 [SMILES: COCO[C@@H](c1ccc(Cl)cc1Cl)[C@@H](OC(N)=O)C(C)C]

$^1$H NMR (400 MHz, CDCl$_3$) δ1.07 (t, J=7.6 Hz, 6H), 1.83~1.89 (m, 1H), 3.30 (s, 3H), 4.71 (d, J=6.8 Hz, 1H), 4.73 (br s, 2H), 4.82~4.88 (m, 1H), 5.45 (s, 2H), 7.24~7.30 (m, 2H), 7.73 (d, J=1.5 Hz, 1H)

Example 63

Synthesis of 1-(2,4-dichlorophenyl)-(S)-1-methoxymethoxyhexyl-(S)-2-carbamate

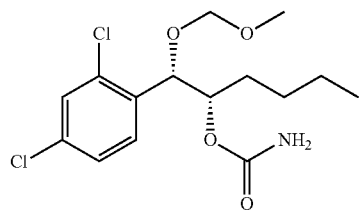

¹H NMR (400 MHz, CDCl₃) δ0.90 (t, J=7.6 Hz, 3H), 1.35~1.65 (m, 6H), 3.30 (s, 3H), 4.71 (d, J=6.8, 1H), 4.73 (br s, 2H), 4.82~4.88 (m, 1H), 5.45 (s, 2H), 7.24~7.30 (m, 2H), 7.73 (d, J=1.5 Hz, 1H)

Example 64

Synthesis of 1-(2,6-dichlorophenyl)-(S)-1-methoxymethoxypropyl-(S)-2-carbamate

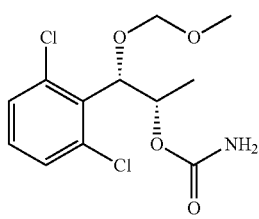 [SMILES: COCO[C@@H](c1c(Cl)cccc1Cl)[C@H](C)OC(N)=O]

¹H NMR (400 MHz, CDCl₃) δ1.37 (d, J=6.8 Hz, 3H), 3.30 (s, 3H), 4.71 (d, J=6.8, 1H), 4.82~4.88 (m, 1H), 5.45 (s, 2H), 7.57~7.58 (m, 3H)

Example 65

Synthesis of 1-(2,6-dichlorophenyl)-(S)-1-methoxymethoxybutyl-(S)-2-carbamate

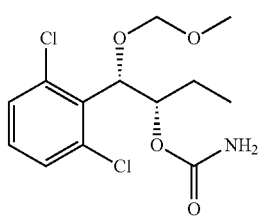 [SMILES: CC[C@H](OC(N)=O)[C@@H](OCOC)c1c(Cl)cccc1Cl]

¹H NMR (400 MHz, CDCl₃) δ1.04 (t, J=7.6 Hz, 3H), 1.60~1.71 (m, 2H), 3.30 (s, 3H), 4.71 (d, J=6.8, 1H), 4.73 (br s, 2H), 4.82~4.88 (m, 1H), 5.45 (s, 2H), 7.54~7.57 (m, 3H)

Example 66

Synthesis of 1-(2,6-dichlorophenyl)-(S)-1-methoxymethoxy-3-methyl-butyl-(S)-2-carbamate

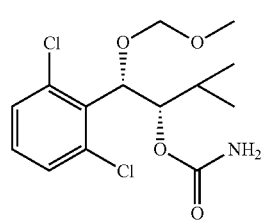 [SMILES: COCO[C@@H](c1c(Cl)cccc1Cl)[C@@H](OC(N)=O)C(C)C]

¹H NMR (400 MHz, CDCl₃) δ1.07 (t, J=7.6 Hz, 6H), 1.83~1.89 (m, 1H), 3.30 (s, 3H), 4.71 (d, J=6.8, 1H), 4.73 (br s, 2H), 4.82~4.88 (m, 1H), 5.45 (s, 2H), 7.55~7.57 (m, 3H)

Example 67

Synthesis of 1-(2,4-dichlorophenyl)-(S)-1-methoxymethoxyhexyl-(S)-2-carbamate

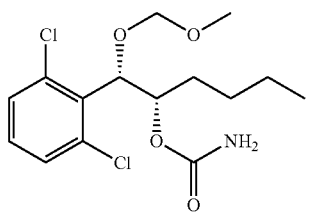

¹H NMR (400 MHz, CDCl₃) δ0.90 (t, J=7.6 Hz, 3H), 1.35~1.65 (m, 6H), 3.30 (s, 3H), 4.71 (d, J=6.8, 1H), 4.73 (br s, 2H), 4.82~4.88 (m, 1H), 5.45 (s, 2H), 7.54~7.59 (m, 3H)

Example 68

Synthesis of 1-(2,3-dichlorophenyl)-(S)-1-methoxymethoxypropyl-(S)-2-carbamate

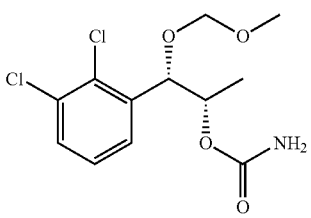 [SMILES: COCO[C@@H](c1cccc(Cl)c1Cl)[C@H](C)OC(N)=O]

¹H NMR (400 MHz, CDCl₃) δ1.37 (d, J=6.8 Hz, 3H), 3.30 (s, 3H), 4.71 (d, J=6.8, 1H), 4.82~4.88 (m, 1H), 5.45 (s, 2H), 7.01~7.14 (m, 3H)

Example 69

Synthesis of 1-(2-chlorophenyl)-(R)-1-methoxymethoxypropyl-(R)-2-carbamate

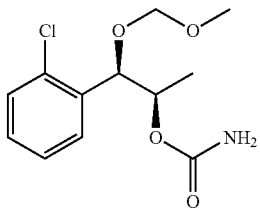 [SMILES: COCO[C@H](c1ccccc1Cl)[C@@H](C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.26~7.70 (m, 4H)

Example 70

Synthesis of 1-(2-chlorophenyl)-1-methoxymethoxypropyl-2-carbamate

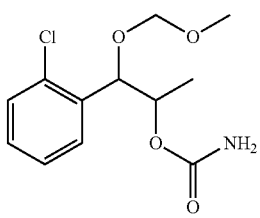 [SMILES: COCOC(c1ccccc1Cl)C(C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.26~7.70 (m, 4H)

Example 71

Synthesis of 1-(2-chlorophenyl)-(R)-1-methoxymethoxypropyl-(S)-2-carbamate

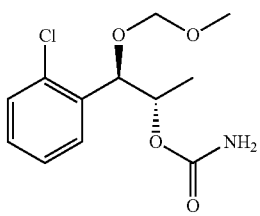 [SMILES: COCO[C@H](c1ccccc1Cl)[C@H](C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.26~7.70 (m, 4H)

Example 72

Synthesis of 1-(2-chlorophenyl)-(S)-1-methoxymethoxypropyl-(R)-2-carbamate

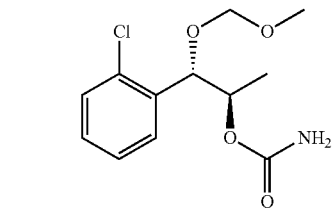 [SMILES: COCO[C@@H](c1ccccc1Cl)[C@@H](C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.26~7.70 (m, 4H)

Example 73

Synthesis of 1-(2-chlorophenyl)-(R)-1-methoxymethoxybutyl-(R)-2-carbamate

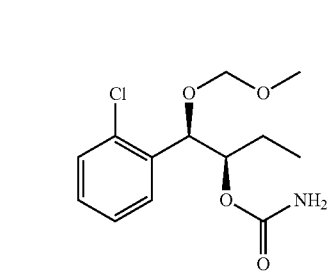 [SMILES: CC[C@@H](OC(N)=O)[C@H](OCOC)c1ccccc1Cl]

$^1$H NMR (400 MHz, CDCl$_3$) δ1.04 (t, J=7.6 Hz, 3H), 1.60~1.71 (m, 2H), 3.30 (s, 3H), 4.71 (d, J=6.8 Hz, 1H), 4.73 (br s, 2H), 4.82~4.88 (m, 1H), 5.45 (s, 2H), 7.26~7.70 (m, 4H)

Example 74

Synthesis of 1-(2-chlorophenyl)-1-methoxymethoxybutyl-2-carbamate

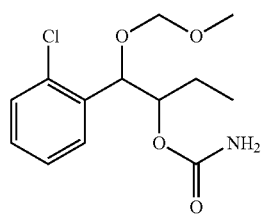 [SMILES: CCC(OC(N)=O)C(OCOC)c1ccccc1Cl]

$^1$H NMR (400 MHz, CDCl$_3$) δ1.04 (1, J=7.6 Hz, 3H), 1.60~1.71 (m, 2H), 3.30 (s, 3H), 4.71 (d, J=6.8 Hz, 1H), 4.73 (br s, 2H), 4.82~4.88 (m, 1H), 5.45 (s, 2H), 7.26~7.70 (m, 4H)

Example 75

Synthesis of 1-(2-chlorophenyl)-(R)-1-methoxymethoxy-3-methyl-butyl-(R)-2-carbamate

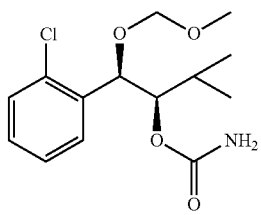 [SMILES: COCO[C@H](c1ccccc1Cl)[C@H](OC(N)=O)C(C)C]

¹H NMR (400 MHz, CDCl₃) δ1.04 (1, J=7.6 Hz, 3H), 1.60~1.71 (m, 2H), 3.30 (s, 3H), 4.71 (d, J=6.8, 1H), 4.73 (br s, 2H), 4.82~4.88 (m, 1H), 5.45 (s, 2H), 7.26~7.70 (m, 4H)

Example 76

Synthesis of 1-(2-chlorophenyl)-1-methoxymethoxy-3-methyl-butyl-2-carbamate

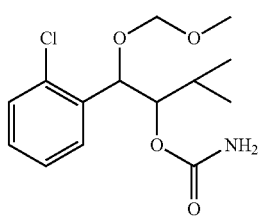 [SMILES: COCOC(c1ccccc1Cl)C(OC(N)=O)C(C)C]

¹H NMR (400 MHz, CDCl₃) δ1.07 (1, J=7.6 Hz, 6H), 1.83~1.89 (m, 1H), 3.30 (s, 3H), 4.71 (d, J=6.8, 1H), 4.73 (br s, 2H), 4.82~4.88 (m, 1H), 5.45 (s, 2H), 7.26~7.70 (m, 4H)

Example 77

Synthesis of 1-(2-chlorophenyl)-(R)-1-methoxymethoxyhexyl-(R)-2-carbamate

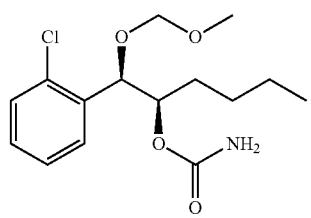 [SMILES: CCCC[C@@H](OC(N)=O)[C@H](OCOC)c1ccccc1Cl]

¹H NMR (400 MHz, CDCl₃) δ0.90 (t, J=7.6 Hz, 3H), 1.35~1.65 (m, 6H), 3.30 (s, 3H), 4.71 (d, J=6.8, 1H), 4.73 (br s, 2H), 4.82~4.88 (m, 1H), 5.45 (s, 2H), 7.26~7.70 (m, 4H)

Example 78

Synthesis of 1-(2-chlorophenyl)-1-methoxymethoxyhexyl-2-carbamate

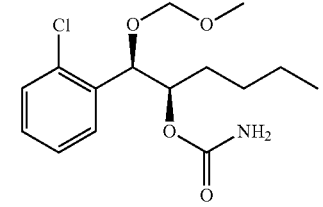 [SMILES: CCCC[C@@H](OC(N)=O)[C@H](OCOC)c1ccccc1Cl]

¹H NMR (400 MHz, CDCl₃) δ0.90 (t, J=7.6 Hz, 3H), 1.35~1.65 (m, 6H), 3.30 (s, 3H), 4.71 (d, J=6.8, 1H), 4.73 (br s, 2H), 4.82~4.88 (m, 1H), 5.45 (s, 2H), 7.26~7.70 (m, 4H)

Example 79

Synthesis of 1-(2-chlorophenyl)-(R)-1-methoxymethoxypropyl-(R)-2-methylcarbamate

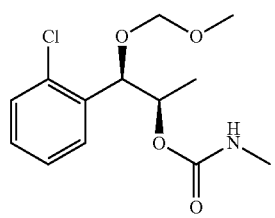 [SMILES: CNC(=O)O[C@H](C)[C@H](OCOC)c1ccccc1Cl]

¹H NMR (400 MHz, CDCl₃) δ1.37 (d, J=6.8 Hz, 3H), 2.58 (s, 3H), 3.30 (s, 3H), 4.71 (d, J=6.8, 1H), 4.82~4.88 (m, 1H), 5.45 (s, 2H), 7.26~7.70 (m, 4H)

Example 80

Synthesis of 1-(2-chlorophenyl)-(R)-1-methoxymethoxypropyl-(R)-2-propylcarbamate

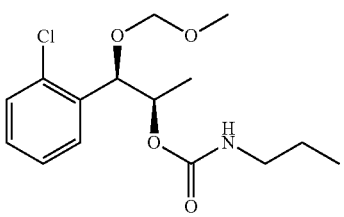 [SMILES: CCCNC(=O)O[C@H](C)[C@H](OCOC)c1ccccc1Cl]

¹H NMR (400 MHz, CDCl₃) δ0.90 (t, J=6.8 Hz, 3H), 1.37 (d, J=6.8 Hz, 3H), 1.60 (m, 2H), 3.18 (t, J=7.1 Hz, 2H), 3.30 (s, 3H), 4.71 (d, J=6.8, 1H), 4.82~4.88 (m, 1H), 5.45 (s, 2H), 7.26~7.70 (m, 4H)

Example 81

Synthesis of 1-(2-chlorophenyl)-(R)-1-methoxymethoxypropyl-(R)-2-isopropylcarbamate

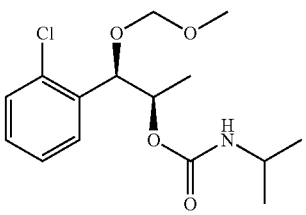 [SMILES: COCO[C@H](c1ccccc1Cl)[C@@H](C)OC(=O)NC(C)C]

¹H NMR (400 MHz, CDCl₃) δ, 1.27 (d, J=6.8 Hz, 6H), 1.37 (d, J=6.8 Hz, 3H), 3.30 (s, 3H), 4.17 (m, 1H), 4.71 (d, J=6.8, 1H), 4.82~4.88 (m, 1H), 5.45 (s, 2H), 7.26~7.70 (m, 4H)

Example 82

Synthesis of 1-(2-chlorophenyl)-(R)-1-methoxymethoxypropyl-(R)-2-cyclopropylcarbamate

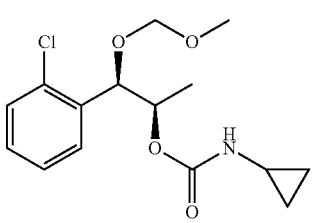 [SMILES: COCO[C@H](c1ccccc1Cl)[C@@H](C)OC(=O)NC1CC1]

¹H NMR (400 MHz, CDCl₃) δ0.57 (m, 2H), 0.82 (m, 2H), 1.37 (d, J=6.8 Hz, 3H), 2.75 (m, 1H), 3.30 (s, 3H), 4.71 (d, J=6.8, 1H), 4.82~4.88 (m, 1H), 5.45 (s, 2H), 7.26~7.70 (m, 4H)

Example 83

Synthesis of 1-(2-chlorophenyl)-(R)-1-methoxymethoxypropyl-(R)-2-cyclohexylcarbamate

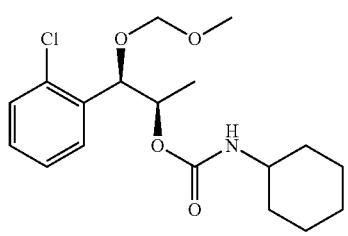 [SMILES: COCO[C@H](c1ccccc1Cl)[C@@H](C)OC(=O)NC1CCCCC1]

¹H NMR (400 MHz, CDCl₃) δ1.11~1.21 (m, 4H), 1.37 (d, J=6.8 Hz, 3H), 1.47~1.49 (m, 4H), 1.74 (m, 2H), 3.30 (s, 3H), 3.54 (m, 1H), 4.71 (d, J=6.8, 1H), 4.82~4.88 (m, 1H), 5.45 (s, 2H), 7.26~7.70 (m, 4H)

Example 84

Synthesis of 1-(2-chlorophenyl)-(R)-1-methoxymethoxypropyl-(R)-2-cyclohexylcarbamate

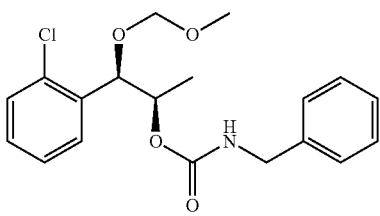 [SMILES: COCO[C@H](c1ccccc1Cl)[C@@H](C)OC(=O)NCc1ccccc1]

¹H NMR (400 MHz, CDCl₃) δ1.37 (d, J=6.8 Hz, 3H), 3.30 (s, 3H), 4.20 (m, 2H), 4.71 (d, J=6.8, 1H), 4.82~4.88 (m, 1H), 5.45 (s, 2H), 7.13~7.19 (m, 4H), 7.37~7.88 (m, 5H)

Example 85

Synthesis of 1-(2-chlorophenyl)-(R)-1-methoxymethoxypropyl-(R)-2-bicyclo[2,2,1]heptan-escarbamate

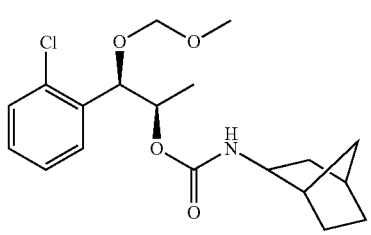 [SMILES: COCO[C@H](c1ccccc1Cl)[C@@H](C)OC(=O)NC1CC2CCC1C2]

¹H NMR (400 MHz, CDCl₃) δ1.33~1.58 (m, 9H), 1.75~1.88 (m, 2H), 2.06~2.13 (m, 2H), 3.30 (s, 3H), 3.53 (m, 1H), 4.71 (d, J=6.8, 1H), 4.82~4.88 (m, 1H), 5.45 (s, 2H), 7.13~7.19 (m, 4H), 7.37~7.88 (m, 5H)

Example 86

Synthesis of 1-(2-fluorophenyl)-(R)-1-methoxymethoxypropyl-(R)-2-carbamate

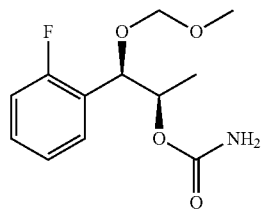 [SMILES: COCO[C@H](c1ccccc1F)[C@@H](C)OC(N)=O]

¹H NMR (400 MHz, CDCl₃) δ1.37 (d, J=6.8 Hz, 3H), 3.30 (s, 3H), 4.71 (d, J=6.8, 1H), 4.82~4.88 (m, 1H), 5.45 (s, 2H), 7.15~7.68 (m, 4H)

Example 87

Synthesis of 1-(4-fluorophenyl)-(R)-1-methoxymethoxypropyl-(R)-2-carbamate

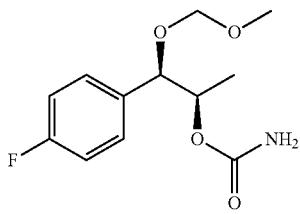 [SMILES: COCO[C@H](c1ccc(F)cc1)[C@@H](C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 6.96~7.17 (m, 4H)

Example 88

Synthesis of 1-(4-fluorophenyl)-(R)-1-methoxymethoxybutyl-(R)-2-carbamate

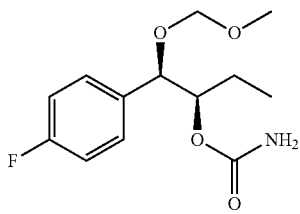 [SMILES: CC[C@@H](OC(N)=O)[C@H](OCOC)c1ccc(F)cc1]

$^1$H NMR (400 MHz, CDCl$_3$) δ1.04 (t, J=7.6 Hz, 3H), 1.60~1.71 (m, 2H), 3.30 (s, 3H), 4.71 (d, J=6.8, 1H), 4.73 (br s, 2H), 4.82~4.88 (m, 1H), 5.45 (s, 2H), 6.90~7.20 (m, 4H)

Example 89

Synthesis of 1-(4-fluorophenyl)-(R)-1-methoxymethoxy-3-methyl-butyl-(R)-2-carbamate

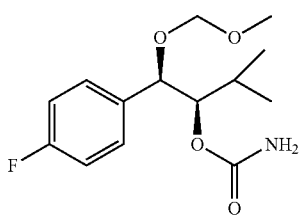 [SMILES: COCO[C@H](c1ccc(F)cc1)[C@H](OC(N)=O)C(C)C]

$^1$H NMR (400 MHz, CDCl$_3$) δ1.07 (t, J=7.6 Hz, 6H), 1.83~1.89 (m, 1H), 3.30 (s, 3H), 4.71 (d, J=6.8, 1H), 4.73 (br s, 2H), 4.82~4.88 (m, 1H), 5.45 (s, 2H), 6.92~7.17 (m, 4H)

Example 90

Synthesis of 1-(4-fluorophenyl)-(R)-1-methoxymethoxyhexyl-(R)-2-carbamate

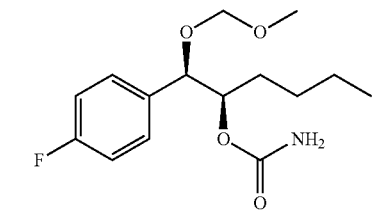 [SMILES: CCCC[C@@H](OC(N)=O)[C@H](OCOC)c1ccc(F)cc1]

$^1$H NMR (400 MHz, CDCl$_3$) δ0.90 (t, J=7.6 Hz, 3H), 1.35~1.65 (m, 6H), 3.30 (s, 3H), 4.71 (d, J=6.8, 1H), 4.73 (br s, 2H), 4.82~4.88 (m, 1H), 5.45 (s, 2H), 6.96~7.19 (m, 4H)

Example 91

Synthesis of 1-(2-iodophenyl)-(R)-1-methoxymethoxypropyl-(R)-2-carbamate

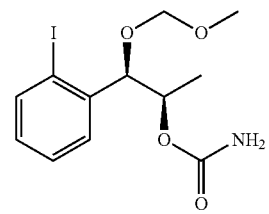 [SMILES: COCO[C@H](c1ccccc1I)[C@@H](C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.13~7.88 (m, 4H)

Example 92

Synthesis of 1-(2-iodophenyl)-(R)-1-methoxymethoxybutyl-(R)-2-carbamate

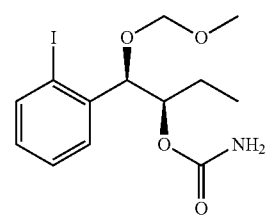 [SMILES: CC[C@@H](OC(N)=O)[C@H](OCOC)c1ccccc1I]

$^1$H NMR (400 MHz, CDCl$_3$) δ1.04 (t, J=7.6 Hz, 3H), 1.60~1.71 (m, 2H), 3.30 (s, 3H), 4.71 (d, J=6.8, 1H), 4.82~4.88 (m, 1H), 5.45 (s, 2H), 7.26~7.70 (m, 4H)

Example 93

Synthesis of 1-(2-iodophenyl)-(R)-1-methoxymethoxy-3-methyl-butyl-(R)-2-carbamate

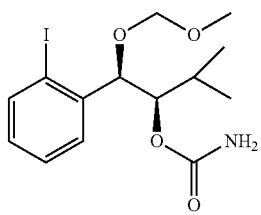 [SMILES: COCO[C@H](c1ccccc1I)[C@H](OC(N)=O)C(C)C]

$^1$H NMR (400 MHz, CDCl$_3$) δ1.07 (d, J=7.6 Hz, 3H), 1.83~1.89 (m, 1H), 3.30 (s, 3H), 4.71 (d, J=6.8, 1H), 4.82=4.88 (m, 1H), 5.45 (s, 2H), 7.26~7.70 (m, 4H)

Example 94

Synthesis of 1-(2-iodophenyl)-(R)-1-methoxymethoxyhexyl-(R)-2-carbamate

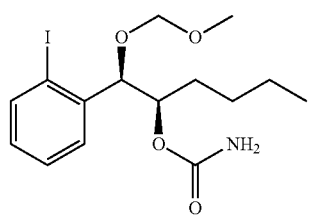 [SMILES: CCCC[C@@H](OC(N)=O)[C@H](OCOC)c1ccccc1I]

$^1$H NMR (400 MHz, CDCl$_3$) δ0.84 (1, J=7.0 Hz, 3H), 1.20~1.35 (m, 4H), 1.36~1.41 (m, 1H), 1.59~1.63 (m, 1H), 3.30 (s, 3H), 4.47 (br s, 2H), 4.71 (d, J=6.8, 1H), 4.82~4.88 (m, 1H), 5.45 (s, 2H), 7.26~7.70 (m, 4H)

Example 95

Synthesis of 1-(3-iodophenyl)-(R)-1-methoxymethoxypropyl-(R)-2-carbamate

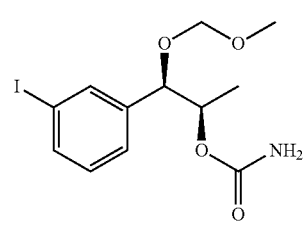 [SMILES: COCO[C@H](c1cccc(I)c1)[C@@H](C)OC(N)=O]

$^1$H NMR (400 MHz, CDCl$_3$) δ1.16 (d, J=6.4 Hz, 3H), 3.39 (s, 3H), 4.54~4.63 (m, 6H), 5.04~5.10 (m, 1H), 7.09~7.73 (m, 4H)

Example 96

Synthesis of 1-(3-iodophenyl)-(R)-1-methoxymethoxybutyl-(R)-2-carbamate

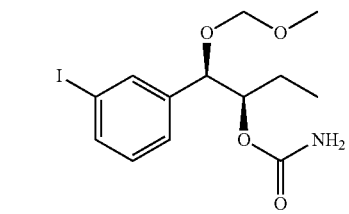 [SMILES: CC[C@@H](OC(N)=O)[C@H](OCOC)c1cccc(I)c1]

$^1$H NMR (400 MHz, CDCl$_3$) δ1.04 (t, J=7.6 Hz, 3H), 1.60~1.71 (m, 2H), 3.30 (s, 3H), 4.71 (d, J=6.8, 1H), 4.82~4.88 (m, 1H), 5.45 (s, 2H), 7.26~7.70 (m, 4H)

Example 97

Synthesis of 1-(3-iodophenyl)-(R)-1-methoxymethoxy-3-methyl-butyl-(R)-2-carbamate

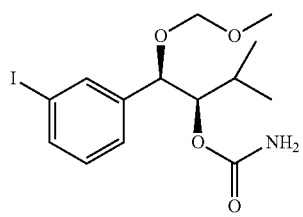 [SMILES: COCO[C@H](c1cccc(I)c1)[C@H](OC(N)=O)C(C)C]

$^1$H NMR (400 MHz, CDCl$_3$) δ1.07 (d, J=7.6 Hz, 3H), 1.83~1.89 (m, 1H), 3.30 (s, 3H), 4.71 (d, J=6.8, 1H), 4.82~4.88 (m, 1H), 5.45 (s, 2H), 7.26~7.70 (m, 4H)

Example 98

Synthesis of 1-(3-iodophenyl)-(R)-1-methoxymethoxyhexyl-(R)-2-carbamate

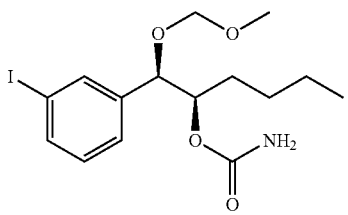 [SMILES: CCCC[C@@H](OC(N)=O)[C@H](OCOC)c1cccc(I)c1]

$^1$H NMR (400 MHz, CDCl$_3$) δ0.84 (1, J=7.0 Hz, 3H), 1.20~1.35 (m, 4H), 1.36~1.41 (m, 1H), 1.59~1.63 (m, 1H), 3.30 (s, 3H), 4.47 (br s, 2H), 4.71 (d, J=6.8, 1H), 4.82~4.88 (m, 1H), 5.45 (s, 2H), 7.26~7.70 (m, 4H)

Example 99

Synthesis of 1-(2-chlorophenyl)-(R)-1-methoxymethoxypropyl-(R)-2-methylcarbamate

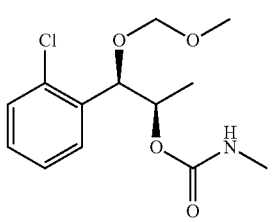 [SMILES: CNC(=O)O[C@H](C)[C@H](OCOC)c1ccccc1Cl]

$^1$H NMR (400 MHz, CDCl$_3$) δ1.37 (d, J=6.8 Hz, 3H), 2.58 (s, 3H), 3.30 (s, 3H), 4.71 (d, J=6.8, 1H), 4.82~4.88 (m, 1H), 5.45 (s, 2H), 7.26~7.70 (m, 4H)

Example 100

Synthesis of 1-(2-chlorophenyl)-(R)-1-methoxymethoxypropyl-(R)-2-propylcarbamate

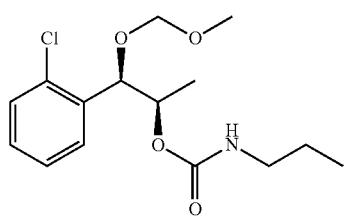 [SMILES: CCCNC(=O)O[C@H](C)[C@H](OCOC)c1ccccc1Cl]

$^1$H NMR (400 MHz, CDCl$_3$) δ0.90 (1, J=6.8 Hz, 3H), 1.37 (d, J=6.8 Hz, 3H), 1.60 (m, 2H), 3.18 (t, J=7.1 Hz, 2H), 3.30 (s, 3H), 4.71 (d, J=6.8, 1H), 4.82~4.88 (m, 1H), 5.45 (s, 2H), 7.26~7.70 (m, 4H)

Example 101

Synthesis of 1-(2-chlorophenyl)-(R)-1-methoxymethoxypropyl-(R)-2-isopropylcarbamate

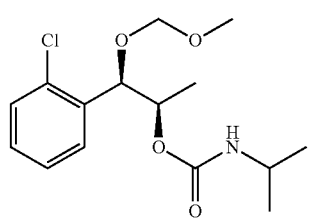 [SMILES: COCO[C@H](c1ccccc1Cl)[C@@H](C)OC(=O)NC(C)C]

$^1$H NMR (400 MHz, CDCl$_3$) δ, 1.27 (d, J=6.8 Hz, 6H), 1.37 (d, J=6.8 Hz, 3H), 3.30 (s, 3H), 4.17 (m, 1H), 4.71 (d, J=6.8, 1H), 4.82~4.88 (m, 1H), 5.45 (s, 2H), 7.26~7.70 (m, 4H)

Example 102

Synthesis of 1-(2-chlorophenyl)-(R)-1-methoxymethoxypropyl-(R)-2-cyclopropylcarbamate

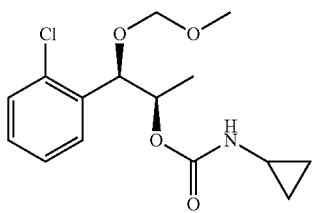 [SMILES: COCO[C@H](c1ccccc1Cl)[C@@H](C)OC(=O)NC1CC1]

$^1$H NMR (400 MHz, CDCl$_3$) δ0.57 (m, 2H), 0.82 (m, 2H), 1.37 (d, J=6.8 Hz, 3H), 2.75 (m, 1H), 3.30 (s, 3H), 4.71 (d, J=6.8, 1H), 4.82~4.88 (m, 1H), 5.45 (s, 2H), 7.26~7.70 (m, 4H)

Example 103

Synthesis of 1-(2-chlorophenyl)-(R)-1-methoxymethoxypropyl-(R)-2-cyclohexylcarbamate

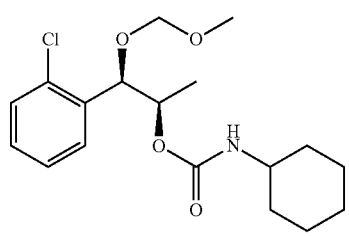 [SMILES: COCO[C@H](c1ccccc1Cl)[C@@H](C)OC(=O)NC1CCCCC1]

$^1$H NMR (400 MHz, CDCl$_3$) δ1.11~1.21 (m, 4H), 1.37 (d, J=6.8 Hz, 3H), 1.47~1.49 (m, 4H), 1.74 (m, 2H), 3.30 (s, 3H), 3.54 (m, 1H), 4.71 (d, J=6.8, 1H), 4.82~4.88 (m, 1H), 5.45 (s, 2H), 7.26~7.70 (m, 4H)

Example 104

Synthesis of 1-(2-chlorophenyl)-(R)-1-methoxymethoxypropyl-(R)-2-cyclohexylcarbamate

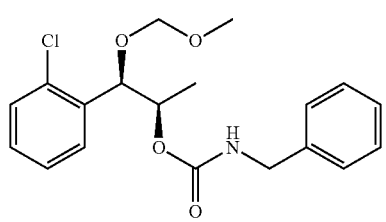 [SMILES: COCO[C@H](c1ccccc1Cl)[C@@H](C)OC(=O)NCc1ccccc1]

$^1$H NMR (400 MHz, CDCl$_3$) δ1.37 (d, J=6.8 Hz, 3H), 3.30 (s, 3H), 4.20 (m, 2H), 4.71 (d, J=6.8, 1H), 4.82~4.88 (m, 1H), 5.45 (s, 2H), 7.13~7.19 (m, 4H), 7.37~7.88 (m, 5H)

Example 105

Synthesis of 1-(2-chlorophenyl)-(R)-1-methoxymethoxypropyl-(R)-2-bicyclo[2,2,1]heptan-escarbamate

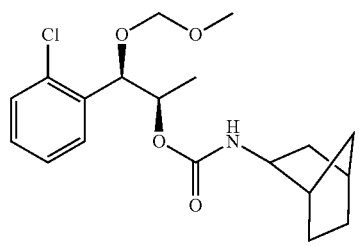 [SMILES: COCO[C@H](c1ccccc1Cl)[C@@H](C)OC(=O)NC1CC2CCC1C2]

$^1$H NMR (400 MHz, CDCl$_3$) δ1.33~1.58 (m, 9H), 1.75~1.88 (m, 2H), 2.06~2.13 (m, 2H), 3.30 (s, 3H), 3.53 (m, 1H), 4.71 (d, J=6.8, 1H), 4.82~4.88 (m, 1H), 5.45 (s, 2H), 7.13~7.19 (m, 4H), 7.37~7.88 (m, 5H)

Example 106

Synthesis of 1-(2,4-dichlorophenyl)-(R)-1-methoxymethoxypropyl-(R)-2-carbamate

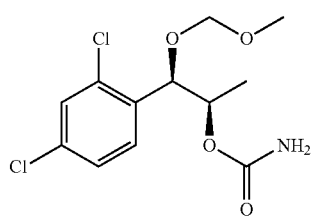 [SMILES: COCO[C@H](c1ccc(Cl)cc1Cl)[C@@H](C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.24~7.30 (m, 2H), 7.73 (d, J=1.5 Hz, 1H)

Example 107

Synthesis of 1-(2,6-dichlorophenyl)-(R)-1-methoxymethoxypropyl-(R)-2-carbamate

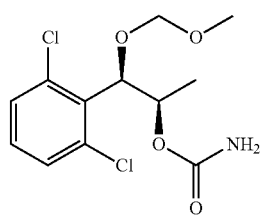 [SMILES: COCO[C@H](c1c(Cl)cccc1Cl)[C@@H](C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.57~7.58 (m, 3H)

Example 108

Synthesis of 1-(2,3-dichlorophenyl)-(R)-1-methoxymethoxypropyl-(R)-2-carbamate

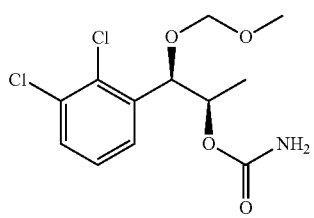 [SMILES: COCO[C@H](c1cccc(Cl)c1Cl)[C@@H](C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.01~7.14 (m, 3H)

Example 109

Synthesis of 1-(2,4-dichlorophenyl)-(R)-1-methoxymethoxybutyl-(R)-2-carbamate

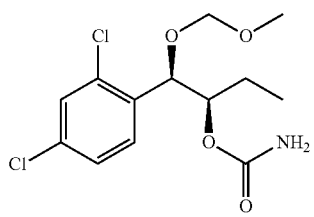 [SMILES: CC[C@@H](OC(N)=O)[C@H](OCOC)c1ccc(Cl)cc1Cl]

$^1$H NMR (400 MHz, CDCl$_3$) δ1.04 (t, J=7.6 Hz, 3H), 1.60~1.71 (m, 2H), 3.30 (s, 3H), 4.71 (d, J=6.8, 1H), 4.73 (br s, 2H), 4.82~4.88 (m, 1H), 5.45 (s, 2H), 7.24~7.30 (m, 2H), 7.73 (d, J=1.5 Hz, 1H)

Example 110

Synthesis of 1-(2,6-dichlorophenyl)-(R)-1-methoxymethoxybutyl-(R)-2-carbamate

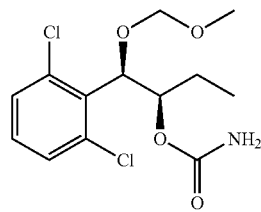 [SMILES: CC[C@@H](OC(N)=O)[C@H](OCOC)c1c(Cl)cccc1Cl]

$^1$H NMR (400 MHz, CDCl$_3$) δ1.04 (t, J=7.6 Hz, 3H), 1.60~1.71 (m, 2H), 3.30 (s, 3H), 4.71 (d, J=6.8, 1H), 4.73 (br s, 2H), 4.82~4.88 (m, 1H), 5.45 (s, 2H), 7.54~7.57 (m, 3H)

Example 111

Synthesis of 1-(2,4-dichlorophenyl)-(R)-1-methoxymethoxy-3-methyl-butyl-(R)-2-carbamate

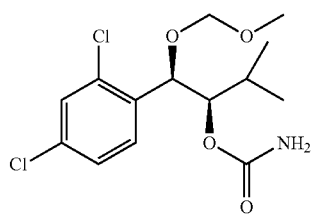 [SMILES: COCO[C@H](c1ccc(Cl)cc1Cl)[C@H](OC(N)=O)C(C)C]

¹H NMR (400 MHz, CDCl₃) δ1.07 (1, J=7.6 Hz, 6H), 1.83~1.89 (m, 1H), 3.30 (s, 3H), 4.71 (d, J=6.8, 1H), 4.73 (br s, 2H), 4.82~4.88 (m, 1H), 5.45 (s, 2H), 7.24~7.30 (m, 2H), 7.73 (d, J=1.5 Hz, 1H)

Example 112

Synthesis of 1-(2,6-dichlorophenyl)-(R)-1-methoxymethoxy-3-methyl-butyl-(R)-2-carbamate

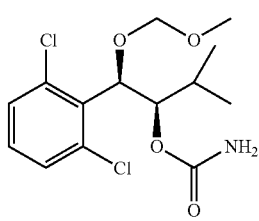 [SMILES: COCO[C@H](c1c(Cl)cccc1Cl)[C@H](OC(N)=O)C(C)C]

¹H NMR (400 MHz, CDCl₃) δ1.07 (t, J=7.6 Hz, 6H), 1.83~1.89 (m, 1H), 3.30 (s, 3H), 4.71 (d, J=6.8, 1H), 4.73 (br s, 2H), 4.82~4.88 (m, 1H), 5.45 (s, 2H), 7.55~7.57 (m, 3H)

Example 113

Synthesis of 1-(2,4-dichlorophenyl)-(R)-1-methoxymethoxyhexyl-(R)-2-carbamate

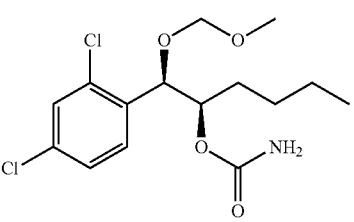 [SMILES: CCCC[C@@H](OC(N)=O)[C@H](OCOC)c1ccc(Cl)cc1Cl]

¹H NMR (400 MHz, CDCl₃) δ0.90 (1, J=7.6 Hz, 3H), 1.35~1.65 (m, 6H), 3.30 (s, 3H), 4.71 (d, J=6.8, 1H), 4.73 (br s, 2H), 4.82~4.88 (m, 1H), 5.45 (s, 2H), 7.24~7.30 (m, 2H), 7.73 (d, J=1.5 Hz, 1H)

Example 114

Synthesis of 1-(2,4-dichlorophenyl)-(R)-1-methoxymethoxyhexyl-(R)-2-carbamate

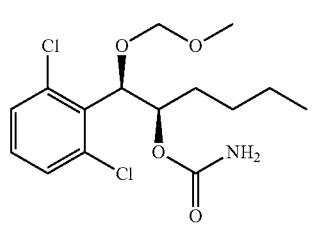 [SMILES: CCCC[C@@H](OC(N)=O)[C@H](OCOC)c1c(Cl)cccc1Cl]

¹H NMR (400 MHz, CDCl₃) δ0.90 (t, J=7.6 Hz, 3H), 1.35~1.65 (m, 6H), 3.30 (s, 3H), 4.71 (d, J=6.8, 1H), 4.73 (br s, 2H), 4.82~4.88 (m, 1H), 5.45 (s, 2H), 7.54~7.59 (m, 3H)

Example 115

Synthesis of 1-(2,4-dichlorophenyl)-1-methoxymethoxypropyl-2-carbamate

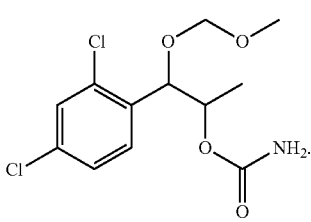 [SMILES: COCOC(c1ccc(Cl)cc1Cl)C(C)OC(N)=O]

¹H NMR (400 MHz, CDCl₃) δ1.37 (d, J=6.8 Hz, 3H), 3.30 (s, 3H), 4.71 (d, J=6.8, 1H), 4.82~4.88 (m, 1H), 5.45 (s, 2H), 7.24~7.30 (m, 2H), 7.73 (d, J=1.5 Hz, 1H)

Example 116

Synthesis of 1-(2,6-dichlorophenyl)-1-methoxymethoxypropyl-2-carbamate

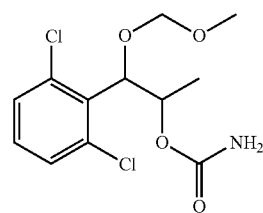 [SMILES: COCOC(c1c(Cl)cccc1Cl)C(C)OC(N)=O]

¹H NMR (400 MHz, CDCl₃) δ1.37 (d, J=6.8 Hz, 3H), 3.30 (s, 3H), 4.71 (d, J=6.8, 1H), 4.82~4.88 (m, 1H), 5.45 (s, 2H), 7.57~7.58 (m, 3H)

Example 117

Synthesis of 1-(2,3-dichlorophenyl)-1-methoxymethoxypropyl-2-carbamate

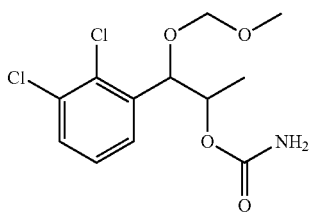 [SMILES: COCOC(c1cccc(Cl)c1Cl)C(C)OC(N)=O]

¹H NMR (400 MHz, CDCl₃) δ1.37 (d, J=6.8 Hz, 3H), 3.30 (s, 3H), 4.71 (d, J=6.8, 1H), 4.82~4.88 (m, 1H), 5.45 (s, 2H), 7.01~7.14 (m, 3H)

Example 118

Synthesis of 1-(2,4-dichlorophenyl)-1-methoxymethoxybutyl-2-carbamate

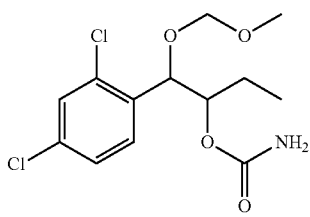 [SMILES: CCC(OC(N)=O)C(OCOC)c1ccc(Cl)cc1Cl]

¹H NMR (400 MHz, CDCl₃) δ1.04 (t, J=7.6 Hz, 3H), 1.60~1.71 (m, 2H), 3.30 (s, 3H), 4.71 (d, J=6.8, 1H), 4.73 (br s, 2H), 4.82~4.88 (m, 1H), 5.45 (s, 2H), 7.24~7.30 (m, 2H), 7.73 (d, J=1.5 Hz, 1H)

Example 119

Synthesis of 1-(2,6-dichlorophenyl)-1-methoxymethoxybutyl-2-carbamate

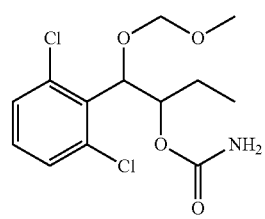 [SMILES: CCC(OC(N)=O)C(OCOC)c1c(Cl)cccc1Cl]

¹H NMR (400 MHz, CDCl₃) δ1.04 (t, J=7.6 Hz, 3H), 1.60~1.71 (m, 2H), 3.30 (s, 3H), 4.71 (d, J=6.8, 1H), 4.73 (br s, 2H), 4.82~4.88 (m, 1H), 5.45 (s, 2H), 7.54~7.57 (m, 3H)

Example 120

Synthesis of 1-(2,4-dichlorophenyl)-1-methoxymethoxy-3-methyl-butyl-2-carbamate

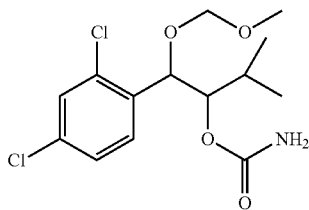 [SMILES: COCOC(c1ccc(Cl)cc1Cl)C(OC(N)=O)C(C)C]

¹H NMR (400 MHz, CDCl₃) δ1.07 (1, J=7.6 Hz, 6H), 1.83~1.89 (m, 1H), 3.30 (s, 3H), 4.71 (d, J=6.8, 1H), 4.73 (br s, 2H), 4.82~4.88 (m, 1H), 5.45 (s, 2H), 7.24~7.30 (m, 2H), 7.73 (d, J=1.5 Hz, 1H)

Example 121

Synthesis of 1-(2,6-dichlorophenyl)-1-methoxymethoxy-3-methyl-butyl-2-carbamate

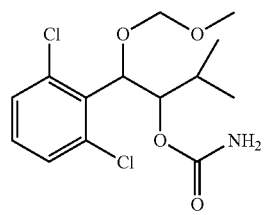 [SMILES: COCOC(c1c(Cl)cccc1Cl)C(OC(N)=O)C(C)C]

¹H NMR (400 MHz, CDCl₃) δ1.07 (t, J=7.6 Hz, 6H), 1.83~1.89 (m, 1H), 3.30 (s, 3H), 4.71 (d, J=6.8, 1H), 4.73 (br s, 2H), 4.82~4.88 (m, 1H), 5.45 (s, 2H), 7.55~7.57 (m, 3H)

Example 122

Synthesis of 1-(2,4-dichlorophenyl)-1-methoxymethoxyhexyl-2-carbamate

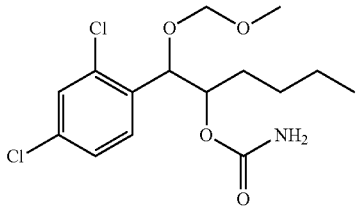 [SMILES: CCCCC(OC(N)=O)C(OCOC)c1ccc(Cl)cc1Cl]

¹H NMR (400 MHz, CDCl₃) δ0.90 (t, J=7.6 Hz, 3H), 1.35~1.65 (m, 6H), 3.30 (s, 3H), 4.71 (d, J=6.8, 1H), 4.73 (br s, 2H), 4.82~4.88 (m, 1H), 5.45 (s, 2H), 7.24~7.30 (m, 2H), 7.73 (d, J=1.5 Hz, 1H)

Example 123

Synthesis of 1-(2,4-dichlorophenyl)-1-methoxymethoxyhexyl-2-carbamate

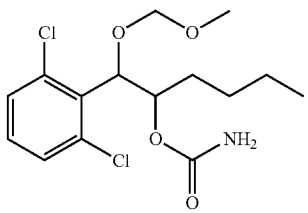

¹H NMR (400 MHz, CDCl₃) δ0.90 (t, J=7.6 Hz, 3H), 1.35~1.65 (m, 6H), 3.30 (s, 3H), 4.71 (d, J=6.8, 1H), 4.73 (br s, 2H), 4.82~4.88 (m, 1H), 5.45 (s, 2H), 7.54~7.59 (m, 3H)

Example 124

Synthesis of 1-(2-chlorophenyl)-(S)-1-methoxypropyl-(S)-2-carbamate

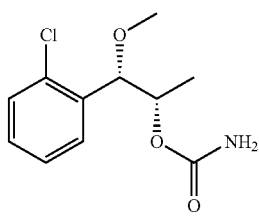

1-(2-chlorophenyl)-1-hydorxyalkyl-2-alkylcarbamate (Preparation Example 103, 0.5 g), THF (Tetrahydrofuran), MeI (Methyliodide, 5 eq, 0.5 ml) and t-BuOH (Potassium tert-butoxide, 1.5 eq, 0.26 g) were put into a flask and stirred at the 0° C. When the reaction was completed, the obtained product was washed with 1M HCl solution and EA (Ethylacetate). The separated organic layer was dehydrated with anhydrous MgSO₄(Magnesium sulfate), filtrated, and concentrated under reduced pressure. The concentrated residue was purified by a silicagel aolumn chromatography, to obtain title compound.

¹H NMR (400 MHz, CDCl₃) δ1.40 (d, J=6.0 Hz, 3H), 3.24 (s, 3H), 4.71 (d, J=6.4 Hz, 1H), 4.80~4.85 (m, 1H), 7.01 (br s, 1H), 7.07~7.20 (m, 4H)

According to the method described in Example 124, the following compounds of Examples 124 to 123246 were prepared:

Example 125

Synthesis of 1-(2-chlorophenyl)-(S)-1-methoxypropyl-(S)-2-methylcarbamate

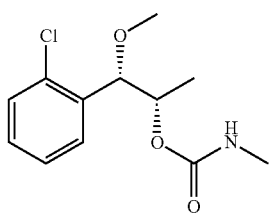 [SMILES: CNC(=O)O[C@@H](C)[C@@H](OC)c1ccccc1Cl]

¹H NMR (400 MHz, CDCl₃) δ1.40 (d, J=6.0 Hz, 3H), 2.74 (s, 3H), 3.24 (s, 3H), 4.71 (d, J=6.4 Hz, 1H), 4.80~4.85 (m, 1H), 7.01 (br s, 1H), 7.07~7.20 (m, 4H)

Example 126

Synthesis of 1-(2-chlorophenyl)-(S)-1-methoxypropyl-(S)-2-propylcarbamate

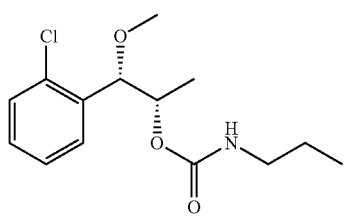

¹H NMR (400 MHz, CDCl₃) δ0.96 (t, J=6.4 Hz, 3H), 1.40 (d, J=6.0 Hz, 3H), 1.55~1.60 (m, 2H), 2.96 (t, J=6.0 Hz, 2H), 3.24 (s, 3H), 4.71 (d, J=6.0 Hz, 1H), 4.82~4.88 (m, 1H), 6.76 (br s, 2H), 7.07~7.21 (m, 4H)

Example 127

Synthesis of 1-(2-chlorophenyl)-(S)-1-methoxypropyl-(S)-2-isopropylcarbamate

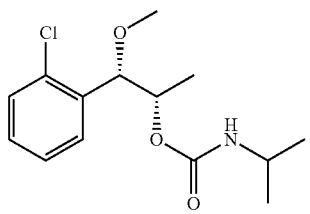 [SMILES: CO[C@@H](c1ccccc1Cl)[C@H](C)OC(=O)NC(C)C]

¹H NMR (400 MHz, CDCl₃) δ, 1.15 (d, J=6.0 Hz, 3H), 1.35 (d, J=6.4 Hz, 3H), 1.50 (d, J=6.8 Hz, 3H), 3.24 (s, 3H), 3.75 (br s, 1H), 4.48 (br s, 1H), 4.50 (d, J=4.8 Hz, 1H), 5.09~5.20 (m, 1H), 7.07~7.20 (m, 4H)

Example 128

Synthesis of 1-(2-chlorophenyl)-(S)-1-methoxypropyl-(S)-2-cyclopropylcarbamate

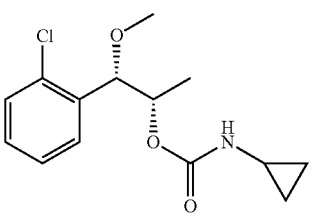

¹H NMR (400 MHz, CDCl₃) δ0.30~0.34 (m, 2H), 0.54~0.58 (m, 2H), 1.30 (d, J=6.8 Hz, 3H), 2.55 (m, 1H), 3.24 (s, 3H), 4.55 (d, J=4.8 Hz, 1H), 4.90 (br m, 1H), 5.09~5.15 (br s, 1H), 7.06~7.21 (m, 4H)

Example 129

Synthesis of 1-(2-chlorophenyl)-(S)-1-methoxypropyl-(S)-2-cyclohexylcarbamate

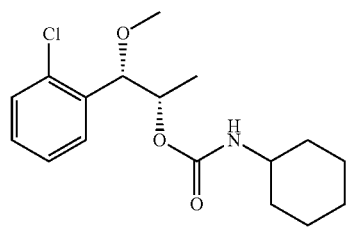

¹H NMR (400 MHz, CDCl₃) δ1.11~1.21 (m, 4H), 1.37 (d, J=6.8 Hz, 3H), 1.47~1.49 (m, 4H), 1.74 (m, 2H), 3.30 (s, 3H), 3.54 (m, 1H), 4.71 (d, J=6.8, 1H), 4.82~4.88 (m, 1H), 5.45 (s, 2H), 7.26~7.70 (m, 4H)

Example 130

Synthesis of 1-(2-chlorophenyl)-(S)-1-methoxypropyl-(S)-2-cyclohexylcarbamate

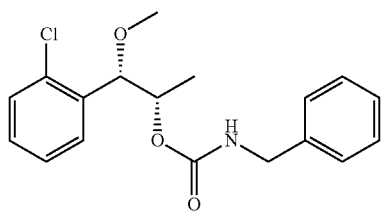

¹H NMR (400 MHz, CDCl₃) δ1.40 (d, J=6.8 Hz, 3H), 3.24 (s, 3H), 4.20 (m, 2H), 4.71 (d, J=6.8 Hz, 1H), 4.82~4.88 (m, 1H), 7.13~7.19 (m, 4H), 7.32~7.46 (m, 5H)

Example 131

Synthesis of 1-(2-chlorophenyl)-(S)-1-methoxypropyl-(S)-2-bicyclo[2,2,1]heptanescarbamate

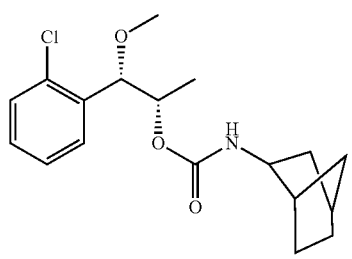 [SMILES: CO[C@@H](c1ccccc1Cl)[C@H](C)OC(=O)NC1CC2CCC1C2]

¹H NMR (400 MHz, CDCl₃) δ1.40 (d, J=6.4 Hz, 3H), 1.44~1.50 (m, 7H), 1.70~1.73 (m, 1H), 2.03~2.07 (m, 1H), 3.24 (s, 3H), 3.50~3.55 (m, 2H), 4.71 (d, J=6.4 Hz, 1H), 4.80~4.87 (m, 1H), 7.07~7.19 (m, 4H)

Example 132

Synthesis of 1-(2-chlorophenyl)-(S)-1-methoxybutyl-(S)-2-carbamate

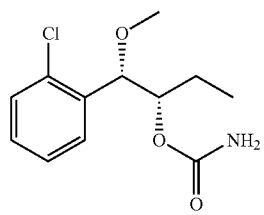

¹H NMR (400 MHz, CDCl₃) δ1.04 (t, J=7.6 Hz, 3H), 1.60~1.71 (m, 2H), 3.22 (s, 3H), 4.71 (d, J=6.8, 1H), 4.73 (br s, 2H), 4.82~4.88 (m, 1H), 7.26~7.70 (m, 4H)

Example 133

Synthesis of 1-(2-chlorophenyl)-(S)-1-methoxy-3-methyl-butyl-(S)-2-carbamate

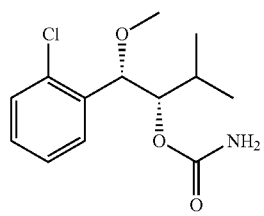

¹H NMR (400 MHz, CDCl₃) δ1.07 (t, J=7.6 Hz, 6H), 1.83~1.89 (m, 1H), 3.26 (s, 3H), 4.71 (d, J=6.8, 1H), 4.73 (br s, 2H), 4.82~4.88 (m, 1H), 7.26~7.70 (m, 4H)

Example 134

Synthesis of 1-(2-chlorophenyl)-(S)-1-methoxyhexyl-(S)-2-carbamate

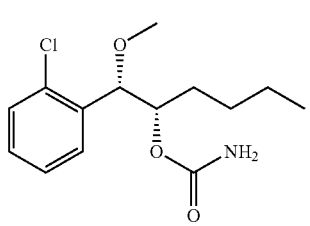 [SMILES: CCCC[C@H](OC(N)=O)[C@@H](OC)c1ccccc1Cl]

¹H NMR (400 MHz, CDCl₃) δ0.90 (t, J=7.6 Hz, 3H), 1.35~1.65 (m, 6H), 3.23 (s, 3H), 4.71 (d, J=6.8, 1H), 4.73 (br s, 2H), 4.82~4.88 (m, 1H), 7.26~7.70 (m, 4H)

Example 135

Synthesis of 1-(2-fluorophenyl)-(S)-1-methoxypropyl-(S)-2-carbamate

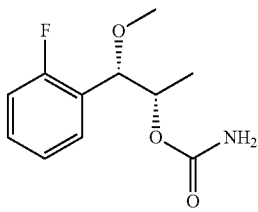

$^1$H NMR (400 MHz, CDCl$_3$) δ1.37 (d, J=6.8 Hz, 3H), 3.23 (s, 3H), 4.71 (d, J=6.8, 1H), 4.82~4.88 (m, 1H), 7.15~7.68 (m, 4H)

Example 136

Synthesis of 1-(2-fluorophenyl)-(S)-1-methoxypropyl-(S)-2-methylcarbamate

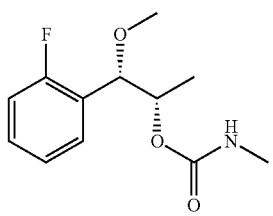

$^1$H NMR (400 MHz, CDCl$_3$) δ1.37 (d, J=6.8 Hz, 3H), 2.58 (s, 3H), 3.24 (s, 3H), 4.71 (d, J=6.8, 1H), 4.82~4.88 (m, 1H), 7.15~7.68 (m, 4H)

Example 137

Synthesis of 1-(2-fluorophenyl)-(S)-1-methoxypropyl-(S)-2-propylcarbamate

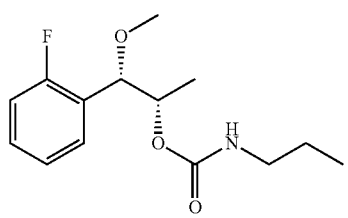

$^1$H NMR (400 MHz, CDCl$_3$) δ0.90 (t, J=6.8 Hz, 3H), 1.37 (d, J=6.8 Hz, 3H), 1.60 (m, 2H), 3.18 (t, J=7.1 Hz, 2H), 3.22 (s, 3H), 4.71 (d, J=6.8, 1H), 4.82~4.88 (m, 1H), 7.15~7.68 (m, 4H)

Example 138

Synthesis of 1-(2-fluorophenyl)-(S)-1-methoxypropyl-(S)-2-isopropylcarbamate

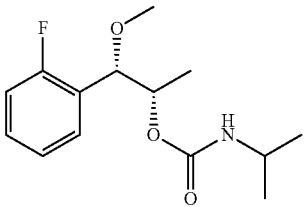 [SMILES: CO[C@@H](c1ccccc1F)[C@H](C)OC(=O)NC(C)C]

$^1$H NMR (400 MHz, CDCl$_3$) δ, 1.27 (d, J=6.8 Hz, 6H), 1.37 (d, J=6.8 Hz, 3H), 3.25 (s, 3H), 4.17 (m, 1H), 4.71 (d, J=6.8, 1H), 4.82~4.88 (m, 1H), 7.15~7.69 (m, 4H)

Example 139

Synthesis of 1-(2-fluorophenyl)-(S)-1-methoxypropyl-(S)-2-cyclopropylcarbamate

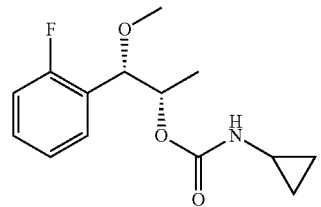

$^1$H NMR (400 MHz, CDCl$_3$) δ0.57 (m, 2H), 0.82 (m, 2H), 1.37 (d, J=6.8 Hz, 3H), 2.75 (m, 1H), 3.24 (s, 3H), 4.71 (d, J=6.8, 1H), 4.82~4.88 (m, 1H), 7.16~7.70 (m, 4H)

Example 140

Synthesis of 1-(2-fluorophenyl)-(S)-1-methoxypropyl-(S)-2-cyclohexylcarbamate

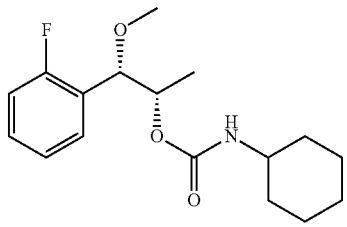 [SMILES: CO[C@@H](c1ccccc1F)[C@H](C)OC(=O)NC1CCCCC1]

$^1$H NMR (400 MHz, CDCl$_3$) δ1.11~1.21 (m, 4H), 1.37 (d, J=6.8 Hz, 3H), 1.47~1.49 (m, 4H), 1.74 (m, 2H), 3.26 (s, 3H), 3.54 (m, 1H), 4.71 (d, J=6.8, 1H), 4.82~4.88 (m, 1H), 7.15~7.66 (m, 4H)

Example 141

Synthesis of 1-(2-fluorophenyl)-(S)-1-methoxymethoxypropyl-(S)-2-cyclohexylcarbamate

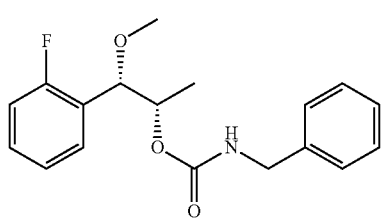

¹H NMR (400 MHz, CDCl₃) δ1.37 (d, J=6.8 Hz, 3H), 3.24 (s, 3H), 4.20 (m, 2H), 4.71 (d, J=6.8, 1H), 4.82~4.88 (m, 1H), 7.15~7.68 (m, 4H), 7.72~7.88 (m, 5H)

Example 142

Synthesis of 1-(2fluorophenyl)-(S)-1-methoxypropyl-(S)-2-bicyclo[2,2,1]heptanescarbamate

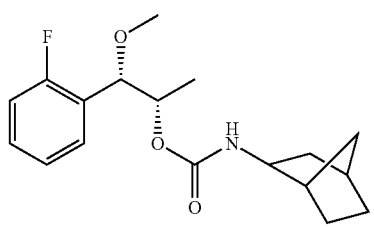

¹H NMR (400 MHz, CDCl₃) δ1.33~1.58 (m, 9H), 1.75~1.88 (m, 2H), 2.06~2.13 (m, 2H), 3.23 (s, 3H), 3.53 (m, 1H), 4.71 (d, J=6.8, 1H), 4.82~4.88 (m, 1H), 7.15~7.68 (m, 4H), 7.37~7.88 (m, 5H)

Example 143

Synthesis of 1-(2-iodophenyl)-(S)-1-methoxypropyl-(S)-2-carbamate

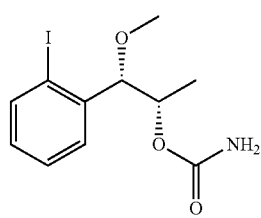 [SMILES: CO[C@@H](c1ccccc1I)[C@H](C)OC(N)=O]

¹H NMR (400 MHz, CDCl₃) δ1.37 (d, J=6.8 Hz, 3H), 3.21 (s, 3H), 4.71 (d, J=6.8, 1H), 4.82~4.88 (m, 1H), 7.13~7.88 (m, 4H)

Example 144

Synthesis of 1-(2-iodophenyl)-(S)-1-methoxypropyl-(S)-2-methylcarbamate

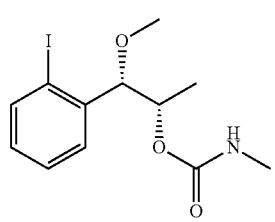 [SMILES: CNC(=O)O[C@@H](C)[C@@H](OC)c1ccccc1I]

¹H NMR (400 MHz, CDCl₃) δ1.37 (d, J=6.8 Hz, 3H), 2.58 (s, 3H), 3.24 (s, 3H), 4.71 (d, J=6.8, 1H), 4.82~4.88 (m, 1H), 7.13~7.898 (m, 4H)

Example 145

Synthesis of 1-(2-iodophenyl)-(S)-1-methoxypropyl-(S)-2-propylcarbamate

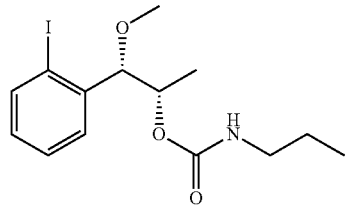 [SMILES: CCCNC(=O)O[C@@H](C)[C@@H](OC)c1ccccc1I]

¹H NMR (400 MHz, CDCl₃) δ0.90 (1, J=6.8 Hz, 3H), 1.37 (d, J=6.8 Hz, 3H), 1.60 (m, 2H), 3.18 (t, J=7.1 Hz, 2H), 3.24 (s, 3H), 4.71 (d, J=6.8, 1H), 4.82~4.88 (m, 1H), 7.14~7.87 (m, 4H)

Example 146

Synthesis of 1-(2-iodophenyl)-(S)-1-methoxypropyl-(S)-2-isopropylcarbamate

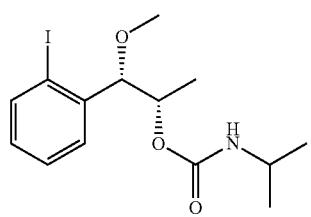 [SMILES: CO[C@@H](c1ccccc1I)[C@H](C)OC(=O)NC(C)C]

¹H NMR (400 MHz, CDCl₃) δ, 1.27 (d, J=6.8 Hz, 6H), 1.37 (d, J=6.8 Hz, 3H), 3.30 (s, 3H), 4.17 (m, 1H), 4.71 (d, J=6.8, 1H), 4.82~4.88 (m, 1H), 5.45 (s, 2H), 7.15~7.89 (m, 4H)

Example 147

Synthesis of 1-(2-iodophenyl)-(S)-1-methoxypropyl-(S)-2-cyclopropylcarbamate

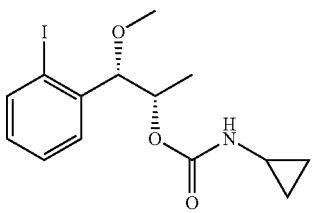

¹H NMR (400 MHz, CDCl₃) δ0.57 (m, 2H), 0.82 (m, 2H), 1.37 (d, J=6.8 Hz, 3H), 2.75 (m, 1H), 3.30 (s, 3H), 4.71 (d, J=6.8, 1H), 4.82=4.88 (m, 1H), 5.45 (s, 2H), 7.16~7.87 (m, 4H)

Example 148

Synthesis of 1-(2-iodophenyl)-(S)-1-methoxypropyl-(S)-2-cyclohexylcarbamate

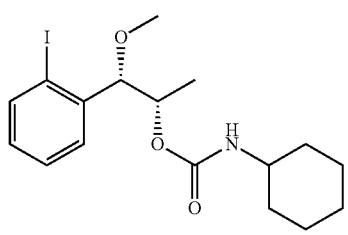 [SMILES: CO[C@@H](c1ccccc1I)[C@H](C)OC(=O)NC1CCCCC1]

¹H NMR (400 MHz, CDCl₃) δ1.11~1.21 (m, 4H), 1.37 (d, J=6.8 Hz, 3H), 1.47~1.49 (m, 4H), 1.74 (m, 2H), 3.30 (s, 3H), 3.54 (m, 1H), 4.71 (d, J=6.8, 1H), 4.82~4.88 (m, 1H), 5.45 (s, 2H), 7.18~7.91 (m, 4H)

Example 149

Synthesis of 1-(2-iodophenyl)-(S)-1-methoxypropyl-(S)-2-cyclohexylcarbamate

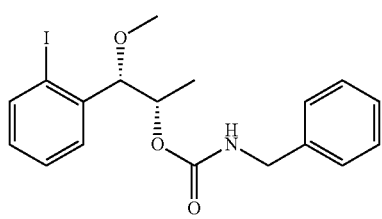 [SMILES: CO[C@@H](c1ccccc1I)[C@H](C)OC(=O)NCc1ccccc1]

¹H NMR (400 MHz, CDCl₃) δ1.37 (d, J=6.8 Hz, 3H), 3.24 (s, 3H), 4.20 (m, 2H), 4.71 (d, J=6.8, 1H), 4.82~4.88 (m, 1H), 7.15~7.68 (m, 4H), 7.72~7.88 (m, 5H)

Example 150

Synthesis of 1-(2-iodophenyl)-(S)-1-methoxypropyl-(S)-2-bicyclo[2,2,1]heptanescarbamate

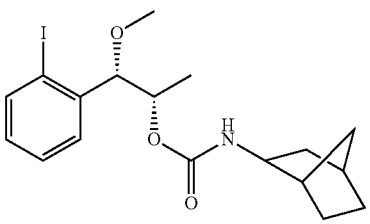 [SMILES: CO[C@@H](c1ccccc1I)[C@H](C)OC(=O)NC1CC2CCC1C2]

¹H NMR (400 MHz, CDCl₃) δ1.33~1.58 (m, 9H), 1.75~1.88 (m, 2H), 2.06~2.13 (m, 2H), 3.22 (s, 3H), 3.53 (m, 1H), 4.71 (d, J=6.8, 1H), 4.82~4.88 (m, 1H), 7.15~7.68 (m, 4H), 7.37~7.88 (m, 5H)

Example 151

Synthesis of 1-(2-iodophenyl)-(S)-1-methoxybutyl-(S)-2-carbamate

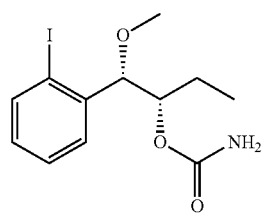 [SMILES: CC[C@H](OC(N)=O)[C@@H](OC)c1ccccc1I]

¹H NMR (400 MHz, CDCl₃) δ1.04 (t, J=7.6 Hz, 3H), 1.60~1.71 (m, 2H), 3.24 (s, 3H), 4.71 (d, 1H), 4.82~4.88 (m, 1H), 7.26~7.70 (m, 4H)

Example 152

Synthesis of 1-(2-iodophenyl)-(S)-1-methoxybutyl-(S)-2-methylcarbamate

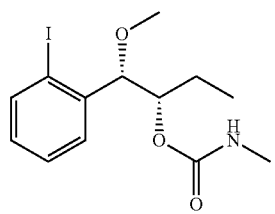 [SMILES: CC[C@H](OC(=O)NC)[C@@H](OC)c1ccccc1I]

¹H NMR (400 MHz, CDCl₃) δ1.04 (t, J=7.6 Hz, 3H), 1.60~1.71 (m, 2H), 2.58 (s, 3H), 3.23 (s, 3H), 4.71 (d, J=6.8, 1H), 4.82~4.88 (m, 1H), 7.13~7.88 (m, 4H)

Example 153

Synthesis of 1-(2-iodophenyl)-(S)-1-methoxybutyl-(S)-2-propylcarbamate

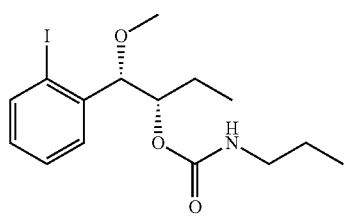 [SMILES: CCCNC(=O)O[C@@H](CC)[C@@H](OC)c1ccccc1I]

$^1$H NMR (400 MHz, CDCl$_3$) δ 0.90 (t, J=6.8 Hz, 3H), 1.04 (t, J=7.6 Hz, 3H), 1.58~1.71 (m, 4H), 3.18 (t, J=7.1 Hz, 2H), 3.22 (s, 3H), 4.71 (d, J=6.8, 1H), 4.82~4.88 (m, 1H), 7.14~7.89 (m, 4H)

Example 154

Synthesis of 1-(2-iodophenyl)-(S)-1-methoxybutyl-(S)-2-isopropylcarbamate

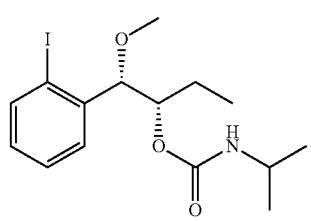 [SMILES: CC[C@H](OC(=O)NC(C)C)[C@@H](OC)c1ccccc1I]

$^1$H NMR (400 MHz, CDCl$_3$) δ 1.04 (1, J=7.6 Hz, 3H), 1.27 (d, J=6.8 Hz, 6H), 1.60~1.71 (m, 2H), 3.23 (s, 3H), 4.17 (m, 1H), 4.71 (d, J=6.8 Hz, 1H), 4.82~4.88 (m, 1H), 7.15~7.90 (m, 4H)

Example 155

Synthesis of 1-(2-iodophenyl)-(S)-1-methoxybutyl-(S)-2-cyclopropylcarbamate

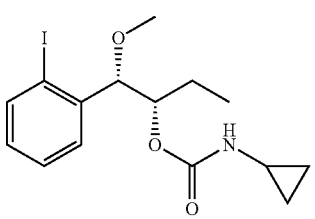 [SMILES: CC[C@H](OC(=O)NC1CC1)[C@@H](OC)c1ccccc1I]

$^1$H NMR (400 MHz, CDCl$_3$) δ 0.57 (m, 2H), 0.82 (m, 2H), 1.04 (t, J=7.6 Hz, 3H), 1.60~1.71 (m, 2H), 2.75 (m, 1H), 3.24 (s, 3H), 4.71 (d, J=6.8, 1H), 4.82~4.88 (m, 1H), 7.16~7.90 (m, 4H)

Example 156

Synthesis of 1-(2-iodophenyl)-(S)-1-methoxybutyl-(S)-2-cyclohexylcarbamate

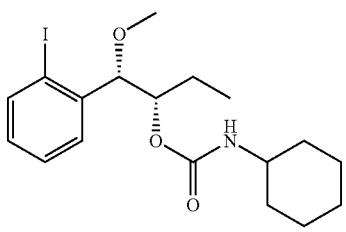 [SMILES: CC[C@H](OC(=O)NC1CCCCC1)[C@@H](OC)c1ccccc1I]

$^1$H NMR (400 MHz, CDCl$_3$) δ 1.04 (1, J=7.6 Hz, 3H), 1.11~1.21 (m, 4H), 1.47~1.49 (m, 4H), 1.60~1.71 (m, 2H), 1.74 (m, 2H), 3.23 (s, 3H), 3.54 (m, 1H), 4.71 (d, J=6.8, 1H), 4.82~4.88 (m, 1H), 7.14~7.87 (m, 4H)

Example 157

Synthesis of 1-(2-iodophenyl)-(S)-1-methoxybutyl-(S)-2-cyclohexylcarbamate

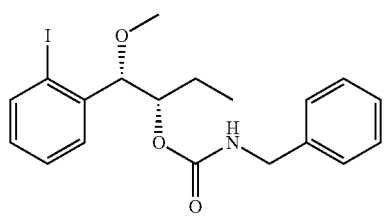 [SMILES: CC[C@H](OC(=O)NCc1ccccc1)[C@@H](OC)c1ccccc1I]

$^1$H NMR (400 MHz, CDCl$_3$) δ 1.04 (1, J=7.6 Hz, 3H), 1.60~1.71 (m, 2H), 3.23 (s, 3H), 4.20 (m, 2H), 4.71 (d, J=6.8, 1H), 4.82~4.88 (m, 1H), 7.14~7.19 (m, 4H), 7.37~7.88 (m, 5H)

Example 158

Synthesis of 1-(2-iodophenyl)-(S)-1-methoxybutyl-(S)-2-bicyclo[2,2,1]heptanescarbamate

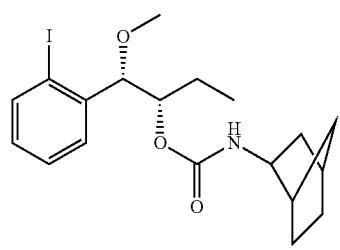 [SMILES: CC[C@H](OC(=O)NC1CC2CCC1C2)[C@@H](OC)c1ccccc1I]

$^1$H NMR (400 MHz, CDCl$_3$) δ 1.04 (t, J=7.6 Hz, 3H), 1.33~1.58 (m, 6H), 1.60~1.71 (m, 2H), 1.75~1.88 (m, 2H), 2.06~2.13 (m, 2H), 3.24 (s, 3H), 3.53 (m, 1H), 4.71 (d, J=6.8, 1H), 4.82~4.88 (m, 1H), 7.15~7.19 (m, 4H), 7.37~7.88 (m, 5H)

Example 159

Synthesis of 1-(2-iodophenyl)-(S)-1-methoxy-3-methyl-butyl-(S)-2-carbamate

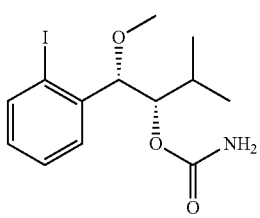 [SMILES: CO[C@@H](c1ccccc1I)[C@@H](OC(N)=O)C(C)C]

¹H NMR (400 MHz, CDCl₃) δ1.07 (d, J=7.6 Hz, 3H), 1.83~1.89 (m, 1H), 3.23 (s, 3H), 4.71 (d, J=6.8, 1H), 4.82~4.88 (m, 1H), 7.26~7.70 (m, 4H)

Example 160

Synthesis of 1-(2-iodophenyl)-(S)-1-methoxy-3-methyl-butyl-(S)-2-methylcarbamate

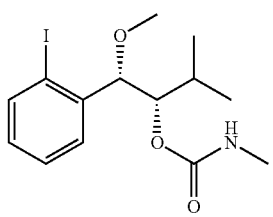 [SMILES: CNC(=O)O[C@@H](C(C)C)[C@@H](OC)c1ccccc1I]

¹H NMR (400 MHz, CDCl₃) δ1.04 (d, J=7.6 Hz, 6H), 1.60~1.71 (m, 1H), 2.58 (s, 3H), 3.24 (s, 3H), 4.71 (d, J=6.8, 1H), 4.82~4.88 (m, 1H), 7.13~7.88 (m, 4H)

Example 161

Synthesis of 1-(2-iodophenyl)-(S)-1-methoxy-3-methyl-butyl-(S)-2-propylcarbamate

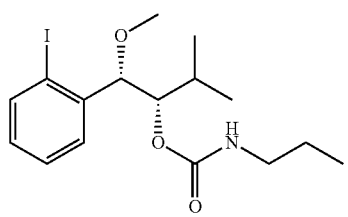 [SMILES: CCCNC(=O)O[C@@H](C(C)C)[C@@H](OC)c1ccccc1I]

¹H NMR (400 MHz, CDCl₃) δ0.90 (t, J=6.8 Hz, 3H), 1.04 (d, J=7.6 Hz, 6H), 1.58~1.71 (m, 5H), 3.18 (t, J=7.1 Hz, 2H), 3.23 (s, 3H), 4.71 (d, J=6.8, 1H), 4.82~4.88 (m, 1H), 7.14~7.89 (m, 4H)

Example 162

Synthesis of 1-(2-iodophenyl)-(S)-1-methoxy-3-methyl-butyl-(S)-2-isopropylcarbamate

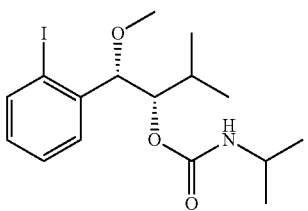 [SMILES: CO[C@@H](c1ccccc1I)[C@@H](OC(=O)NC(C)C)C(C)C]

¹H NMR (400 MHz, CDCl₃) δ1.04 (t, J=7.6 Hz, 6H), 1.27 (d, J=6.8 Hz, 6H), 1.60~1.71 (m, 1H), 3.24 (s, 3H), 4.17 (m, 1H), 4.71 (d, J=6.8, 1H), 4.82~4.88 (m, 1H), 7.15~7.90 (m, 4H)

Example 163

Synthesis of 1-(2-iodophenyl)-(S)-1-methoxy-3-methyl-butyl-(S)-2-cyclopropylcarbamate

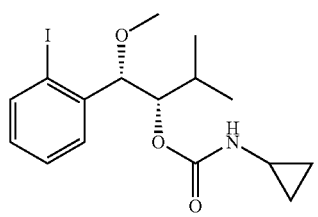 [SMILES: CO[C@@H](c1ccccc1I)[C@@H](OC(=O)NC1CC1)C(C)C]

¹H NMR (400 MHz, CDCl₃) δ0.57 (m, 2H), 0.82 (m, 2H), 1.04 (d, J=7.6 Hz, 6H), 1.60~1.71 (m, 1H), 2.75 (m, 1H), 3.24 (s, 3H), 4.71 (d, J=6.8, 1H), 4.82~4.88 (m, 1H), 7.16~7.90 (m, 4H)

Example 164

Synthesis of 1-(2-iodophenyl)-(S)-1-methoxy-3-methyl-butyl-(S)-2-cyclohexylcarbamate

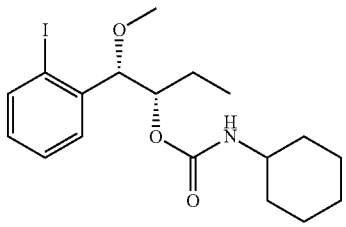 [SMILES: CC[C@H](OC(=O)NC1CCCCC1)[C@@H](OC)c1ccccc1I]

¹H NMR (400 MHz, CDCl₃) δ1.04 (d, J=7.6 Hz, 6H), 1.11~1.21 (m, 4H), 1.47~1.49 (m, 4H), 1.74 (m, 2H), 1.84~1.90 (m, 1H), 3.23 (s, 3H), 3.54 (m, 1H), 4.71 (d, J=6.8, 1H), 4.82~4.88 (m, 1H), 7.14~7.87 (m, 4H)

Example 165

Synthesis of 1-(2-iodophenyl)-(S)-1-methoxy-3-methyl-butyl-(S)-2-cyclohexylcarbamate

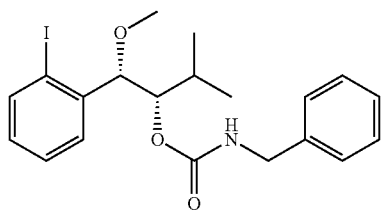 [SMILES: CO[C@@H](c1ccccc1I)[C@@H](OC(=O)NCc1ccccc1)C(C)C]

¹H NMR (400 MHz, CDCl₃) δ1.04 (d, J=7.6 Hz, 6H), 1.87~1.90 (m, 1H), 3.24 (s, 3H), 4.20 (m, 2H), 4.71 (d, J=6.8, 1H), 4.82~4.88 (m, 1H), 7.14~7.19 (m, 4H), 7.37~7.88 (m, 5H)

Example 166

Synthesis of 1-(2-iodophenyl)-(S)-1-methoxy-3-methyl-butyl-(S)-2-bicyclo[2,2,1]heptanescarbamate

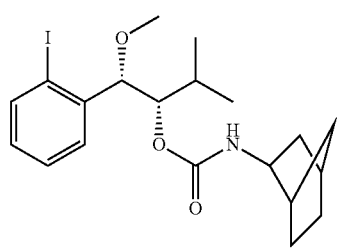 [SMILES: CO[C@@H](c1ccccc1I)[C@@H](OC(=O)NC1CC2CCC1C2)C(C)C]

¹H NMR (400 MHz, CDCl₃) δ1.04 (d, J=7.6 Hz, 6H), 1.33~1.58 (m, 6H), 1.75~1.88 (m, 2H), 1.88~1.93 (m, 1H), 2.06~2.13 (m, 2H), 3.22 (s, 3H), 3.53 (m, 1H), 4.71 (d, J=6.8, 1H), 4.82~4.88 (m, 1H), 7.15~7.19 (m, 4H), 7.37~7.88 (m, 5H)

Example 167

Synthesis of 1-(2-iodophenyl)-(S)-1-methoxyhexyl-(S)-2-carbamate

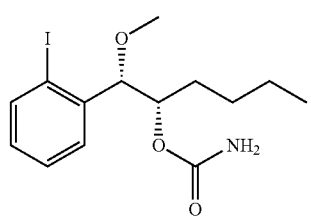 [SMILES: CCCC[C@H](OC(N)=O)[C@@H](OC)c1ccccc1I]

¹H NMR (400 MHz, CDCl₃) δ0.84 (1, J=7.0 Hz, 3H), 1.20~1.35 (m, 4H), 1.36~1.41 (m, 1H), 1.59~1.63 (m, 1H), 3.23 (s, 3H), 4.47 (br s, 2H), 4.71 (d, J=6.8, 1H), 4.82~4.88 (m, 1H), 7.26~7.70 (m, 4H)

Example 168

Synthesis of 1-(2-iodophenyl)-(S)-1-methoxyhexyl-(S)-2-methylcarbamate

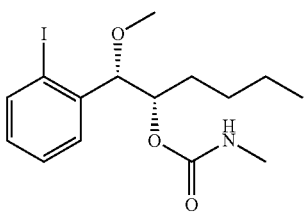 [SMILES: CCCC[C@H](OC(=O)NC)[C@@H](OC)c1ccccc1I]

¹H NMR (400 MHz, CDCl₃) δ0.89 (t, J=7.2 Hz, 3H), 1.20~1.35 (m, 4H), 1.36~1.41 (m, 1H), 1.59~1.63 (m, 1H), 2.58 (s, 3H), 3.23 (s, 3H), 4.71 (d, J=6.8, 1H), 4.82~4.88 (m, 1H), 7.13~7.88 (m, 4H)

Example 169

Synthesis of 1-(2-iodophenyl)-(S)-1-methoxyhexyl-(S)-2-propylcarbamate

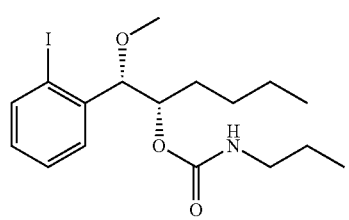 [SMILES: CCCC[C@H](OC(=O)NCCC)[C@@H](OC)c1ccccc1I]

¹H NMR (400 MHz, CDCl₃) δ0.87 (1, J=6.8 Hz, 3H), 0.90 (t, J=6.8 Hz, 3H), 1.21~1.35 (m, 4H), 1.36~1.40 (m, 1H), 1.58~1.62 (m, 1H), 3.18 (t, J=7.1 Hz, 2H), 3.24 (s, 3H), 4.71 (d, J=6.8, 1H), 4.82~4.88 (m, 1H), 7.14~7.89 (m, 4H)

Example 170

Synthesis of 1-(2-iodophenyl)-(S)-1-methoxyhexyl-(5)-2-isopropylcarbamate

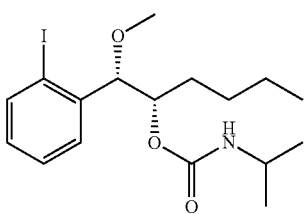 [SMILES: CCCC[C@H](OC(=O)NC(C)C)[C@@H](OC)c1ccccc1I]

¹H NMR (400 MHz, CDCl₃) δ0.84 (t, J=7.6 Hz, 3H), 1.22~1.35 (m, 4H), 1.27 (d, J=6.8 Hz, 6H), 1.36~1.40 (m, 1H), 1.58~1.62 (m, 1H), 3.23 (s, 3H), 4.17 (m, 1H), 4.71 (d, J=6.8, 1H), 4.82~4.88 (m, 1H), 7.15~7.90 (m, 4H)

Example 171

Synthesis of 1-(2-iodophenyl)-(S)-1-methoxyhexyl-(S)-2-cyclopropylcarbamate

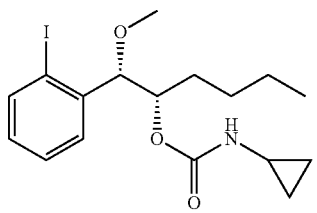 [SMILES: CCCC[C@H](OC(=O)NC1CC1)[C@@H](OC)c1ccccc1I]

¹H NMR (400 MHz, CDCl₃) δ0.57 (m, 2H), 0.82 (m, 2H), 0.88 (t, J=7.6 Hz, 3H), 1.22~1.35 (m, 4H), 1.36~1.40 (m, 1H), 1.58~1.62 (m, 1H), 2.75 (m, 1H), 3.23 (s, 3H), 4.71 (d, J=6.8, 1H), 4.82~4.88 (m, 1H), 7.16~7.90 (m, 4H)

Example 172

Synthesis of 1-(2-iodophenyl)-(S)-1-methoxyhexyl-(S)-2-cyclohexylcarbamate

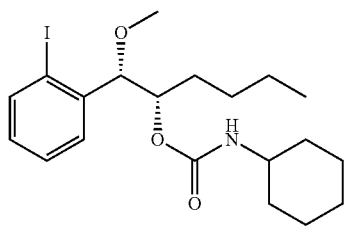 [SMILES: CCCC[C@H](OC(=O)NC1CCCCC1)[C@@H](OC)c1ccccc1I]

¹H NMR (400 MHz, CDCl₃) δ0.98 (1, J=7.6 Hz, 3H), 1.11~1.21 (m, 4H), 1.26~1.33 (m, 4H), 1.47~1.49 (m, 2H), 1.52~1.54 (m, 2H), 1.74 (m, 2H), 1.84~1.90 (m, 1H), 3.23 (s, 3H), 3.54 (m, 1H), 4.71 (d, J=6.8, 1H), 4.82~4.88 (m, 1H), 7.14~7.87 (m, 4H)

Example 173

Synthesis of 1-(2-iodophenyl)-(S)-1-methoxyhexyl-(S)-2-cyclohexylcarbamate

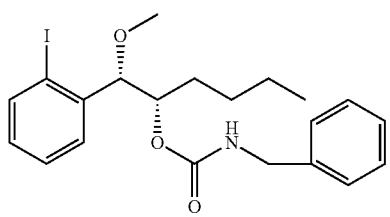 [SMILES: CCCC[C@H](OC(=O)NCc1ccccc1)[C@@H](OC)c1ccccc1I]

¹H NMR (400 MHz, CDCl₃) δ0.94 (t, J=7.6 Hz, 3H), 1.26~1.33 (m, 4H), 1.51~1.55 (m, 2H), 3.23 (s, 3H), 4.20 (m, 2H), 4.71 (d, J=6.8, 1H), 4.82~4.88 (m, 1H), 7.14~7.19 (m, 4H), 7.37~7.88 (m, 5H)

Example 174

Synthesis of 1-(2-iodophenyl)-(S)-1-methoxyhexyl-(S)-2-bicyclo[2,2,1]heptanescarbamate

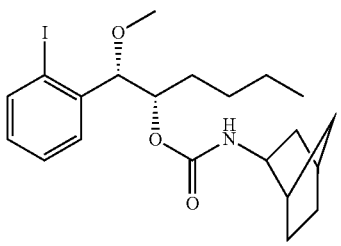 [SMILES: CCCC[C@H](OC(=O)NC1CC2CCC1C2)[C@@H](OC)c1ccccc1I]

¹H NMR (400 MHz, CDCl₃) δ0.97 (t, J=7.0 Hz, 3H), 1.25~1.32 (m, 4H), 1.33~1.58 (m, 8H), 1.60~1.71 (m, 2H), 1.75~1.88 (m, 2H), 2.06~2.13 (m, 2H), 3.24 (s, 3H), 3.53 (m, 1H), 4.71 (d, J=6.8, 1H), 4.82~4.88 (m, 1H), 7.15~7.19 (m, 4H), 7.37~7.88 (m, 5H)

Example 175

Synthesis of 1-(3-iodophenyl)-(S)-1-methoxypropyl-(S)-2-carbamate

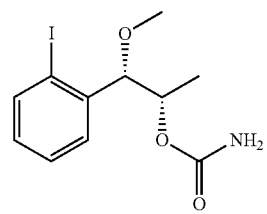 [SMILES: CO[C@@H](c1ccccc1I)[C@H](C)OC(N)=O]

¹H NMR (400 MHz, CDCl₃) δ1.16 (d, J=6.4 Hz, 3H), 3.24 (s, 3H), 4.54~4.63 (m, 4H), 5.04~5.10 (m, 1H), 7.09~7.73 (m, 4H)

Example 176

Synthesis of 1-(3-iodophenyl)-(S)-1-methoxybutyl-(S)-2-carbamate

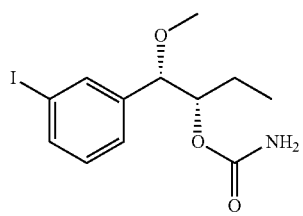 [SMILES: CC[C@H](OC(N)=O)[C@@H](OC)c1cccc(I)c1]

¹H NMR (400 MHz, CDCl₃) δ1.04 (t, J=7.6 Hz, 3H), 1.60~1.71 (m, 2H), 3.24 (s, 3H), 4.71 (d, J=6.8, 1H), 4.73 (br s, 2H), 4.82~4.88 (m, 1H), 6.96~7.57 (m, 4H)

Example 177

Synthesis of 1-(3-iodophenyl)-(S)-1-methoxy-3-methyl-butyl-(S)-2-carbamate

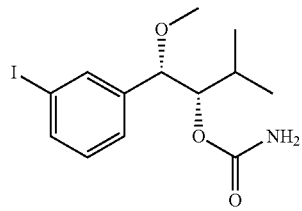 [SMILES: CO[C@@H](c1cccc(I)c1)[C@@H](OC(N)=O)C(C)C]

$^1$H NMR (400 MHz, CDCl$_3$) δ1.07 (t, J=7.6 Hz, 6H), 1.83~1.89 (m, 1H), 3.24 (s, 3H), 4.71 (d, J=6.8, 1H), 4.73 (br s, 2H), 4.82~4.88 (m, 1H), 7.00~7.58 (m, 4H)

Example 178

Synthesis of 1-(3-iodophenyl)-(S)-1-methoxyhexyl-(S)-2-carbamate

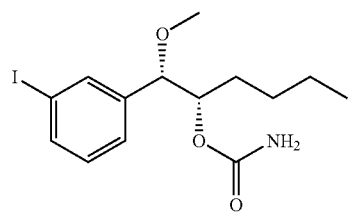 [SMILES: CCCC[C@H](OC(N)=O)[C@@H](OC)c1cccc(I)c1]

$^1$H NMR (400 MHz, CDCl$_3$) δ0.90 (t, J=7.6 Hz, 3H), 1.35~1.65 (m, 6H), 3.23 (s, 3H), 4.71 (d, J=6.8, 1H), 4.73 (br s, 2H), 4.82~4.88 (m, 1H), 7.01~7.59 (m, 4H)

Example 179

Synthesis of 1-(4-fluorophenyl)-(S)-1-methoxypropyl-(S)-2-carbamate

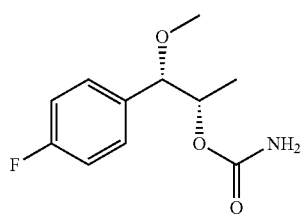 [SMILES: CO[C@@H](c1ccc(F)cc1)[C@H](C)OC(N)=O]

$^1$H NMR (400 MHz, CDCl$_3$) δ1.37 (d, J=6.8 Hz, 3H), 3.23 (s, 3H), 4.71 (d, J=6.8, 1H), 4.82~4.88 (m, 1H), 6.96~7.17 (m, 4H)

Example 180

Synthesis of 1-(4-fluorophenyl)-(S)-1-methoxybutyl-(S)-2-carbamate

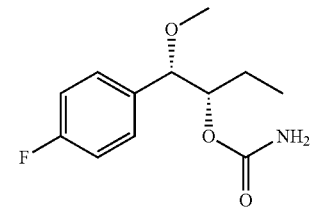 [SMILES: CC[C@H](OC(N)=O)[C@@H](OC)c1ccc(F)cc1]

$^1$H NMR (400 MHz, CDCl$_3$) δ1.04 (t, J=7.6 Hz, 3H), 1.60~1.71 (m, 2H), 3.24 (s, 3H), 4.71 (d, J=6.8, 1H), 4.73 (br s, 2H), 4.82~4.88 (m, 1H), 6.90~7.20 (m, 4H)

Example 181

Synthesis of 1-(4-fluorophenyl)-(S)-1-methoxy-3-methyl-butyl-(S)-2-carbamate

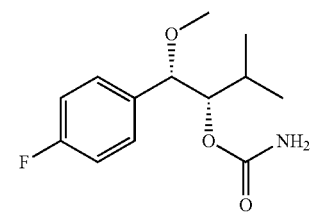 [SMILES: CO[C@@H](c1ccc(F)cc1)[C@@H](OC(N)=O)C(C)C]

$^1$H NMR (400 MHz, CDCl$_3$) δ1.07 (t, J=7.6 Hz, 6H), 1.83~1.89 (m, 1H), 3.24 (s, 3H), 4.71 (d, J=6.8, 1H), 4.73 (br s, 2H), 4.82~4.88 (m, 1H), 6.92~7.17 (m, 4H)

Example 182

Synthesis of 1-(4-fluorophenyl)-(S)-1-methoxy-hexyl-(S)-2-carbamate

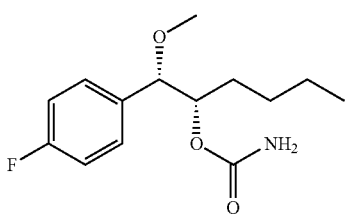 [SMILES: CCCC[C@H](OC(N)=O)[C@@H](OC)c1ccc(F)cc1]

$^1$H NMR (400 MHz, CDCl$_3$) δ0.90 (t, J=7.6 Hz, 3H), 1.35~1.65 (m, 6H), 3.23 (s, 3H), 4.71 (d, J=6.8, 1H), 4.73 (br s, 2H), 4.82~4.88 (m, 1H), 6.96~7.19 (m, 4H)

Example 183

Synthesis of 1-(2,4-dichlorophenyl)-(S)-1-methoxy-propyl-(S)-2-carbamate

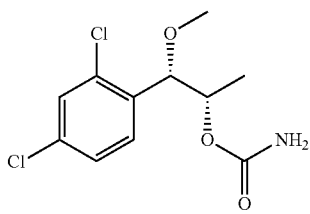 [SMILES: CO[C@@H](c1ccc(Cl)cc1Cl)[C@H](C)OC(N)=O]

¹H NMR (400 MHz, CDCl₃) δ1.37 (d, J=6.8 Hz, 3H), 3.24 (s, 3H), 4.71 (d, J=6.8, 1H), 4.82~4.88 (m, 1H), 7.24~7.30 (m, 2H), 7.73 (d, J=1.5 Hz, 1H)

Example 184

Synthesis of 1-(2,4-dichlorophenyl)-(S)-1-methoxy-butyl-(S)-2-carbamate

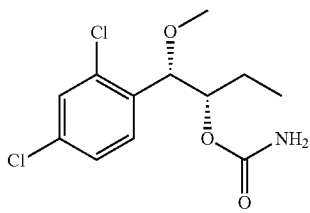 [SMILES: CC[C@H](OC(N)=O)[C@@H](OC)c1ccc(Cl)cc1Cl]

¹H NMR (400 MHz, CDCl₃) δ1.04 (t, J=7.6 Hz, 3H), 1.60~1.71 (m, 2H), 3.24 (s, 3H), 4.71 (d, J=6.8, 1H), 4.73 (br s, 2H), 4.82~4.88 (m, 1H), 7.24~7.30 (m, 2H), 7.73 (d, J=1.5 Hz, 1H)

Example 185

Synthesis of 1-(2,4-dichlorophenyl)-(S)-1-methoxy-3-methyl-butyl-(S)-2-carbamate

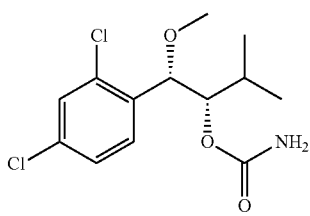 [SMILES: CO[C@@H](c1ccc(Cl)cc1Cl)[C@@H](OC(N)=O)C(C)C]

¹H NMR (400 MHz, CDCl₃) δ1.07 (1, J=7.6 Hz, 6H), 1.83~1.89 (m, 1H), 3.24 (s, 3H), 4.71 (d, J=6.8, 1H), 4.73 (br s, 2H), 4.82~4.88 (m, 1H), 7.24~7.30 (m, 2H), 7.73 (d, J=1.5 Hz, 1H)

Example 186

Synthesis of 1-(2,4-dichlorophenyl)-(S)-1-methoxy-hexyl-(S)-2-carbamate

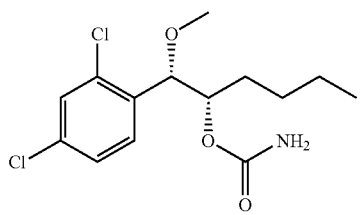 [SMILES: CCCC[C@H](OC(N)=O)[C@@H](OC)c1ccc(Cl)cc1Cl]

¹H NMR (400 MHz, CDCl₃) δ0.90 (t, J=7.6 Hz, 3H), 1.35~1.65 (m, 6H), 3.24 (s, 3H), 4.71 (d, J=6.8, 1H), 4.73 (br s, 2H), 4.82~4.88 (m, 1H), 7.24~7.30 (m, 2H), 7.73 (d, J=1.5 Hz, 1H)

Example 187

Synthesis of 1-(2,6-dichlorophenyl)-(S)-1-methoxy-propyl-(S)-2-carbamate

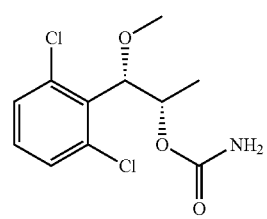 [SMILES: CO[C@@H](c1c(Cl)cccc1Cl)[C@H](C)OC(N)=O]

¹H NMR (400 MHz, CDCl₃) δ1.37 (d, J=6.8 Hz, 3H), 3.24 (s, 3H), 4.71 (d, J=6.8, 1H), 4.82~4.88 (m, 1H), 7.57~7.58 (m, 3H)

Example 188

Synthesis of 1-(2,6-dichlorophenyl)-(S)-1-methoxy-butyl-(S)-2-carbamate

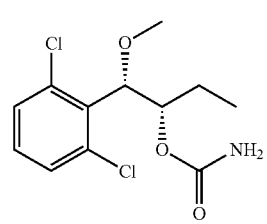 [SMILES: CC[C@H](OC(N)=O)[C@@H](OC)c1c(Cl)cccc1Cl]

¹H NMR (400 MHz, CDCl₃) δ1.04 (t, J=7.6 Hz, 3H), 1.60~1.71 (m, 2H), 3.24 (s, 3H), 4.71 (d, J=6.8, 1H), 4.73 (br s, 2H), 4.82~4.88 (m, 1H), 7.54~7.57 (m, 3H)

Example 189

Synthesis of 1-(2,6-dichlorophenyl)-(S)-1-methoxy-3-methyl-butyl-(S)-2-carbamate

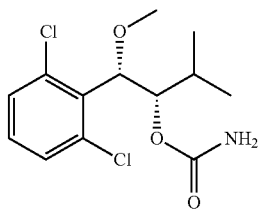 [SMILES: CO[C@@H](c1c(Cl)cccc1Cl)[C@@H](OC(N)=O)C(C)C]

¹H NMR (400 MHz, CDCl₃) δ1.07 (t, J=7.6 Hz, 6H), 1.83~1.89 (m, 1H), 3.24 (s, 3H), 4.71 (d, J=6.8, 1H), 4.73 (br s, 2H), 4.82~4.88 (m, 1H), 7.55~7.57 (m, 3H)

Example 190

Synthesis of 1-(2,4-dichlorophenyl)-(S)-1-methoxy-hexyl-(S)-2-carbamate

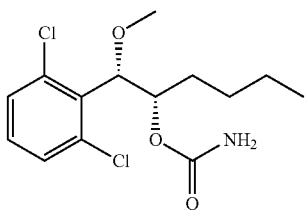 [SMILES: CCCC[C@H](OC(N)=O)[C@@H](OC)c1c(Cl)cccc1Cl]

¹H NMR (400 MHz, CDCl₃) δ0.90 (l, J=7.6 Hz, 3H), 1.35~1.65 (m, 6H), 3.23 (s, 3H), 4.71 (d, J=6.8, 1H), 4.73 (br s, 2H), 4.82~4.88 (m, 1H), 7.54~7.59 (m, 3H)

Example 191

Synthesis of 1-(2,3-dichlorophenyl)-(S)-1-methoxy-propyl-(S)-2-carbamate

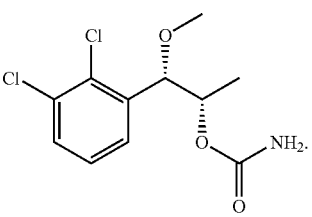 [SMILES: CO[C@@H](c1cccc(Cl)c1Cl)[C@H](C)OC(N)=O]

¹H NMR (400 MHz, CDCl₃) δ1.37 (d, J=6.8 Hz, 3H), 3.24 (s, 3H), 4.71 (d, J=6.8, 1H), 4.82~4.88 (m, 1H), 7.01~7.14 (m, 3H)

Example 192

Synthesis of 1-(2-chlorophenyl)-(R)-1-methoxypropyl-(12)-2-carbamate

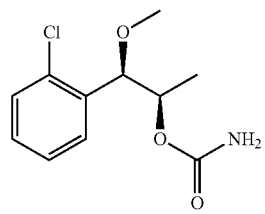 [SMILES: CO[C@H](c1ccccc1Cl)[C@@H](C)OC(N)=O]

¹H NMR (400 MHz, CDCl₃) δ1.37 (d, J=6.8 Hz, 3H), 3.24 (s, 3H), 4.71 (d, J=6.8, 1H), 4.82~4.88 (m, 1H), 7.26~7.70 (m, 4H)

Example 193

Synthesis of 1-(2-chlorophenyl)-1-methoxypropyl-2-carbamate

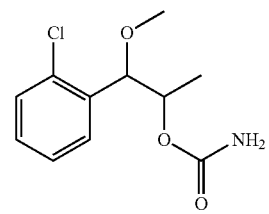 [SMILES: COC(c1ccccc1Cl)C(C)OC(N)=O]

¹H NMR (400 MHz, CDCl₃) δ1.37 (d, J=6.8 Hz, 3H), 3.24 (s, 3H), 4.71 (d, J=6.8, 1H), 4.82~4.88 (m, 1H), 7.26~7.70 (m, 4H)

Example 194

Synthesis of 1-(2-chlorophenyl)-(R)-1-methoxypropyl-(S)-2-carbamate

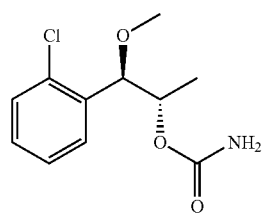 [SMILES: CO[C@H](c1ccccc1Cl)[C@H](C)OC(N)=O]

¹H NMR (400 MHz, CDCl₃) δ1.37 (d, J=6.8 Hz, 3H), 3.24 (s, 3H), 4.71 (d, J=6.8, 1H), 4.82~4.88 (m, 1H), 7.26~7.70 (m, 4H)

Example 195

Synthesis of 1-(2-chlorophenyl)-(S)-1-methoxypropyl-(R)-2-carbamate

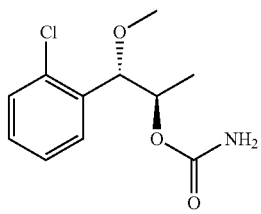 [SMILES: CO[C@@H](c1ccccc1Cl)[C@@H](C)OC(N)=O]

$^1$H NMR (400 MHz, CDCl$_3$) δ1.37 (d, J=6.8 Hz, 3H), 3.24 (s, 3H), 4.71 (d, J=6.8, 1H), 4.82~4.88 (m, 1H), 7.26~7.70 (m, 4H)

Example 196

Synthesis of 1-(2-chlorophenyl)-(R)-1-methoxybutyl-(R)-2-carbamate

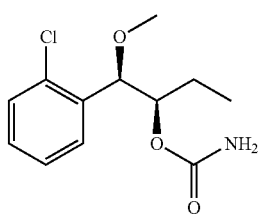 [SMILES: CC[C@@H](OC(N)=O)[C@H](OC)c1ccccc1Cl]

$^1$H NMR (400 MHz, CDCl$_3$) δ1.04 (t, J=7.6 Hz, 3H), 1.60~1.71 (m, 2H), 3.24 (s, 3H), 4.71 (d, J=6.8, 1H), 4.73 (br s, 2H), 4.82~4.88 (m, 1H), 7.26~7.70 (m, 4H)

Example 197

Synthesis of 1-(2-chlorophenyl)-1-methoxybutyl-2-carbamate

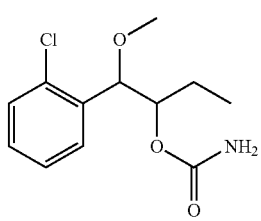 [SMILES: CCC(OC(N)=O)C(OC)c1ccccc1Cl]

$^1$H NMR (400 MHz, CDCl$_3$) δ1.04 (t, J=7.6 Hz, 3H), 1.60~1.71 (m, 2H), 3.23 (s, 3H), 4.71 (d, J=6.8, 1H), 4.73 (br s, 2H), 4.82~4.88 (m, 1H), 7.26~7.70 (m, 4H)

Example 198

Synthesis of 1-(2-chlorophenyl)-(R)-1-methoxy-3-methyl-butyl-(R)-2-carbamate

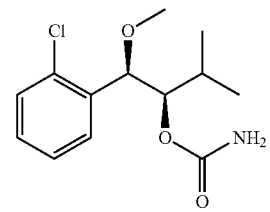 [SMILES: CO[C@H](c1ccccc1Cl)[C@H](OC(N)=O)C(C)C]

$^1$H NMR (400 MHz, CDCl$_3$) δ1.04 (1, J=7.6 Hz, 3H), 1.60~1.71 (m, 2H), 3.24 (s, 3H), 4.71 (d, J=6.8, 1H), 4.73 (br s, 2H), 4.82~4.88 (m, 1H), 7.26~7.70 (m, 4H)

Example 199

Synthesis of 1-(2-chlorophenyl)-1-methoxy-3-methyl-butyl-2-carbamate

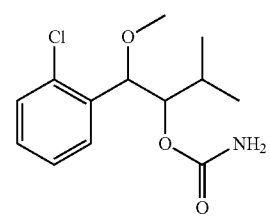 [SMILES: COC(c1ccccc1Cl)C(OC(N)=O)C(C)C]

$^1$H NMR (400 MHz, CDCl$_3$) δ1.07 (t, J=7.6 Hz, 6H), 1.83~1.89 (m, 1H), 3.24 (s, 3H), 4.71 (d, J=6.8, 1H), 4.73 (br s, 2H), 4.82~4.88 (m, 1H), 7.26~7.70 (m, 4H)

Example 200

Synthesis of 1-(2-chlorophenyl)-(R)-1-methoxy-hexyl-(R)-2-carbamate

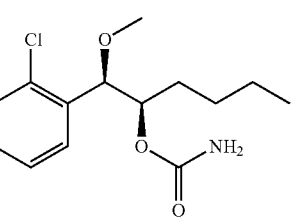

$^1$H NMR (400 MHz, CDCl$_3$) δ0.90 (1, J=7.6 Hz, 3H), 1.35~1.65 (m, 6H), 3.24 (s, 3H), 4.71 (d, J=6.8, 1H), 4.73 (br s, 2H), 4.82~4.88 (m, 1H), 7.26~7.70 (m, 4H)

Example 201

Synthesis of 1-(2-chlorophenyl)-1-methoxyhexyl-2-carbamate

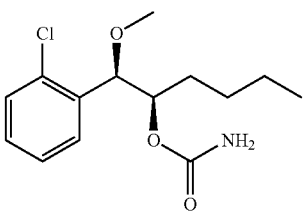 [SMILES: CCCC[C@@H](OC(N)=O)[C@H](OC)c1ccccc1Cl]

¹H NMR (400 MHz, CDCl₃) δ0.90 (1, J=7.6 Hz, 3H), 1.35~1.65 (m, 6H), 3.24 (s, 3H), 4.71 (d, J=6.8, 1H), 4.73 (br s, 2H), 4.82~4.88 (m, 1H), 7.26~7.70 (m, 4H)

Example 202

Synthesis of 1-(2-chlorophenyl)-(R)-1-methoxypropyl-(R)-2-methylcarbamate

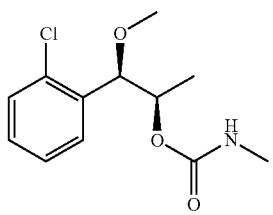 [SMILES: CNC(=O)O[C@H](C)[C@H](OC)c1ccccc1Cl]

¹H NMR (400 MHz, CDCl₃) δ1.37 (d, J=6.8 Hz, 3H), 2.58 (s, 3H), 3.24 (s, 3H), 4.71 (d, J=6.8, 1H), 4.82~4.88 (m, 1H), 7.26~7.70 (m, 4H)

Example 203

Synthesis of 1-(2-chlorophenyl)-(R)-1-methoxypropyl-(R)-2-propylcarbamate

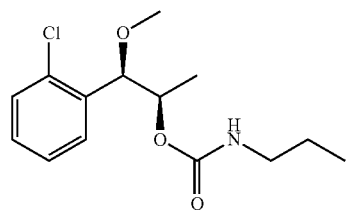 [SMILES: CCCNC(=O)O[C@H](C)[C@H](OC)c1ccccc1Cl]

¹H NMR (400 MHz, CDCl₃) δ0.90 (t, J=6.8 Hz, 3H), 1.37 (d, J=6.8 Hz, 3H), 1.60 (m, 2H), 3.18 (t, J=7.1 Hz, 2H), 3.23 (s, 3H), 4.71 (d, J=6.8, 1H), 4.82~4.88 (m, 1H), 7.26~7.70 (m, 4H)

Example 204

Synthesis of 1-(2-chlorophenyl)-(R)-1-thoxypropyl-(R)-2-isopropylcarbamate

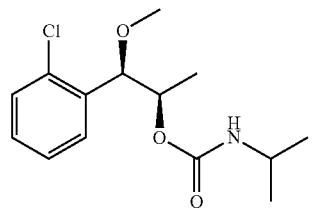 [SMILES: CO[C@H](c1ccccc1Cl)[C@@H](C)OC(=O)NC(C)C]

¹H NMR (400 MHz, CDCl₃) δ, 1.27 (d, J=6.8 Hz, 6H), 1.37 (d, J=6.8 Hz, 3H), 3.23 (s, 3H), 4.17 (m, 1H), 4.71 (d, J=6.8, 1H), 4.82~4.88 (m, 1HH), 7.26~7.70 (m, 4H)

Example 205

Synthesis of 1-(2-chlorophenyl)-(R)-1-methoxypropyl-(R)-2-cyclopropylcarbamate

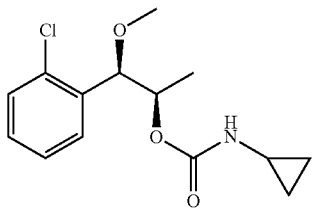 [SMILES: CO[C@H](c1ccccc1Cl)[C@@H](C)OC(=O)NC1CC1]

¹H NMR (400 MHz, CDCl₃) δ0.57 (m, 2H), 0.82 (m, 2H), 1.37 (d, J=6.8 Hz, 3H), 2.75 (m, 1H), 3.24 (s, 3H), 4.71 (d, J=6.8, 1H), 4.82~4.88 (m, 1H), 7.26~7.70 (m, 4H)

Example 206

Synthesis of 1-(2-chlorophenyl)-(R)-1-methoxypropyl-(R)-2-cyclohexylcarbamate

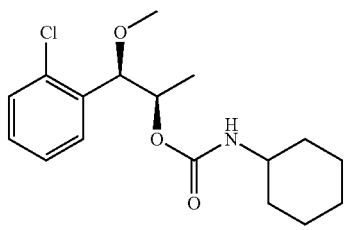 [SMILES: CO[C@H](c1ccccc1Cl)[C@@H](C)OC(=O)NC1CCCCC1]

¹H NMR (400 MHz, CDCl₃) δ1.11~1.21 (in, 4H), 1.37 (d, J=6.8 Hz, 3H), 1.47~1.49 (m, 4H), 1.74 (m, 2H), 3.24 (s, 3H), 3.54 (m, 1H), 4.71 (d, J=6.8, 1H), 4.82~4.88 (m, 1H), 7.26~7.70 (m, 4H)

Example 207

Synthesis of 1-(2-chlorophenyl)-(R)-1-methoxypropyl-(R)-2-cyclohexylcarbamate

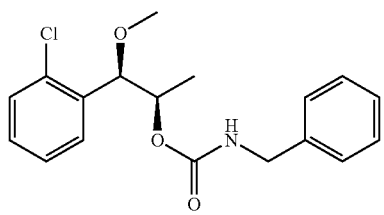 [SMILES: CO[C@H](c1ccccc1Cl)[C@@H](C)OC(=O)NCc1ccccc1]

¹H NMR (400 MHz, CDCl₃) δ1.37 (d, J=6.8 Hz, 3H), 3.24 (s, 3H), 4.20 (m, 2H), 4.71 (d, J=6.8, 1H), 4.82~4.88 (m, 1H), 7.13~7.19 (m, 4H), 7.37~7.88 (m, 5H)

Example 208

Synthesis of 1-(2-chlorophenyl)-(R)-1-methoxypropyl-(R)-2-bicyclo[2,2,1]heptanescarbamate

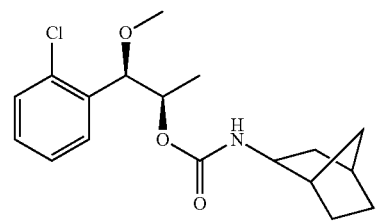 [SMILES: CO[C@H](c1ccccc1Cl)[C@@H](C)OC(=O)NC1CC2CCC1C2]

¹H NMR (400 MHz, CDCl₃) δ1.33~1.58 (m, 9H), 1.75~1.88 (m, 2H), 2.06~2.13 (m, 2H), 3.22 (s, 3H), 3.53 (m, 1H), 4.71 (d, J=6.8, 1H), 4.82~4.88 (m, 1H), 7.13~7.19 (m, 4H), 7.37~7.88 (m, 5H)

Example 209

Synthesis of 1-(2-fluorophenyl)-(R)-1-methoxypropyl-(R)-2-carbamate

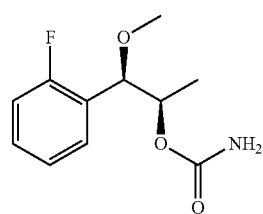

¹H NMR (400 MHz, CDCl₃) δ1.37 (d, J=6.8 Hz, 3H), 3.23 (s, 3H), 4.71 (d, J=6.8, 1H), 4.82~4.88 (m, 1H), 7.15~7.68 (m, 4H)

Example 210

Synthesis of 1-(4-fluorophenyl)-(R)-1-methoxypropyl-(R)-2-carbamate

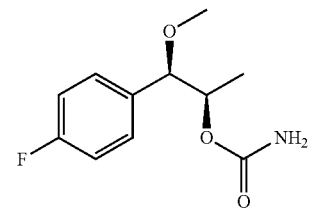 [SMILES: CO[C@H](c1ccc(F)cc1)[C@@H](C)OC(N)=O]

¹H NMR (400 MHz, CDCl₃) δ1.37 (d, J=6.8 Hz, 3H), 3.23 (s, 3H), 4.71 (d, J=6.8, 1H), 4.82~4.88 (m, 1H), 6.96~7.17 (m, 4H)

Example 211

Synthesis of 1-(4-fluorophenyl)-(R)-1-methoxybutyl-(R)-2-carbamate

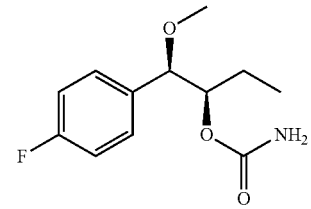 [SMILES: CC[C@@H](OC(N)=O)[C@H](OC)c1ccc(F)cc1]

¹H NMR (400 MHz, CDCl₃) δ1.04 (t, J=7.6 Hz, 3H), 1.60~1.71 (m, 2H), 3.24 (s, 3H), 4.71 (d, J=6.8 Hz, 1H), 4.73 (br s, 2H), 4.82~4.88 (m, 1H), 6.90~7.20 (m, 4H)

Example 212

Synthesis of 1-(4-fluorophenyl)-(R)-1-methoxy-3-methyl-butyl-(R)-2-carbamate

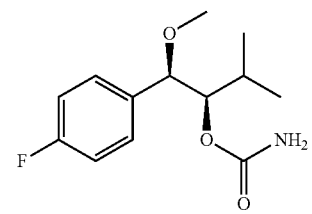 [SMILES: CO[C@H](c1ccc(F)cc1)[C@H](OC(N)=O)C(C)C]

¹H NMR (400 MHz, CDCl₃) δ1.07 (t, J=7.6 Hz, 6H), 1.83~1.89 (m, 1H), 3.23 (s, 3H), 4.71 (d, J=6.8 Hz, 1H), 4.73 (br s, 2H), 4.82~4.88 (m, 1H), 6.92~7.17 (m, 4H)

Example 213

Synthesis of 1-(4-fluorophenyl)-(R)-1-methoxy-hexyl-(R)-2-carbamate

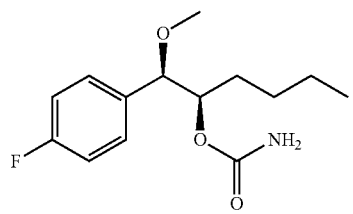 [SMILES: CCCC[C@@H](OC(N)=O)[C@H](OC)c1ccc(F)cc1]

¹H NMR (400 MHz, CDCl₃) δ0.90 (t, J=7.6 Hz, 3H), 1.35~1.65 (m, 6H), 3.23 (s, 3H), 4.71 (d, J=6.8, 1H), 4.73 (br s, 2H), 4.82~4.88 (m, 1H), 6.96~7.19 (m, 4H)

Example 214

Synthesis of 1-(2-iodophenyl)-(R)-1-methoxypropyl-(R)-2-carbamate

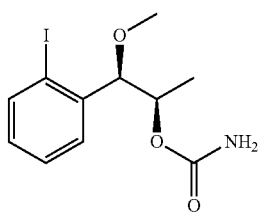

¹H NMR (400 MHz, CDCl₃) δ1.37 (d, J=6.8 Hz, 3H), 3.24 (s, 3H), 4.71 (d, J=6.8, 1H), 4.82~4.88 (m, 1H), 7.13~7.88 (m, 4H)

Example 215

Synthesis of 1-(2-iodophenyl)-(R)-1-methoxybutyl-(R)-2-carbamate

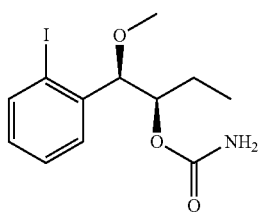

¹H NMR (400 MHz, CDCl₃) δ1.04 (t, J=7.6 Hz, 3H), 1.60~1.71 (m, 2H), 3.23 (s, 3H), 4.71 (d, J=6.8, 1H), 4.82~4.88 (m, 1H), 7.26~7.70 (m, 4H)

Example 216

Synthesis of 1-(2-iodophenyl)-(R)-1-methoxy-3-methyl-butyl-(R)-2-carbamate

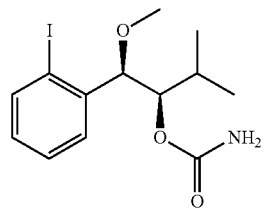

¹H NMR (400 MHz, CDCl₃) δ1.07 (d, J=7.6 Hz, 3H), 1.83~1.89 (m, 1H), 3.24 (s, 3H), 4.71 (d, J=6.8, 1H), 4.82~4.88 (m, 1H), 7.26~7.70 (m, 4H)

Example 217

Synthesis of 1-(2-iodophenyl)-(R)-1-methoxyhexyl-(R)-2-carbamate

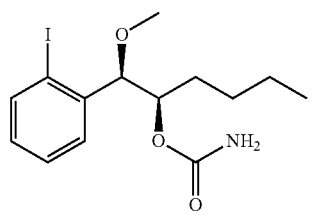 [SMILES: CCCC[C@@H](OC(N)=O)[C@H](OC)c1ccccc1I]

¹H NMR (400 MHz, CDCl₃) δ0.84 (t, J=7.0 Hz, 3H), 1.20~1.35 (m, 4H), 1.36~1.41 (m, 1H), 1.59~1.63 (m, 1H), 3.30 (s, 3H), 4.47 (br s, 2H), 4.71 (d, J=6.8, 1H), 4.82~4.88 (m, 1H), 5.45 (s, 2H), 7.26~7.70 (m, 4H)

Example 218

Synthesis of 1-(3-iodophenyl)-(R)-1-methoxypropyl-(R)-2-carbamate

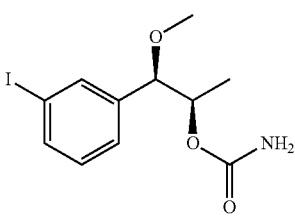 [SMILES: CO[C@H](c1cccc(I)c1)[C@@H](C)OC(N)=O]

¹H NMR (400 MHz, CDCl₃) δ1.16 (d, J=6.4 Hz, 3H), 3.23 (s, 3H), 4.54~4.63 (m, 4H), 5.04~5.10 (m, 1H), 7.09~7.73 (m, 4H)

Example 219

Synthesis of 1-(3-iodophenyl)-(R)-1-methoxybutyl-(R)-2-carbamate

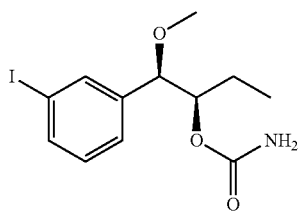 [SMILES: CC[C@@H](OC(N)=O)[C@H](OC)c1cccc(I)c1]

¹H NMR (400 MHz, CDCl₃) δ1.04 (t, J=7.6 Hz, 3H), 1.60~1.71 (m, 2H), 3.24 (s, 3H), 4.71 (d, J=6.8, 1H), 4.82~4.88 (m, 1H), 7.26~7.70 (m, 4H)

Example 220

Synthesis of 1-(3-iodophenyl)-(R)-1-methoxy-3-methyl-butyl-(R)-2-carbamate

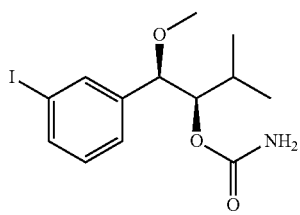 [SMILES: CO[C@H](c1cccc(I)c1)[C@H](OC(N)=O)C(C)C]

¹H NMR (400 MHz, CDCl₃) δ1.07 (d, J=7.6 Hz, 3H), 1.83~1.89 (m, 1H), 3.24 (s, 3H), 4.71 (d, J=6.8, 1H), 4.82~4.88 (m, 1H), 7.26~7.70 (m, 4H)

Example 221

Synthesis of 1-(3-iodophenyl)-(R)-1-methoxyhexyl-(R)-2-carbamate

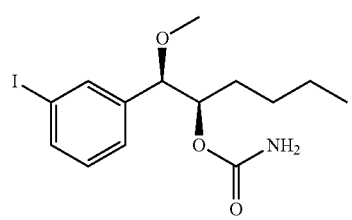 [SMILES: CCCC[C@@H](OC(N)=O)[C@H](OC)c1cccc(I)c1]

¹H NMR (400 MHz, CDCl₃) δ0.84 (1, J=7.0 Hz, 3H), 1.20~1.35 (m, 4H), 1.36~1.41 (m, 1H), 1.59~1.63 (m, 1H), 3.30 (s, 3H), 4.47 (br s, 2H), 4.71 (d, J=6.8, 1H), 4.82~4.88 (m, 1H), 7.26~7.70 (m, 4H)

Example 222

Synthesis of 1-(2-chlorophenyl)-(R)-1-methoxypropyl-(R)-2-methylcarbamate

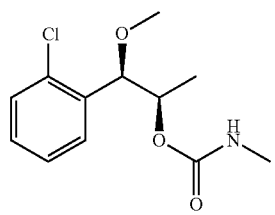 [SMILES: CNC(=O)O[C@H](C)[C@H](OC)c1ccccc1Cl]

¹H NMR (400 MHz, CDCl₃) δ1.37 (d, J=6.8 Hz, 3H), 2.58 (s, 3H), 2.24 (s, 3H), 4.71 (d, J=6.8, 1H), 4.82~4.88 (m, 1H), 7.26~7.70 (m, 4H)

Example 223

Synthesis of 1-(2-chlorophenyl)-(R)-1-methoxypropyl-(R)-2-propylcarbamate

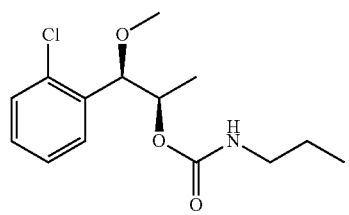 [SMILES: CCCNC(=O)O[C@H](C)[C@H](OC)c1ccccc1Cl]

¹H NMR (400 MHz, CDCl₃) δ0.90 (1, J=6.8 Hz, 3H), 1.37 (d, J=6.8 Hz, 3H), 1.60 (m, 2H), 3.18 (t, J=7.1 Hz, 2H), 3.23 (s, 3H), 4.71 (d, J=6.8, 1H), 4.82~4.88 (m, 1H), 7.26~7.70 (m, 4H)

Example 224

Synthesis of 1-(2-chlorophenyl)-(R)-1-methoxypropyl-(R)-2-isopropylcarbamate

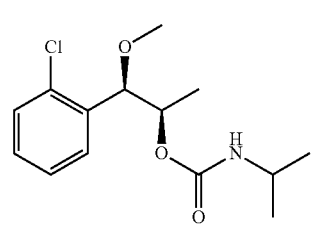 [SMILES: CO[C@H](c1ccccc1Cl)[C@@H](C)OC(=O)NC(C)C]

¹H NMR (400 MHz, CDCl₃) δ, 1.27 (d, J=6.8 Hz, 6H), 1.37 (d, J=6.8 Hz, 3H), 3.24 (s, 3H), 4.17 (m, 1H), 4.71 (d, J=6.8, 1H), 4.82~4.88 (m, 1H), 7.26~7.70 (m, 4H)

Example 225

Synthesis of 1-(2-chlorophenyl)-(R)-1-methoxypropyl-(R)-2-cyclopropylcarbamate

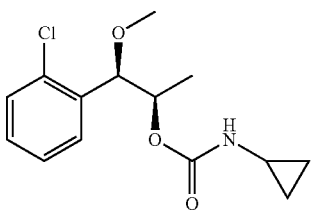 [SMILES: CO[C@H](c1ccccc1Cl)[C@@H](C)OC(=O)NC1CC1]

¹H NMR (400 MHz, CDCl₃) δ0.57 (m, 2H), 0.82 (m, 2H), 1.37 (d, J=6.8 Hz, 3H), 2.75 (m, 1H), 3.24 (s, 3H), 4.71 (d, J=6.8, 1H), 4.82~4.88 (m, 1H), 7.26~7.70 (m, 4H)

Example 226

Synthesis of 1-(2-chlorophenyl)-(R)-1-methoxypropyl-(R)-2-cyclohexylcarbamate

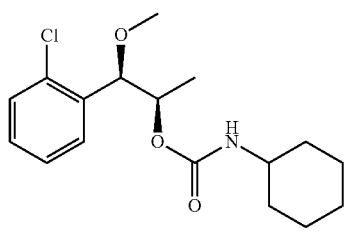 [SMILES: CO[C@H](c1ccccc1Cl)[C@@H](C)OC(=O)NC1CCCCC1]

¹H NMR (400 MHz, CDCl₃) δ1.11~1.21 (m, 4H), 1.37 (d, J=6.8 Hz, 3H), 1.47~1.49 (m, 4H), 1.74 (m, 2H), 3.24 (s, 3H), 3.54 (m, 1H), 4.71 (d, J=6.8, 1H), 4.82~4.88 (m, 1H), 7.26~7.70 (m, 4H)

Example 227

Synthesis of 1-(2-chlorophenyl)-(R)-1-methoxypropyl-(R)-2-cyclohexylcarbamate

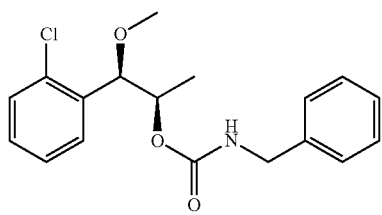 [SMILES: CO[C@H](c1ccccc1Cl)[C@@H](C)OC(=O)NCc1ccccc1]

¹H NMR (400 MHz, CDCl₃) δ1.37 (d, J=6.8 Hz, 3H), 3.24 (s, 3H), 4.20 (m, 2H), 4.71 (d, J=6.8, 1H), 4.82~4.88 (m, 1H), 7.13~7.19 (m, 4H), 7.37~7.88 (m, 5H)

Example 228

Synthesis of 1-(2-chlorophenyl)-(R)-1-methoxypropyl-(R)-2-bicyclo[2,2,1]heptanescarbamate

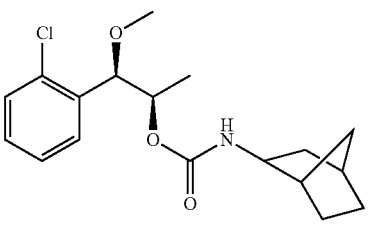 [SMILES: CO[C@H](c1ccccc1Cl)[C@@H](C)OC(=O)NC1CC2CCC1C2]

¹H NMR (400 MHz, CDCl₃) δ1.33~1.58 (m, 9H), 1.75~1.88 (m, 2H), 2.06~2.13 (m, 2H), 3.24 (s, 3H), 3.53 (m, 1H), 4.71 (d, J=6.8, 1H), 4.82~4.88 (m, 1H), 7.13~7.19 (m, 4H), 7.37~7.88 (m, 5H)

Example 229

Synthesis of 1-(2,4-dichlorophenyl)-(R)-1-methoxypropyl-(R)-2-carbamate

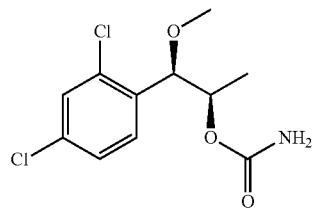 [SMILES: CO[C@H](c1ccc(Cl)cc1Cl)[C@@H](C)OC(N)=O]

¹H NMR (400 MHz, CDCl₃) δ1.37 (d, J=6.8 Hz, 3H), 3.24 (s, 3H), 4.71 (d, J=6.8, 1H), 4.82~4.88 (m, 1H), 7.24~7.30 (m, 2H), 7.73 (d, J=1.5 Hz, 1H)

Example 230

Synthesis of 1-(2,6-dichlorophenyl)-(R)-1-methoxypropyl-(R)-2-carbamate

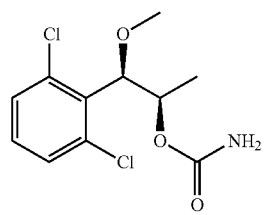 [SMILES: CO[C@H](c1c(Cl)cccc1Cl)[C@@H](C)OC(N)=O]

¹H NMR (400 MHz, CDCl₃) δ1.37 (d, J=6.8 Hz, 3H), 3.24 (s, 3H), 4.71 (d, J=6.8, 1H), 4.82~4.88 (m, 1H), 7.57~7.58 (m, 3H)

Example 231

Synthesis of 1-(2,3-dichlorophenyl)-(R)-1-methoxy-propyl-(R)-2-carbamate

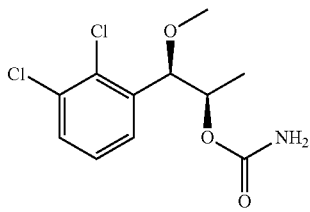 [SMILES: CO[C@H](c1cccc(Cl)c1Cl)[C@@H](C)OC(N)=O]

¹H NMR (400 MHz, CDCl₃) δ1.37 (d, J=6.8 Hz, 3H), 3.24 (s, 3H), 4.71 (d, J=6.8, 1H), 4.82~4.88 (m, 1H), 7.01~7.14 (m, 3H)

Example 232

Synthesis of 1-(2,4-dichlorophenyl)-(R)-1-methoxy-butyl-(R)-2-carbamate

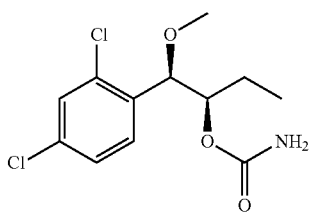 [SMILES: CC[C@@H](OC(N)=O)[C@H](OC)c1ccc(Cl)cc1Cl]

¹H NMR (400 MHz, CDCl₃) δ1.04 (t, J=7.6 Hz, 3H), 1.60~1.71 (m, 2H), 3.24 (s, 3H), 4.71 (d, J=6.8, 1H), 4.73 (br s, 2H), 4.82~4.88 (m, 1H), 7.24~7.30 (m, 2H), 7.73 (d, J=1.5 Hz, 1H)

Example 233

Synthesis of 1-(2,6-dichlorophenyl)-(R)-1-methoxy-butyl-(R)-2-carbamate

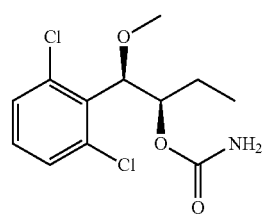 [SMILES: CC[C@@H](OC(N)=O)[C@H](OC)c1c(Cl)cccc1Cl]

¹H NMR (400 MHz, CDCl₃) δ1.04 (t, J=7.6 Hz, 3H), 1.60~1.71 (m, 2H), 3.24 (s, 3H), 4.71 (d, J=6.8, 1H), 4.73 (br s, 2H), 4.82~4.88 (m, 1H), 7.54~7.57 (m, 3H)

Example 234

Synthesis of 1-(2,4-dichlorophenyl)-(R)-1-methoxy-3-methyl-butyl-(R)-2-carbamate

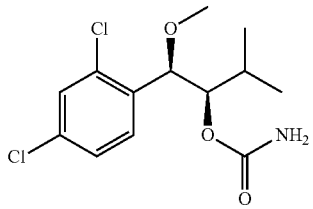 [SMILES: CO[C@H](c1ccc(Cl)cc1Cl)[C@H](OC(N)=O)C(C)C]

¹H NMR (400 MHz, CDCl₃) δ1.07 (t, J=7.6 Hz, 6H), 1.83~1.89 (m, 1H), 3.24 (s, 3H), 4.71 (d, J=6.8, 1H), 4.73 (br s, 2H), 4.82~4.88 (m, 1H), 7.24~7.30 (m, 2H), 7.73 (d, J=1.5 Hz, 1H)

Example 235

Synthesis of 1-(2,6-dichlorophenyl)-(R)-1-methoxy-3-methyl-butyl-(R)-2-carbamate

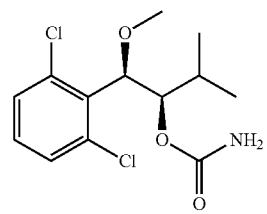 [SMILES: CO[C@H](c1c(Cl)cccc1Cl)[C@H](OC(N)=O)C(C)C]

¹H NMR (400 MHz, CDCl₃) δ1.07 (t, J=7.6 Hz, 6H), 1.83~1.89 (m, 1H), 3.24 (s, 3H), 4.71 (d, J=6.8, 1H), 4.73 (br s, 2H), 4.82~4.88 (m, 1H), 7.55~7.57 (m, 3H)

Example 236

Synthesis of 1-(2,4-dichlorophenyl)-(R)-1-methoxy-hexyl-(R)-2-carbamate

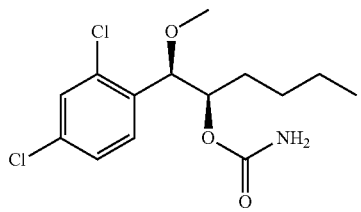 [SMILES: CCCC[C@@H](OC(N)=O)[C@H](OC)c1ccc(Cl)cc1Cl]

¹H NMR (400 MHz, CDCl₃) δ0.90 (t, J=7.6 Hz, 3H), 1.35~1.65 (m, 6H), 3.24 (s, 3H), 4.71 (d, J=6.8, 1H), 4.73 (br s, 2H), 4.82~4.88 (m, 1H), 7.24~7.30 (m, 2H), 7.73 (d, J=1.5 Hz, 1H)

Example 237

Synthesis of 1-(2,4-dichlorophenyl)-(R)-1-methoxy-hexyl-(R)-2-carbamate

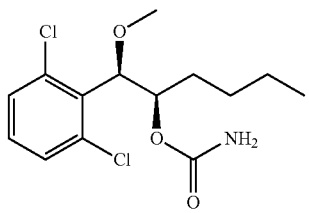 [SMILES: CCCC[C@@H](OC(N)=O)[C@H](OC)c1c(Cl)cccc1Cl]

¹H NMR (400 MHz, CDCl₃) δ0.90 (t, J=7.6 Hz, 3H), 1.35~1.65 (m, 6H), 3.23 (s, 3H), 4.71 (d, J=6.8, 1H), 4.73 (br s, 2H), 4.82~4.88 (m, 1H), 7.54~7.59 (m, 3H)

Example 238

Synthesis of 1-(2,4-dichlorophenyl)-1-methoxypropyl-2-carbamate

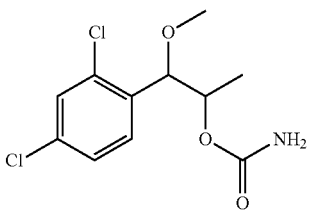 [SMILES: COC(c1ccc(Cl)cc1Cl)C(C)OC(N)=O]

¹H NMR (400 MHz, CDCl₃) δ1.37 (d, J=6.8 Hz, 3H), 3.23 (s, 3H), 4.71 (d, J=6.8, 1H), 4.82~4.88 (m, 1H), 7.24~7.30 (m, 2H), 7.73 (d, J=1.5 Hz, 1H)

Example 239

Synthesis of 1-(2,6-dichlorophenyl)-1-methoxypropyl-2-carbamate

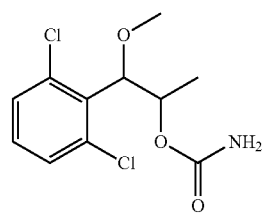

¹H NMR (400 MHz, CDCl₃) δ1.37 (d, J=6.8 Hz, 3H), 3.24 (s, 3H), 4.71 (d, J=6.8, 1H), 4.82~4.88 (m, 1H), 7.57~7.58 (m, 3H)

Example 240

Synthesis of 1-(2,3-dichlorophenyl)-1-methoxypropyl-2-carbamate

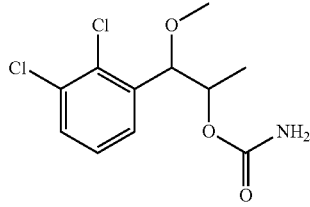 [SMILES: COC(c1cccc(Cl)c1Cl)C(C)OC(N)=O]

¹H NMR (400 MHz, CDCl₃) δ1.37 (d, J=6.8 Hz, 3H), 3.24 (s, 3H), 4.71 (d, J=6.8, 1H), 4.82~4.88 (m, 1H), 7.01~7.14 (m, 3H)

Example 241

Synthesis of 1-(2,4-dichlorophenyl)-1-methoxybutyl-2-carbamate

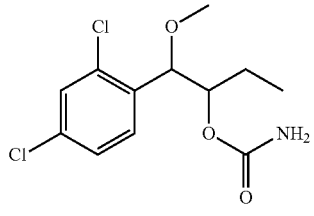

¹H NMR (400 MHz, CDCl₃) δ1.04 (t, J=7.6 Hz, 3H), 1.60~1.71 (m, 2H), 3.23 (s, 3H), 4.71 (d, J=6.8, 1H), 4.73 (br s, 2H), 4.82~4.88 (m, 1H), 7.24~7.30 (m, 2H), 7.73 (d, J=1.5 Hz, 1H)

Example 242

Synthesis of 1-(2,6-dichlorophenyl)-1-methoxybutyl-2-carbamate

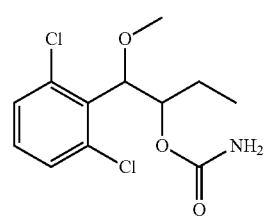

¹H NMR (400 MHz, CDCl₃) δ1.04 (t, J=7.6 Hz, 3H), 1.60~1.71 (m, 2H), 3.24 (s, 3H), 4.71 (d, J=6.8, 1H), 4.73 (br s, 2H), 4.82~4.88 (m, 1H), 7.54~7.57 (m, 3H)

Example 243

Synthesis of 1-(2,4-dichlorophenyl)-1-methoxy-3-methyl-butyl-2-carbamate

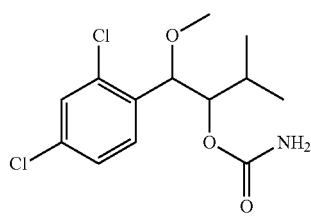 [SMILES: COC(c1ccc(Cl)cc1Cl)C(OC(N)=O)C(C)C]

$^1$H NMR (400 MHz, CDCl$_3$) δ1.07 (1, J=7.6 Hz, 6H), 1.83~1.89 (m, 1H), 3.24 (s, 3H), 4.71 (d, J=6.8, 1H), 4.73 (br s, 2H), 4.82~4.88 (m, 1H), 7.24~7.30 (m, 2H), 7.73 (d, J=1.5 Hz, 1H)

Example 244

Synthesis of 1-(2,6-dichlorophenyl)-1-methoxy-3-methyl-butyl-2-carbamate

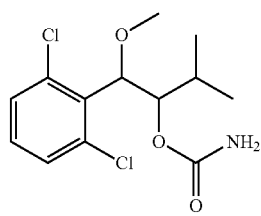

$^1$H NMR (400 MHz, CDCl$_3$) δ1.07 (1, J=7.6 Hz, 6H), 1.83~1.89 (m, 1H), 3.24 (s, 3H), 4.71 (d, J=6.8, 1H), 4.73 (br s, 2H), 4.82~4.88 (m, 1H), 7.55~7.57 (m, 3H)

Example 245

Synthesis of 1-(2,4-dichlorophenyl)-1-methoxyhexyl-2-carbamate

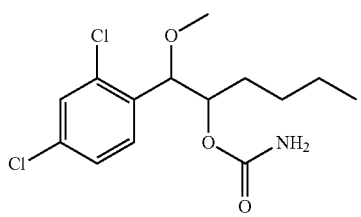

$^1$H NMR (400 MHz, CDCl$_3$) δ0.90 (1, J=7.6 Hz, 3H), 1.35~1.65 (m, 6H), 3.24 (s, 3H), 4.71 (d, J=6.8, 1H), 4.73 (br s, 2H), 4.82~4.88 (m, 1H), 7.24~7.30 (m, 2H), 7.73 (d, J=1.5 Hz, 1H)

Example 246

Synthesis of 1-(2,4-dichlorophenyl)-1-methoxyhexyl-2-carbamate

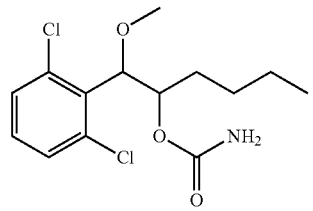 [SMILES: CCCCC(OC(N)=O)C(OC)c1c(Cl)cccc1Cl]

$^1$H NMR (400 MHz, CDCl$_3$) δ0.90 (t, J=7.6 Hz, 3H), 1.35~1.65 (m, 6H), 3.24 (s, 3H), 4.71 (d, J=6.8, 1H), 4.73 (br s, 2H), 4.82~4.88 (m, 1H), 7.54~7.59 (m, 3H)

Example 247

Synthesis of 1-(2-chlorophenyl)-(S)-1-carbamoyloxypropyl-(S)-2-carbamate

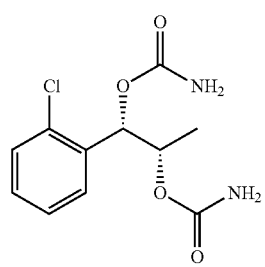 [SMILES: C[C@H](OC(N)=O)[C@@H](OC(N)=O)c1ccccc1Cl]

1-(2-chlorophenyl)-1-hydroxypropyl-1-carbamate (Preparation Example 103, 8 g), tetrahydrofuran (THF), and carbonyldiimidazole (CDI, 1.5 eq, 9.1 g) were put into a flask and stirred at the room temperature. After approximately 3 hours, ammonia solution (NH$_4$OH, 3 eq, 4.4 ml) was added thereto. When the reaction was completed, the obtained product was washed with 1M HCl solution and ethylacetate (EA). The separated organic layer was dehydrated with anhydrous MgSO$_4$(Magnesium sulfate), filtrated, and concentrated under reduced pressure. The concentrated residue was purified by a silica gel column chromatography, to obtain the title compound.

$^1$H NMR (400 MHz, DMSO-d$_6$) δ1.12 (d, J=6.4 Hz, 3H), 4.97~5.03 (m, 1H), 5.91 (d, J=5.2 Hz, 1H), 6.31~6.92 (m, 4H), 7.30~7.42 (m, 4H)

According to the method described in Example 247, the following compounds of Examples 248 to 256 were prepared:

Example 248

Synthesis of 1-(2-chlorophenyl)-(S)-1-carbamoyloxypropyl-(S)-2-methylcarbamate

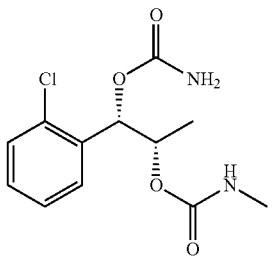 [SMILES: CNC(=O)O[C@@H](C)[C@@H](OC(N)=O)c1ccccc1Cl]

$^1$H NMR (400 MHz, CDCl$_3$) δ1.40 (d, J=6.0 Hz, 3H), 2.74 (s, 3H), 4.71 (d, J=6.4 Hz, 1H), 4.80~4.85 (m, 1H), 6.30~6.90 (br s, 3H), 7.28~7.43 (m, 4H)

Example 249

Synthesis of 1-(2-chlorophenyl)-(S)-1-carbamoyloxypropyl-(S)-2-propylcarbamate

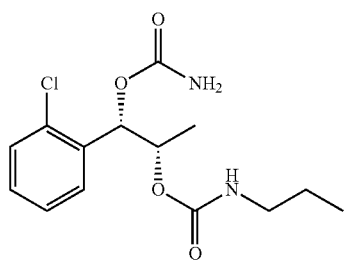 [SMILES: CCCNC(=O)O[C@@H](C)[C@@H](OC(N)=O)c1ccccc1Cl]

$^1$H NMR (400 MHz, CDCl$_3$) δ0.96 (t, J=6.4 Hz, 3H), 1.40 (d, J=6.0 Hz, 3H), 1.55~1.60 (m, 2H), 2.96 (t, J=6.0 Hz, 2H), 4.71 (d, J=6.0 Hz, 1H), 4.82~4.88 (m, 1H), 6.76 (br s, 3H), 7.07~7.21 (m, 4H)

Example 250

Synthesis of 1-(2-chlorophenyl)-(R)-2-carbamoyloxypropyl-(R)-1-carbamate (2)

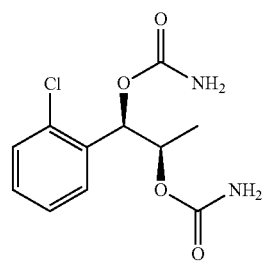

$^1$H NMR (400 MHz, DMSO-d$_6$) δ1.12 (d, J=6.4 Hz, 3H), 4.97~5.04 (m, 1H), 5.92 (d, J=5.2 Hz, 1H), 6.25~6.83 (m, 4H), 7.30~7.44 (m, 4H)

Example 251

Synthesis of 1-(2-chlorophenyl)-2-carbamoyloxypropyl-1-carbamate (3)

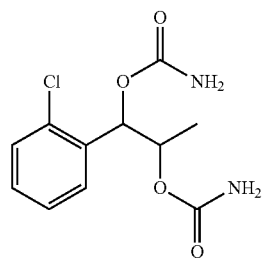 [SMILES: CC(OC(N)=O)C(OC(N)=O)c1ccccc1Cl]

$^1$H NMR (400 MHz, DMSO-d$_6$) δ1.12 (d, J=6.4 Hz, 3H), 4.97~5.03 (m, 1H), 5.91 (d, J=5.2 Hz, 1H), 6.31~6.92 (m, 4H), 7.30~7.42 (m, 4H)

Example 252

Synthesis of 1-(2-chlorophenyl)-(S)-1-carbamoyloxybutyl-(S)-2-carbamate

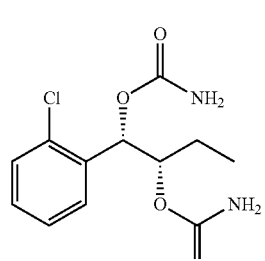

$^1$H NMR (400 MHz, CDCl$_3$) δ1.04 (t, J=7.6 Hz, 3H), 1.60~1.71 (m, 2H), 4.71 (d, J=6.8, 1H), 4.73 (br s, 2H), 5.82~5.88 (m, 1H), 7.26~7.70 (m, 4H)

Example 253

Synthesis of 1-(2-chlorophenyl)-(S)-1-carbamoyloxy-3-methyl-butyl-(S)-2-carbamate

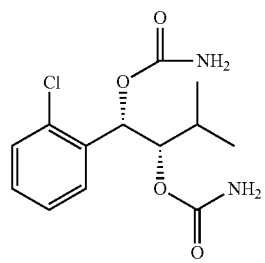 [SMILES: CC(C)[C@H](OC(N)=O)[C@@H](OC(N)=O)c1ccccc1Cl]

$^1$H NMR (400 MHz, CDCl$_3$) δ1.07 (t, J=7.6 Hz, 6H), 1.83~1.89 (m, 1H), 4.71 (d, J=6.8, 1H), 4.73 (br s, 2H), 5.80~5.88 (m, 1H), 7.26~7.70 (m, 4H)

Example 254

Synthesis of 1-(2-chlorophenyl)-(S)-1-carbamoyloxyhexyl-(S)-2-carbamate

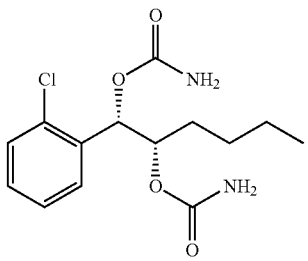 [SMILES: CCCC[C@H](OC(N)=O)[C@@H](OC(N)=O)c1ccccc1Cl]

¹H NMR (400 MHz, CDCl₃) δ0.90 (1, J=7.6 Hz, 3H), 1.35~1.65 (m, 6H), 4.71 (d, J=6.8, 1H), 4.73 (br s, 2H), 5.82~5.88 (m, 1H), 7.26~7.70 (m, 4H)

Example 255

Synthesis of 1-(2-fluorophenyl)-(S)-1-carbamoyloxypropyl-(S)-2-carbamate

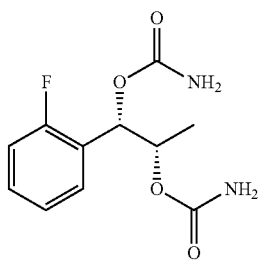

¹H NMR (400 MHz, DMSO-d₆) δ1.37 (d, J=6.8 Hz, 3H), 4.71 (d, J=6.8, 1H), 5.82~5.88 (m, 1H), 7.15~7.68 (m, 4H)

Example 256

Synthesis of 1-(2-fluorophenyl)-(S)-1-carbamoyloxybutyl-(S)-2-carbamate

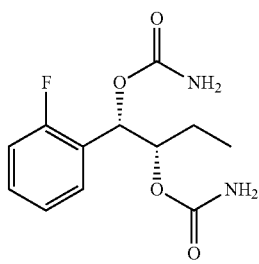

¹H NMR (400 MHz, CDCl₃) δ1.02 (1, J=7.2 Hz, 3H), 1.60~1.71 (m, 2H), 4.71 (d, J=6.8 Hz, 1H), 4.73 (br s, 2H), 5.82~5.88 (m, 1H), 6.09~7.17 (m, 4H)

Example 257

Synthesis of 1-(2-fluorophenyl)-(S)-1-carbamoyloxy-3-methyl-butyl-(S)-2-carbamate

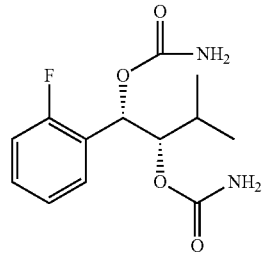 [SMILES: CC(C)[C@H](OC(N)=O)[C@@H](OC(N)=O)c1ccccc1F]

¹H NMR (400 MHz, CDCl₃) δ1.07 (t, J=7.6 Hz, 6H), 1.83~1.89 (m, 1H), 4.71 (d, J=6.8 Hz, 1H), 4.73 (br s, 2H), 5.80~5.88 (m, 1H), 6.10~7.20 (m, 4H)

Example 258

Synthesis of 1-(2-fluorophenyl)-(S)-1-carbamoyloxyhexyl-(S)-2-carbamate

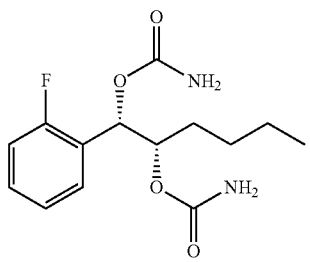 [SMILES: CCCC[C@H](OC(N)=O)[C@@H](OC(N)=O)c1ccccc1F]

¹H NMR (400 MHz, CDCl₃) δ0.90 (t, J=7.6 Hz, 3H), 1.35~1.65 (m, 6H), 4.71 (d, J=6.8 Hz, 1H), 4.73 (br s, 2H), 5.82~5.88 (m, 1H), 7.16~7.69 (m, 4H)

Example 259

Synthesis of 1-(2-iodophenyl)-(S)-1-carbamoyloxypropyl-(S)-2-carbamate

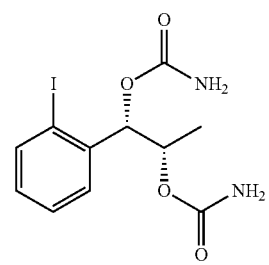 [SMILES: C[C@H](OC(N)=O)[C@@H](OC(N)=O)c1ccccc1I]

¹H NMR (400 MHz, DMSO-d₆) δ1.37 (d, J=6.8 Hz, 3H), 4.71 (d, J=6.8 Hz, 1H), 4.82~4.88 (m, 1H), 7.13~7.88 (m, 4H)

Example 260

Synthesis of 1-(2-iodophenyl)-(S)-1-carbamoyloxy-butyl-(S)-2-carbamate

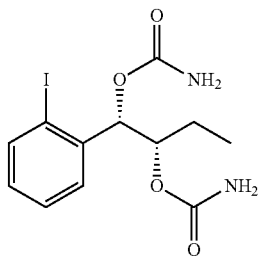 [SMILES: CC[C@H](OC(N)=O)[C@@H](OC(N)=O)c1ccccc1I]

¹H NMR (400 MHz, CDCl₃) δ1.02 (1, J=7.2 Hz, 3H), 1.60~1.71 (m, 2H), 4.71 (d, J=6.8 Hz, 1H), 4.73 (br s, 2H), 5.82~5.88 (m, 1H), 6.96~7.57 (m, 4H)

Example 261

Synthesis of 1-(2-iodophenyl)-(S)-1-carbamoyloxy-3-methyl-butyl-(S)-2-carbamate

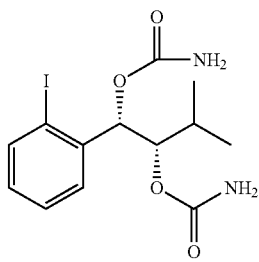 [SMILES: CC(C)[C@H](OC(N)=O)[C@@H](OC(N)=O)c1ccccc1I]

¹H NMR (400 MHz, CDCl₃) δ1.07 (t, J=7.6 Hz, 6H), 1.83~1.89 (m, 1H), 4.71 (d, J=6.8 Hz, 1H), 4.73 (br s, 2H), 5.80~5.88 (m, 1H), 6.98~7.61 (m, 4H)

Example 262

Synthesis of 1-(2-iodophenyl)-(S)-1-carbamoyloxy-hexyl-(S)-2-carbamate

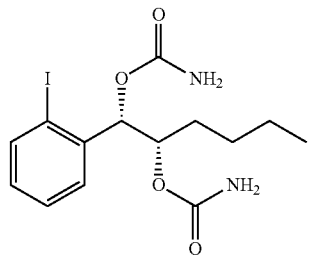 [SMILES: CCCC[C@H](OC(N)=O)[C@@H](OC(N)=O)c1ccccc1I]

¹H NMR (400 MHz, CDCl₃) δ0.90 (1, J=7.6 Hz, 3H), 1.35~1.65 (m, 6H), 4.71 (d, J=6.8 Hz, 1H), 4.73 (br s, 2H), 5.82~5.88 (m, 1H), 6.95~7.61 (m, 4H)

Example 263

Synthesis of 1-(2,4-dichlorophenyl)-(S)-1-carbamoyloxypropyl-(S)-2-carbamate

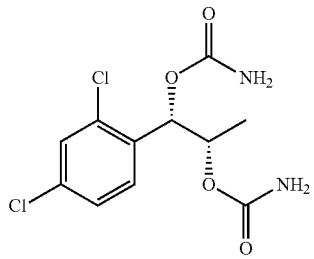 [SMILES: C[C@H](OC(N)=O)[C@@H](OC(N)=O)c1ccc(Cl)cc1Cl]

¹H NMR (400 MHz, DMSO-d₆) δ1.37 (d, J=6.8 Hz, 3H), 4.71 (d, J=6.8 Hz, 1H), 4.82~4.88 (m, 1H), 7.07~7.21 (m, 3H)

Example 264

Synthesis of 1-(2,4-dichlorophenyl)-(S)-1-carbamoyloxybutyl-(S)-2-carbamate

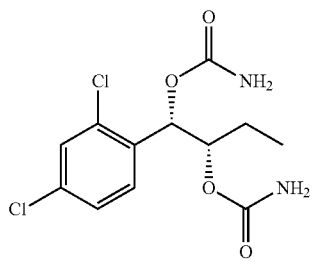 [SMILES: CC[C@H](OC(N)=O)[C@@H](OC(N)=O)c1ccc(Cl)cc1Cl]

¹H NMR (400 MHz, CDCl₃) δ1.02 (1, J=7.2 Hz, 3H), 1.60~1.71 (m, 2H), 4.71 (d, J=6.8 Hz, 1H), 4.73 (br s, 2H), 5.82~5.88 (m, 1H), 7.05~7.19 (m, 3H)

Example 265

Synthesis of 1-(2,4-dichlorophenyl)-(S)-1-carbamoyloxy-3-methyl-butyl-(S)-2-carbamate

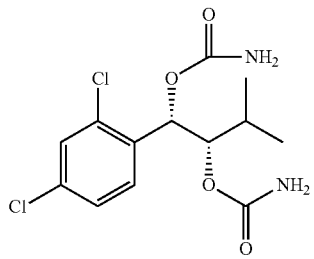 [SMILES: CC(C)[C@H](OC(N)=O)[C@@H](OC(N)=O)c1ccc(Cl)cc1Cl]

¹H NMR (400 MHz, CDCl₃) δ1.07 (t, J=7.6 Hz, 6H), 1.83~1.89 (m, 1H), 4.71 (d, J=6.8 Hz, 1H), 4.73 (br s, 2H), 5.80~5.88 (m, 1H), 7.02~7.17 (m, 3H)

Example 266

Synthesis of 1-(2,4-dichlorophenyl)-(S)-1-carbamoyloxyhexyl-(S)-2-carbamate

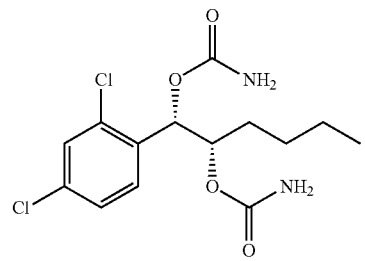 [SMILES: CCCC[C@H](OC(N)=O)[C@@H](OC(N)=O)c1ccc(Cl)cc1Cl]

¹H NMR (400 MHz, CDCl₃) δ0.90 (t, J=7.6 Hz, 3H), 1.35~1.65 (m, 6H), 4.71 (d, J=6.8 Hz, 1H), 4.73 (br s, 2H), 5.82~5.88 (m, 1H), 7.08~7.22 (m, 3H)

Example 267

Synthesis of 1-(2,6-dichlorophenyl)-(S)-1-carbamoyloxypropyl-(S)-2-carbamate

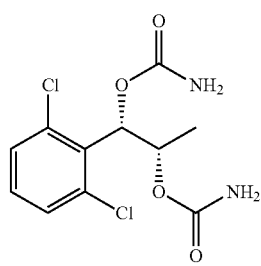

¹H NMR (400 MHz, DMSO-d₆) δ1.37 (d, J=6.8 Hz, 3H), 4.71 (d, J=6.8 Hz, 1H), 4.82~4.88 (m, 1H), 7.07~7.11 (m, 3H)

Example 268

Synthesis of 1-(2,6-dichlorophenyl)-(S)-1-carbamoyloxybutyl-(S)-2-carbamate

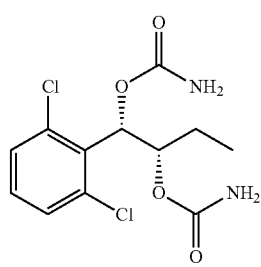 [SMILES: CC[C@H](OC(N)=O)[C@@H](OC(N)=O)c1c(Cl)cccc1Cl]

¹H NMR (400 MHz, CDCl₃) δ1.02 (t, J=7.2 Hz, 3H), 1.60~1.71 (m, 2H), 4.71 (d, J=6.8 Hz, 1H), 4.73 (br s, 2H), 5.82~5.88 (m, 1H), 7.05~7.10 (m, 3H)

Example 269

Synthesis of 1-(2,6-dichlorophenyl)-(S)-1-carbamoyloxy-3-methyl-butyl-(S)-2-carbamate

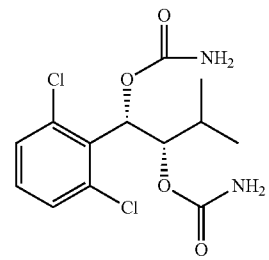 [SMILES: CC(C)[C@H](OC(N)=O)[C@@H](OC(N)=O)c1c(Cl)cccc1Cl]

¹H NMR (400 MHz, CDCl₃) δ1.07 (t, J=7.6 Hz, 6H), 1.83~1.89 (m, 1H), 4.71 (d, J=6.8 Hz, 1H), 4.73 (br s, 2H), 5.80~5.88 (m, 1H), 7.02~7.08 (m, 3H)

Example 270

Synthesis of 1-(2,6-dichlorophenyl)-(S)-1-carbamoyloxyhexyl-(S)-2-carbamate

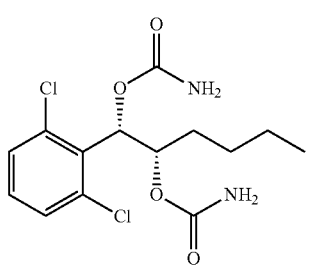 [SMILES: CCCC[C@H](OC(N)=O)[C@@H](OC(N)=O)c1c(Cl)cccc1Cl]

¹H NMR (400 MHz, CDCl₃) δ0.90 (t, J=7.6 Hz, 3H), 1.35~1.65 (m, 6H), 4.71 (d, J=6.8 Hz, 1H), 4.73 (br s, 2H), 5.82~5.88 (m, 1H), 7.05~7.12 (m, 3H)

Example 271

Synthesis of 1-(2,6-difluorophenyl)-(S)-1-methoxymethoxypropyl-(S)-2-carbamate

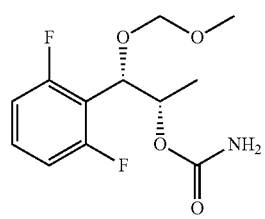 [SMILES: COCO[C@@H](c1c(F)cccc1F)[C@H](C)OC(N)=O]

¹H NMR (400 MHz, CDCl₃) δ1.37 (d, J=6.8 Hz, 3H), 3.30 (s, 3H), 4.71 (d, J=6.8, 1H), 4.82~4.88 (m, 1H), 5.45 (s, 2H), 6.67~7.15 (m, 3H)

Example 272

Synthesis of 1-(2,5-dichlorophenyl)-(S)-1-methoxymethoxypropyl-(S)-2-carbamate

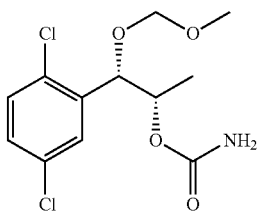 [SMILES: COCO[C@@H](c1cc(Cl)ccc1Cl)[C@H](C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.13~7.26 (m, 3H)

Example 273

Synthesis of 1-(2,5-dichlorophenyl)-(R)-1-methoxymethoxypropyl-(R)-2-carbamate

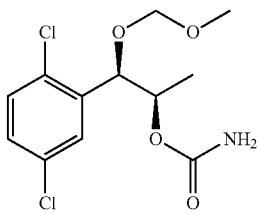 [SMILES: COCO[C@H](c1cc(Cl)ccc1Cl)[C@@H](C)OC(N)=O]

$^1$H NMR (400 MHz, CDCl$_3$) δ1.37 (d, J=6.8 Hz, 3H), 3.30 (s, 3H), 4.71 (d, J=6.8, 1H), 4.82~4.88 (m, 1H), 5.45 (s, 2H), 7.13~7.26 (m, 3H)

Example 274

Synthesis of 1-(2-chlorophenyl)-(S)-2-methoxymethoxypropyl-(S)-1-carbamate

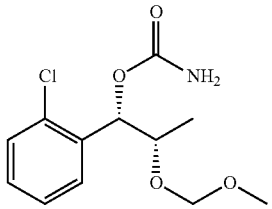 [SMILES: COCO[C@@H](C)[C@@H](OC(N)=O)c1ccccc1Cl]

$^1$H NMR (400 MHz, CDCl$_3$) δ1.21 (d, J=6.8 Hz, 3H), 3.24 (s, 3H), 3.94~4.05 (m, 1H), 5.45 (s, 2H), 5.56 (d, J=6.8 Hz, 1H), 7.07~7.20 (m, 4H)

Example 275

Synthesis of 1-(2-chlorophenyl)-(S)-2-methoxypropyl-(S)-1-carbamate

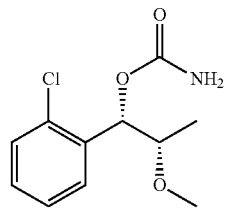 [SMILES: CO[C@@H](C)[C@@H](OC(N)=O)c1ccccc1Cl]

$^1$H NMR (400 MHz, CDCl$_3$) δ1.23 (d, J=6.4 Hz, 3H), 3.22 (s, 3H), 3.99 (m, 1H), 5.52 (d, J=6.4 Hz, 1H), 7.07~7.21 (m, 4H)

Example 276

Synthesis of 1-(2-chlorophenyl)-(S)-1-methoxymethoxyethyl-2-carbamate

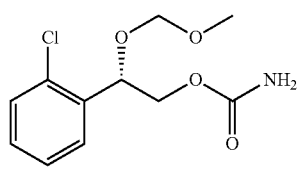

$^1$H NMR (400 MHz, DMSO-d$_6$) δ3.30 (s, 3H), 4.71 (d, J=6.8, 1H), 4.82~4.88 (m, 1H), 5.45 (s, 2H), 7.26~7.70 (m, 4H)

Example 277

Synthesis of 1-(2-fluorophenyl)-(S)-1-methoxymethoxyethyl-2-carbamate

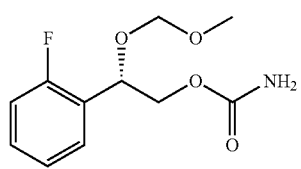 [SMILES: COCO[C@H](COC(N)=O)c1ccccc1F]

$^1$H NMR (400 MHz, CDCl$_3$) δ3.30 (s, 3H), 4.71 (d, J=6.8, 1H), 4.82~4.88 (m, 1H), 5.45 (s, 2H), 7.26~7.70 (m, 4H)

Example 278

Synthesis of 1-(2-iodophenyl)-(S)-1-methoxymethoxyethyl-2-carbamate

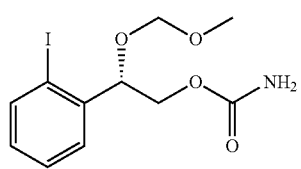

¹H NMR (400 MHz, DMSO-d₆) δ3.26 (s, 3H), 3.94~4.09 (m, 1H), 4.47 (d, J=6.8 Hz, 1H), 4.60 (d, J=6.8 Hz, 1H), 4.97 (m, 1H), 6.55 (br 2H), 7.07~7.87 (m, 4H)

Example 279

Synthesis of 1-(2-chlorophenyl)-(S)-1-methoxy-ethyl-2-carbamate

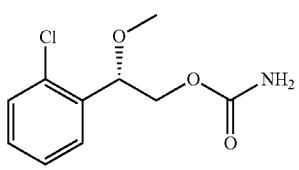

¹H NMR (400 MHz, DMSO-d₆) δ3.27 (s, 3H), 4.71 (d, J=6.8, 1H), 4.82~4.88 (m, 1H), 6.47~6.63 (br 2H), 7.26~7.70 (m, 4H)

Example 280

Synthesis of 1-(2-fluorophenyl)-(S)-1-methoxy-ethyl-2-carbamate

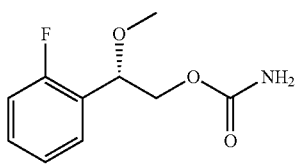

¹H NMR (400 MHz, DMSO-d₆) δ3.29 (s, 3H), 4.71 (d, J=6.8, 1H), 4.82~4.88 (m, 1H), 7.26~7.70 (m, 4H)

Example 281

Synthesis of 1-(2-iodophenyl)-(S)-1-methoxyethyl-2-carbamate

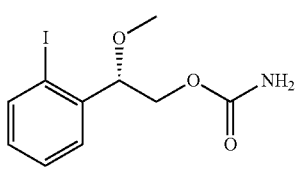

¹H NMR (400 MHz, DMSO-d₆) δ3.28 (s, 3H), 3.94~4.09 (m, 1H), 4.97 (m, 1H), 7.07~7.87 (m, 4H)

Example 282

Synthesis of 1-(2-iodophenyl)-(S)-2-methoxymethoxypropyl-1-carbamate

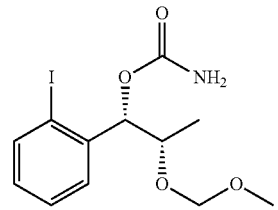 [SMILES: COCO[C@@H](C)[C@@H](OC(N)=O)c1ccccc1I]

¹H NMR (400 MHz, CDCl₃) δ1.31 (d, J=9.6, 3H), 3.08 (s, 3H), 4.15~4.20 (m, 1H), 4.33 (d, J=6.8, 1H), 4.56 (d, J=7.2, 1H) 4.79 (brs, 2H), 5.88 (d, J=4.0, 1H), 6.98~7.02 (m, 1H), 7.33~7.42 (m, 2H), 7.85 (dd, J=7.80, 0.8, 1H)

Example 283

Synthesis of 1-(2-iodophenyl)-(S)-2-methoxypropyl-1-carbamate

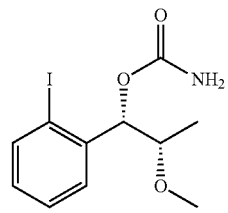 [SMILES: CO[C@@H](C)[C@@H](OC(N)=O)c1ccccc1I]

¹H NMR (400 MHz, CDCl₃) δ1.29 (d, J=6.4, 3H), 3.29 (s, 3H), 4.56 (d, J=5.3, 1H), 4.55 (brs, 2H), 5.08~5.11 (m, 1H), 7.01~7.05 (m, 1H), 7.38~7.86 (m, 3H)

Example 284

Synthesis of 1-(2-fluorophenyl)-(S)-2-methoxymethoxypropyl-1-carbamate

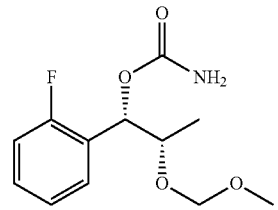

¹H NMR (400 MHz, CDCl₃) δ1.19 (d, J=6.4, 3H), 3.15 (s, 3H), 4.03~4.18 (m, 1H), 4.49 (d, J=6.8, 1H), 4.61 (d, J=7.2, 1H), 4.81 (s, 2H), 5.95 (d, J=5.2, 1H), 7.00~7.43 (m, 4H)

Example 285

Synthesis of 1-(2-fluorophenyl)-(S)-2-methoxypropyl-(S)-1-carbamate

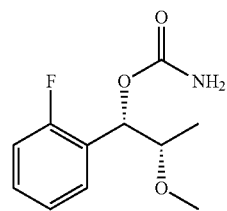

¹H NMR (400 MHz, CDCl₃) δ1.18 (d, J=6.4, 3H), 3.30 (s, 3H), 3.99 (d, J=5.3, 1H), 4.65 (brs, 2H), 4.89~5.01 (m, 1H), 7.01~7.05 (m, 1H), 7.38~7.68 (m, 3H)

Example 286

Synthesis of 1-(2-chloro-6-fluorophenyl)-(S)-1-carbamoyloxypropyl-(S)-2-carbamate

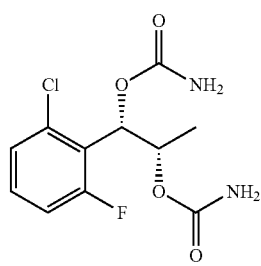 [SMILES: C[C@H](OC(N)=O)[C@@H](OC(N)=O)c1c(F)cccc1Cl]

¹H NMR (400 MHz, DMSO) δ0.97 (d, J=6.4, 3H), 5.28~5.31 (m, 1H), 6.48 (d, J=8.4, 1H), 6.48~6.77 (br 4H), 7.23~7.45 (m, 3H).

Example 287

Synthesis of 1-(2-chloro-6-fluorophenyl)-(R)-1-carbamoyloxypropyl-(R)-2-carbamate

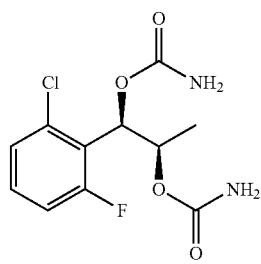 [SMILES: C[C@@H](OC(N)=O)[C@H](OC(N)=O)c1c(F)cccc1Cl]

¹H NMR (400 MHz, CDCl₃) δ1.17 (d, J=6.4, 3H), 4.74 (br s, 4H), 5.52~5.60 (m, 1H), 6.29 (d, J=8.4, 1H), 7.00~7.05 (m, 1H), 7.22~7.23 (m, 2H).

Example 288

Synthesis of 1-(2-iodophenyl)-(R)-1-carbamoyloxypropyl-(R)-2-carbamate

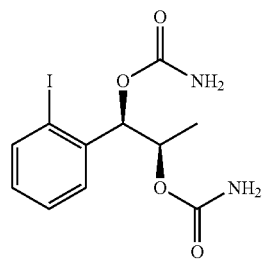 [SMILES: C[C@@H](OC(N)=O)[C@H](OC(N)=O)c1ccccc1I]

¹H NMR (400 MHz, DMSO) δ1.15 (d, J=6.8, 3H), 4.96~5.00 (m, 1H), 5.72 (d, J=4.4, 1H), 6.43 (br s, 2H), 6.57 (br s, 1H), 6.79 (br s, 1H), 7.04~7.12 (m, 1H), 7.33~7.49 (m, 2H), 7.84 (d, J=8.0, 1H).

Example 289

Synthesis of 1-(2-fluorophenyl)-(R)-1-carbamoyloxypropyl-(R)-2-carbamate

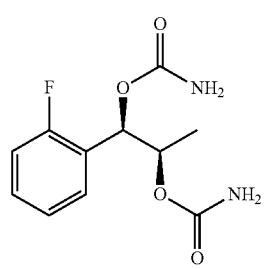

¹H NMR (400 MHz, DMSO) δ1.06 (d, J=6.4, 3H), 4.95~5.01 (m, 1H), 5.80 (d, J=6.0, 1H), 6.50 (br s, 2H), 6.82 (br s, 2H), 7.17~7.24 (m, 2H), 7.34~7.37 (m, 2H).

Example 290

Synthesis of 1-(2,6-dichlorophenyl)-(R)-1-carbamoyloxypropyl-(R)-2-carbamate

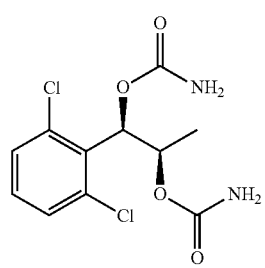 [SMILES: C[C@@H](OC(N)=O)[C@H](OC(N)=O)c1c(Cl)cccc1Cl]

¹H NMR (400 MHz, CDCl3) δ1.64 (d, J=6.4, 314), 4.59 (br s, 2H), 4.86 (br s, 211), 4.97~5.02 (m, 1H), 6.02 (d, J=8.0, 1H), 7.31~7.35 (m, 1H), 7.41~7.44 (m, 2H).

Example 291

Synthesis of 1-(2,4-difluorophenyl)-(R)-1-carbamoyloxypropyl-(R)-2-carbamate

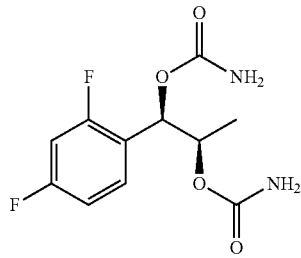 [SMILES: C[C@@H](OC(N)=O)[C@H](OC(N)=O)c1ccc(F)cc1F]

$^1$H NMR (400 MHz, CDCl3) δ1.18 (d, J=6.4, 3H), 4.65 (br s, 2H), 4.75 (br s, 2H), 5.17~5.24 (m, 1H), 5.95 (d, J=7.2, 1H), 6.81~6.93 (m, 2H), 7.36~7.42 (m, 1H).

Example 292

Synthesis of 1-(2,6-difluorophenyl)-(R)-1-carbamoyloxypropyl-(R)-2-carbamate

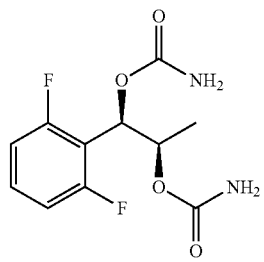 [SMILES: C[C@@H](OC(N)=O)[C@H](OC(N)=O)c1c(F)cccc1F]

$^1$H NMR (400 MHz, CDCl3) δ1.16 (d, J=6.8, 3H), 4.76 (br s, 4H), 5.44~5.48 (m, 1H), 6.10 (d, J=8.4, 1H), 6.90~6.95 (m, 2H), 7.28~7.35 (m, 2H).

Example 293

Synthesis of 1-(2,5-difluorophenyl)-(R)-1-carbamoyloxypropyl-(R)-2-carbamate

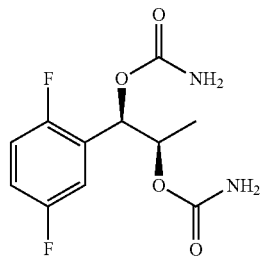 [SMILES: C[C@@H](OC(N)=O)[C@H](OC(N)=O)c1cc(F)ccc1F]

$^1$H NMR (400 MHz, CDCl3) δ1.23 (d, J=6.8, 3H), 4.64 (br s, 2H), 4.77 (br s, 2H), 5.15~5.22 (m, 1H), 5.97 (d, J=6.4, 1H), 6.98~7.07 (m, 2H), 7.08~7.13 (m, 1H).

Example 294

Synthesis of 1-(2-chlorophenyl)-(S)-1-carbamoyloxypropyl-(R)-2-carbamate

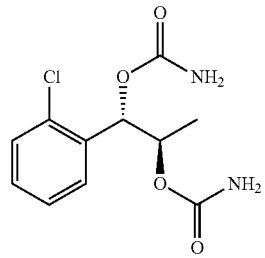 [SMILES: C[C@@H](OC(N)=O)[C@@H](OC(N)=O)c1ccccc1Cl]

$^1$H NMR (400 MHz, DMSO) δ1.09 (d, J=6.8, 3H), 4.95~5.01 (m, 1H), 5.95 (d, J=3.6, 1H), 6.53 (br s, 2H), 6.86 (br s, 2H), 7.32~7.42 (m, 2H), 7.44~7.47 (m, 2H).

Example 295

Synthesis of 1-(2-chlorophenyl)-(R)-1-carbamoyloxypropyl-(S)-2-carbamate

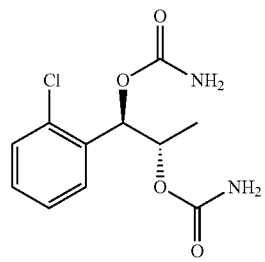 [SMILES: C[C@H](OC(N)=O)[C@H](OC(N)=O)c1ccccc1Cl]

$^1$H NMR (400 MHz, DMSO) δ1.09 (d, J=6.4, 3H), 4.95~5.01 (m, 1H), 5.95 (d, J=3.6, 1H), 6.47 (br s, 2H), 6.82 (br s, 2H), 7.32~7.41 (m, 2H), 7.44~7.47 (m, 2H).

Example 296

Measurement of Anti-epilepsy activity using MES (Maximal ElectroShock)

In the MES test (Ref., G. Villetti et al. Neuropharmacology 40 (2001) 866~878), An electrical stimulus (50 mA, 60 Hz, 0.2 s in Mice or Rats) supplied by 11A Shocker (IITC Life Science Company) was delivered through corneal electrodes. All mice (or rats) assigned to any electroshock at peak time were treated with test sample which was dissolved in 30% PEG400 prepared by saline solvent applied to oral before the test, If mice stretching their hind limb in a straight line wasn't observed in the MES test, This results were shown that the test sample had an anti-epilepsy activity. Three doses of test sample were administered orally (p.o.) to over 18 mice (3 mice per dose) for evaluating the respective doses at which 50% of the animals are protected from seizure ($ED_{50}$). The value of $ED_{50}$ is calculated by Litchfield and Wicoxon log-probit method which is a dose-response relationship. Then, the test results are shown as table 3.

[Statistical Analysis]

The obtained results are shown as mean±sem. The difference between the groups was statistically analyzed by ANOVA, and then, further examined by Dunnett's test or Bonferroni test. If p is less than 0.05, it was determined that the difference between the groups had statistical significance.

TABLE 3

Measurement results of anti-epilepsy activity of compounds in Mice

| Compound No. | MES test (p, o.) | |
|---|---|---|
| | $ED_{50}$ (mg/kg) | Peak Time (h) |
| 1 | 21.6 | 1 |
| 9 | 90[a] (100%) | — |
| 10 | 90[a] (100%) | — |
| 11 | 90[a] (100%) | — |
| 20 | 29.5 | 0.5 |
| 28 | 90[a] (33.3%) | — |
| 36 | 90[a] (100%) | — |
| 44 | 90[a] (100%) | — |
| 52 | 24.7 | 1 |
| 68 | 90[a] (100%) | — |
| 69 | 90[a] (66.6%) | — |
| 71 | 90[a] (100%) | — |
| 72 | 90[a] (100%) | — |
| 107 | 30[a] (33.3%) | — |
| 124 | 15.6 | 1 |
| 135 | 12.5 | 0.5 |
| 143 | 15.7 | 1 |
| 151 | 37 | 1 |
| 167 | 90[a] (33.3%) | — |
| 177 | 90[a] (66.6%) | — |
| 179 | 90[a] (33.3%) | — |
| 183 | 90[a] (100%) | — |
| 190 | 90[a] (66.6%) | — |
| 191 | 90[a] (100%) | — |
| 194 | 90[a] (100%) | — |
| 195 | 90[a] (100%) | — |
| 213 | 90[a] (33.3%) | — |
| 232 | 90[a] (33.3%) | — |
| 250 | 46.3 | 4 |
| 251 | 100[a] (33.3%) | — |
| 259 | 90[a] (66.6%) | — |
| 267 | 50[a] (16.6%) | — |
| 273 | 30[a] (33.3%) | — |
| 274 | 90[a] (100%) | — |
| 275 | 90[a] (100%) | — |
| 278 | 30[a] (33.3%) | — |
| 282 | 90[a] (33.3%) | — |
| 283 | 90[a] (100%) | — |
| 284 | 90[a] (33.3%) | — |
| 286 | 90[a] (33.3%) | — |
| 289 | 56.2 | 2 |
| 290 | 30[a] (33.3%) | — |
| 292 | 56[a] (33.3%) | — |
| 294 | 90[a] (66.6%) | — |
| 295 | 90[a] (100%) | — |

[a]Injection amount (mg/kg)
Protection % = the percentage of effect compared to the vehicle only.

Example 297

Lithium-Pilocarpine Induced Status Epilepticus Model

Prevention Study

Male Sprague-Dawley rats (purchased from Orient Bio Inc. Korea) of body weight 200~230 g were used for these studies and housed 4-5 rats per a cage for 4-5 days. On the day prior to status epilepsy (SE), rats received 127 mg/kg lithium chloride (Sigma, St. Louis, Mo., U.S.A.) intraperitoneally (i.p.). Approximately 18-20 h following this treatment, the rats were given 43 mg/kg pilocarpine (Sigma) intraperitoneally. An i.p. injection of 2 mg/kg methyl-scopolamine (Sigma) was administered 30 min prior to pilocarpine to block the effects of the muscarinic agonist on peripheral cholinergic receptors. The test drug was administered intraperitoneally (i.p.) in a volume of 2 ul/g body weight. Pharmacological effects of all the test materials were evaluated to compare the test groups (n=6) with a control group (n=6). Control group was administrated vehicle, only. The peak time was determined by administration test material's random dose for 0.5, 1, 2, 4 hour. The time that the most protect was defined peak time and ED50 was determined by other dose administration at peak time. The animals were then transferred to observation cages and observed continuously for 90 min. The seizure activity was elicited in approximately 95% of control group. Protection was defined as a complete absence of seizure grade 4~5 based on Racine scale (Racine, 1972) over the 90-min observation period. The effective dose of compound necessary to protect against seizures to 50% of controls (i.e. ED50) was determined by log probit analysis using SPSS software program (SPSS Inc.). The obtained results are shown in following Table 4.

Intervention Study

Male Sprague-Dawley rats (purchased from Orient Bio Inc. Korea) of body weight 200-230 g were used for these studies and housed 4-5 rats per a cage for 4-5 days. On the day prior to SE, rats received 127 mg/kg lithium chloride (Sigma, St. Louis, Mo., U.S.A.) intraperitoneally (i.p.). Approximately 18-20 h following this treatment, the rats were given 43 mg/kg pilocarpine (Sigma) intraperitoneally. An i.p. injection of 2 mg/kg methyl-scopolamine (Sigma) was administered 30 min prior to pilocarpine to block the effects of the muscarinic agonist on peripheral cholinergic receptors. The effects of compounds dissolved in 30% Poly Ethylene Glycol 400 (Acros Organics, Geel, Belgium) 20% Tween80 were studied at various times or 30 min after the occurrence of the first motor seizure or SE onset. The drug was administered intraperitoneally in a volume of 2 ul/g body weight. Pharmacological effects was evaluated to compare the test groups with a control group (n=8). Control group was administrated vehicle, only. The obtained results are shown in following Tables 5 (Reference; Racine R. J. (1972). Modification of seizure activity by electrical stimulation: II Motor seizure. Electroenceph. Clin. Neurophysiol. 32: 281-294.)

TABLE 4

Measurement results of Lithium-pilocarpine induced status epilepticus of compounds in the prevention test (Rats)

| | Therapeutic effect Prevention (rat, ip) | |
|---|---|---|
| Compound (Example) No. | ED50 (mg/kg) | Peak Time (h) |
| 1 | 26.6 | 0.5 |
| 20 | 25.9 | 1 |
| 28 | [a]50 (100%) | — |
| 52 | [a]20 (16.7%) | — |
| 135 | [a]20 (16.7%) | — |
| 143 | 19.6 | 1 |
| 151 | [a]60 (100%) | — |
| 250 | [a]60 (16.7%) | — |
| 289 | [a]80 (16.7%) | — |

[a]Injection amount (mg/kg),
Protection % = the percentage of prevention activity compared to the vehicle only, respectively.

TABLE 5

Measurement results of Lithium-pilocarpine induced status epilepticus of compounds in the intervention test (Rats)

| Compound (Example) No. | Intervention (rat, iv) [a]Dose (Protection %) |
|---|---|
| 1 | 46 (50%) |
| 9 | 46 (33.3%) |
| 10 | 46 (66.7%) |
| 11 | 46 (66.7%) |
| 20 | 46 (16.7%) |
| 28 | 46 (33.3%) |
| 52 | 46 (100%) |
| 68 | 46 (40%) |
| 71 | 46 (100%) |
| 72 | 46 (50%) |
| 135 | 46 (100%) |
| 143 | 23 (66.7%) |
| 151 | 46 (100%) |
| 183 | 46 (100%) |
| 191 | 46 (100%) |
| 194 | 46 (83.3%) |
| 195 | 46 (50%) |
| 274 | 46 (33.3%) |

[a]Injection amount (mg/kg),
% = the percentage of intervention activity compared to the vehicle only, respectively.

What is claimed is:

1. A method for treating an epilepsy or an epilepsy-related syndrome in a subject in need thereof comprising administering to the subject a pharmaceutically effective amount of a pharmaceutical composition comprising a compound represented by the following Chemical Formula I or a pharmaceutically acceptable salt thereof, as an active ingredient:

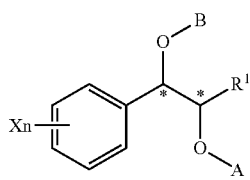

[Chemical Formula I]

wherein,

X is a halogen, n means the number of substituent X and is an integer from 1 to 5, wherein X is the same or different from each other, when n is 2 or larger, $R^1$ is a linear or branched $C_1$-$C_4$ alkyl group, A is selected from the group consisting of an allyl, a $C_1$-$C_{19}$ linear or branched alkyl group, a $C_2$-$C_8$ alkoxy alky ether group and a carbamoyl derivative represented by

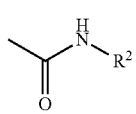

B is selected from the group consisting of an allyl, a $C_1$-$C_{19}$ linear or branched alkyl group, a $C_2$-$C_8$ alkoxy alky ether group and a carbamoyl derivative represented by and

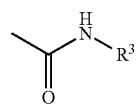

and $R^2$ and $R^3$ may be the same as or different from each other, and independently selected from the group consisting of hydrogen, a linear or branched alkyl group of $C_1$-$C_4$, a cycloalkyl group of $C_3$-$C_8$, and benzyl group.

2. The method according to claim 1, wherein A is a carbamoyl group, B is $C_1$-$C_{19}$ linear or branched alkyl group or a $C_2$-$C_8$ alkoxy alky ether group.

3. The method according to claim 1, wherein B is a carbamoyl group, A is $C_1$-$C_{19}$ linear or branched alkyl group or a $C_2$-$C_8$ alkoxy alky ether group.

4. The method according to claim 1, wherein the substituents of A and B are each a carbamoyl group at the same time.

5. The method according to claim 1, wherein the $C_2$-$C_8$ alkoxy alky ether group is methoxy methy(MOM), methoxyethoxymethyl(MEM), thertahydropyranyl(THP), benzyloxymethyl(BOM), methylthiomethyl(MTM), trimethylsilylethoxymethyl(SEM) or ethoxyethyl(EE) group.

6. The method according to claim 1, wherein the $C_1$-$C_{19}$ linear or branched alkyl group in the substituents A and B is a linear or branched $C_1$-$C_6$ lower aliphatic alkyl, a $C_3$-$C_{19}$ cycloaliphatic ring and a $C_6$-$C_{18}$ aromatic group which may be substituted with at least one selected from the group consisting of hydrogen, $C_1$-$C_6$ lower alkyl and $C_1$-$C_6$ alkoxy group.

7. The method according to claim 1, wherein X is chlorine, fluorine, iodine, or bromine; n is 1 or 2; and $R^2$ and $R^3$ are the same as or different from each other, and independently selected from the group consisting of hydrogen, methyl group, propyl group, isopropyl group, cyclopropyl group, cyclohexyl group, bicycloheptane group, and benzyl group.

8. The method according to claim 1, wherein the phenyl alkyl carbamate compound is selected from the group consisting of:

1-(2-chlorophenyl)-1-carbamoyloxypropyl-2-carbamate,
1-(2-chlorophenyl)-1-carbamoyloxypropyl-2-N-methyl-carbamate,
1-(2-chlorophenyl)-1-carbamoyloxypropyl 2-N-propyl-carbamate,
1-(2-chlorophenyl)-1-carbamoyloxybutyl-2-carbamate,
1-(2-chlorophenyl)-1-carbamoyloxy-3-methyl-butyl-2-carbamate,
1-(2-chlorophenyl)-1-carbamoyloxyhexyl-2-carbamate,
1-(2-iodophenyl)-1-carbamoyloxypropyl-2-carbamate,
1-(2-iodophenyl)-1-carbamoyloxybutyl-2-carbamate,
1-(2-iodophenyl)-1-carbamoyloxy-3-methyl-butyl-2-carbamate,
1-(2-iodophenyl)-1-carbamoyloxyhexyl-2-carbamate,
1-(2-fluorophenyl)-1-carbamoyloxypropyl-2-carbamate,
1-(2-fluorophenyl)-1-carbamoyloxybutyl-2-carbamate,
1-(2-fluorophenyl)-1-carbamoyloxy-3-methyl-butyl-2-carbamate,
1-(2-fluorophenyl)-1-carbamoyloxyhexyl-2-carbamate,
1-(2,4-dichlorophenyl)-1-carbamoyloxypropyl-2-carbamate,
1-(2,4-dichlorophenyl)-1-carbamoyloxybutyl-2-carbamate, 1-(2,4-dichlorophenyl)-1-carbamoyloxy-3-methyl-butyl-2-carbamate,
1-(2,4-dichlorophenyl)-1-carbamoyloxyhexyl-2-carbamate,
1-(2,6-dichlorophenyl)-1-carbamoyloxypropyl-2-carbamate,
1-(2,6-dichlorophenyl)-1-carbamoyloxybutyl-2-carbamate,
1-(2,6-dichlorophenyl)-1-carbamoyloxy-3-methyl-butyl-2-carbamate,
1-(2,6-dichlorophenyl)-1-carbamoyloxyhexyl-2-carbamate,
1-(2,4-difluorophenyl)-1-carbamoyloxypropyl 2-carbamate,
1-(2,5-difluorophenyl)-1-carbamoyloxypropyl 2-carbamate,
1-(2,6-difluorophenyl)-1-carbamoyloxypropyl 2-carbamate,
1-(2-chloro-6-fluorophenyl)-1-carbamoyloxypropyl 2-carbamate,
1-(2-iodophenyl)-1-(methoxy)-propyl-2-carbamate,
1-(2-iodophenyl)-1-(methoxy)-propyl-2-N-methylcarbamate,
1-(2-iodophenyl)-1-(methoxy)-propyl-2-N-propylcarbamate,
1-(2-iodophenyl)-1-(methoxy)-propyl-2-N-isopropylcarbamate,
1-(2-iodophenyl)-1-(methoxy)-propyl-2-N-cyclopropylcarbamate,
1-(2-iodophenyl)-1-(methoxy)-propyl-2-N-cyclohexylcarbamate,
1-(2-iodophenyl)-1-(methoxy)-propyl-2-N-benzylcarbamate,
1-(2-iodophenyl)-1-(methoxy)-propyl-2-N-bicyclo[2,2,1]heptanecarbamate,
1-(2-iodophenyl)-1-(methoxy)-butyl-2-carbamate,
1-(2-iodophenyl)-1-(methoxy)-butyl-2-N-methylcarbamate,
1-(2-iodophenyl)-1-(methoxy)-butyl-2-N-propylcarbamate,
1-(2-iodophenyl)-1-(methoxy)-butyl-2-N-isopropylcarbamate,
1-(2-iodophenyl)-1-(methoxy)-butyl-2-N-cyclopropylcarbamate,
1-(2-iodophenyl)-1-(methoxy)-butyl-2-N-cyclohexylcarbamate,
1-(2-iodophenyl)-1-(methoxy)-butyl-2-N-benzylcarbamate,
1-(2-iodophenyl)-1-(methoxy)-butyl-2-N-bicyclo[2,2,1]heptanecarbamate,
1-(2-iodophenyl)-1-(methoxy)-3-methyl-butyl-2-carbamate,
1-(2-iodophenyl)-1-(methoxy)-3-methyl-butyl-2-N-methylcarbamate,
1-(2-iodophenyl)-1-(methoxy)-3-methyl-butyl-2-N-propylcarbamate,
1-(2-iodophenyl)-1-(methoxy)-3-methyl-butyl-2-N-isopropylcarbamate,
1-(2-iodophenyl)-1-(methoxy)-3-methyl-butyl-2-N-cyclopropylcarbamate,
1-(2-iodophenyl)-1-(methoxy)-3-methyl-butyl-2-N-cyclohexylcarbamate,
1-(2-iodophenyl)-1-(methoxy)-3-methyl-butyl-2-N-benzylcarbamate,
1-(2-iodophenyl)-1-(methoxy)-3-methyl-butyl-2-N-bicyclo[2,2,1]heptanecarbamate,
1-(2-iodophenyl)-1-(methoxy)-hexyl-2-carbamate,
1-(2-iodophenyl)-1-(methoxy)-hexyl-2-N-methylcarbamate,
1-(2-iodophenyl)-1-(methoxy)-hexyl-2-N-propylcarbamate,
1-(2-iodophenyl)-1-(methoxy)-hexyl-2-N-isopropylcarbamate,
1-(2-iodophenyl)-1-(methoxy)-hexyl-2-N-cyclopropylcarbamate,
1-(2-iodophenyl)-1-(methoxy)-hexyl-2-N-cyclohexylcarbamate,
1-(2-iodophenyl)-1-(methoxy)-hexyl-2-N-benzylcarbamate,
1-(2-iodophenyl)-1-(methoxy)-hexyl-2-N-bicyclo[2,2,1]heptanecarbamate,
1-(3-iodophenyl)-1-(methoxy)-propyl-2-carbamate,
1-(3-iodophenyl)-1-(methoxy)-butyl-2-carbamate,
1-(3-iodophenyl)-1-(methoxy)-3-methyl-butyl-2-carbamate,
1-(3-iodophenyl)-1-(methoxy)-hexyl-2-carbamate,
1-(2-fluorophenyl)-1-(methoxy)-propyl-2-carbamate,
1-(2-fluorophenyl)-1-(methoxy)-propyl-2-N-methylcarbamate,
1-(2-fluorophenyl)-1-(methoxy)-propyl-2-N-propylcarbamate,
1-(2-fluorophenyl)-1-(methoxy)-propyl-2-N-isopropylcarbamate,
1-(2-fluorophenyl)-1-(methoxy)-propyl-2-N-cyclopropylcarbamate,
1-(2-fluorophenyl)-1-(methoxy)-propyl-2-N-cyclohexylcarbamate,
1-(2-fluorophenyl)-1-(methoxy)-propyl-2-N-benzylcarbamate,
1-(2-fluorophenyl)-1-(methoxy)-propyl-2-N-bicyclo[2,2,1]heptanecarbamate,
1-(2-fluorophenyl)-1-(methoxy)-butyl-2-carbamate,
1-(2-fluorophenyl)-1-(methoxy)-3-methyl-butyl-2-carbamate,
1-(2-fluorophenyl)-1-(methoxy)-hexyl-2-carbamate,
1-(4-fluorophenyl)-1-(methoxy)-proyl-2-carbamate,
1-(4-fluorophenyl)-1-(methoxy)-butyl-2-carbamate,
1-(4-fluorophenyl)-1-(methoxy)-3-methyl-butyl-2-carbamate,
1-(4-fluorophenyl)-1-(methoxy)-hexyl-2-carbamate,
1-(2-chlorophenyl)-1-(methoxy)-propyl-2-carbamate,
1-(2-chlorophenyl)-1-(methoxy)-propyl-2-N-methylcarbamate,
1-(2-chlorophenyl)-1-(methoxy)-propyl-2-N-propylcarbamate,
1-(2-chlorophenyl)-1-(methoxy)-propyl-2-N-isopropylcarbamate,
1-(2-chlorophenyl)-1-(methoxy)-propyl-2-N-cyclopropylcarbamate,
1-(2-chlorophenyl)-1-(methoxy)-propyl-2-N-cyclohexylcarbamate,
1-(2-chlorophenyl)-1-(methoxy)-propyl-2-N-benzylcarbamate,
1-(2-chlorophenyl)-1-(methoxy)-propyl-2-N-bicyclo[2,2,1]heptanecarbamate,
1-(2-chlorophenyl)-1-(methoxy)-butyl-2-carbamate,
1-(2-chlorophenyl)-1-(methoxy)-3-methyl-butyl-2-carbamate,
1-(2-chlorophenyl)-1-(methoxy)-hexyl-2-carbamate,
1-(2,3-dichlorophenyl)-1-(methoxy)-propyl-2-carbamate,
1-(2,4-dichlorophenyl)-1-(methoxy)-propyl-2-carbamate,
1-(2,4-dichlorophenyl)-1-(methoxy)-butyl-2-carbamate,
1-(2,4-dichlorophenyl)-1-(methoxy)-3-methyl-butyl-2-carbamate, 1-(2,4-dichlorophenyl)-1-(methoxy)-hexyl-2-carbamate,
1-(2,6-dichlorophenyl)-1-(methoxy)-propyl-2-carbamate,
1-(2,6-dichlorophenyl)-1-(methoxy)-butyl-2-carbamate,
1-(2,6-dichlorophenyl)-1-(methoxy)-3-methyl-butyl-2-carbamate,
1-(2,6-dichlorophenyl)-1-(methoxy)-hexyl-2-carbamate,
1-(2-chlorophenyl)-1-(methoxymethoxy)-propyl-2-carbamate,
1-(2-chlorophenyl)-1-(methoxymethoxy)-propyl-2-N-methylcarbamate,
1-(2-chlorophenyl)-1-(methoxymethoxy)-propyl-2-N-propylcarbamate,
1-(2-chlorophenyl)-1-(methoxymethoxy)-propyl-2-N-isopropylcarbamate,
1-(2-chlorophenyl)-1-(methoxymethoxy)-propyl-2-N-cyclopropylcarbamate,
1-(2-chlorophenyl)-1-(methoxymethoxy)-propyl-2-N-cyclohexylcarbamate,
1-(2-chlorophenyl)-1-(methoxymethoxy)-propyl-2-N-benzylcarbamate,
1-(2-chlorophenyl)-1-(methoxymethoxy)-propyl-2-N-bicyclo[2,2,1]heptanecarbamate,
1-(2-chlorophenyl)-1-(methoxymethoxy)-butyl-2-carbamate,
1-(2-chlorophenyl)-1-(methoxymethoxy)-3-methyl-butyl-2-carbamate,
1-(2-chlorophenyl)-1-(methoxymethoxy)-hexyl-2-carbamate,
1-(2,3-dichlorophenyl)-1-(methoxymethoxy)-propyl-2-carbamate,
1-(2,4-dichlorophenyl)-1-(methoxymethoxy)-propyl-2-carbamate,
1-(2,4-dichlorophenyl)-1-(methoxymethoxy)-butyl-2-carbamate,
1-(2,4-dichlorophenyl)-1-(methoxymethoxy)-3-methyl-butyl-2-carbamate,
1-(2,4-dichlorophenyl)-1-(methoxymethoxy)-hexyl-2-carbamate,
1-(2,5-dichlorophenyl)-1-(methoxymethoxy)-propyl-2-carbamate,
1-(2,6-dichlorophenyl)-1-(methoxymethoxy)-propyl-2-carbamate,
1-(2,6-dichlorophenyl)-1-(methoxymethoxy)-butyl-2-carbamate,
1-(2,6-dichlorophenyl)-1-(methoxymethoxy)-3-methyl-butyl-2-carbamate,
1-(2,6-dichlorophenyl)-1-(methoxymethoxy)-hexyl-2-carbamate,
1-(2-fluorophenyl)-1-(methoxymethoxy)-propyl-2-carbamate,
1-(2-fluorophenyl)-1-(methoxymethoxy)-propyl-2-N-methylcarbamate,
1-(2-fluorophenyl)-1-(methoxymethoxy)-propyl-2-N-propylcarbamate,
1-(2-fluorophenyl)-1-(methoxymethoxy)-propyl-2-N-isopropylcarbamate,
1-(2-fluorophenyl)-1-(methoxymethoxy)-propyl-2-N-cyclopropylcarbamate,
1-(2-fluorophenyl)-1-(methoxymethoxy)-propyl-2-N-cyclohexylcarbamate,
1-(2-fluorophenyl)-1-(methoxymethoxy)-propyl-2-N-benzylcarbamate,
1-(2-fluorophenyl)-1-(methoxymethoxy)-propyl-2-N-bicyclo[2,2,1]heptanecarbamate,
1-(2-fluorophenyl)-1-(methoxymethoxy)-butyl-2-carbamate,
1-(2-fluorophenyl)-1-(methoxymethoxy)-3-methyl-butyl-2-carbamate,
1-(2-fluorophenyl)-1-(methoxymethoxy)-hexyl-2-carbamate,
1-(4-fluorophenyl)-1-(methoxymethoxy)-propyl-2-carbamate,
1-(4-fluorophenyl)-1-(methoxymethoxy)-butyl-2-carbamate,
1-(4-fluorophenyl)-1-(methoxymethoxy)-3-methyl-butyl-2-carbamate,
1-(4-fluorophenyl)-1-(methoxymethoxy)-hexyl-2-carbamate,
1-(2,6-difluorophenyl)-1-(methoxymethoxy)-propyl-2-carbamate,
1-(2-iodophenyl)-1-(methoxymethoxy)-propyl-2-carbamate,
1-(2-iodophenyl)-1-(methoxymethoxy)-propyl-2-N-methylcarbamate,
1-(2-iodophenyl)-1-(methoxymethoxy)-propyl-2-N-propylcarbamate,
1-(2-iodophenyl)-1-(methoxymethoxy)-propyl-2-N-isopropylcarbamate,
1-(2-iodophenyl)-1-(methoxymethoxy)-propyl-2-N-cyclopropylcarbamate,
1-(2-iodophenyl)-1-(methoxymethoxy)-propyl-2-N-cyclohexylcarbamate,
1-(2-iodophenyl)-1-(methoxymethoxy)-propyl-2-N-benzylcarbamate,
1-(2-iodophenyl)-1-(methoxymethoxy)-propyl-2-N-bicyclo[2,2,1]heptanecarbamate,
1-(2-iodophenyl)-1-(methoxymethoxy)-butyl-2-carbamate,
1-(2-iodophenyl)-1-(methoxymethoxy)-butyl-2-N-methylcarbamate,
1-(2-iodophenyl)-1-(methoxymethoxy)-butyl-2-N-propylcarbamate,
1-(2-iodophenyl)-1-(methoxymethoxy)-butyl-2-N-isopropylcarbamate,
1-(2-iodophenyl)-1-(methoxymethoxy)-butyl-2-N-cyclopropylcarbamate,
1-(2-iodophenyl)-1-(methoxymethoxy)-butyl-2-N-cyclohexylcarbamate,
1-(2-iodophenyl)-1-(methoxymethoxy)-butyl-2-N-benzylcarbamate,
1-(2-iodophenyl)-1-(methoxymethoxy)-butyl-2-N-bicyclo[2,2,1]heptanecarbamate,
1-(2-iodophenyl)-1-(methoxymethoxy)-3-methyl-butyl-2-carbamate,
1-(2-iodophenyl)-1-(methoxymethoxy)-3-methyl-butyl-2-N-methylcarbamate,
1-(2-iodophenyl)-1-(methoxymethoxy)-3-methyl-butyl-2-N-propylcarbamate,
1-(2-iodophenyl)-1-(methoxymethoxy)-3-methyl-butyl-2-N-isopropylcarbamate,
1-(2-iodophenyl)-1-(methoxymethoxy)-3-methyl-butyl-2-N-cyclopropylcarbamate,
1-(2-iodophenyl)-1-(methoxymethoxy)-3-methyl-butyl-2-N-cyclohexylcarbamate,
1-(2-iodophenyl)-1-(methoxymethoxy)-3-methyl-butyl-2-N-benzylcarbamate,
1-(2-iodophenyl)-1-(methoxymethoxy)-3-methyl-butyl-2-N-bicyclo[2,2,1]heptanecarbamate,
1-(2-iodophenyl)-1-(methoxymethoxy)-hexyl-2-carbamate,
1-(2-iodophenyl)-1-(methoxymethoxy)-hexyl-2-N-methylcarbamate, 1-(2-iodophenyl)-1-(methoxymethoxy)-hexyl-2-N-propylcarbamate,
1-(2-iodophenyl)-1-(methoxymethoxy)-hexyl-2-N-isopropylcarbamate,
1-(2-iodophenyl)-1-(methoxymethoxy)-hexyl-2-N-cyclopropylcarbamate,
1-(2-iodophenyl)-1-(methoxymethoxy)-hexyl-2-N-cyclohexylcarbamate,
1-(2-iodophenyl)-1-(methoxymethoxy)-hexyl-2-N-benzylcarbamate,
1-(2-iodophenyl)-1-(methoxymethoxy)-hexyl-2-N-bicyclo[2,2,1]heptanecarbamate,
1-(3-iodophenyl)-1-(methoxymethoxy)-propyl-2-carbamate,
1-(3-iodophenyl)-1-(methoxymethoxy)-butyl-2-carbamate,
1-(3-iodophenyl)-1-(methoxymethoxy)-3-methyl-butyl-2-carbamate,
1-(3-iodophenyl)-1-(methoxymethoxy)-hexyl-2-carbamate,
1-(2-chlorophenyl)-2-(methoxymethoxy)-propyl-1-carbamate,
1-(2-chlorophenyl)-2-(methoxy)-propyl-1-carbamate,
1-(2-fluorophenyl)-2-(methoxymethoxy)-propyl-1-carbamate,
1-(2-fluorophenyl)-2-(methoxy)-propyl 1-carbamate,
1-(2-iodophenyl)-2-(methoxymethoxy)-propyl-1-carbamate, and
1-(2-iodophenyl)-2-(methoxy)-propyl-1-carbamate.

9. The method according to claim 1, wherein the compound is in the form of racemate, enantiomer, diastereomer, a mixture of enantiomer, or a mixture of diastereomer.

10. The method according to claim 9, wherein the compound is selected from the group consisting of:
1-(2-chlorophenyl)-(S)-1-carbamoyloxypropyl-(S)-2-carbamate,
1-(2-chlorophenyl)-(S)-1-carbamoyloxypropyl-(S)-2-N-methylcarbamate,
1-(2-chlorophenyl)-(S)-1-carbamoyloxypropyl-(S)-2-N-propylcarbamate,
1-(2-chlorophenyl)-(S)-1-carbamoyloxybutyl-(S)-2-carbamate,
1-(2-chlorophenyl)-(S)-1-carbamoyloxy-3-methyl-butyl-(S)-2-carbamate,
1-(2-chlorophenyl)-(S)-1-carbamoyloxyhexyl-(S)-2-carbamate,
1-(2-iodophenyl)-(S)-1-carbamoyloxypropyl-(S)-2-carbamate,
1-(2-iodophenyl)-(S)-1-carbamoyloxybutyl-(S)-2-carbamate,
1-(2-iodophenyl)-(S)-1-carbamoyloxy-3-methyl-butyl-(S)-2-carbamate,
1-(2-iodophenyl)-(S)-1-carbamoyloxyhexyl-(S)-2-carbamate,
1-(2-fluorophenyl)-(S)-1-carbamoyloxypropyl-(S)-2-carbamate,
1-(2-fluorophenyl)-(S)-1-carbamoyloxybutyl-(S)-2-carbamate,
1-(2-fluorophenyl)-(S)-1-carbamoyloxy-3-methyl-butyl-(S)-2-carbamate,
1-(2-fluorophenyl)-(S)-1-carbamoyloxyhexyl-(S)-2-carbamate,
1-(2,4-dichlorophenyl)-(S)-1-carbamoyloxypropyl-(S)-2-carbamate,
1-(2,4-dichlorophenyl)-(S)-1-carbamoyloxybutyl-(S)-2-carbamate,
1-(2,4-dichlorophenyl)-(S)-1-carbamoyloxy-3-methyl-butyl-2-carbamate,
1-(2,4-dichlorophenyl)-(S)-1-carbamoyloxyhexyl-(S)-2-carbamate,
1-(2,6-dichlorophenyl)-(S)-1-carbamoyloxypropyl-(S)-2-carbamate,
1-(2,6-dichlorophenyl)-(S)-1-carbamoyloxybutyl-(S)-2-carbamate,
1-(2,6-dichlorophenyl)-(S)-1-carbamoyloxy-3-methyl-butyl-(S)-2-carbamate,
1-(2,6-dichlorophenyl)-(S)-1-carbamoyloxyhexyl-(S)-2-carbamate,
1-(2-chloro-6-fluorophenyl)-(S)-1-carbamoyloxypropyl-(S) 2-carbamate,
1-(2-iodophenyl)-(S)-1-(methoxy)-propyl-(S)-2-carbamate,
1-(2-iodophenyl)-(S)-1-(methoxy)-propyl-(S)-2-N-methylcarbamate,
1-(2-iodophenyl)-(S)-1-(methoxy)-propyl-(S)-2-N-propylcarbamate,
1-(2-iodophenyl)-(S)-1-(methoxy)-propyl-(S)-2-N-isopropylcarbamate,
1-(2-iodophenyl)-(S)-1-(methoxy)-propyl-(S)-2-N-cyclopropylcarbamate,
1-(2-iodophenyl)-(S)-1-(methoxy)-propyl-(S)-2-N-cyclohexylcarbamate,
1-(2-iodophenyl)-(S)-1-(methoxy)-propyl-(S)-2-N-benzylcarbamate,
1-(2-iodophenyl)-(S)-1-(methoxy)-propyl-(S)-2-N-bicyclo[2,2,1]heptanecarbamate,
1-(2-iodophenyl)-(S)-1-(methoxy)-butyl-(S)-2-carbamate,
1-(2-iodophenyl)-(S)-1-(methoxy)-butyl-(S)-2-N-methylcarbamate,
1-(2-iodophenyl)-(S)-1-(methoxy)-butyl-(S)-2-N-propylcarbamate,
1-(2-iodophenyl)-(S)-1-(methoxy)-butyl-(S)-2-N-isopropylcarbamate,
1-(2-iodophenyl)-(S)-1-(methoxy)-butyl-(S)-2-N-cyclopropylcarbamate,
1-(2-iodophenyl)-(S)-1-(methoxy)-butyl-(S)-2-N-cyclohexylcarbamate,
1-(2-iodophenyl)-(S)-1-(methoxy)-butyl-(S)-2-N-benzylcarbamate,
1-(2-iodophenyl)-(S)-1-(methoxy)-butyl-(S)-2-N-bicyclo[2,2,1]heptanecarbamate,
1-(2-iodophenyl)-(S)-1-(methoxy)-3-methyl-butyl-(S)-2-carbamate,
1-(2-iodophenyl)-(S)-1-(methoxy)-3-methyl-butyl-(S)-2-N-methylcarbamate,
1-(2-iodophenyl)-(S)-1-(methoxy)-3-methyl-butyl-(S)-2-N-propylcarbamate,
1-(2-iodophenyl)-(S)-1-(methoxy)-3-methyl-butyl-(S)-2-N-isopropylcarbamate,
1-(2-iodophenyl)-(S)-1-(methoxy)-3-methyl-butyl-(S)-2-N-cyclopropylcarbamate,
1-(2-iodophenyl)-(S)-1-(methoxy)-3-methyl-butyl-(S)-2-N-cyclohexylcarbamate,
1-(2-iodophenyl)-(S)-1-(methoxy)-3-methyl-butyl-(S)-2-N-benzylcarbamate,
1-(2-iodophenyl)-(S)-1-(methoxy)-3-methyl-butyl-(S)-2-N-bicyclo[2,2,1]heptanecarbamate,
1-(2-iodophenyl)-(S)-1-(methoxy)-hexyl-(S)-2-carbamate,
1-(2-iodophenyl)-(S)-1-(methoxy)-hexyl-(S)-2-N-methylcarbamate, 1-(2-iodophenyl)-(S)-1-(methoxy)-hexyl-(S)-2-N-propylcarbamate,
1-(2-iodophenyl)-(S)-1-(methoxy)-hexyl-(S)-2-N-isopropylcarbamate,
1-(2-iodophenyl)-(S)-1-(methoxy)-hexyl-(S)-2-N-cyclopropylcarbamate,
1-(2-iodophenyl)-(S)-1-(methoxy)-hexyl-(S)-2-N-cyclohexylcarbamate,
1-(2-iodophenyl)-(S)-1-(methoxy)-hexyl-(S)-2-N-benzylcarbamate,
1-(2-iodophenyl)-(S)-1-(methoxy)-hexyl-(S)-2-N-bicyclo[2,2,1]heptanecarbamate,
1-(3-iodophenyl)-(S)-1-(methoxy)-propyl-(S)-2-carbamate,
1-(3-iodophenyl)-(S)-1-(methoxy)-butyl-(S)-2-carbamate,
1-(3-iodophenyl)-(S)-1-(methoxy)-3-methyl-butyl-(S)-2-carbamate,
1-(3-iodophenyl)-(S)-1-(methoxy)-hexyl-(S)-2-carbamate,
1-(2-fluorophenyl)-(S)-1-(methoxy)-propyl-(S)-2-carbamate,
1-(2-fluorophenyl)-(S)-1-(methoxy)-propyl-(S)-2-N-methylcarbamate,
1-(2-fluorophenyl)-(S)-1-(methoxy)-propyl-(S)-2-N-propylcarbamate,
1-(2-fluorophenyl)-(S)-1-(methoxy)-propyl-(S)-2-N-isopropylcarbamate,
1-(2-fluorophenyl)-(S)-1-(methoxy)-propyl-(S)-2-N-cyclopropylcarbamate,
1-(2-fluorophenyl)-(S)-1-(methoxy)-propyl-(S)-2-N-cyclohexylcarbamate,
1-(2-fluorophenyl)-(S)-1-(methoxy)-propyl-(S)-2-N-benzylcarbamate,
1-(2-fluorophenyl)-(S)-1-(methoxy)-propyl-(S)-2-N-bicyclo[2,2,1]heptanecarbamate,
1-(4-fluorophenyl)-(S)-1-(methoxy)-proyl-(S)-2-carbamate,
1-(4-fluorophenyl)-(S)-1-(methoxy)-butyl-(S)-2-carbamate,
1-(4-fluorophenyl)-(S)-1-(methoxy)-3-methyl-butyl-(S)-2-carbamate,
1-(4-fluorophenyl)-(S)-1-(methoxy)-hexyl-(S)-2-carbamate,
1-(2-chlorophenyl)-(S)-1-(methoxy)-propyl-(S)-2-carbamate,
1-(2-chlorophenyl)-(S)-1-(methoxy)-propyl-(S)-2-N-methylcarbamate,
1-(2-chlorophenyl)-(S)-1-(methoxy)-propyl-(S)-2-N-propylcarbamate,
1-(2-chlorophenyl)-(S)-1-(methoxy)-propyl-(S)-2-N-isopropylcarbamate,
1-(2-chlorophenyl)-(S)-1-(methoxy)-propyl-(S)-2-N-cyclopropylcarbamate,
1-(2-chlorophenyl)-(S)-1-(methoxy)-propyl-(S)-2-N-cyclohexylcarbamate,
1-(2-chlorophenyl)-(S)-1-(methoxy)-propyl-(S)-2-N-benzylcarbamate,
1-(2-chlorophenyl)-(S)-1-(methoxy)-propyl-(S)-2-N-bicyclo[2,2,1]heptanecarbamate,
1-(2-chlorophenyl)-(S)-1-(methoxy)-butyl-(S)-2-carbamate,
1-(2-chlorophenyl)-(S)-1-(methoxy)-3-methyl-butyl-(S)-2-carbamate,
1-(2-chlorophenyl)-(S)-1-(methoxy)-hexyl-(S)-2-carbamate,
1-(2,3-dichlorophenyl)-(S)-1-(methoxy)-propyl-(S)-2-carbamate,
1-(2,4-dichlorophenyl)-(S)-1-(methoxy)-propyl-(S)-2-carbamate,
1-(2,4-dichlorophenyl)-(S)-1-(methoxy)-butyl-(S)-2-carbamate,
1-(2,4-dichlorophenyl)-(S)-1-(methoxy)-3-methyl-butyl-(S)-2-carbamate,
1-(2,4-dichlorophenyl)-(S)-1-(methoxy)-hexyl-(S)-2-carbamate,
1-(2,6-dichlorophenyl)-(S)-1-(methoxy)-propyl-(S)-2-carbamate,
1-(2,6-dichlorophenyl)-(S)-1-(methoxy)-butyl-(S)-2-carbamate,
1-(2,6-dichlorophenyl)-(S)-1-(methoxy)-3-methyl-butyl-(S)-2-carbamate,
1-(2,6-dichlorophenyl)-(S)-1-(methoxy)-hexyl-(S)-2-carbamate,
1-(2-chlorophenyl)-(S)-1-(methoxymethoxy)-propyl-(S)-2-carbamate,
1-(2-chlorophenyl)-(S)-1-(methoxymethoxy)-propyl-(S)-2-N-methylcarbamate,
1-(2-chlorophenyl)-(S)-1-(methoxymethoxy)-propyl-(S)-2-N-propylcarbamate,
1-(2-chlorophenyl)-(S)-1-(methoxymethoxy)-propyl-(S)-2-N-isopropylcarbamate,
1-(2-chlorophenyl)-(S)-1-(methoxymethoxy)-propyl-(S)-2-N-cyclopropylcarbamate,
1-(2-chlorophenyl)-(S)-1-(methoxymethoxy)-propyl-(S)-2-N-cyclohexylcarbamate,
1-(2-chlorophenyl)-(S)-1-(methoxymethoxy)-propyl-2-N-benzylcarbamate,
1-(2-chlorophenyl)-(S)-1-(methoxymethoxy)-propyl-2-N-bicyclo[2,2,1]heptanecarbamate,
1-(2-chlorophenyl)-(S)-1-(methoxymethoxy)-butyl-(S)-2-carbamate,
1-(2-chlorophenyl)-(S)-1-(methoxymethoxy)-3-methyl-butyl-(S)-2-carbamate,
1-(2-chlorophenyl)-(S)-1-(methoxymethoxy)-hexyl-(S)-2-carbamate,
1-(2,3-dichlorophenyl)-(S)-1-(methoxymethoxy)-propyl-(S)-2-carbamate,
1-(2,4-dichlorophenyl)-(S)-1-(methoxymethoxy)-propyl-(S)-2-carbamate,
1-(2,4-dichlorophenyl)-(S)-1-(methoxymethoxy)-butyl-(S)-2-carbamate,
1-(2,4-dichlorophenyl)-(S)-1-(methoxymethoxy)-3-methyl-butyl-(S)-2-carbamate,
1-(2,4-dichlorophenyl)-(S)-1-(methoxymethoxy)-hexyl-(S)-2-carbamate,
1-(2,5-dichlorophenyl)-(S)-1-(methoxymethoxy)-propyl-(S)-2-carbamate,
1-(2,6-dichlorophenyl)-(S)-1-(methoxymethoxy)-propyl-(S)-2-carbamate,
1-(2,6-dichlorophenyl)-(S)-1-(methoxymethoxy)-butyl-(S)-2-carbamate,
1-(2,6-dichlorophenyl)-(S)-1-(methoxymethoxy)-3-methyl-butyl-(S)-2-carbamate,
1-(2,6-dichlorophenyl)-(S)-1-(methoxymethoxy)-hexyl-(S)-2-carbamate,
1-(2-fluorophenyl)-(S)-1-(methoxymethoxy)-propyl-(S)-2-carbamate,
1-(2-fluorophenyl)-(S)-1-(methoxymethoxy)-propyl-(S)-2-N-methylcarbamate,
1-(2-fluorophenyl)-(S)-1-(methoxymethoxy)-propyl-(S)-2-N-propylcarbamate, 1-(2-fluorophenyl)-(S)-1-(methoxymethoxy)-propyl-(S)-2-N-isopropylcarbamate,
1-(2-fluorophenyl)-(S)-1-(methoxymethoxy)-propyl-(S)-2-N-cyclopropylcarbamate,
1-(2-fluorophenyl)-(S)-1-(methoxymethoxy)-propyl-(S)-2-N-cyclohexylcarbamate,
1-(2-fluorophenyl)-(S)-1-(methoxymethoxy)-propyl-(S)-2-N-benzylcarbamate,
1-(2-fluorophenyl)-(S)-1-(methoxymethoxy)-propyl-(S)-2-N-bicyclo[2,2,1]heptanecarbamate,
1-(2-fluorophenyl)-(S)-1-(methoxymethoxy)-butyl-(S)-2-carbamate,
1-(2-fluorophenyl)-(S)-1-(methoxymethoxy)-3-methyl-butyl-(S)-2-carbamate,
1-(2-fluorophenyl)-(S)-1-(methoxymethoxy)-hexyl-(S)-2-carbamate,
1-(4-fluorophenyl)-(S)-1-(methoxymethoxy)-propyl-(S)-2-carbamate,
1-(4-fluorophenyl)-(S)-1-(methoxymethoxy)-butyl-(S)-2-carbamate,
1-(4-fluorophenyl)-(S)-1-(methoxymethoxy)-3-methyl-butyl-(S)-2-carbamate,
1-(4-fluorophenyl)-(S)-1-(methoxymethoxy)-hexyl-(S)-2-carbamate,
1-(2,6-difluorophenyl)-(S)-1-(methoxymethoxy)-propyl-(S)-2-carbamate,
1-(2-iodophenyl)-(S)-1-(methoxymethoxy)-propyl-(S)-2-carbamate,
1-(2-iodophenyl)-(S)-1-(methoxymethoxy)-propyl-(S)-2-N-methylcarbamate,
1-(2-iodophenyl)-(S)-1-(methoxymethoxy)-propyl-(S)-2-N-propylcarbamate,
1-(2-iodophenyl)-(S)-1-(methoxymethoxy)-propyl-(S)-2-N-isopropylcarbamate,
1-(2-iodophenyl)-(S)-1-(methoxymethoxy)-propyl-(S)-2-N-cyclopropylcarbamate,
1-(2-iodophenyl)-(S)-1-(methoxymethoxy)-propyl-(S)-2-N-cyclohexylcarbamate,
1-(2-iodophenyl)-(S)-1-(methoxymethoxy)-propyl-(S)-2-N-benzylcarbamate,
1-(2-iodophenyl)-(S)-1-(methoxymethoxy)-propyl-2-N-bicyclo[2,2,1]heptanecarbamate,
1-(2-iodophenyl)-(S)-1-(methoxymethoxy)-butyl-(S)-2-carbamate,
1-(2-iodophenyl)-(S)-1-(methoxymethoxy)-butyl-(S)-2-N-methylcarbamate,
1-(2-iodophenyl)-(S)-1-(methoxymethoxy)-butyl-(S)-2-N-propylcarbamate,
1-(2-iodophenyl)-(S)-1-(methoxymethoxy)-butyl-(S)-2-N-isopropylcarbamate,
1-(2-iodophenyl)-(S)-1-(methoxymethoxy)-butyl-(S)-2-N-cyclopropylcarbamate,
1-(2-iodophenyl)-(S)-1-(methoxymethoxy)-butyl-(S)-2-N-cyclohexylcarbamate,
1-(2-iodophenyl)-(S)-1-(methoxymethoxy)-butyl-(S)-2-N-benzylcarbamate,
1-(2-iodophenyl)-(S)-1-(methoxymethoxy)-butyl-(S)-2-N-bicyclo[2,2,1]heptanecarbamate,
1-(2-iodophenyl)-(S)-1-(methoxymethoxy)-3-methyl-butyl-(S)-2-carbamate,
1-(2-iodophenyl)-(S)-1-(methoxymethoxy)-3-methyl-butyl-(S)-2-N-methylcarbamate,
1-(2-iodophenyl)-(S)-1-(methoxymethoxy)-3-methyl-butyl-(S)-2-N-propylcarbamate,
1-(2-iodophenyl)-(S)-1-(methoxymethoxy)-3-methyl-butyl-(S)-2-N-isopropylcarbamate,
1-(2-iodophenyl)-(S)-1-(methoxymethoxy)-3-methyl-butyl-(S)-2-N-cyclopropylcarbamate,
1-(2-iodophenyl)-(S)-1-(methoxymethoxy)-3-methyl-butyl-(S)-2-N-cyclohexylcarbamate,
1-(2-iodophenyl)-(S)-1-(methoxymethoxy)-3-methyl-butyl-(S)-2-N-benzylcarbamate,
1-(2-iodophenyl)-(S)-1-(methoxymethoxy)-3-methyl-butyl-(S)-2-N-bicyclo[2,2,1]heptanecarbamate,
1-(2-iodophenyl)-(S)-1-(methoxymethoxy)-hexyl-2-carbamate,
1-(2-iodophenyl)-(S)-1-(methoxymethoxy)-hexyl-(S)-2-N-methylcarbamate,
1-(2-iodophenyl)-(S)-1-(methoxymethoxy)-hexyl-(S)-2-N-propylcarbamate,
1-(2-iodophenyl)-(S)-1-(methoxymethoxy)-hexyl-(S)-2-N-isopropylcarbamate,
1-(2-iodophenyl)-(S)-1-(methoxymethoxy)-hexyl-(S)-2-N-cyclopropylcarbamate,
1-(2-iodophenyl)-(S)-1-(methoxymethoxy)-hexyl-(S)-2-N-cyclohexylcarbamate,
1-(2-iodophenyl)-(S)-1-(methoxymethoxy)-hexyl-(S)-2-N-benzylcarbamate,
1-(2-iodophenyl)-(S)-1-(methoxymethoxy)-hexyl-(S)-2-N-bicyclo[2,2,1]heptanecarbamate,
1-(3-iodophenyl)-(S)-1-(methoxymethoxy)-propyl-(S)-2-carbamate,
1-(3-iodophenyl)-(S)-1-(methoxymethoxy)-butyl-(S)-2-carbamate,
1-(3-iodophenyl)-(S)-1-(methoxymethoxy)-3-methyl-butyl-(S)-2-carbamate,
1-(3-iodophenyl)-(S)-1-(methoxymethoxy)-hexyl-(S)-2-carbamate,
1-(2-chlorophenyl)-(S)-2-(methoxymethoxy)-propyl-(S)-1-carbamate,
1-(2-chlorophenyl)-(S)-2-(methoxy)-propyl-(S)-1-carbamate,
1-(2-fluorophenyl)-(S)-2-(methoxymethoxy)-propyl-(S)-1-carbamate,
1-(2-fluorophenyl)-(S)-2-(methoxy)-propyl-(S) 1-carbamate,
1-(2-iodophenyl)-(S)-2-(methoxymethoxy)-propyl-(S)-1-carbamate,
1-(2-iodophenyl)-(S)-2-(methoxy)-propyl-(S) 1 carbamate,
1-(2-chlorophenyl)-(R)-1-carbamoyloxypropyl-(R)-2-carbamate,
1-(2-iodophenyl)-(R)-1-carbamoyloxypropyl-(R)-2-carbamate,
1-(2-fluorophenyl)-(R)-1-carbamoyloxypropyl-(R)-2-carbamate,
1-(2,4-dichlorophenyl)-(R)-1-carbamoyloxypropyl-(R)-2-carbamate,
1-(2,6-dichlorophenyl)-(R)-1-carbamoyloxypropyl-(R)-2-carbamate,
1-(2,4-difluorophenyl)-(R)-1-carbamoyloxypropyl(R) 2-carbamate,
1-(2,5-difluorophenyl)-(R)-1-carbamoyloxypropyl-(R) 2-carbamate,
1-(2,6-difluorophenyl)-(R)-1-carbamoyloxypropyl-(R) 2 carbamate,
1-(2-chloro-6-fluorophenyl)-(R)-1-carbamoyloxypropyl-(R) 2-carbamate,
1-(2-iodophenyl)-(R)-1-(methoxy)-propyl-(R)-2-carbamate,
1-(2-iodophenyl)-(R)-1-(methoxy)-butyl(R)-2-carbamate, 1-(2-iodophenyl)-(R)-1-(methoxy)3-methyl-butyl-(R)-2-carbamate,
1-(2-iodophenyl)-(R)-1-(methoxy)-hexyl-(R)-2-carbamate,
1-(3-iodophenyl)-(R)-1-(methoxy)-propyl-(R)-2-carbamate,
1-(3-iodophenyl)-(R)-1-(methoxy)-butyl-(R)-2-carbamate,
1-(3-iodophenyl)-(R)-1-(methoxy)3-methyl-butyl-(R)-2-carbamate,
1-(3-iodophenyl)-(R)-1-(methoxy)-hexyl-(R)-2-carbamate,
1-(2-fluorophenyl)-(R)-1-(methoxy)-propyl-(R)-2-carbamate,
1-(4-fluorophenyl)-(R)-1-(methoxy)-proyl-(R)-2-carbamate,
1-(4-fluorophenyl)-(R)-1-(methoxy)-butyl-(R)-2-carbamate,
1-(4-fluorophenyl)-(R)-1-(methoxy)-3-methyl-butyl-(R)-2-carbamate,
1-(4-fluorophenyl)-(R)-1-(methoxy)-hexyl-(R)-2-carbamate,
1-(2-chlorophenyl)-(R)-1-(methoxy)-propyl-(R)-2-carbamate,
1-(2-chlorophenyl)-(R)-1-(methoxy)-propyl-(R)-2-N-methylcarbamate,
1-(2-chlorophenyl)-(R)-1-(methoxy)-propyl-(R)-2-N-propylcarbamate,
1-(2-chlorophenyl)-(R)-1-(methoxy)-propyl-(R)-2-N-isopropylcarbamate,
1-(2-chlorophenyl)-(R)-1-(methoxy)-propyl-(R)-2-N-cyclopropylcarbamate,
1-(2-chlorophenyl)-(R)-1-(methoxy)-propyl-(R)-2-N-cyclohexylcarbamate,
1-(2-chlorophenyl)-(R)-1-(methoxy)-propyl-(R)-2-N-benzylcarbamate,
1-(2-chlorophenyl)-(R)-1-(methoxy)-propyl-(R)-2-N-bicyclo[2,2,1]heptanecarbamate,
1-(2-chlorophenyl)-(R)-1-(methoxy)-butyl-(R)-2-carbamate,
1-(2-chlorophenyl)-(R)-1-(methoxy)-3-methyl-butyl-(R)-2-carbamate,
1-(2-chlorophenyl)-(R)-1-(methoxy)-hexyl-(R)-2-carbamate,
1-(2,3-dichlorophenyl)-(R)-1-(methoxy)-propyl-(R)-2-carbamate,
1-(2,4-dichlorophenyl)-(R)-1-(methoxy)-propyl-(R)-2-carbamate,
1-(2,4-dichlorophenyl)-(R)-1-(methoxy)-butyl-(R)-2-carbamate,
1-(2,4-dichlorophenyl)-(R)-1-(methoxy)-3-methyl-butyl-(R)-2-carbamate,
1-(2,4-dichlorophenyl)-(R)-1-(methoxy)-hexyl-(R)-2-carbamate,
1-(2,6-dichlorophenyl)-(R)-1-(methoxy)-propyl-(R)-2-carbamate,
1-(2,6-dichlorophenyl)-(R)-1-(methoxy)-butyl-(R)-2-carbamate,
1-(2,6-dichlorophenyl)-(R)-1-(methoxy)-3-methyl-butyl-(R)-2-carbamate,
1-(2,6-dichlorophenyl)-(R)-1-(methoxy)-hexyl-(R)-2-carbamate,
1-(2-chlorophenyl)-(R)-1-(methoxymethoxy)-propyl-(R)-2-carbamate,
1-(2-chlorophenyl)-(R)-1-(methoxymethoxy)-propyl-(R)-2-N-methylcarbamate,
1-(2-chlorophenyl)-(R)-1-(methoxymethoxy)-propyl-(R)-2-N-propylcarbamate,
1-(2-chlorophenyl)-(R)-1-(methoxymethoxy)-propyl-(R)-2-N-isopropylcarbamate,
1-(2-chlorophenyl)-(R)-1-(methoxymethoxy)-propyl-(R)-2-N-cyclopropylcarbamate,
1-(2-chlorophenyl)-(R)-1-(methoxymethoxy)-propyl-(R)-2-N-cyclohexylcarbamate,
1-(2-chlorophenyl)-(R)-1-(methoxymethoxy)-propyl-(R)-2-N-benzylcarbamate,
1-(2-chlorophenyl)-(R)-1-(methoxymethoxy)-propyl-(R)-2-N-bicyclo[2,2,1]heptanecarbamate,
1-(2-chlorophenyl)-(R)-1-(methoxymethoxy)-butyl-(R)-2-carbamate,
1-(2-chlorophenyl)-(R)-1-(methoxymethoxy)-3-methyl-butyl-(R)-2-carbamate,
1-(2-chlorophenyl)-(R)-1-(methoxymethoxy)-hexyl-(R)-2-carbamate,
1-(2,3-dichlorophenyl)-(R)-1-(methoxymethoxy)-propyl-(R)-2-carbamate,
1-(2,4-dichlorophenyl)-(R)-1-(methoxymethoxy)-propyl-(R)-2-carbamate,
1-(2,4-dichlorophenyl)-(R)-1-(methoxymethoxy)-butyl-(R)-2-carbamate,
1-(2,4-dichlorophenyl)-(R)-1-(methoxymethoxy)-3-methyl-butyl-(R)-2-carbamate,
1-(2,4-dichlorophenyl)-(R)-1-(methoxymethoxy)-hexyl-(R)-2-carbamate,
1-(2,5-dichlorophenyl)-(R)-1-(methoxymethoxy)-propyl-(R)-2-carbamate,
1-(2,6-dichlorophenyl)-(R)-1-(methoxymethoxy)-propyl-(R)-carbamate,
1-(2,6-dichlorophenyl)-(R)-1-(methoxymethoxy)-butyl-(R)-2-carbamate,
1-(2,6-dichlorophenyl)-(R)-1-(methoxymethoxy)-3-methyl-butyl-(R)-2-carbamate,
1-(2,6-dichlorophenyl)-(R)-1-(methoxymethoxy)-hexyl-(R)-2-carbamate,
1-(2-fluorophenyl)-(R)-1-(methoxymethoxy)-propyl-(R)-2-carbamate,
1-(4-fluorophenyl)-(R)-1-(methoxymethoxy)-propyl-(R)-2-carbamate,
1-(4-fluorophenyl)-(R)-1-(methoxymethoxy)-butyl-(R)-2-carbamate,
1-(4-fluorophenyl)-(R)-1-(methoxymethoxy)-3-methyl-butyl-(R)-2-carbamate,
1-(4-fluorophenyl)-(R)-1-(methoxymethoxy)-hexyl-(R)-2-carbamate,
1-(2-iodophenyl)-(R)-1-(methoxymethoxy)-propyl-(R)-2-carbamate,
1-(2-iodophenyl)-(R)-1-(methoxymethoxy)-butyl-(R)-2-carbamate,
1-(2-iodophenyl)-(R)-1-(methoxymethoxy)-3-methyl-butyl-(R)-2-carbamate,
1-(2-iodophenyl)-(R)-1-(methoxymethoxy)-hexyl-(R)-2-carbamate,
1-(3-iodophenyl)-(R)-1-(methoxymethoxy)-propyl-(R)-2-carbamate,
1-(3-iodophenyl)-(R)-1-(methoxymethoxy)-butyl-(R)-2-carbamate,
1-(3-iodophenyl)-(R)-1-(methoxymethoxy)-3-methyl-butyl-(R)-2-carbamate,
1-(3-iodophenyl)-(R)-1-(methoxymethoxy)-hexyl-(R)-2-carbamate,
1-(2-chlorophenyl)-(S)-1-carbamoyloxypropyl-(R)-2-carbamate, 1-(2-chlorophenyl)-(R)-1-carbamoyloxypropyl-(S)-2-carbamate, 1-(2-chlorophenyl)-(S)-1-(methoxy)-propyl-(R)-2-carbamate, 1-(2-chlorophenyl)-(R)-1-(methoxy)-propyl-(S)-2-carbamate, 1-(2-chlorophenyl)-(S)-1-(methoxymethoxy)-propyl-(R)-2-carbamate, and 1-(2-chlorophenyl)-(R)-1-(methoxymethoxy)-propyl-(S)-2-carbamate.

11. The method according to claim 1, wherein the epilepsy is an intractable epilepsy.

12. The method according to claim 11, wherein the intractable epilepsy is selected from the group consisting of localization-related epilepsy, generalized epilepsy and syndromes thereof.

13. The method according to claim 12, wherein the localization-related epilepsy is cortical epilepsy or temporal lobe epilepsy.

14. The method according to claim 13, wherein the cortical epilepsy is a frontal lobe epilepsy, parietal lobe epilepsy, or occipital lobe epilepsy.

15. The method according to claim 1, wherein the epilepsy-related syndrome is an epileptic seizure.

16. The method according to claim 15, wherein the epileptic seizure is an intractable localization-related epilepsy, an intractable secondary generalized seizure, an intractable complex partial seizure or an intractable status epilepticus.

* * * * *